(12) United States Patent
Aicher et al.

(10) Patent No.: US 8,754,226 B2
(45) Date of Patent: Jun. 17, 2014

(54) PIPERIDINYL-SUBSTITUTED LACTAMS AS GPR119 MODULATORS

(75) Inventors: Thomas Daniel Aicher, Ann Arbor, MI (US); Josef Roland Bencsik, LaSalle (CA); Kevin Ronald Condroski, San Diego, CA (US); Jay Bradford Fell, Boulder, CO (US); John P. Fischer, Boulder, CO (US); Ronald Jay Hinklin, Boulder, CO (US); Scott Alan Pratt, Longmont, CO (US); Ajay Singh, Broomfield, CO (US); Timothy M. Turner, Longmont, CO (US); David A. Mareska, McMurray, PA (US); Steven Armen Boyd, Pittsburgh, PA (US)

(73) Assignee: Array BioPharma Inc., Boulder, CO (US)

( * ) Notice: Subject to any disclaimer, the term of this patent is extended or adjusted under 35 U.S.C. 154(b) by 0 days.

(21) Appl. No.: 13/698,257

(22) PCT Filed: May 13, 2011

(86) PCT No.: PCT/US2011/036443
§ 371 (c)(1),
(2), (4) Date: Nov. 15, 2012

(87) PCT Pub. No.: WO2011/146335
PCT Pub. Date: Nov. 24, 2011

(65) Prior Publication Data
US 2013/0158009 A1 Jun. 20, 2013

Related U.S. Application Data

(60) Provisional application No. 61/345,461, filed on May 17, 2010.

(51) Int. Cl.
| | | |
|---|---|---|
| A01N 43/40 | (2006.01) | |
| A61K 31/445 | (2006.01) | |
| A61K 31/44 | (2006.01) | |
| C07D 401/00 | (2006.01) | |
| C07D 405/00 | (2006.01) | |
| C07D 409/00 | (2006.01) | |
| C07D 411/00 | (2006.01) | |
| C07D 413/00 | (2006.01) | |
| C07D 417/00 | (2006.01) | |
| C07D 419/00 | (2006.01) | |
| C07D 421/00 | (2006.01) | |

(52) U.S. Cl.
USPC ........ 546/208; 546/278.4; 546/256; 546/304; 514/318; 514/329; 514/333

(58) Field of Classification Search
USPC ................. 514/318, 329; 546/192
See application file for complete search history.

(56) References Cited

U.S. PATENT DOCUMENTS

| | | | | |
|---|---|---|---|---|
| 2006/0189638 | A1* | 8/2006 | Rawlins et al. | 514/265.1 |
| 2008/0146588 | A1* | 6/2008 | Devita et al. | 514/255.05 |
| 2009/0264650 | A1* | 10/2009 | Cho et al. | 544/141 |
| 2013/0184257 | A1 | 7/2013 | Aicher et al. | |

FOREIGN PATENT DOCUMENTS

| | | | |
|---|---|---|---|
| WO | WO 2002/102380 A1 | 12/2002 | |
| WO | WO 2005/061489 A1 | 7/2005 | |
| WO | WO 2005/082849 A1 | 9/2005 | |
| WO | WO 2005/101989 A2 | 11/2005 | |
| WO | WO 2005/121121 A2 | 12/2005 | |
| WO | WO 2006/117677 A1 | 11/2006 | |
| WO | WO 2007/003962 A2 | 1/2007 | |
| WO | WO 2007/003964 A1 | 1/2007 | |
| WO | WO 2008/025798 A1 | 3/2008 | |
| WO | WO 2008025798 | * | 6/2008 |
| WO | WO 2008/085316 A1 | 7/2008 | |
| WO | WO 2009/014910 A2 | 1/2009 | |
| WO | WO 2010/004344 A1 | 1/2010 | |
| WO | WO2010009183 A1 | 1/2010 | |
| WO | WO2011/029046 | * | 3/2011 |
| WO | WO2011127051 A1 | 10/2011 | |
| WO | WO 2011/146335 A1 | 11/2011 | |
| WO | WO 2013/066869 A1 | 5/2013 | |
| WO | WO 2013/074641 A1 | 5/2013 | |

OTHER PUBLICATIONS

Wermuth (The Practice of Medicinal Chemistry, Third edition, Elsevier, Amsterdam, 2008, chapter 16.*
Katz; Diabetes Obes. Metab., 2012, 14, 709-716, pubmed abstract.*
Overton; British Journal of Pharmacology (2008) 153, S76-S81.*
Di Dalmazi; Endocrine, 2013, published online May 13, 2013.*
Wu et al., "2,5-Disubstituted pyridines as potent GPR119 agonists", Bioorganic & Medicinal Chemistry Letters, vol. 20 (8), 2577-2581 (2010).
Boyd, Steven A., "AR-7947, a GPR119 Agonist with Durable Reductions in Post-Prandial and Fasted Blood Glucose in Preclinical Models of Type 2 Diabetes", GTCbio Diabetes Summit, Philadelphia, PA, Mar. 7-8, 2011, 14 pages.

(Continued)

Primary Examiner — John Mabry
Assistant Examiner — Daniel Carcanague
(74) Attorney, Agent, or Firm — Viksnins Harris & Padys PLLP; Sarah S. Mastous

(57) ABSTRACT

Compounds of Formula (I): and pharmaceutically acceptable salts thereof in which $X^1$, $X^2$, L, $R^3$, $R^4$, $R^5$, $R^6$, $R^{6a}$, $R^7$, $R^9$, $R^{9a}$, and n have the meanings given in the specification, are modulators of GPR119 and are useful in the treatment or prevention of diseases such as such as, but not limited to, type 2 diabetes, diabetic complications, symptoms of diabetes, metabolic syndrome, obesity, dyslipidemia, and related conditions.

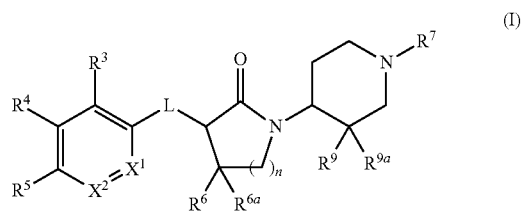

(I)

71 Claims, No Drawings

(56) References Cited

OTHER PUBLICATIONS

Fyfe et al., "GPR119 agonists as potential new oral agents for the treatment of type 2 diabetes and obesity", *Expert Opin. Drug Discov.*, 3(4), 403-413 (2008).

Jones et al., "GPR119 agonists for the treatment of type 2 diabetes", *Expert Opin. Ther. Patents*, 19(10), 1339-1359 (2009).

Patent Cooperation Treaty, International Searching Authority, Search Report and Written Opinion for PCT/US2011/036443, 10 pages, dated Oct. 24, 2011.

Shah, "GPR119 agonists: A promising new approach for the treatment of type 2 diabetes and related metabolic disorders", *Current Opinion in Drug Discovery & Development*, 12(4), 519-532 (2009).

Koch et al., ARRY-981: A GPR119 Agonist for Diabetes, Non-Confidential Slide Set, Bio International Convention, Washington D.C., 17 pages, Jun. 27-30, 2011.

Semple et al., "Discovery of the First Potent and Orally Efficacious Agonist of the Orphan G-Protein Coupled Receptor 119", *J. Med. Chem.*, 51, 5172-5175 (2008).

* cited by examiner

PIPERIDINYL-SUBSTITUTED LACTAMS AS GPR119 MODULATORS

The present invention relates to novel compounds, to pharmaceutical compositions comprising the compounds, to processes for making the compounds, and to the use of the compounds in therapy. More particularly, it relates to certain piperidinyl-substituted lactams which are modulators of GPR119 and are useful in the treatment or prevention of diseases such as, but not limited to, type 2 diabetes, diabetic complications, symptoms of diabetes, metabolic syndrome, obesity, dyslipidemia, and related conditions. In addition, the compounds are useful in decreasing food intake, decreasing weight gain, and increasing satiety in mammals.

Diabetes is diagnosed by elevated fasting plasma glucose levels ≥126 mg/dL or by plasma glucose levels after an oral glucose tolerance test ≥200 mg/dL. Diabetes is associated with the classic symptoms of polydipsia, polyphagia and polyuria (The Expert Committee on the Diagnosis and Classification of Diabetes Mellitus, *Diabetes Care,* 1998, 21, S5-19). Of the two major forms of diabetes, insulin dependent diabetes mellitus (Type I) accounts for 5-10% of the diabetic population. Type I diabetes is characterized by near total beta cell loss in the pancreas and little or no circulating insulin. Non-insulin dependent diabetes mellitus (type 2 diabetes) is the more common form of diabetes. Type 2 diabetes is a chronic metabolic disease that develops from a combination of insulin resistance in the muscle, fat, and liver and from partial beta cell loss in the pancreas. The disease progresses with the inability of the pancreas to secrete sufficient insulin to overcome such resistance. Uncontrolled type 2 diabetes is associated with an increased risk of heart disease, stroke, neuropathy, retinopathy and nephropathy among other diseases.

Obesity is a medical condition characterized by high levels of adipose tissue in the body. Body mass index is calculated by dividing weight by height squared (BMI=$kg/m^2$), where a person with a BMI of ≥30 is considered obese and medical intervention is recommended (For the Clinical Efficacy Assessment Subcommittee of the American College of Physicans. Pharmacological and surgical management of obesity in primary care: a clinical practice guideline from the American College of Physicians. *Ann Intern Med,* 2005, 142, 525-531). The main causes of obesity are increased calorie intake accompanied with a lack of physical activity and genetic predisposition. Obesity leads to an increased risk of many diseases including but not limited to diabetes, heart disease, stroke, dementia, cancer, and osteoarthritis.

Metabolic syndrome is present when a group of risk factors are found in a mammal (Grundy, S. M.; Brewer, H. B. Jr; et al *Circulation,* 2004, 109, 433-438). Abdominal obesity, dyslipidemia, high blood pressure and insulin resistance predominate in this disease. Similar to obesity, metabolic syndrome results from increased calorie intake, physical inactivity, and aging. Of major concern is that this condition can lead to coronary artery disease and type 2 diabetes.

Clinically there are a number of treatments currently being used to lower blood glucose in type 2 diabetic patients. Metformin (De Fronzo, R. A.; Goodman, A. M. *N Engl. J. Med.,* 1995, 333, 541-549) and the PPAR agonists (Wilson, T. M., et al., *J. Med. Chem.,* 1996, 39, 665-668) partially ameliorate insulin resistance by improving glucose utilization in cells. Treatment with sulfonylureas (Blickle, J F. *Diabetes Metab.* 2006 32, 113-120) has been shown to promote insulin secretion by affecting the pancreatic KATP channel; however, the increase in insulin is not glucose dependent and such treatment can lead to hypoglycemia. The recently approved DPP4 inhibitors and GLP-1 mimetics promote insulin secretion by the beta cell through an incretin mechanism, and administration of these agents causes insulin release in a glucose dependent manner (Vahl, T. P., D'Alessio, D. A., *Expert Opinion on Invest. Drugs,* 2004, 13, 177-188). However, even with these newer treatments, it is difficult to achieve precise control of blood glucose levels in type 2 diabetic patients in accordance with the guidelines recommended by the American Diabetes Association.

GPR119 is a Gs-coupled receptor that is predominately expressed in the pancreatic beta cells and in the enteroendocrine K and L cells of the GI tract. In the gut, this receptor is activated by endogenous lipid-derived ligands such as oleoylethanolamide (Lauffer, L. M., et al., *Diabetes,* 2009, 58, 1058-1066). Upon activation of GPR119 by an agonist, the enteroendocrine cells release the gut hormones glucagon-like peptide 1 (GLP-1), glucose-dependent insulinotropic peptide (GIP), and peptide YY (PYY) among others. GLP-1 and GIP have multiple mechanisms of action that are important for controlling blood glucose levels (Parker, H. E., et al., *Diabetologia,* 2009, 52, 289-298). One action of these hormones is to bind to GPCRs on the surface of beta cells leading to a rise in intracellular c-AMP levels. This rise results in a glucose dependent release of insulin by the pancreas (Drucker, D. J. *J. Clin. Investigation,* 2007, 117, 24-32; Winzell, M. S. *Pharmacol. and Therap.* 2007, 116, 437-448). In addition, GLP-1 and GIP have been shown to increase beta cell proliferation and decrease the rate of apoptosis in vivo in animal models of diabetes and in vitro with human beta cells (Farilla, L.; et al., *Endocrinology,* 2002, 143, 4397-4408; Farilla, L.; et al., *Endocrinology,* 2003, 144 5149-5158; and Hughes, T. E., *Current Opin. Chem. Biol.,* 2009, 13, 1-6). Current GLP-1 mechanism based therapies, such as sitagliptin and Byetta® (exenatide), have been clinically validated to improve glucose control in type 2 diabetic patients.

GPR119 receptors are also expressed on the pancreatic beta cells. A GPR119 agonist can bind to the pancreatic GPR119 receptor and cause a rise in cellular c-AMP levels consistent with a Gs-coupled GPCR signaling mechanism. The increased c-AMP then leads to a release of insulin in a glucose dependent manner. The ability of GPR119 agonists to enhance glucose-dependent insulin release by direct action on the pancreas has been demonstrated in vitro and in vivo (Chu Z., et al., Endocrinology 2007, 148:2601-9). This dual mechanism of action of the release of incretin hormones in the gut and binding directly to receptors on the pancreas may offer an advantage for GPR119 agonists over current therapies for treating diabetes.

GPR119 agonists, by increasing the release of PYY, may also be of benefit in treating many of comorbidities associated with diabetes and to treat these diseases in the absence of diabetes. Administration of $PYY_{3-36}$ has been reported to reduce food intake in animals (Batterham, R. L., et al., *Nature,* 2002, 418, 650-654), increase satiety and decrease food intake in humans (Batterham, R. L., et al., *Nature,* 2002, 418, 650-654), increase resting body metabolism (Sloth B., et al., *Am. J. Physiol. Endocrinol. Metab.,* 2007, 292, E1062-1068 and Guo, Y., et al., *Obesity,* 2006, 14, 1562-1570), increase fat oxidation (Adams, S. H., et al., *J. Nutr.,* 2006, 136, 195-201 and van den Hoek, A. M., et al., *Diabetes,* 2004, 53, 1949-1952), increase thyroid hormone activity, and increase adiponectin levels. PYY release caused by GPR119 agonists can therefore be beneficial in treating the metabolic syndrome and obesity.

Several classes of small molecule GPR119 agonists are known (Fyfe, M. T. E. et al., *Expert Opin. Drug. Discov.,*

2008, 3(4):403-413; Jones, R. M., et al., *Expert Opin. Ther. Patents*, 2009, 19(10), 1339-1359).

There remains, however, a need for compounds and methods for the treatment or prevention of diabetes, dyslipidemia, diabetic complications, and obesity.

SUMMARY OF THE INVENTION

It has now been found that certain novel piperidinyl-substituted lactams are modulators of GPR119 and are useful for treating type 2 diabetes, diabetic complications, metabolic syndrome, obesity, dyslipidemia, and related conditions.

Accordingly, in one aspect of the present invention there is provided compounds having the general Formula I

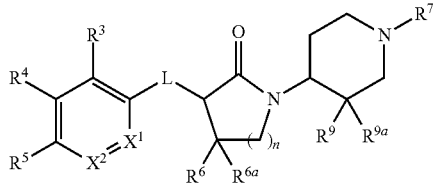

and pharmaceutically acceptable salts thereof, wherein $X^1$, $X^2$, L, $R^3$, $R^4$, $R^5$, $R^6$, $R^{6a}$, $R^7$, $R^9$, $R^{9a}$ and n are as defined herein. In one embodiment of Formula I, $R^{6a}$ is hydrogen, and $R^9$ and $R^{9a}$ are hydrogen.

In another aspect of the invention, there are provided pharmaceutical compositions comprising a compound of Formula I or a pharmaceutically acceptable salt thereof and a pharmaceutically acceptable carrier, diluent or excipient.

In another aspect of the invention, there is provided a method of treating a disease or condition selected from type 2 diabetes, symptoms of diabetes, diabetic complications, metabolic syndrome (including hyperglycemia, impaired glucose tolerance, and insulin resistance), obesity, dyslipidemia, dyslipoproteinemia, vascular restenosis, diabetic retinopathy, hypertension, cardiovascular disease, Alzheimer's disease, schizophrenia, and multiple sclerosis in a mammal, which comprises administering to said mammal in need thereof a therapeutically effective amount of a compound of Formula I or a pharmaceutically acceptable salt thereof.

In another aspect of the invention, there is provided the use of a compound of Formula I in the treatment of a disease or condition selected type 2 diabetes, symptoms of diabetes, diabetic complications, metabolic syndrome (including hyperglycemia, impaired glucose tolerance, and insulin resistance), obesity, dyslipidemia, dyslipoproteinemia, vascular restenosis, diabetic retinopathy, hypertension, cardiovascular disease, Alzheimer's disease, schizophrenia, and multiple sclerosis.

In another aspect of the invention, there is provided compounds of Formula I or pharmaceutically acceptable salts thereof, for use in therapy.

Another aspect of the invention provides intermediates for preparing compounds of Formula I. In one embodiment, certain compounds of Formula I may be used as intermediates for the preparation of other compounds of Formula I.

Another aspect of the invention includes processes for preparing, methods of separation, and methods of purification of the compounds described herein.

DETAILED DESCRIPTION OF THE INVENTION

One embodiment of this invention provides compounds of the general Formula I

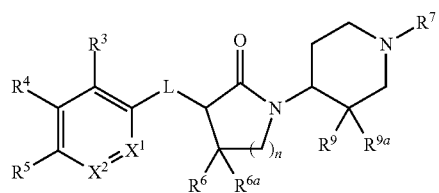

and pharmaceutically acceptable salts and solvates thereof, wherein:

L is O or $NR^x$;

$R^x$ is H or (1-3C)alkyl;

$X^1$ is N or $CR^1$ and $X^2$ is N or $CR^2$, wherein only one of $X^1$ and $X^2$ may be N;

$R^1$, $R^2$, $R^3$ and $R^4$ are independently selected from H, halogen, $CF_3$, (1-6C)alkyl and (1-6C)alkoxy;

$R^5$ is (1-3C)alkylsulfonyl, (3-6C)cycloalkylsulfonyl, (cyclopropylmethyl) sulfonyl, phenylsulfonyl, CN, Br, $CF_3$, triazolyl, (1-4C)alkoxycarbonyl, $R^xR^yNHC(=O)—$, oxadiazolyl optionally substituted with (1-3C)alkyl, and tetrazolyl optionally substituted with (1-3C)alkyl;

or when $X^1$ is $CR^1$ and $X^2$ is $CR^2$, then $R^4$ and $R^5$ optionally together with the atoms to which they are attached form a 5-6 membered saturated heterocyclic ring having 1-2 ring heteroatoms independently selected from O and S and optionally substituted with an oxo group, wherein the S when present is optionally oxidized;

$R^x$ and $R^y$ are independently (1-4C)alkyl optionally substituted with OH, or $R^x$ and $R^y$ together with the atom to which they are attached form a 5-6 membered saturated azacyclic ring optionally substituted with OH;

$R^6$ is H, OH or methyl;

$R^{6a}$ is H or methyl;

$R^7$ is a group having the structure

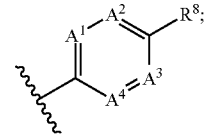

$A^1$ is N or $CR^a$;

$A^2$ is N or $CR^b$;

$A^3$ is N or $CR^c$;

$A^4$ is N or $CR^d$, wherein at least one of $A^1$, $A^2$, $A^3$ and $A^4$ is N, and no more than two of $A^1$, $A^2$, $A^3$ and $A^4$ may be N;

$R^a$, $R^b$, $R^c$ and $R^d$ are independently H, $CF_3$, halogen, (1-4C)alkyl or CN;

$R^{6a}$ is hydrogen;

$R^8$ is selected from hydrogen, halogen, $CF_3$, CN, (1-10C)alkyl, hydroxy(1-6C)alkyl, (1-6C)alkoxy, (1-6C alkyl)sulfanyl, phenyl, pyridyl, pyrimidyl, pyrazolyl, and di(1-3C)alkylcarbamyl, wherein each of said phenyl, pyridyl, pyrimidyl, and pyrazolyl is optionally substituted with one or more substituents independently selected from halogen, (1-4C)alkyl, (1-4C)alkoxy and $CF_3$; $R^9$ and $R^{9a}$ are independently hydrogen or methyl; and n is 1, 2 or 3.

One embodiment of this invention provides compounds of the general Formula I and pharmaceutically acceptable salts and solvates thereof, wherein:

L is O or NR$^x$;

R$^x$ is H or (1-3C)alkyl;

X$^1$ is N or CR$^1$ and X$^2$ is N or CR$^2$, wherein only one of X$^1$ and X$^2$ may be N;

R$^1$, R$^2$, R$^3$ and R$^4$ are independently selected from H, halogen, CF$_3$, (1-6C)alkyl and (1-6C)alkoxy;

R$^5$ is (1-3C)alkylsulfonyl, (3-6C)cycloalkylsulfonyl, (cyclopropylmethyl)sulfonyl, phenylsulfonyl, CN, Br, CF$_3$, oxadiazolyl optionally substituted with (1-3C)alkyl, or tetrazolyl optionally substituted with (1-3C)alkyl;

or when X$^1$ is CR$^1$ and X$^2$ is CR$^2$, then R$^4$ and R$^5$ optionally together with the atoms to which they are attached form a 5-6 membered saturated heterocyclic ring having 1-2 ring heteroatoms independently selected from O and S and optionally substituted with an oxo group, wherein the S when present is optionally oxidized;

R$^6$ is H or OH;

R$^{6a}$ is H;

R$^7$ is a group having the structure

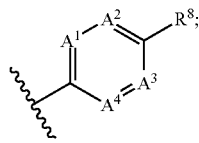

A$^1$ is N or CR$^a$;

A$^2$ is N or CR$^b$;

A$^3$ is N or CR$^c$;

A$^4$ is N or CR$^d$, wherein at least one of A$^1$, A$^2$, A$^3$ and A$^4$ is N, and no more than two of A$^1$, A$^2$, A$^3$ and A$^4$ may be N;

R$^a$, R$^b$, R$^c$ and R$^d$ are independently H, CF$_3$, halogen, (1-4C)alkyl or CN;

R$^8$ is selected from hydrogen, halogen, CF$_3$, CN, (1-10C)alkyl, hydroxy(1-6C)alkyl, (1-6C)alkoxy, (1-6C alkyl)sulfanyl, phenyl, pyridyl, pyrimidyl and pyrazolyl, wherein each of said phenyl, pyridyl, pyrimidyl, and pyrazolyl is optionally substituted with one or more substituents independently selected from halogen, (1-4C)alkyl, (1-4C)alkoxy and CF$_3$;

R$^9$ and R$^{9a}$ are hydrogen; and n is 1, 2 or 3.

In one embodiment, n is 1 or 3.

In one embodiment of Formula I, n is 1.

In one embodiment of Formula I, n is 2.

In one embodiment of Formula I, n is 2, provided that at least two of R$^1$, R$^2$, R$^3$ and R$^4$ is not H.

In one embodiment of Formula I, n is 3.

In one embodiment of Formula I, L is O.

In one embodiment of Formula I, L is NR$^x$.

In one embodiment, L is NH.

In one embodiment, L is N(1-3C)alkyl. Particular examples include NMe and NEt.

In one embodiment, R$^1$ is H, F, Cl or CF$_3$.

In one embodiment, R$^1$ is H, F or Cl.

In one embodiment, R$^1$ is H.

In one embodiment, R$^1$ is F.

In one embodiment, R$^1$ is Cl.

In one embodiment, R$^1$ is CF$_3$.

In one embodiment, R$^2$ is H, F or Me.

In one embodiment, R$^2$ is H.

In one embodiment, R$^2$ is F.

In one embodiment, R$^2$ is Me.

In one embodiment, R$^3$ is H, F, Cl or CF$_3$.

In one embodiment, R$^3$ is H.

In one embodiment, R$^3$ is F.

In one embodiment, R$^3$ is Cl.

In one embodiment, R$^3$ is CF$_3$.

In one embodiment, R$^4$ is H, Me, F, or Cl.

In one embodiment, R$^4$ is H.

In one embodiment, R$^4$ is Me.

In one embodiment, R$^4$ is F.

In one embodiment, R$^4$ is Cl.

In one embodiment of Formula I, the residue:

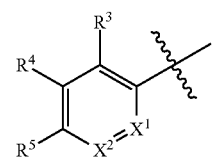

of Formula I, wherein the wavy line represents the point of attachment of the residue in Formula I, is selected from a residue wherein X$^1$ is CR$^1$ and X$^2$ is CR$^2$, such that the residue can be represented as:

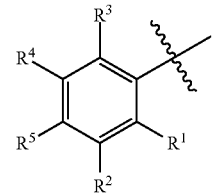

wherein R$^1$, R$^2$, R$^3$, R$^4$ and R$^5$ are as defined for Formula I.

In one embodiment of Formula I, R$^1$, R$^2$, R$^3$ and R$^4$ are independently selected from H, halogen, CF$_3$, (1-6C)alkyl and (1-6C)alkoxy.

In one embodiment, R$^1$, R$^2$, R$^3$ and R$^4$ are independently selected from H, F, Cl, CF$_3$, methyl, ethyl, propyl, isopropyl, methoxy, ethoxy, propoxy and isopropoxy.

In one embodiment of Formula I, R$^1$, R$^2$, R$^3$ and R$^4$ are independently selected from H, (1-6C)alkyl, CF$_3$ and halogen.

In one embodiment, R$^1$ and R$^2$ are independently selected from H, F and Cl, and R$^3$ and R$^4$ are independently selected from H, Me, F, Cl and CF$_3$.

In one embodiment, R$^1$ is H or F, R$^2$ is H, F or Cl, R$^3$ is H, F, or CF$_3$, and R$^4$ is H, Me, F, or Cl.

In one embodiment, R$^1$, R$^2$ and R$^4$ are H, and R$^3$ is F.

In one embodiment, R$^1$ and R$^3$ are F, and R$^2$ and R$^4$ are H.

In one embodiment, R$^1$ and R$^4$ are H, and R$^2$ and R$^3$ are F.

In one embodiment, R$^1$ and R$^4$ are H, R$^2$ is Cl and R$^3$ is F.

In one embodiment, R$^1$ and R$^4$ are H, R$^2$ is Me and R$^3$ is F.

In one embodiment, R$^1$, R$^2$ and R$^4$ are H, and R$^3$ is CF$_3$.

In one embodiment, R$^1$, R$^2$ and R$^3$ are H, and R$^4$ is F.

In one embodiment, R$^1$, R$^2$ and R$^3$ are H, and R$^4$ is Cl.

In one embodiment, R$^1$ is F, R$^2$ and R$^3$ are H, and R$^4$ is Me.

In one embodiment of Formula I, the residue:

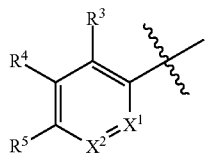

of Formula I, wherein the wavy line represents the point of attachment of the residue in Formula I, is selected from a residue wherein $X^1$ is N and $X^2$ is $CR^2$, such that the residue can be represented as:

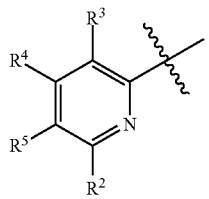

wherein $R^2$, $R^3$, $R^4$ and $R^5$ are as defined for Formula I. In one embodiment, $R^2$, $R^3$ and $R^4$ are independently selected from H, F, Cl, $CF_3$, methyl, ethyl, propyl, isopropyl, methoxy, ethoxy, propoxy and isopropoxy. In one embodiment, $R^2$, $R^3$ and $R^4$ are independently selected from H, halogen, $CF_3$ and (1-6C)alkyl. In one embodiment, $R^2$, $R^3$ and $R^4$ are independently selected from H, halogen and (1-6C)alkyl. In one embodiment, $R^2$, $R^3$ and $R^4$ are independently selected from H, F, Cl and Me. In one embodiment, $R^2$, $R^3$ and $R^4$ are independently selected from H or Cl. In one embodiment, $R^2$ is H. In one embodiment, $R^3$ is H. In one embodiment, $R^3$ is Cl. In one embodiment, $R^4$ is H. In one embodiment, $R^2$, $R^3$ and $R^4$ are each H. In one embodiment, $R^2$ and $R^4$ are H and $R^3$ is Cl.

In one embodiment of Formula I, the residue:

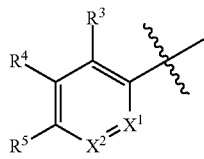

of Formula I, wherein the wavy line represents the point of attachment of the residue in Formula I, is selected from a residue wherein $X^1$ is $CR^1$ and $X^2$ is N, such that the residue can be represented as:

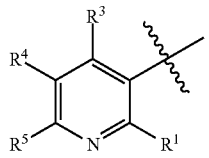

wherein $R^1$, $R^3$, $R^4$ and $R^5$ are as defined for Formula I. In one embodiment, $R^1$, $R^3$ and $R^4$ are independently selected from H, F, Cl, $CF_3$, methyl, ethyl, propyl, isopropyl, methoxy, ethoxy, propoxy and isopropoxy. In one embodiment, $R^1$, $R^3$ and $R^4$ are independently selected from H, halogen, $CF_3$ and (1-6C)alkyl. In one embodiment, $R^1$, $R^3$ and $R^4$ are independently selected from H, halogen, and (1-6C)alkyl. In one embodiment, $R^1$, $R^3$ and $R^4$ are independently selected from H, F, Cl and Me. In one embodiment, $R^1$, $R^3$ and $R^4$ are independently selected from H or Cl. In one embodiment, $R^1$ is H. In one embodiment, $R^3$ is H. In one embodiment, $R^3$ is Cl. In one embodiment, $R^4$ is H. In one embodiment, each of $R^1$, $R^3$ and $R^4$ is H.

In one embodiment, the residue:

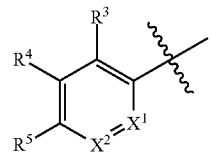

of Formula I, wherein the wavy line represents the point of attachment of the residue in Formula I, is selected from a residue wherein $X^1$ and $X^2$ are N, such that the residue can be represented as:

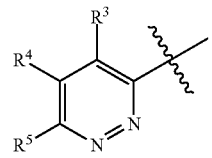

where $R^3$, $R^4$ and $R^5$ are as defined for Formula I. In one embodiment, $R^3$ and $R^4$ are hydrogen.

In one embodiment of Formula I, $X^1$ is N or $CR^1$ and $X^2$ is N or $CR^2$, wherein only one of $X^1$ and $X^2$ may be N; $R^1$, $R^2$, $R^3$ and $R^4$ are independently selected from H, halogen, $CF_3$, (1-6C)alkyl and (1-6C)alkoxy; and $R^5$ is (1-3C)alkylsulfonyl, (3-6C)cycloalkylsulfonyl, cyclopropylmethylsulfonyl-, phenylsulfonyl-, CN, Br, $CF_3$, oxadiazolyl optionally substituted with (1-3C)alkyl, or tetrazolyl optionally substituted with (1-3C)alkyl.

In one embodiment of Formula I, $X^1$ is $CR^1$, $X^2$ is $CR^2$, and $R^4$ and $R^5$ together with the atoms to which they are attached form a 5-6 membered saturated heterocyclic ring having 1-2 ring heteroatoms independently selected from O and S, wherein the heterocyclic ring is optionally substituted with an oxo group, and the S is optionally oxidized.

In one embodiment, $R^4$ and $R^5$ together with the atoms to which they are attached form a six-membered oxacyclic ring optionally substituted with oxo. In one embodiment, the residue:

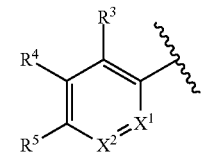

of Formula I wherein the wavy line represents the point of attachment of the residue in Formula I, has the structure:

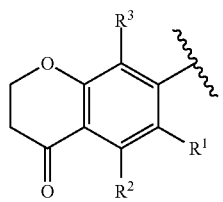

wherein $R^1$, $R^2$ and $R^3$ are independently selected from H, halogen, $CF_3$, (1-6C)alkyl and (1-6C)alkoxy. In one embodiment, $R^1$, $R^2$ and $R^3$ independently selected from H, F, Cl, $CF_3$, methyl, ethyl, propyl, isopropyl, methoxy, ethoxy, propoxy and isopropoxy. In one embodiment, $R^1$, $R^2$ and $R^3$ are independently selected from H, F, Me or $CF_3$. In one embodiment, $R^1$ is H or F. In one embodiment, $R^2$ is H or Me. In one embodiment, $R^3$ is H, F or $CF_3$. In one embodiment, $R^1$, $R^2$ and $R^3$ are H.

In one embodiment of Formula I, $X^1$ is $CR^1$, $X^2$ is $CR^2$, and $R^4$ and $R^5$ together with the atoms to which they are attached form a 5-membered heterocyclic ring having a ring S atom which is oxidized. In one embodiment, the residue:

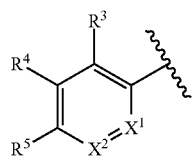

of Formula I has the structure:

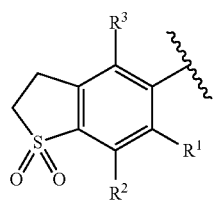

wherein $R^1$, $R^2$ and $R^3$ are independently selected from H, halogen, $CF_3$, (1-6C)alkyl and (1-6C)alkoxy. In one embodiment, $R^1$, $R^2$ and $R^3$ are independently selected from H, F, Cl, $CF_3$, methyl, ethyl, propyl, isopropyl, methoxy, ethoxy, propoxy and isopropoxy. In one embodiment, $R^1$, $R^2$ and $R^3$ are independently selected from H, F, Me or $CF_3$. In one embodiment, $R^1$ is H or F. In one embodiment, $R^2$ is H or Me. In one embodiment, $R^3$ is H, F or $CF_3$. In one embodiment, $R^1$ is F, and $R^2$ and $R^3$ are H. In one embodiment, $R^1$, $R^2$ and $R^3$ are H.

In one embodiment of Formula I, $R^5$ is selected from (1-3C)alkylsulfonyl, (3-6C)cycloalkylsulfonyl, cyclopropylmethylsulfonyl, and phenylsulfonyl ($C_6H_5SO_2$—).

In one embodiment, $R^5$ is (1-3C)alkylsulfonyl. Examples include $CH_3SO_2$— and $CH_3CH_2SO_2$—, $CH_3CH_2CH_2SO_2$— and $(CH_3)_2CHSO_2$—. Particular examples include $MeSO_2$— and $EtSO_2$—. In one embodiment, $R^5$ is $MeSO_2$—. In one embodiment, $R^5$ is $EtSO_2$—.

In one embodiment, $R^5$ is (3-6C)cycloalkylsulfonyl. An example is (cyclopropyl)$SO_2$—.

In one embodiment, $R^5$ is cyclopropylmethylsulfonyl which can be represented by the structure:

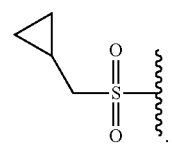 [SMILES: *S(=O)(=O)CC1CC1]

In one embodiment, $R^5$ is phenylsulfonyl ($C_6H_5SO_2$—).
In one embodiment, $R^5$ is selected from CN, Br and $CF_3$.
In one embodiment, $R^5$ is CN.
In one embodiment, $R^5$ is Br.
In one embodiment, $R^5$ is $CF_3$.
In one embodiment, $R^5$ is oxadiazolyl optionally substituted with (1-3C)alkyl. In one embodiment, $R^5$ is oxadiazolyl optionally substituted with methyl. In one embodiment, $R^5$ is 1,3,4-oxadiazolyl optionally substituted with (1-3C)alkyl. A particular example of $R^5$ is a group having the structure:

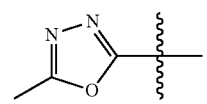

In one embodiment, $R^5$ is tetrazolyl optionally substituted with (1-3C)alkyl. In one embodiment, $R^5$ is tetrazolyl optionally substituted with methyl. Particular examples of $R^5$ include groups having the structures:

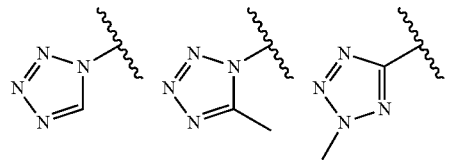

In one embodiment, $R^5$ is triazolyl. A particular example of $R^5$ is 1,2,4-triazol-1-yl having the structure:

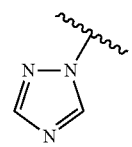

In one embodiment, $R^5$ is (1-4C)alkoxycarbonyl. A particular example of $R^5$ is methoxycarbonyl ($CH_3C(=O)$—).

In one embodiment, $R^5$ is $R^xR^yNHC(=O)$—. In one embodiment, $R^x$ and $R^y$ are independently (1-4C)alkyl optionally substituted with OH. In one embodiment, $R^x$ and $R^y$ are independently methyl, ethyl or 2-hydroxyethyl. Particular example of $R^5$ is the structures:

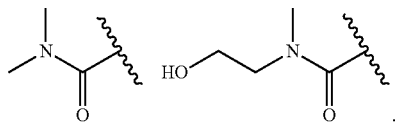

In one embodiment, $R^5$ is $R^xR^yNHC(=O)$— where $R^x$ and $R^y$ together with the atom to which they are attached form a 5-6 membered saturated azacyclic ring optionally substituted with OH. Particular example of $R^5$ is the structures:
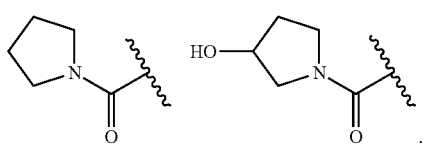 [SMILES: *C(=O)N1CCCC1 ; *C(=O)N1CCC(O)C1]
Particular examples of the group having the structure
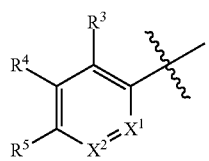
include the following structures:
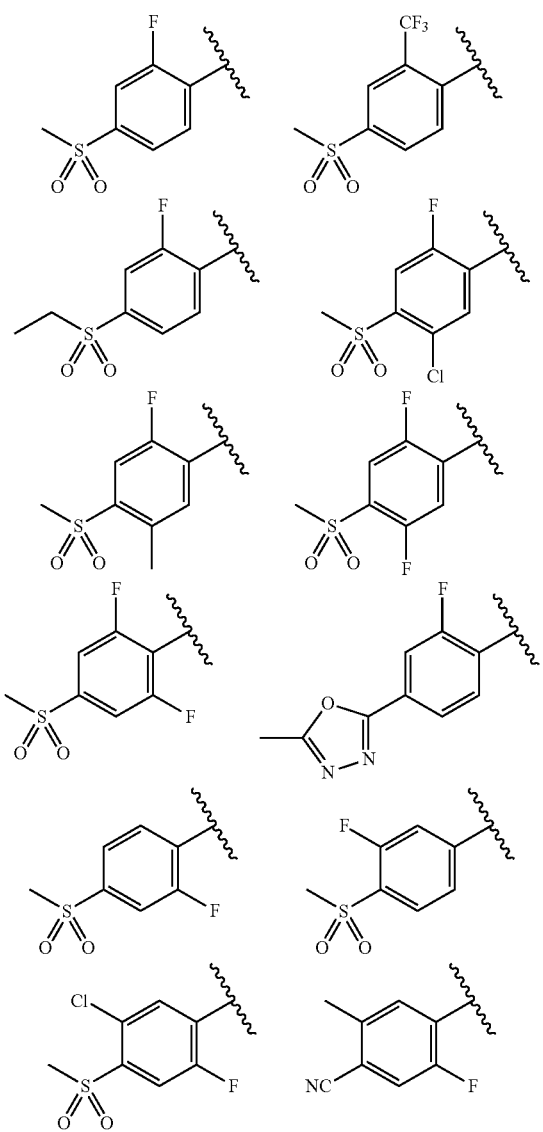
-continued
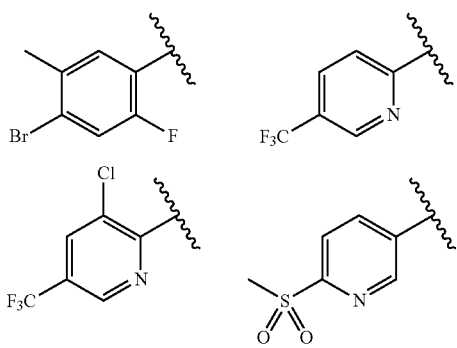
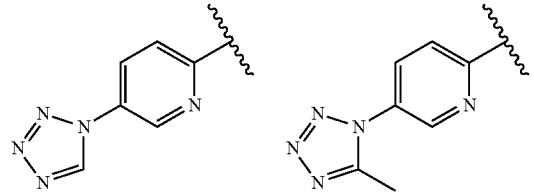
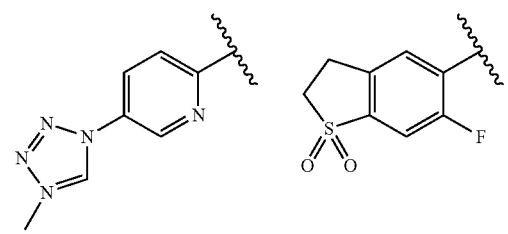
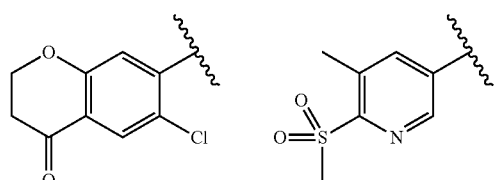
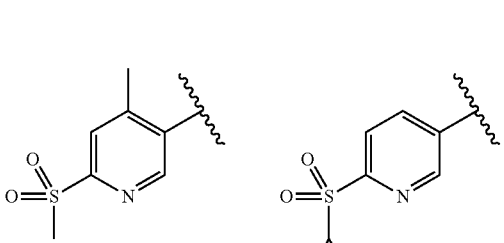
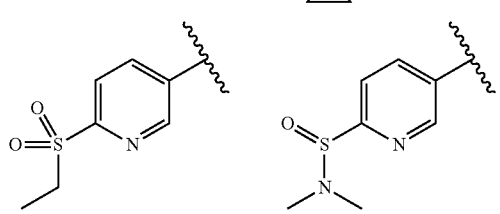
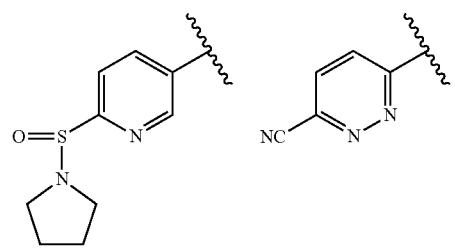

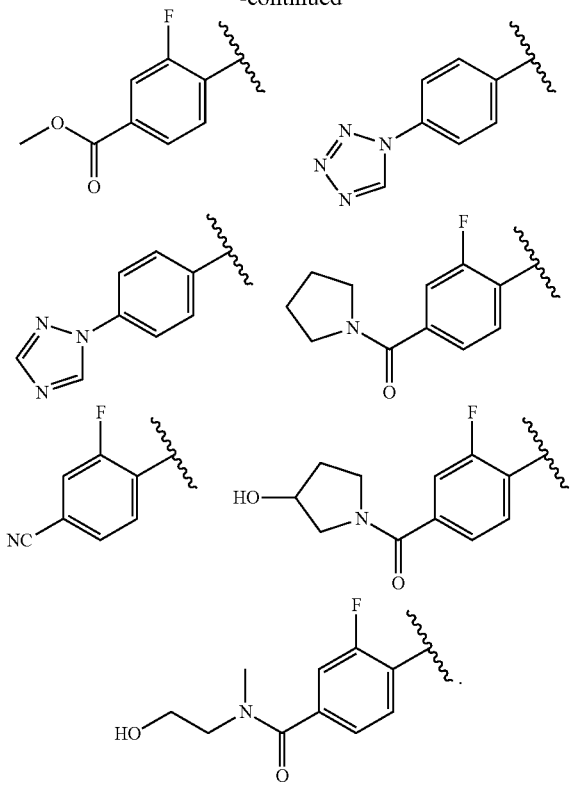

In one embodiment of Formula I, $R^6$ is H.
In one embodiment of Formula I, $R^6$ is OH.
In one embodiment of Formula I, $R^6$ is methyl.
In one embodiment of Formula I, $R^{6a}$ is H.
In one embodiment of Formula I, $R^{6a}$ is methyl.
In one embodiment of Formula I, $R^6$ and $R^{6a}$ are both hydrogen.
In one embodiment of Formula I, $R^6$ and $R^{6a}$ are both methyl.
In one embodiment of Formula I, $R^7$ is a group having the structure:

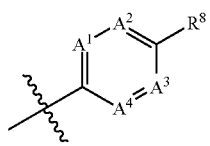

in which $A^1$ is $CR^a$, $A^2$ is $CR^b$, $A^3$ is $CR^c$, and $A^4$ is N, such that $R^7$ is a group having the formula $R^{7a}$

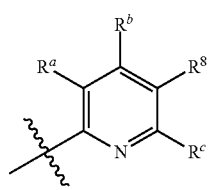

where $R^8$ is as defined for Formula I, and $R^a$, $R^b$ and $R^c$ are independently H, $CF_3$, halogen, (1-4C)alkyl or CN. In one embodiment, $R^a$, $R^b$ and $R^c$ are independently selected from hydrogen, halogen, (1-4C)alkyl and CN. In one embodiment, $R^a$, $R^b$ and $R^c$ are independently selected from hydrogen, halogen and (1-4C)alkyl. In one embodiment, at least one of $R^a$, $R^b$ and $R^c$ is hydrogen. In one embodiment, two of $R^a$, $R^b$ and $R^c$ are hydrogen and the other is selected from hydrogen, methyl, Cl, F and CN. In one embodiment, two of $R^a$, $R^b$ and $R^c$ are hydrogen and the other is selected from hydrogen, methyl and Cl. In one embodiment, two of $R^a$, $R^b$ and $R^c$ are hydrogen and the other is fluoro. In one embodiment, each of $R^a$, $R^b$ and $R^c$ is hydrogen.

In one embodiment of Formula I, $R^7$ is a group having the structure:

in which $A^1$ is N, $A^2$ is $CR^b$, $A^3$ is $CR^c$, and $A^4$ is N, such that $R^7$ is a group having the formula $R^{7b}$:

where $R^8$ is as defined for Formula I, and $R^b$ and $R^c$ are independently H, $CF_3$, halogen, (1-4C)alkyl or CN. In one embodiment of the group $R^{7b}$, one of $R^b$ and $R^c$ is hydrogen and the other is selected from H, $CF_3$, halogen, (1-4C)alkyl or CN. In one embodiment of the group $R^{7b}$, one of $R^b$ and $R^c$ is hydrogen and the other is selected from hydrogen and (1-4C)alkyl. In one embodiment, $R^b$ and $R^c$ are both hydrogen.

In one embodiment of Formula I, $R^7$ is a group having the structure:

in which $A^1$ is $CR^a$, $A^2$ is N, $A^3$ is $CR^c$, and $A^4$ is N, such that $R^7$ is a group having the formula $R^{7c}$:

where $R^8$ is as defined for Formula I, and $R^a$ and $R^c$ are independently selected from H, $CF_3$, halogen, (1-4C)alkyl and CN. In one embodiment, one of $R^a$ and $R^c$ is hydrogen and the other is selected from hydrogen, halogen, CN and (1-4C)alkyl. In one embodiment, one of $R^a$ and $R^c$ is hydrogen and the other is selected from hydrogen, Cl, CN and methyl. In one embodiment, each of $R^a$ and $R^c$ is hydrogen.

In one embodiment of Formula I, $R^7$ is a group having the structure:

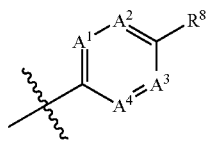

in which $A^1$ is $CR^a$, $A^2$ is $CR^b$, $A^3$ is N, and $A^4$ is N, such that $R^7$ is a group having the formula $R^{7d}$

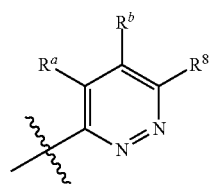

where $R^8$ is as defined for Formula I, and $R^a$ and $R^b$ are independently selected from H, $CF_3$, halogen, (1-4C)alkyl and CN. In one embodiment, one of $R^a$ and $R^b$ is hydrogen and the other is selected from hydrogen and (1-4C)alkyl. In one embodiment, one of $R^a$ and $R^b$ is hydrogen and the other is selected from hydrogen and methyl. In one embodiment, each of $R^a$ and $R^b$ is hydrogen.

In one embodiment of Formula I, $R^7$ is a group having the structure:

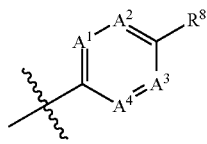

in which $A^1$ is $CR^a$, $A^2$ and $A^3$ are N, and $A^4$ is $CR^4$, such that $R^7$ is a group having the formula $R^{7e}$

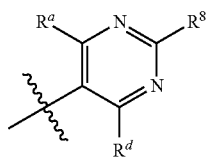

where $R^8$ is as defined for Formula I, and $R^a$ and $R^d$ are independently selected from H, $CF_3$, halogen, (1-4C)alkyl and CN. In one embodiment, one of $R^a$ and $R^d$ is hydrogen and the other is selected from hydrogen and (1-4C)alkyl. In one embodiment, one of $R^a$ and $R^d$ is hydrogen and the other is selected from hydrogen and methyl. In one embodiment, each of $R^a$ and $R^d$ is hydrogen.

In one embodiment of Formula I, $R^8$ is hydrogen.

In one embodiment of Formula I, $R^8$ is halogen. In one embodiment, $R^8$ is selected from Cl, Br and I. In one embodiment, $R^8$ is Cl.

In one embodiment of Formula I, $R^8$ is $CF_3$.

In one embodiment of Formula I, $R^8$ is CN.

In one embodiment of Formula I, $R^8$ is (1-10C)alkyl. In one embodiment, $R^8$ is selected from methyl, ethyl, propyl, isopropyl, butyl, heptyl and decyl. In one embodiment, $R^8$ is heptyl or decyl. In one embodiment, $R^8$ is selected from (1-3C)alkyl. In one embodiment, $R^8$ is selected from methyl and ethyl. In one embodiment, $R^8$ is methyl. In one embodiment, $R^8$ is ethyl.

In one embodiment of Formula I, $R^8$ is hydroxy(1-6C)alkyl. In one embodiment, $R^8$ is selected from 2-hydroxyprop-2-yl, 1-hydroxyethyl, 2-hydroxyethyl and hydroxymethyl. In one embodiment, $R^8$ is selected from 2-hydroxyprop-2-yl, 1-hydroxyethyl and 2-hydroxyethyl. In one embodiment, $R^8$ is 2-hydroxyprop-2-yl.

In one embodiment of Formula I, $R^8$ is (1-6C)alkoxy. In one embodiment of Formula I, $R^8$ is methoxy.

In one embodiment of Formula I, $R^8$ is (1-6C alkyl)sulfanyl. In one embodiment of Formula I, $R^8$ is $CH_3S$—.

In one embodiment of Formula I, $R^8$ is phenyl optionally substituted with one or more substituents independently selected from halogen, (1-4C)alkyl, (1-4C)alkoxy and $CF_3$. In one embodiment, $R^8$ is phenyl optionally substituted with one or more substituents independently selected from F, Cl, methyl, ethyl and $CF_3$. In one embodiment, $R^8$ is phenyl optionally substituted with one of said substituents. In one embodiment, $R^8$ is phenyl or methylphenyl, for example phenyl or 2-methylphenyl.

In one embodiment of Formula I, $R^8$ is pyridyl, pyrimidyl, or pyrazolyl, wherein each of said phenyl, pyridyl, pyrimidyl, and pyrazolyl is optionally substituted with one or more substituents independently selected from halogen, (1-4C)alkyl, (1-4C)alkoxy and $CF_3$.

In one embodiment of Formula I, $R^8$ is pyridyl optionally substituted with one or more substituents independently selected from halogen, (1-4C)alkyl, (1-4C)alkoxy and $CF_3$. In one embodiment, $R^8$ is pyridyl optionally substituted with one or more substituents independently selected from F, Cl, methyl, ethyl and $CF_3$. In one embodiment, $R^8$ is pyridyl. In one embodiment, $R^8$ is pyrid-2-yl.

In one embodiment of Formula I, $R^8$ is pyrimidyl optionally substituted with one or more substituents independently selected from halogen, (1-4C)alkyl, (1-4C)alkoxy and $CF_3$. In one embodiment, $R^8$ is pyrimidyl optionally substituted with one or more substituents independently selected from F, Cl, methyl, ethyl and $CF_3$. In one embodiment, $R^8$ is pyrimidyl. In one embodiment, $R^8$ is pyrimid-2-yl.

In one embodiment of Formula I, $R^8$ is pyrazolyl optionally substituted with one or more substituents independently selected from halogen, (1-4C)alkyl, (1-4C)alkoxy and $CF_3$. In one embodiment of Formula I, $R^8$ is pyrazolyl is optionally substituted with one or more substituents independently selected from (1-4C)alkyl. In one embodiment, $R^8$ is pyrazolyl is optionally substituted with methyl. In one embodiment, $R^8$ is pyrazolyl, or methylpyrazolyl. In one embodiment, $R^8$ is 1-methylpyrazol-5-yl, 1-methylpyrazol-4-yl or pyrazol-4-yl.

In one embodiment, $R^8$ is pyridyl, pyrimidyl, or pyrazolyl, wherein said pyrazolyl is optionally substituted with one or more substituents independently selected from (1-4C)alkyl.

In one embodiment, $R^8$ is di(1-3C)alkylcarbamyl. In one embodiment, $R^8$ is $(CH_3)_2NC(=O)$—.

In one embodiment of Formula I, $R^8$ is H, F, Cl, Br, I, $CF_3$, CN, methyl, ethyl, isopropyl, butyl, heptyl, decyl, 2-hydroxyprop-2-yl, 1-hydroxyethyl, 2-hydroxyethyl, hydroxymethyl, methoxy, $CH_3S$—, phenyl, 2-methylphenyl, pyrid-2- yl, pyrimid-2-yl, 1-methylpyrazol-5-yl, 1-methylpyrazol-4-yl, pyrazol-4-yl or (CH$_3$)$_2$NC(=O)—.

In one embodiment of Formula I, R$^8$ is H, F, Cl, Br, I, CF$_3$, CN, methyl, ethyl, isopropyl, butyl, heptyl, decyl, 2-hydroxyprop-2-yl, 1-hydroxyethyl, 2-hydroxyethyl, methoxy, CH$_3$S—, phenyl, 2-methylphenyl, pyrid-2-yl, pyrimid-2-yl, 1-methylpyrazol-5-yl, 1-methylpyrazol-4-yl or pyrazol-4-yl.

In one embodiment of Formula I, R$^8$ is H, halogen, or (1-10C)alkyl.

In one embodiment of Formula I, R$^8$ is CF$_3$, CN, hydroxy(1-6C)alkyl-, (1-6C)alkoxy, (1-6C alkyl)sulfanyl, phenyl optionally substituted with one or more substituents independently selected from halogen, (1-4C)alkyl, (1-4C)alkoxy and CF$_3$, pyrimidyl which is optionally substituted with one or more substituents independently selected from (1-4C)alkyl, or pyrazolyl which is optionally substituted with one or more substituents independently selected from (1-4C)alkyl.

In one embodiment of Formula I, R$^7$ is a group having the formula R$^{7a}$

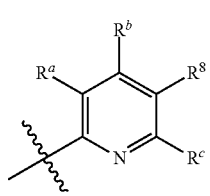

wherein two of R$^a$, R$^b$ and R$^c$ are hydrogen and the other is selected from H, CF$_3$, halogen, (1-4C)alkyl or CN; and R$^8$ is halogen, CN, CF$_3$, (1-10C alkyl), hydroxy(1-6C)alkyl, di(1-4C)alkylaminocarbonyl or phenyl optionally substituted with one or more substituents independently selected from halogen, (1-4C)alkyl, (1-4C)alkoxy or CF$_3$. In one embodiment of Formula I, R$^7$ is a group having the formula R$^{7a}$ wherein two of R$^a$, R$^b$ and R$^c$ are hydrogen and the other is selected from H, CF$_3$, halogen, (1-4C)alkyl or CN; and R$^8$ is halogen, CF$_3$, (1-10C alkyl), hydroxy(1-6C)alkyl, or phenyl optionally substituted with one or more substituents independently selected from halogen, (1-4C)alkyl, (1-4C)alkoxy and CF$_3$.

In one embodiment of Formula I, R$^7$ is a group having the formula R$^{7a}$ wherein two of R$^a$, R$^b$ and R$^c$ are hydrogen and the other is selected from hydrogen, Cl and (1-4C)alkyl; and R$^8$ is F, Cl, CN, CF$_3$, ethyl, hydroxymethyl, 1-hydroxyethyl, 2-hydroxyethyl, (CH$_3$)$_2$NC(=O)— or phenyl. In one embodiment of Formula I, R$^7$ is a group having the formula R$^{7a}$ wherein two of R$^a$, R$^b$ and R$^c$ are hydrogen and the other is selected from hydrogen, Cl and (1-4C)alkyl; and R$^8$ is F, CF$_3$, ethyl, 1-hydroxyethyl, 2-hydroxyethyl or phenyl.

Particular examples of the group R$^{7a}$ include the structures:

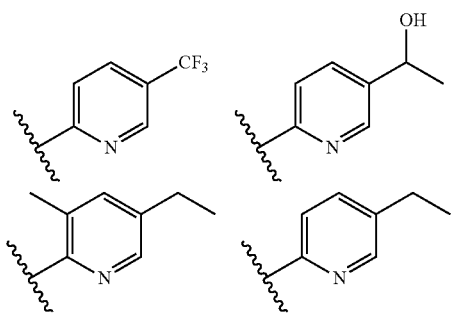

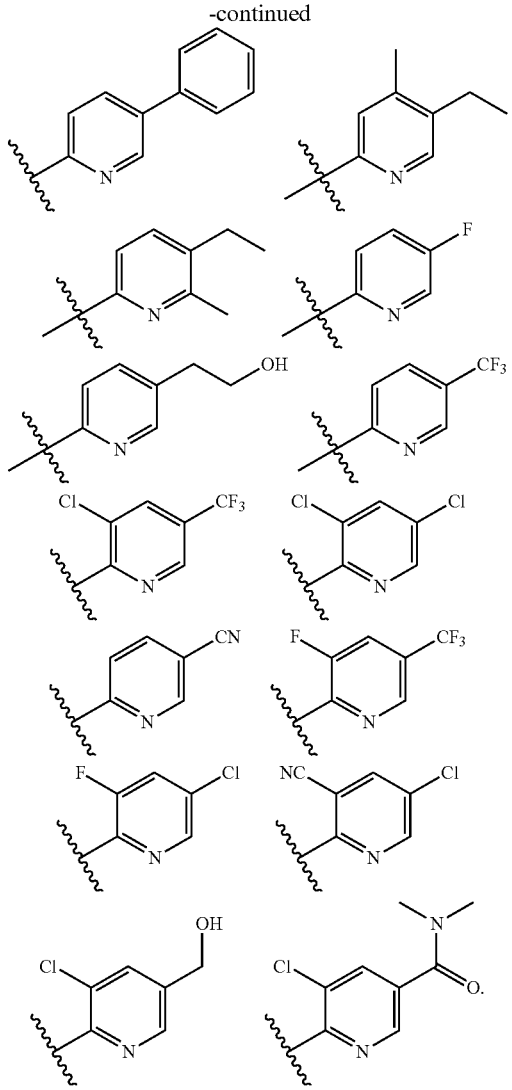

In one embodiment of Formula I, R$^7$ is a group having the formula R$^{7b}$:

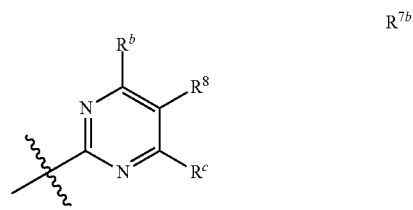

where one of R$^b$ and R$^c$ is hydrogen and the other is selected from H, CF$_3$, halogen, (1-4C)alkyl or CN; and R$^8$ is hydrogen, halogen, CF$_3$, CN, (1-10C alkyl), hydroxy(1-6C) alkyl, (1-6C)alkoxy, (1-6C alkyl)sulfanyl, phenyl, pyridyl, pyrimidyl or pyrazolyl, wherein said phenyl, pyridyl, pyrimidyl and pyrazolyl are optionally substituted with one or more substituents independently selected from halogen, (1-4C) alkyl, (1-4C)alkoxy and CF$_3$.

In one embodiment of Formula I, R$^7$ is a group having the formula R$^{7b}$ wherein one of R$^b$ and R$^c$ is hydrogen and the other is selected from hydrogen and (1-4C)alkyl; and R$^8$ is H, CF$_3$, F, Cl, Br, I, CN, methyl, ethyl, isopropyl, butyl, heptyl, decyl, 2-hydroxyprop-2-yl, methoxy, CH$_3$S—, 2-methylphenyl, pyrid-2-yl, pyrimid-2-yl, 1-methylpyrazol-5-yl, 1-methylpyrazol-4-yl or pyrazol-4-yl.

Particular examples of the group R$^{7b}$ include the structures:

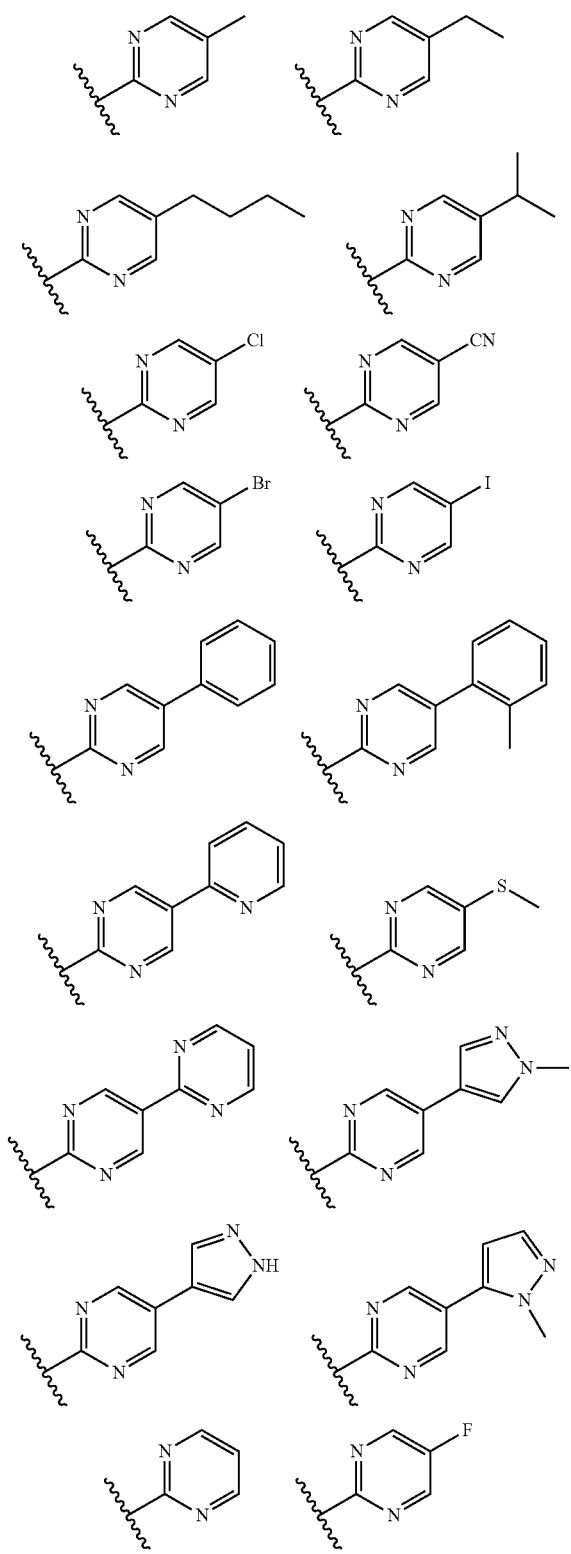

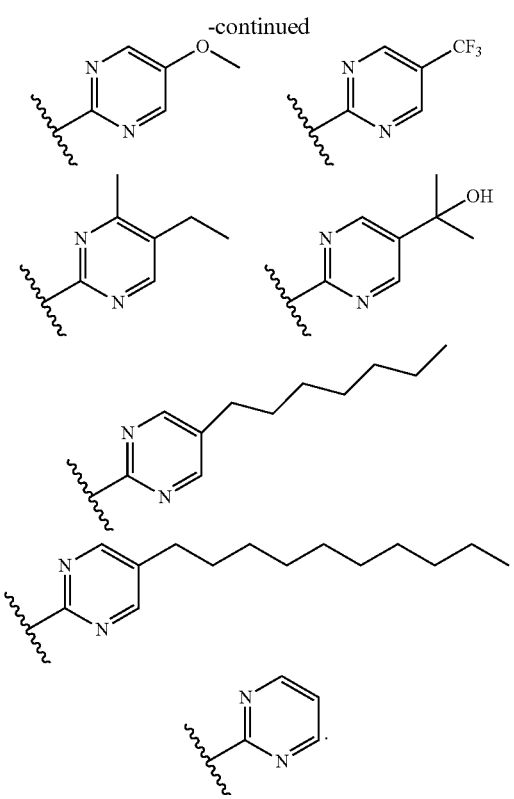

In one embodiment of Formula I, R$^7$ is a group having the formula R$^{7c}$:

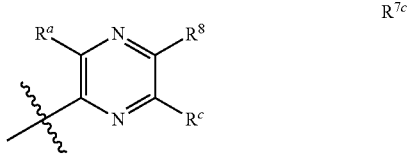

where one of R$^a$ and R$^c$ is hydrogen and the other is H, CF$_3$, halogen, (1-4C)alkyl or CN; and R$^8$ is selected from hydrogen, halogen, CF$_3$, (1-10C)alkyl, (1-6C)alkoxy or phenyl optionally substituted with one or more substituents independently selected from halogen, (1-4C)alkyl, (1-4C)alkoxy and CF$_3$. In one embodiment of Formula I, R$^7$ is a group having the formula R$^{7c}$ where one of R$^a$ and R$^c$ is hydrogen and the other is H, CF$_3$, halogen, (1-4C)alkyl or CN; and R$^8$ is selected from hydrogen, halogen, CF$_3$, (1-10C) alkyl, or phenyl optionally substituted with one or more substituents independently selected from halogen, (1-4C)alkyl, (1-4C)alkoxy and CF$_3$.

In one embodiment of Formula I, R$^7$ is a group having the formula R$^{7c}$ wherein one of R$^a$ and R$^c$ is hydrogen and the other is H, Cl or CN; and R$^8$ is H, (1-4C)alkyl, Cl, Br, CN, methoxy, or phenyl optionally substituted with (1-4C)alkyl.

In one embodiment of Formula I, R$^7$ is a group having the formula R$^{7c}$ wherein one of R$^a$ and R$^c$ is hydrogen and the other is H, Cl or CN; and R$^8$ is H, (1-4C)alkyl, Cl, Br, CN, or phenyl optionally substituted with (1-4C)alkyl.

In one embodiment of Formula I, R$^7$ is a group having the formula R$^{7c}$ wherein one of R$^a$ and R$^c$ is hydrogen and the other is H, Cl or CN; and R$^8$ is H, ethyl, isopropyl, Cl, Br, CN, or methylphenyl.

Particular examples of the group $R^{7c}$ include the structures:

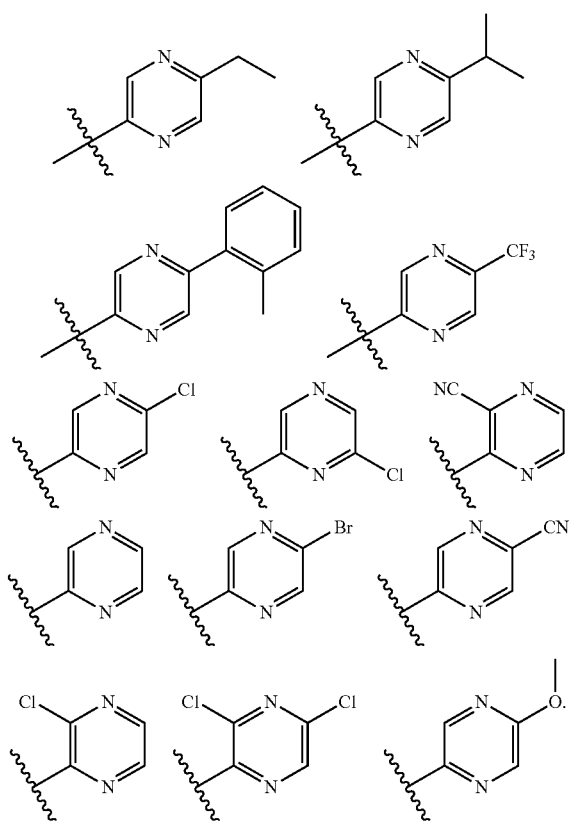

In one embodiment of Formula I, $R^7$ is a group having the formula $R^{7d}$

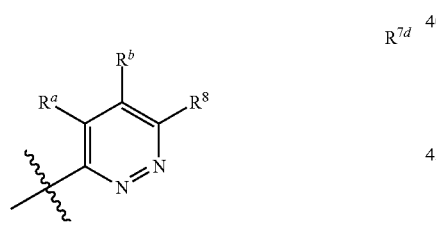

where one of $R^a$ and $R^b$ is hydrogen and the other is H, CF$_3$, halogen, (1-4C)alkyl or CN; and $R^8$ is halogen.

In one embodiment of Formula I, $R^7$ is a group having the formula $R^{7d}$ wherein $R^a$ and $R^b$ are both hydrogen and $R^8$ is halogen.

A particular example of the group $R^{7d}$ is the structure

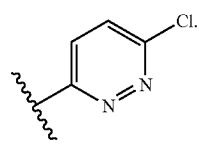 [SMILES: *c1ccc(Cl)nn1]

In one embodiment of Formula I, $R^7$ is a group having the formula $R^{7e}$

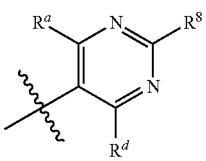

where $R^a$ and $R^d$ are H and $R^8$ is CF$_3$ or (1-10C)alkyl. Particular examples of the group $R^{7e}$ include the structures:

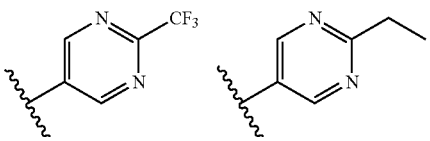

In one embodiment of Formula I, $R^9$ and $R^{9a}$ are hydrogen. In one embodiment of Formula I, $R^9$ and $R^{9a}$ are methyl.

In one embodiment, the following compounds are excluded from Formula I: (S)-3-(2,5-difluoro-4-(methylsulfonyl)phenylamino)-1'-(5-(2-hydroxypropan-2-yl)pyrimidin-2-yl)-1,4'-bipiperidin-2-one; 3-(2-fluoro-4-(methylsulfonyl)phenylamino)-1'-(5-(2-hydroxy-ethyl)pyridin-2-yl)-1,4'-bipiperidin-2-one; (S)-1-(1-(6-chloro-5-(trifluoromethyl)pyridin-2-yl)piperidin-4-yl)-3-((2-fluoro-4-(methylsulfonyl)phenyl)amino)pyrrolidin-2-one; (S)-5-chloro-2-(4-(3-((6-(cyclopropylsulfonyl)pyridin-3-yl)amino)-2-oxopyrrolidin-1-yl)piperidin-1-yl)nicotinonitrile; and (3S)-1-(1-(3-chloro-5-(trifluoromethyl)pyridin-2-yl)-3,3-dimethylpiperidin-4-yl)-3-((2-fluoro-4-(methylsulfonyl)phenyl)amino)pyrrolidin-2-one.

In embodiment, compounds of Formula I include compounds of Formula IA

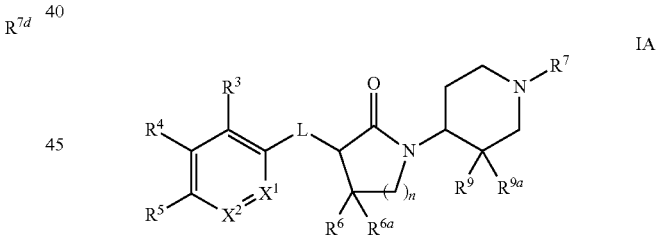

and pharmaceutically acceptable salts thereof, wherein:

L is O or NR$^x$;

$R^x$ is H or (1-3C)alkyl;

$X^1$ is N or CR$^1$ and $X^2$ is N or CR$^2$, wherein only one of $X^1$ and $X^2$ may be N;

$R^1$, $R^2$, $R^3$ and $R^4$ are independently selected from H, halogen, CF$_3$, (1-6C)alkyl and (1-6C)alkoxy;

$R^5$ is (1-3C)alkylsulfonyl, (3-6C)cycloalkylsulfonyl, (cyclopropylmethyl) sulfonyl, phenylsulfonyl, CN, Br, CF$_3$, oxadiazolyl optionally substituted with (1-3C)alkyl, or tetrazolyl optionally substituted with (1-3C)alkyl;

$R^6$ is H or OH;

$R^{6a}$ is H;

$R^7$ is a group having the structure

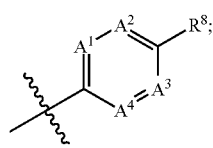

$A^1$ is N or $CR^a$;
$A^2$ is N or $CR^b$;
$A^3$ is N or $CR^c$;
$A^4$ is N or $CR^d$,
wherein at least one of $A^1$, $A^2$, $A^3$ and $A^4$ is N, and no more than two of $A^1$, $A^2$, $A^3$ and $A^4$ may be N;

$R^a$, $R^b$, $R^c$ and $R^d$ are independently H, $CF_3$, halogen, (1-4C)alkyl or CN, wherein only one of $R^a$, $R^b$, $R^c$ and $R^d$ may be $CF_3$, halogen, (1-4C)alkyl or CN, the remainder being hydrogen;

$R^8$ is selected from hydrogen, halogen, $CF_3$, CN, (1-10C)alkyl, hydroxy(1-6C)alkyl, (1-6C)alkoxy, (1-6C alkyl)sulfanyl, phenyl, pyridyl, pyrimidyl, and pyrazolyl, wherein each of said phenyl, pyridyl, pyrimidyl, and pyrazolyl is optionally substituted with one or more substituents independently selected from halogen, (1-4C)alkyl, (1-4C)alkoxy and $CF_3$;

$R^9$ and $R^{9a}$ are hydrogen; and
n is 1, 2 or 3.

It will be appreciated that certain compounds according to the invention may contain one or more centers of asymmetry and may therefore be prepared and isolated as a mixture of isomers such as a racemic or diastereomeric mixture, or in an enantiomerically or diastereomerically pure form. It is intended that all stereoisomeric forms of the compounds of the invention, including but not limited to, diastereomers, enantiomers and atropisomers, as well as mixtures thereof such as racemic mixtures, form part of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The terms "(1-3C)alkyl", "(1-4C)alkyl", "(1-6C)alkyl" and "(1-10C)alkyl" as used herein refer to saturated linear or branched-chain monovalent hydrocarbon radicals of one to three, one to four, one to six carbon, or one to ten atoms, respectively. Examples include, but are not limited to, methyl, ethyl, 1-propyl, isopropyl, 1-butyl, isobutyl, sec-butyl, tert-butyl, 2-methyl-2-propyl, pentyl, hexyl, heptyl and decyl.

The term "hydroxy(1-6C)alkyl" as used herein refers to saturated linear or branched-chain monovalent alkoxy radicals of one to six carbon atoms, wherein one of the carbon atoms is substituted with a hydroxy group.

The terms "(1-4C)alkoxy" and "(1-6C)alkoxy" as used herein refer to saturated linear or branched-chain monovalent alkoxy radicals of one to four or one to six carbon atoms, respectively, wherein the radical is on the oxygen atom. Examples include methoxy, ethoxy, propoxy, isopropoxy, and butoxy.

The term "(1-3C)alkylsulfonyl" as used herein refers to a (1-3C alkyl)$SO_2$— group, wherein the radical is on the sulfur atom and the (1-3C alkyl) portion is as defined above. Examples include methylsulfonyl ($CH_3SO_2$—) and ethylsulfonyl ($CH_3SO_2$—).

The term "(3-6C)cycloalkylsulfonyl" as used herein refers to a (3-6C cycloalkyl)$SO_2$— group, wherein the radical is on the sulfur atom. An example is cyclopropylsulfonyl.

The term "(1-6C alkyl)sulfanyl" as used herein refers to a (1-6C alkyl)S— group, wherein the radical is on the sulfur atom and the (1-6C alkyl) portion is as defined above. Examples include methylsulfanyl ($CH_3S$—) and ethylsulfanyl ($CH_2CH_2S$—).

The term "di(1-3C)alkylcarbamyl" refers to a di(1-3C)alkylNHC(=O)— group.

The term "halogen" includes fluoro, chloro, bromo and iodo.

It will also be appreciated that certain compounds of Formula I may be used as intermediates for the preparation of further compounds of Formula I.

The compounds of Formula I include salts thereof. In certain embodiments, the salts are pharmaceutically acceptable salts. In addition, the compounds of Formula I include other salts of such compounds which are not necessarily pharmaceutically acceptable salts, and which may be useful as intermediates for preparing and/or purifying compounds of Formula I and/or for separating enantiomers of compounds of Formula I. Examples of particular salts include trifluoroacetate and hydrochloride salts.

The term "pharmaceutically acceptable" indicates that the substance or composition is compatible chemically and/or toxicologically, with the other ingredients comprising a formulation, and/or the mammal being treated therewith.

It will further be appreciated that the compounds of Formula I and their salts may be isolated in the form of solvates, and accordingly that any such solvate is included within the scope of the present invention.

Compounds of the invention may also contain unnatural proportions of atomic isotopes at one or more of the atoms that constitute such compounds. That is, an atom, in particular when mentioned in relation to a compound according to Formula I, comprises all isotopes and isotopic mixtures of that atom, either naturally occurring or synthetically produced, either with natural abundance or in an isotopically enriched form. For example, when hydrogen is mentioned, it is understood to refer to $^1H$, $^2H$, $^3H$ or mixtures thereof; when carbon is mentioned, it is understood to refer to $^{11}C$, $^{12}C$, $^{13}C$, $^{14}C$ or mixtures thereof; when nitrogen is mentioned, it is understood to refer to $^{13}N$, $^{14}N$, $^{15}N$ or mixtures thereof; when oxygen is mentioned, it is understood to refer to $^{14}O$, $^{15}O$, $^{16}O$, $^{17}O$, $^{18}O$ or mixtures thereof; and when fluoro is mentioned, it is understood to refer to $^{18}F$, $^{19}F$ or mixtures thereof. The compounds according to the invention therefore also comprise compounds with one or more isotopes of one or more atom, and mixtures thereof, including radioactive compounds, wherein one or more non-radioactive atoms has been replaced by one of its radioactive enriched isotopes. Radiolabeled compounds are useful as therapeutic agents, e.g., cancer therapeutic agents, research reagents, e.g., assay reagents, and diagnostic agents, e.g., in vivo imaging agents. All isotopic variations of the compounds of the present invention, whether radioactive or not, are intended to be encompassed within the scope of the present invention.

The present invention further provides a process for the preparation of a compound of Formula I or a salt thereof as defined herein which comprises:

(a) coupling a corresponding compound having the formula II

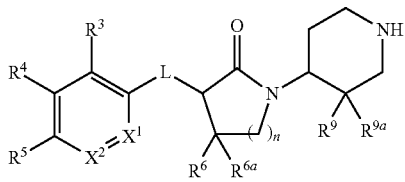

with a corresponding compound having the formula III

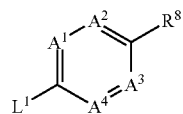

wherein $L^1$ is a leaving atom or group, in the presence of a base and optionally further in the presence of a metal catalyst and optionally in the presence of a ligand; or (b) coupling a corresponding compound having the formula IV

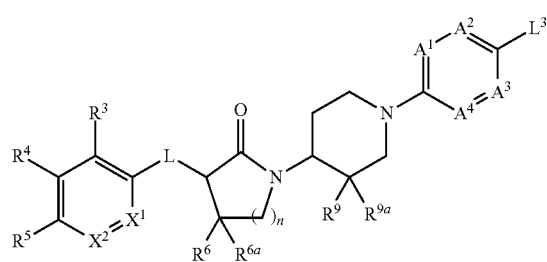

wherein $L^3$ is a leaving atom or group, with a compound having the formula $(R^8)_2Zn$ or $R^8ZnBr$ in the presence of a metal catalyst and a base; or (c) for a compound of Formula I wherein L is $NR^x$, coupling a corresponding compound having the formula V

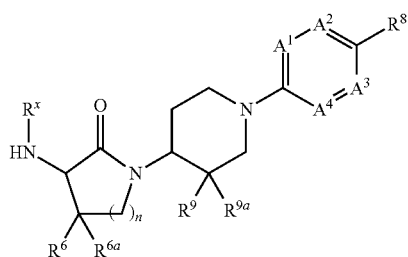

with a corresponding compound having the formula VI

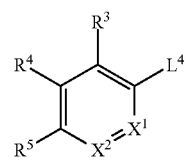

wherein $L^4$ is a leaving atom or group, in the presence of a base and optionally further in the presence of a metal catalyst; or (d) for a compound of Formula I wherein $R^5$ is a group having the $R^{5a}SO_2$— where $R^{5a}$ is (1-3C) alkyl, (3-6C)cycloalkyl, cyclopropylmethyl- or phenyl, reacting a corresponding compound having the formula VII

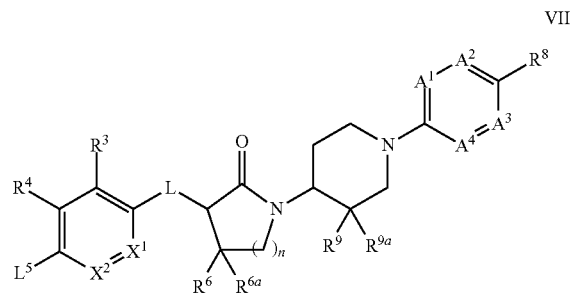

wherein $L^5$ is a leaving atom or group, with a reagent having the formula $R^{5a}SO_2Na$ in the presence of a metal catalyst and a ligand; or (e) for a compound of Formula I wherein $R^8$ is phenyl, pyridyl, pyrimidyl or pyrazolyl, each of which is optionally substituted with one or more substituents independently selected from halogen, (1-4C)alkyl, (1-4C)alkoxy and $CF_3$, reacting a corresponding compound having the formula IV

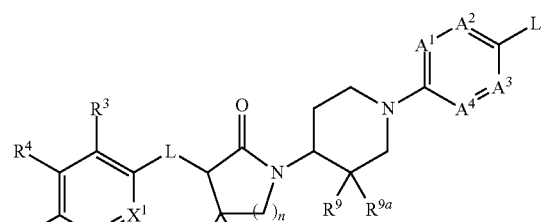

wherein $L^3$ is a leaving atom or group, with a corresponding compound having the formula $R^{8a}B(OR^eR^f)_2$, where $R^{8a}$ is phenyl, pyridyl, pyrimidyl or pyrazolyl, each of which is optionally substituted with one or more substituents independently selected from halogen, (1-4C)alkyl, (1-4C)alkoxy and $CF_3$, and $R^e$ and $R^f$ are H or (1-6C)alkyl, or $R^e$ and $R^f$ together with the atoms to which they are connected form a 5-6 membered ring optionally substituted with 1-4 substituents selected from (1-3C alkyl), wherein said coupling takes place in the presence of a palladium catalyst and a base; or (f) for a compound of Formula I wherein $R^5$ is CN, reacting a corresponding compound having the formula VII

VII

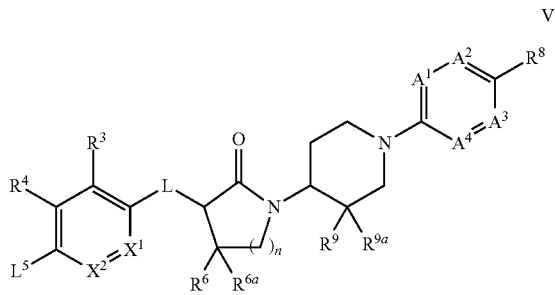

wherein $L^5$ is a leaving atom or group, in the presence of a metal catalyst CuCN; or (g) for a compound of Formula I wherein $R^8$ is CH(OH)(1-5C alkyl), reacting a corresponding compound having the formula VIII

VIII

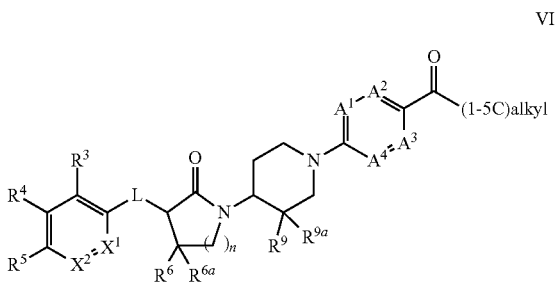

with a reducing agent; or (h) for a compound of Formula I wherein $R^8$ is (1-6C alkyl)sulfanyl, reacting a corresponding compound having the formula IV

IV

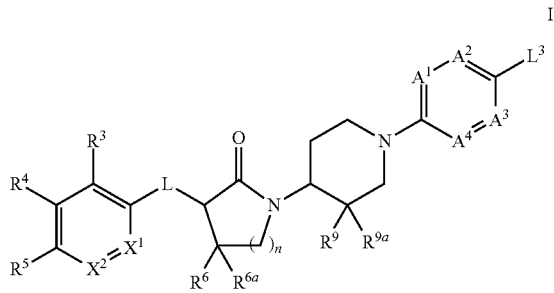

wherein $L^3$ is a leaving atom or group, with a reagent having the formula NaS(1-6C alkyl) in the presence of a palladium catalyst, a ligand and a base; and optionally removing any protecting groups and optionally preparing a salt thereof.

In one embodiment of the methods described above, $R^{6a}$ is hydrogen, and $R^9$ and $R^{9a}$ are hydrogen.

Referring to method (a), the leaving atom $L^1$ may be, for example, a halide such as Cl. Alternatively, $L^1$ may be a leaving group such as an alkylsulfonyl or arylsulfonyl group, for example, a triflate group, an arylsulfonyloxy group or an alkylsulfonyloxy group, such as a mesylate or a tosylate group, $NO_2$, or a diazonium group. In one embodiment, the reaction is performed in the presence of a base. Suitable bases include amine bases, such as tertiary amine bases, such as diisopropylethylamine (DIEA) and triethylamine 1n one embodiment, the reaction is further performed in the presence of a palladium catalyst and a ligand. Suitable metal catalysts include palladium (0), palladium (II), and nickel catalysts. Examples include $Pd_2\,dba_3$, $PdCl_2$, and $Pd(OAc)_2$. Suitable ligands include 2,8,9-triisobutyl-2,5,8,9-tetraaza-1-phosphabicyclo[3.3.3]undecane, XPHOS, DIPHOS or rac-BINAP. Convenient solvents include toluene, aprotic solvents such as ethers (for example tetrahydrofuran or p-dioxane), DMF, DME and DMSO. The reaction is conveniently performed at elevated temperatures, such as 80-130° C., for example 110° C.

Referring to method (b), the leaving atom $L^3$ may be, for example, a halide such as Cl. Alternatively, $L^3$ may be a leaving group such as an alkylsulfonyl or arylsulfonyl group, for example, a triflate group, an arylsulfonyloxy group or an alkylsulfonyloxy group, such as a mesylate or a tosylate group, $NO_2$, or a diazonium group. Suitable metal catalysts include palladium (II) catalysts such as $PdCl_2$-(dppf)-$CH_2Cl_2$, $Pd_2(dba)_3$, $Pd(OAc)_2$ or $Pd(PPh_3)_4$. The base may be, for example, an alkali metal carbonate, such as sodium carbonate, potassium carbonate or cesium carbonate. Convenient solvents include aprotic solvents such as ethers (for example tetrahydrofuran or p-dioxane) or toluene. The reaction is conveniently performed at elevated temperatures, for example between 60 and 110° C.

Referring to method (c), the leaving atom $L^4$ may be, for example, a halide such as F, Cl or Br. Alternatively, $L^4$ may be a leaving group such as an alkylsulfonyl or arylsulfonyl group, for example, a triflate group, an arylsulfonyloxy group or an alkylsulfonyloxy group, such as a mesylate or a tosylate group, $NO_2$, or a diazonium group.

In one embodiment, the reaction may be performed in the presence of a base, such as an alkali metal carbonate, such as sodium carbonate, potassium carbonate or cesium carbonate. Suitable metal catalysts include palladium (0) and palladium (II) catalysts, such as catalysts such as $Pd_2\,dba_3$, $PdCl_2$, and $Pd(OAc)_2$. Suitable ligands include 2,8,9-triisobutyl-2,5,8,9-tetraaza-1-phosphabicyclo[3.3.3]undecane, XPHOS, DIPHOS or rac-BINAP. Convenient solvents include toluene, aprotic solvents such as ethers (for example tetrahydrofuran or p-dioxane), DMF, DME or DMSO. The reaction is conveniently performed at elevated temperatures, such as 80-130° C., for example 90-110° C.

Referring to method (d), the leaving atom $L^5$ may be, for example, a halide such as F, Cl or Br. Alternatively, $L^5$ may be a leaving group such as an alkylsulfonyl or arylsulfonyl group, for example, a triflate group, an arylsulfonyloxy group or an alkylsulfonyloxy group, such as a mesylate or a tosylate group, $NO_2$, or a diazonium group. The metal catalyst may be a Cu(I)triflate benzene-complex, CuI, CuCl, CuBr or $Cu_2O$. The ligand may be, for example, trans-cyclohexane-1,2-diamine Referring to method (e), the leaving atom $L^3$ may be, for example, a halide such as Cl. Alternatively, $L^3$ may be a leaving group such as an alkylsulfonyl or arylsulfonyl group, for example, a triflate group, an arylsulfonyloxy group or an alkylsulfonyloxy group, such as a mesylate or a tosylate group, $NO_2$, or a diazonium group. Examples of $B(OR^e)(OR^f)$ include boronic acid (i.e., where $R^e$ and $R^f$ are both hydrogen), and boronic esters. Examples of boronic esters include dioxaborolanes (i.e., where $R^e$ and $R^f$ together with the atoms to which they are attached form an optionally substituted 5-membered ring) and dioxaborinanes (i.e., where $R^e$ and $R^f$ together with the atoms to which they are attached form an optionally substituted 6-membered ring). A particular example of a dioxoborinane is 4,4,4',4',5,5,5',5'-octamethyl-2,2'-bi(1,3-dioxaborolane) (also known as bis (pinacoloato)diboron). Suitable palladium catalysts include Pd(PPh$_3$)$_4$, Pd$_2$(dba)$_3$, and Pd(OAc)$_2$. Convenient solvents include aprotic solvents such as ethers (for example tetrahydrofuran or p-dioxane), toluene or DMF. The reaction can be conveniently performed at elevated temperatures, for example temperatures ranging from 70 to 110° C. The base may be, for example, an alkali metal carbonate, for example cesium carbonate, sodium carbonate, or potassium carbonate.

Referring to method (f), L$^5$ may be a leaving atom such as a halogen. Alternatively, L$^5$ may be a leaving group such as an alkylsulfonyl or arylsulfonyl group, for example, a triflate group, an arylsulfonyloxy group or an alkylsulfonyloxy group, such as a mesylate or a tosylate group, NO$_2$, or a diazonium group. Suitable solvents include NMP. The reaction can be conveniently performed at elevated temperatures, for example temperatures ranging from 100-180° C., for example 160° C.

Referring to method (g), suitable reducing agents include Na(OAc)$_3$BH and NaCNBH$_3$. Suitable solvents include alcohols such as methanol.

Referring to method (h), L$^3$ may be a leaving atom such as a halogen. Alternatively, L$^3$ may be a leaving group such as an alkylsulfonyl or arylsulfonyl group, for example, a triflate group, an arylsulfonyloxy group or an alkylsulfonyloxy group, such as a mesylate or a tosylate group, NO$_2$, or a diazonium group. Suitable palladium catalysts include Pd(PPh$_3$)$_4$, Pd$_2$(dba)$_3$, and Pd(OAc)$_2$. The base may be, for example, an alkali metal phosphate, such as potassium phosphate. Convenient solvents include aprotic solvents such as ethers (for example tetrahydrofuran or p-dioxane), toluene or DMF. The reaction can be conveniently performed at elevated temperatures, for example temperatures ranging from 80-130° C., for example 100° C.

Compounds of formula II where L is NR$^x$, R$^6$ and R$^{6a}$ are H and n is 1 can be prepared as shown in general Scheme 1.

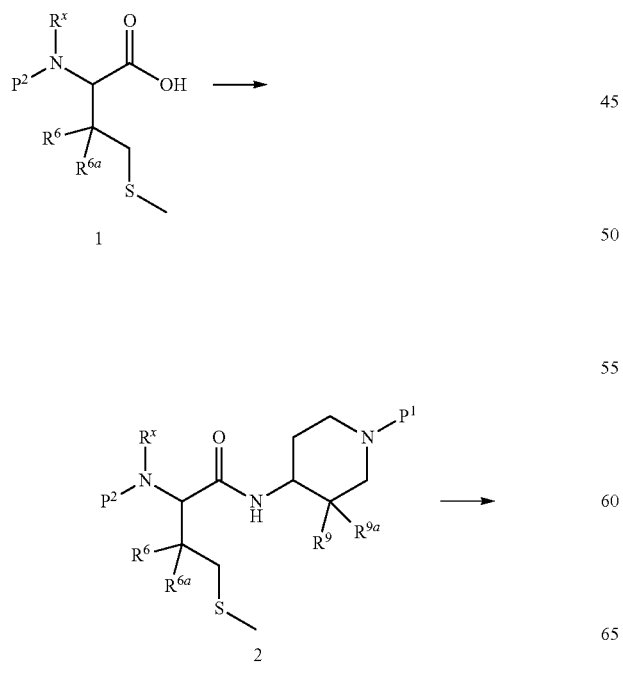

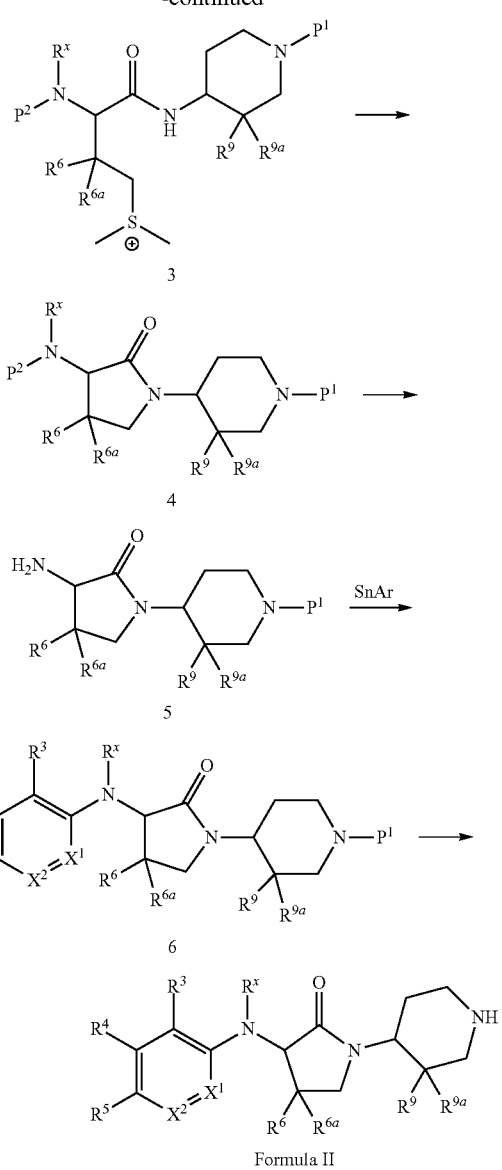

In Scheme 1, P$^1$ and P$^2$ are amine protecting groups. According to Scheme 1, the protected amino piperidine group is coupled to the amino acid intermediate (1) via traditional amide bond forming reagents such as, but not limited to, DCC, to provide compound (2). Compound (2) is activated through methylation reagents such as, but not limited to, methyl iodide to provide compound (3). Cyclization of compound (3) takes place under basic conditions such as, but not limited to, NaH or LHMDS to afford compound (4). Removal of the nitrogen protecting group P$^2$ of compound (4) under standard deprotection conditions to provide compound (5), followed by an SnAr reaction with an appropriately functionalized aryl or heteroaryl group provides compounds of formula II after removal of the protecting group P$^1$ of compound (6) under standard deprotection conditions. In one embodiment of Scheme 1, R$^9$ and R$^{9a}$ are hydrogen.

In one embodiment, compounds of formula II where L is O, R$^6$ and R$^{6a}$ are H and n is 1, 2 or 3 can be prepared as shown in Scheme 2.

Scheme 2

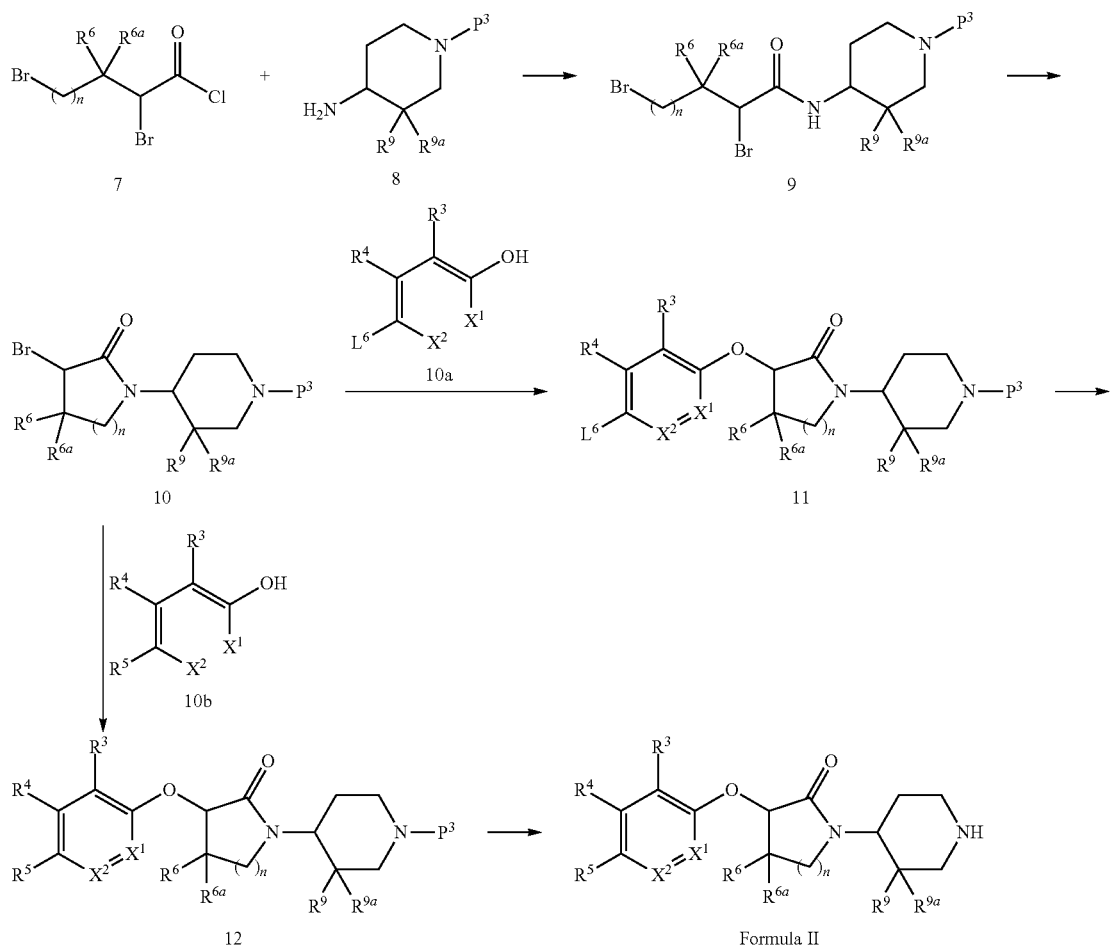

In Scheme 2, $P^3$ is an amine protecting group. According to Scheme 2, acylation of the amino piperidine (8) with acid chloride (7) affords the compound (9). Cyclization of compound (9) to form the lactam (10) is promoted by bases such as, but not limited to, alkali metal hydrides such as NaH, alkali metal amine bases such as lithium diisopropylamide, or silicon-containing alkali metal amides (e.g., sodium hexamethyldisilazide or lithium hexamethyldisilazide). Compound 10 can be coupled with compound 10(a) (where $L^6$ is a leaving group or atom) under basic conditions, for example, in the presence of an alkali metal hydride or carbonate, such as sodium hydride, potassium hydride, sodium carbonate, potassium carbonate or cesium carbonate. When $R^5$ is a group having the $R^{5a}SO_2$— where $R^{5a}$ is (1-3C) alkyl, (3-6C)cycloalkyl, cyclopropylmethyl- or phenyl, compound (11) can be coupled with a corresponding compound having the formula $R^{5a}SO_2Na$ in the presence of a metal catalyst such as, but not limited to, copper and palladium catalysts, to provide compound (12). Alternatively, when $R^5$ is CN, compound (11) can be reacted with CuCN to provide compound (12). Alternatively, compound (10) can be coupled with compound (10b) to provide compound (12). Removal of the protecting group $P^3$ of compound (12) under standard deprotection conditions affords compounds of formula II. In one embodiment of Scheme 2, $R^9$ and $R^{9a}$ are hydrogen.

In one embodiment, compounds of formula II where L is $NR^x$, $R^6$ and $R^{6a}$ are H and n is 2 or 3 can be prepared as shown in Scheme 3.

Scheme 3

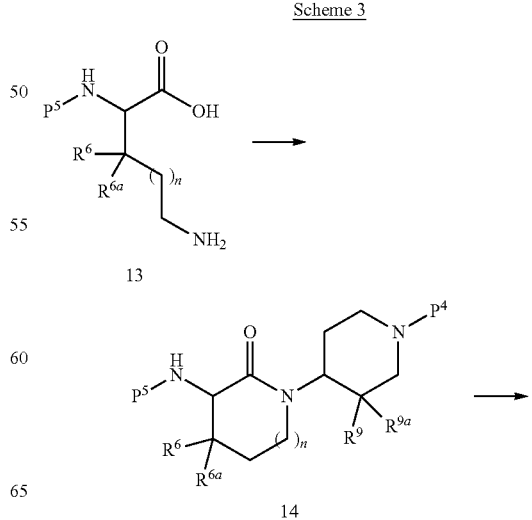

33

-continued

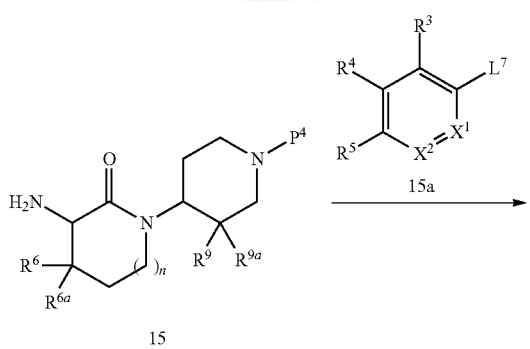

15

16

34

-continued

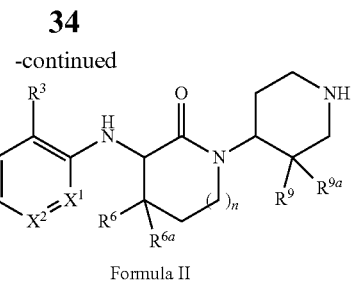

Formula II

In Scheme 3, $P^4$ and $P^5$ are amine protecting groups. According to Scheme 3, amino acid (13) is converted to lactam (14) through sequential reductive amination and amide bond formation. Removal of protecting group $P^5$ of compound (14) under standard deprotection conditions, followed by coupling of the deprotected compound (15) with compound (15a) under standard SnAr conditions affords intermediate (16). The $NH_2$ group of compound (15) can optionally be alkylated under standard alkylation conditions known to persons skilled in the art prior to removal of the protecting group $P^4$. Removal of the protecting group $P^4$ of compound (16) affords compounds of formula II. In one embodiment of Scheme 3, $R^9$ and $R^{9a}$ are hydrogen.

In one embodiment, compounds of formula II where L is O, $R^6$ is OH, $R^{6a}$ is H (not shown in scheme below) and n is 2 can be made according to Scheme 4.

Scheme 4

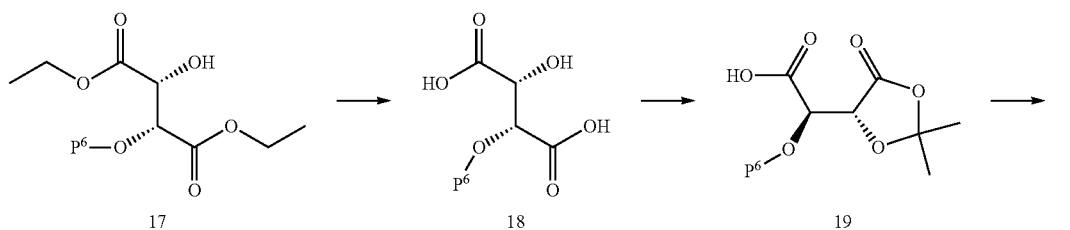

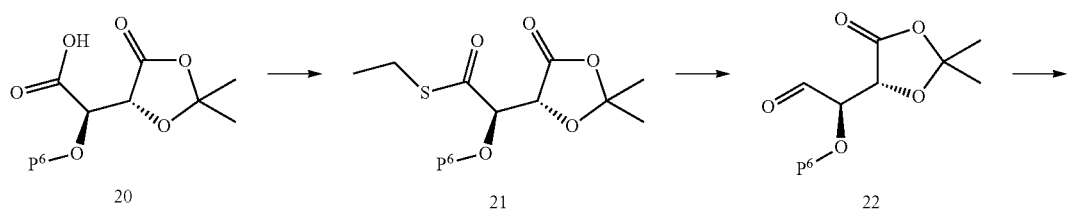

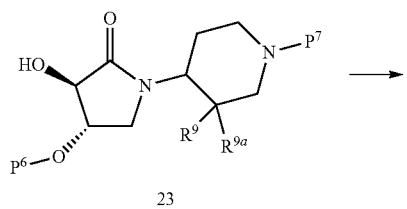

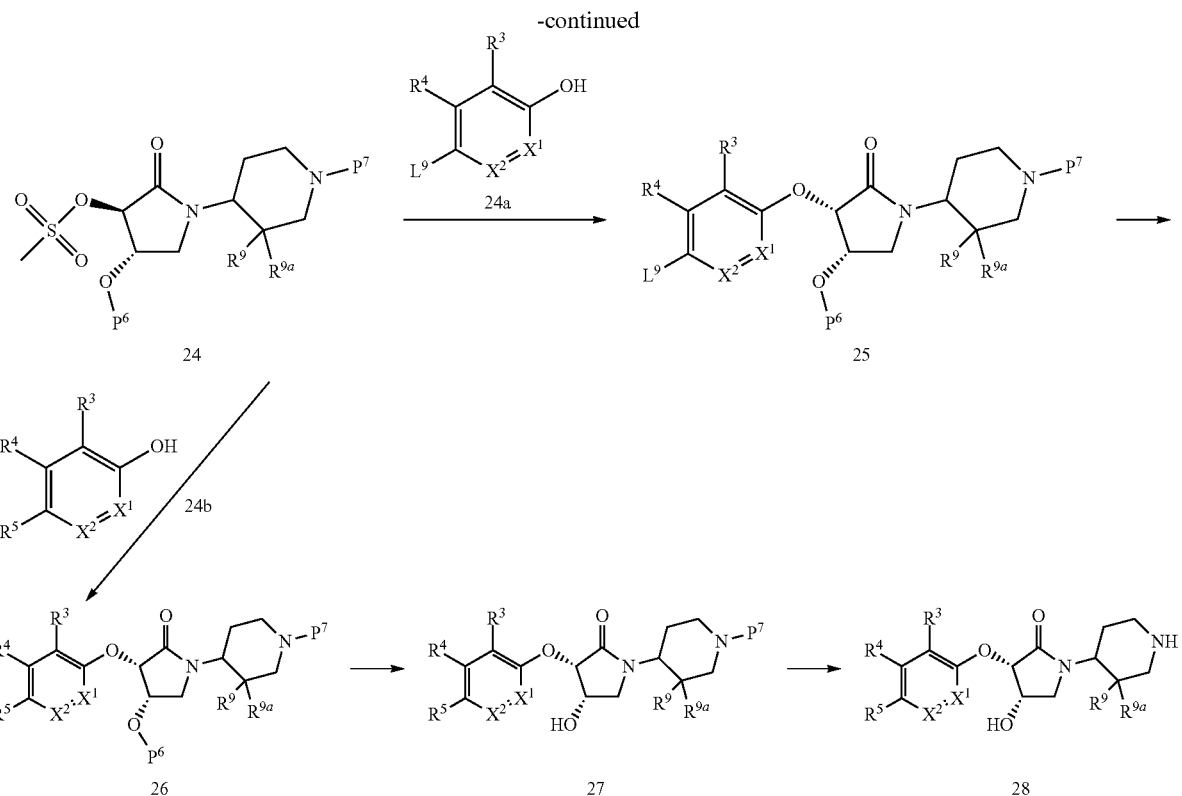

In Scheme 4, $P^6$ is a hydroxyl protecting group, and $P^7$ is an amine protecting group. According to Scheme 4, the monoprotected tartrate ester (17) is hydrolyzed to the bis-acid (18), which is then selectively protected as the acetonide to provide compound (19). The thioester (21) can be formed from compound (19) by various methods such as, but not limited to, in the presence of a coupling reagent such as DCC. The reduction of the thioester (21) to the aldehyde (22) can performed under standard reduction conditions, such as, but not limited to, in the presence of $Et_3SiH$ and Pd/C. Reductive amination of compound (22) with concomitant cyclization to lactam (23) is performed with an appropriate amino piperidine in the presence of a hydride source such as, but not limited to, $Na(OAc)_3BH$ or $NaCNBH_3$. Activation of the alcohol of (23) to a leaving group such as, but not limited to, methanesulfonyl to afford compound (24), allows for the coupling of compound (24a) under basic conditions (for example in the presence of an alkali metal carbonate such as $K_2CO_3$ with inversion of stereochemistry to provide compound (25) in which $L^9$ is a leaving group or atom. When $R^5$ is a group having the $R^{5a}SO_2$— where $R^{5a}$ is (1-3C) alkyl, (3-6C)cycloalkyl, cyclopropylmethyl- or phenyl, compound (25) can be coupled with a corresponding compound having the formula $R^{5a}SO_2Na$ in the presence of a metal catalyst such as, but not limited to, copper and palladium catalysts, to provide compound (26). Alternatively, when $R^5$ is CN, compound (25) can be reacted with CuCN to provide compound (26). Alternatively, compound (24) can be coupled with compound (24b) to provide compound (26). Removal of the protecting group $P^6$ of compound (26), followed by removal or protecting group $P^7$ under standard deprotection conditions affords compound (28). In one embodiment of Scheme 4, $R^9$ and $R^{9a}$ are hydrogen.

In one embodiment, compounds of formula V where L is NH, $R^6$ and $R^{6a}$ are H, and n is 1, 2 or 3 can be made according to Scheme 5.

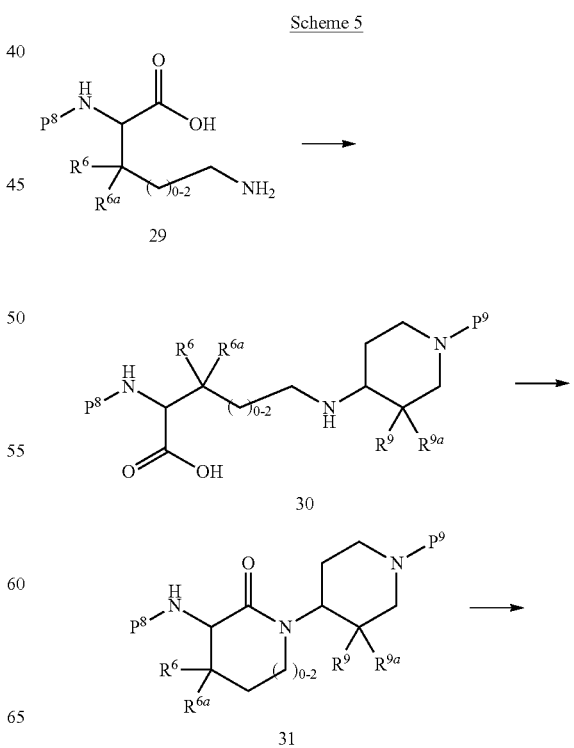

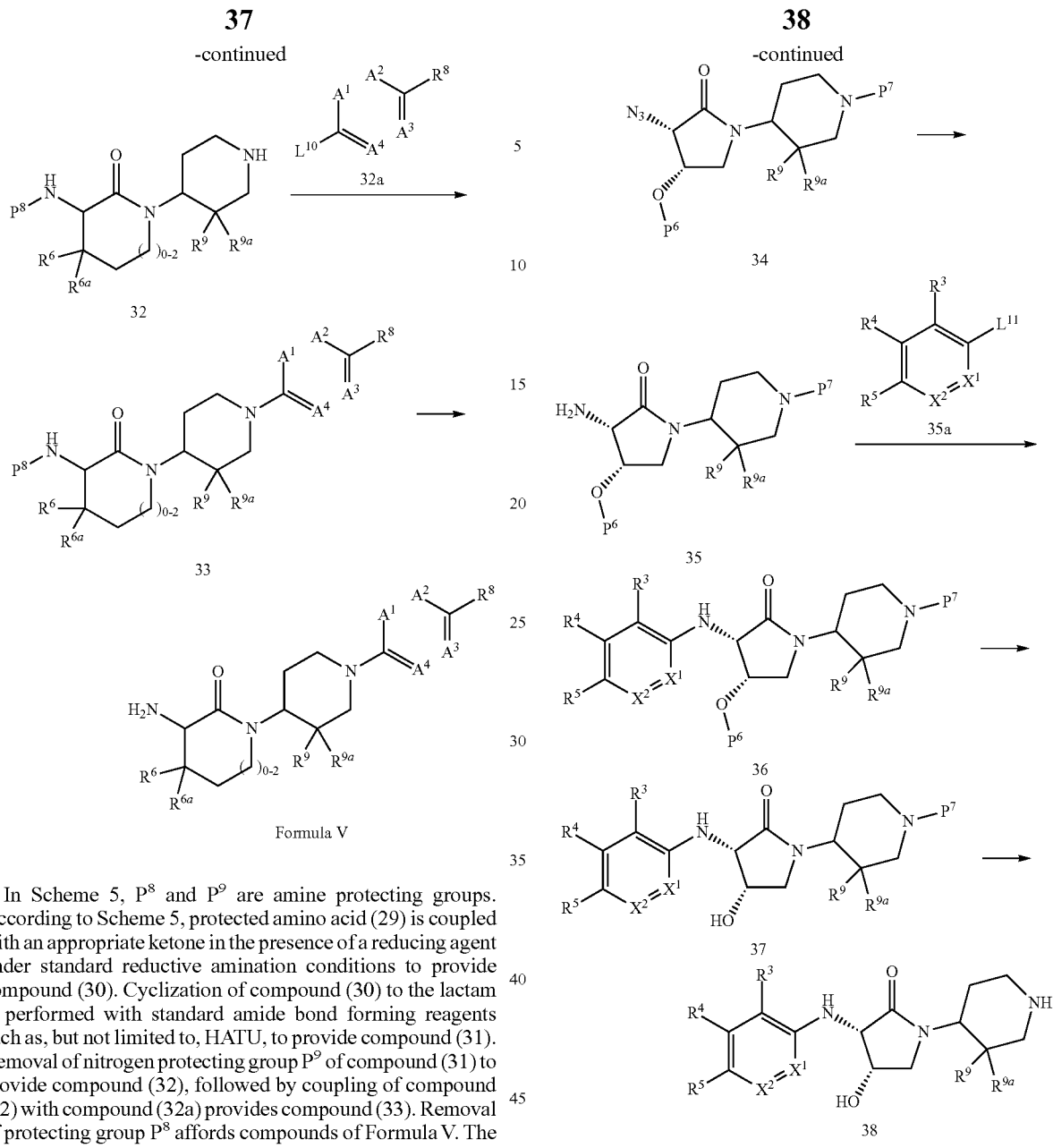

In Scheme 5, $P^8$ and $P^9$ are amine protecting groups. According to Scheme 5, protected amino acid (29) is coupled with an appropriate ketone in the presence of a reducing agent under standard reductive amination conditions to provide compound (30). Cyclization of compound (30) to the lactam is performed with standard amide bond forming reagents such as, but not limited to, HATU, to provide compound (31). Removal of nitrogen protecting group $P^9$ of compound (31) to provide compound (32), followed by coupling of compound (32) with compound (32a) provides compound (33). Removal of protecting group $P^8$ affords compounds of Formula V. The $NH_2$ group of Formula V can optionally be alkylated using standard alkylation conditions known to persons skilled in the art. In one embodiment of Scheme 5, $R^9$ and $R^{9a}$ are hydrogen.

In one embodiment, compounds of formula II where L is NH, $R^6$ is OH, $R^{6a}$ is H (not shown in the scheme below) and n is 2 can be made according to Scheme 6.

Scheme 6

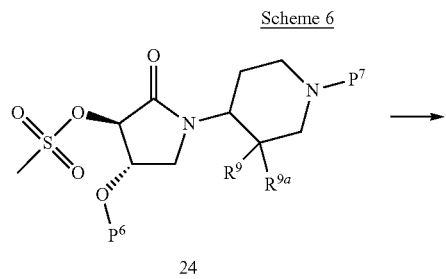

In Scheme 6, $P^6$ is a hydroxyl protecting group, and $P^7$ is an amine protecting group. Starting from compound 24, azide displacement with, for example, $NaN_3$ affords compound (34). Reduction of compound (34) with, for example, aqueous $PPh_3$ affords the compound (35). Coupling of compound (35) with compound (35a) in the presence of a base, such as an alkali metal carbonate, for example $Na_2CO_3$, affords compound (36). Removal of protecting groups $P^6$ and $P^7$ under standard deprotection conditions yields compound 38. In one embodiment of Scheme 6, $R^9$ and $R^{9a}$ are hydrogen.

Amine groups in compounds described in any of the above methods may be protected with any convenient amine protecting group, for example as described in Greene & Wuts, eds., "Protecting Groups in Organic Synthesis", $2^{nd}$ ed. New York; John Wiley & Sons, Inc., 1991. Examples of amine protecting groups include acyl and alkoxycarbonyl groups, such as t-butoxycarbonyl (BOC), and [2-(trimethylsilyl) ethoxy]methyl (SEM). Likewise, carboxyl groups may be protected with any convenient carboxyl protecting group, for example as described in Greene & Wuts, eds., "Protecting Groups in Organic Synthesis", $2^{nd}$ ed. New York; John Wiley & Sons, Inc., 1991. Examples of carboxyl protecting groups include (1-6C)alkyl groups, such as methyl, ethyl and t-butyl. Alcohol groups may be protected with any convenient alcohol protecting group, for example as described in Greene & Wuts, eds., "Protecting Groups in Organic Synthesis", $2^{nd}$ ed. New York; John Wiley & Sons, Inc., 1991. Examples of alcohol (hydroxyl) protecting groups include benzyl, trityl, silyl ethers, and the like.

The compounds of the formulas II, IV, VII, and VIII are also believed to be novel and are provided as further aspects of the invention.

Compounds of Formula I are modulators of GPR119 and are useful for treating or preventing disease including, but not limited to, type 2 diabetes, diabetic complications, symptoms of diabetes, metabolic syndrome, obesity, dyslipidemia, and related conditions.

The ability of compounds of the invention to act as modulators of GPR119 may be demonstrated by the assay described in Example A.

The term "modulate" refers to the treating, prevention, suppression, enhancement or induction of a function or condition. For example, compounds can modulate type 2 diabetes by increasing insulin in a human, thereby suppressing hyperglycemia.

The term "modulator" as used herein includes the terms agonist, antagonist, inverse agonist, and partial agonist.

The term "agonist" refers to a compound that binds to a receptor and triggers a response in a cell. An agonist mimics the effect of an endogenous ligand, a hormone for example, and produces a physiological response similar to that produced by the endogenous ligand.

The term "partial agonist" refers to a compound that binds to a receptor and triggers a partial response in a cell. A partial agonist produces only a partial physiological response of the endogenous ligand.

The term "antagonist" as used herein refers to is a type of receptor ligand or drug that does not provoke a biological response itself upon binding to a receptor, but blocks or dampens agonist-mediated responses.

The term "inverse agonist" as used herein refers to an agent that binds to the same receptor binding-site as an agonist for that receptor and reverses constitutive activity of the receptor.

Certain compounds of Formula I are agonists of GPR119.

Certain compounds of Formula I are inverse agonists of GPR119.

Certain compounds of Formula I are antagonists of GPR119.

In certain embodiments, compound of Formula I are useful for treating or preventing type 2 diabetes mellitus (also known as non-insulin dependent diabetes mellitus, or T2DM). Diabetes mellitus is a condition where the fasting plasma glucose level (glucose concentration in venous plasma) is greater than or equal to 126 mg/dL (tested on two occasions) and the 2-hour plasma glucose level of a 75 g oral glucose tolerance test (OGTT) is greater than or equal to 200 mg/dL. Additional classic symptoms include polydipsia, polyphagia and polyuria.

Accordingly, one aspect of the present invention provides methods for treating or preventing type 2 diabetes mellitus in a mammal, comprising administering to the mammal in need of such treatment a therapeutically effective amount of a compound of Formula I or a pharmaceutically acceptable salt thereof.

In certain embodiments, compound of Formula I are useful for treating or preventing diabetic complications. The term "diabetic complications" includes, but is not limited to, microvascular complications and macrovascular complications. Microvascular complications are those complications that generally result in small blood vessel damage. These complications include, for example, retinopathy (the impairment or loss of vision due to blood vessel damage in the eyes); neuropathy (nerve damage and foot problems due to blood vessel damage to the nervous system); and nephropathy (kidney disease due to blood vessel damage in the kidneys). Macrovascular complications are those complications that generally result from large blood vessel damage. These complications include, e.g., cardiovascular disease and peripheral vascular disease. Cardiovascular disease is generally one of several forms, including, e.g., hypertension (also referred to as high blood pressure), coronary heart disease, stroke, and rheumatic heart disease. Peripheral vascular disease refers to diseases of any of the blood vessels outside of the heart. It is often a narrowing of the blood vessels that carry blood to leg and arm muscles.

Accordingly, one aspect of the present invention provides methods for treating or preventing diabetic complications in a mammal, comprising administering to the mammal in need of such treatment a therapeutically effective amount of a compound of Formula I or a pharmaceutically acceptable salt thereof. In one embodiment, the diabetic complication is retinopathy (also known as diabetic retinopathy).

In certain embodiments, compound of Formula I are useful for treating or preventing symptoms of diabetes. The term "symptom" of diabetes, includes, but is not limited to, polyuria, polydipsia, and polyphagia, as used herein, incorporating their common usage. For example, "polyuria" means the passage of a large volume of urine during a given period; "polydipsia" means chronic, excessive thirst; and "polyphagia" means excessive eating. Other symptoms of diabetes include, e.g., increased susceptibility to certain infections (especially fungal and staphylococcal infections), nausea, and ketoacidosis (enhanced production of ketone bodies in the blood).

Accordingly, one aspect of the present invention provides methods for treating or preventing symptoms of diabetes in a mammal, comprising administering to the mammal in need of such treatment a therapeutically effective amount of a compound of Formula I or a pharmaceutically acceptable salt thereof.

In certain embodiments, compound of Formula I are useful for treating or preventing metabolic syndrome in a mammal. The term "metabolic syndrome" refers to a cluster of metabolic abnormalities including abdominal obesity, insulin resistance, glucose intolerance, hypertension and dyslipidemia. These abnormalities are known to be associated with an increased risk of type 2 diabetes and cardiovascular disease. Compounds of Formula I are also useful for reducing the risks of adverse sequelae associated with metabolic syndrome, and in reducing the risk of developing atherosclerosis, delaying the onset of atherosclerosis, and/or reducing the risk of sequelae of atherosclerosis. Sequelae of atherosclerosis include angina, claudication, heart attack, stroke, and others.

Accordingly, one aspect of the present invention provides methods of treating a metabolic syndrome in a mammal, comprising administering to the mammal in need of such treatment a therapeutically effective amount of a compound of Formula I or a pharmaceutically acceptable salt thereof. In one embodiment, the metabolic syndrome is impaired glucose tolerance. In one embodiment, the metabolic syndrome is insulin resistance. In one embodiment, the metabolic syndrome is atherosclerosis.

In certain embodiments, compound of Formula I are useful for treating or preventing obesity in a mammal. The term "obesity" refers to, according to the World Health Organization, a Body Mass Index ("BMI") greater than 27.8 kg/m$^2$ for men and 27.3 kg/m$^2$ for women (BMI equals weight (kg)/ height (m$^2$). Obesity is linked to a variety of medical conditions including diabetes and hyperlipidemia. Obesity is also a known risk factor for the development of type 2 diabetes.

Accordingly, one aspect of the present invention provides methods of treating or preventing obesity in a mammal, comprising administering to the mammal in need of such treatment a therapeutically effective amount of a compound of Formula I or a pharmaceutically acceptable salt thereof.

Compounds of Formula I may also be useful for treating or preventing diseases and disorders such as, but not limited to, dyslipidemia and dyslipoproteinemia.

The term "dyslipidemia" refers to abnormal levels of lipoproteins in blood plasma including both depressed and/or elevated levels of lipoproteins (e.g., elevated levels of LDL and/or VLDL, and depressed levels of HDL).

The term "dyslipoproteinemia" refers to abnormal lipoproteins in the blood, including hyperlipidemia, hyperlipoproteinemia (excess of lipoproteins in the blood) including type I, II-a (hypercholesterolemia), II-b, III, IV (hypertriglyceridemia) and V (hypertriglyceridemia).

Accordingly, one aspect of the present invention provides methods of treating or preventing dyslipidemia in a mammal, comprising administering to the mammal in need of such treatment a therapeutically effective amount of a compound of Formula I or a pharmaceutically acceptable salt thereof.

Another aspect of the present invention provides methods of treating or preventing dyslipoproteinemia in a mammal, comprising administering to the mammal in need of such treatment a therapeutically effective amount of a compound of Formula I or a pharmaceutically acceptable salt thereof.

By elevating levels of active GLP-1 in vivo, the compounds are useful in treating neurological disorders such as Alzheimer's disease, multiple sclerosis, and schizophrenia.

Accordingly, one aspect of the invention provides methods of treating neurological disorders in a mammal, comprising administering to the mammal in need thereof a therapeutically effective amount of a compound of Formula I or a pharmaceutically acceptable salt thereof. In one embodiment, the neurological disorder is Alzheimer's disease.

Compounds of Formula I generally are useful for treating or preventing diseases and conditions selected from type 2 diabetes, symptoms of diabetes, diabetic complications, metabolic syndrome (including hyperglycemia, impaired glucose tolerance, and insulin resistance), obesity, dyslipidemia, dyslipoproteinemia, vascular restenosis, diabetic retinopathy, hypertension, cardiovascular disease, Alzheimer's disease, schizophrenia, and multiple sclerosis.

Accordingly, one aspect of the invention provides methods for treating or preventing diseases and conditions selected from type 2 diabetes, symptoms of diabetes, diabetic complications, metabolic syndrome (including hyperglycemia, impaired glucose tolerance, and insulin resistance), obesity, dyslipidemia, dyslipoproteinemia, vascular restenosis, diabetic retinopathy, hypertension, cardiovascular disease, Alzheimer's disease, schizophrenia, and multiple sclerosis, comprising administering to the mammal in need of such treatment a therapeutically effective amount of a compound of Formula I or a pharmaceutically acceptable salt thereof. In one embodiment, the disease is selected from type 2 diabetes.

Compounds of Formula I may also be useful for increasing satiety, reducing appetite, and reducing body weight in obese subjects and may therefore be useful in reducing the risk of co-morbidities associated with obesity such as hypertension, atherosclerosis, diabetes, and dyslipidemia.

Accordingly, the present invention provides methods of inducing satiety, reducing appetite, and reducing body weight in a mammal, comprising administering to the mammal in need thereof a therapeutically effective amount of a compound of Formula I or a pharmaceutically acceptable salt thereof.

In one aspect, the present invention provides methods of inducing satiety in a mammal, comprising administering to the mammal in need thereof a therapeutically effective amount of a compound of Formula I or a pharmaceutically acceptable salt thereof.

In one aspect, the present invention provides methods of decreasing food intake in a mammal, comprising administering to the mammal in need thereof a therapeutically effective amount of a compound of Formula I or a pharmaceutically acceptable salt thereof.

In one aspect, the present invention provides methods of controlling or decreasing weight gain of a mammal, comprising administering to the mammal in need thereof a therapeutically effective amount of a compound of Formula I or a pharmaceutically acceptable salt thereof.

Compounds of Formula I may be administered alone as a sole therapy or can be administered in addition with one or more other substances and/or treatments that work by the same or a different mechanism of action. These agents may be administered with one or more compounds of Formula I as part of the same or separate dosage forms, via the same or different routes of administration, and on the same or different administration schedules according to standard pharmaceutical practice known to one skilled in the art.

Accordingly, compounds of Formula I can be used in combination with one or more additional drugs such as insulin preparations, agents for improving insulin resistance (for example PPAR gamma agonists), alpha-glucosidase inhibitors, biguanides, insulin secretagogues, dipeptidylpeptidase IV (DPP4) inhibitors, beta-3 agonists, amylin agonists, phosphotyrosine phosphatase inhibitors, gluconeogenesis inhibitors, sodium-glucose cotransporter inhibitors, known therapeutic agents for diabetic complications, antihyperlipidemic agents, hypotensive agents, antiobesity agents, GLP-I, GIP-I, GLP-I analogs such as exendins, (for example exenatide (Byetta), exenatide-LAR, and liraglutide), and hydroxysterol dehydrogenase-1 (HSD-I) inhibitors.

As used herein, terms "treat" or "treatment" refer to therapeutic, prophylactic, palliative or preventative measures. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder, as well as those prone to have the condition or disorder or those in which the condition or disorder is to be prevented.

In one embodiment, the terms "treatment" or "treating" as used herein, mean an alleviation, in whole or in part, of symptoms associated with a disorder or condition as described herein, or slowing, or halting of further progression or worsening of those symptoms.

In one embodiment, the term "preventing" as used herein means the prevention of the onset, recurrence or spread, in whole or in part, of the disease or condition as described herein, or a symptom thereof.

The terms "effective amount" and "therapeutically effective amount" refer to an amount of compound that, when administered to a mammal in need of such treatment, is sufficient to (i) treat or prevent a particular disease, condition, or disorder, (ii) attenuate, ameliorate, or eliminate one or more symptoms of the particular disease, condition, or disorder, or (iii) prevent or delay the onset of one or more symptoms of the particular disease, condition, or disorder described herein. The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

Compounds of the invention may be administered by any convenient route, for example into the gastrointestinal tract (e.g. rectally or orally), the nose, lungs, musculature or vasculature, or transdermally or dermally. Compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, excipients and further active agents. If parenteral administration is desired, the compositions will be sterile and in a solution or suspension form suitable for injection or infusion. Such compositions form a further aspect of the invention.

The present invention further provides a pharmaceutical composition, which comprises a compound of Formula I or a pharmaceutically acceptable salt thereof, as defined hereinabove, and a pharmaceutically acceptable carrier, diluent or excipient.

An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone ("PVP") K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An aerosol formulation can be prepared by dissolving the compound, for example 5-400 mg, of the invention in a suitable buffer solution, e.g. a phosphate buffer, adding a tonicifier, e.g., a salt such sodium chloride, if desired. The solution is typically filtered, e.g., using a 0.2 micron filter, to remove impurities and contaminants.

The present invention further provides a compound of Formula I or a pharmaceutically acceptable salt thereof, for use in therapy. In one embodiment, the present invention provides a compound of Formula I or a pharmaceutically acceptable salt thereof, for use in treating type 2 diabetes, symptoms of diabetes, diabetic complications, metabolic syndrome (including hyperglycemia, impaired glucose tolerance, and insulin resistance), obesity, dyslipidemia, dyslipoproteinemia, vascular restenosis, diabetic retinopathy, hypertension, cardiovascular disease, Alzheimer's disease, schizophrenia, or multiple sclerosis. In one embodiment, the present invention provides a compound of Formula I or a pharmaceutically acceptable salt thereof, for use in treating type 2 diabetes, symptoms of diabetes, diabetic complications, metabolic syndrome (including hyperglycemia, impaired glucose tolerance, and insulin resistance), obesity, dyslipidemia, or dyslipoproteinemia. In one embodiment, the present invention provides a compound of Formula I or a pharmaceutically acceptable salt thereof, for use in treating type 2 diabetes.

In one embodiment, the invention provides a compound of Formula I or a pharmaceutically acceptable salt thereof, for use in the treatment of type 2 diabetes mellitus in a mammal.

In one embodiment, the invention provides a compound of Formula I or a pharmaceutically acceptable salt thereof, for use in the treatment of diabetic complications in a mammal.

In one embodiment, the invention provides a compound of Formula I or a pharmaceutically acceptable salt thereof, for use in the treatment of symptoms of diabetes in a mammal.

In one embodiment, the invention provides a compound of Formula I or a pharmaceutically acceptable salt thereof, for use in the treatment of metabolic syndrome in a mammal. In one embodiment, the metabolic syndrome is hyperglycemia. In one embodiment, the metabolic syndrome is impaired glucose tolerance. In one embodiment, the metabolic syndrome is insulin resistance. In one embodiment, the metabolic syndrome is atherosclerosis.

In one embodiment, the invention provides a compound of Formula I or a pharmaceutically acceptable salt thereof, for use in the treatment of obesity in a mammal.

In one embodiment, the invention provides a compound of Formula I or a pharmaceutically acceptable salt thereof, for use in the treatment of dyslipidemia in a mammal.

In one embodiment, the invention provides a compound of Formula I or a pharmaceutically acceptable salt thereof, for use in the treatment of dyslipoproteinemia in a mammal.

In one embodiment, the invention provides a compound of Formula I or a pharmaceutically acceptable salt thereof, for use in the treatment of neurological disorders in a mammal. In one embodiment, the neurological disorder is Alzheimer's disease.

In one embodiment, the invention provides a compound of Formula I or a pharmaceutically acceptable salt thereof, for use in inducing satiety in a mammal.

In one embodiment, the invention provides a compound of Formula I or a pharmaceutically acceptable salt thereof, for use in decreasing food intake in a mammal.

In one embodiment, the invention provides a compound of Formula I or a pharmaceutically acceptable salt thereof, for use in controlling or decreasing weight gain in a mammal.

According to a further aspect, the present invention provides the use of a compound of Formula I or a pharmaceutically acceptable salt thereof, in the treatment of a disease or condition selected from type 2 diabetes, symptoms of diabetes, diabetic complications, metabolic syndrome (including hyperglycemia, impaired glucose tolerance, and insulin resistance), obesity, dyslipidemia, dyslipoproteinemia, vascular restenosis, diabetic retinopathy, hypertension, cardiovascular disease, Alzheimer's disease, schizophrenia, and multiple sclerosis.

According to a further aspect, the present invention provides the use of a compound of Formula I or a pharmaceutically acceptable salt thereof, in the treatment of type 2 diabetes mellitus in a mammal.

According to a further aspect, the present invention provides the use of a compound of Formula I or a pharmaceutically acceptable salt thereof, in the treatment of diabetic complications in a mammal.

According to a further aspect, the present invention provides the use of a compound of Formula I or a pharmaceutically acceptable salt thereof, in the treatment of symptoms of diabetes in a mammal.

According to a further aspect, the present invention provides the use of a compound of Formula I or a pharmaceutically acceptable salt thereof, in the treatment of metabolic syndrome in a mammal.

According to a further aspect, the present invention provides the use of a compound of Formula I or a pharmaceutically acceptable salt thereof, in the treatment of metabolic syndrome in a mammal. In one embodiment, the metabolic syndrome is hyperglycemia. In one embodiment, the metabolic syndrome is impaired glucose tolerance.

In one embodiment, the metabolic syndrome is insulin resistance. In one embodiment, the metabolic syndrome is atherosclerosis.

According to a further aspect, the present invention provides the use of a compound of Formula I or a pharmaceutically acceptable salt thereof, in the treatment of obesity in a mammal.

According to a further aspect, the present invention provides the use of a compound of Formula I or a pharmaceutically acceptable salt thereof, in the treatment of dyslipidemia in a mammal.

According to a further aspect, the present invention provides the use of a compound of Formula I or a pharmaceutically acceptable salt thereof, in the treatment of dyslipoproteinemia in a mammal.

According to a further aspect, the present invention provides the use of a compound of Formula I or a pharmaceutically acceptable salt thereof, in the treatment of neurological disorders in a mammal. In one embodiment, the neurological disorder is Alzheimer's disease.

According to a further aspect, the present invention provides the use of a compound of Formula I or a pharmaceutically acceptable salt thereof, in inducing satiety in a mammal.

According to a further aspect, the present invention provides the use of a compound of Formula I or a pharmaceutically acceptable salt thereof, in decreasing food intake in a mammal.

According to a further aspect, the present invention provides the use of a compound of Formula I or a pharmaceutically acceptable salt thereof, in controlling or decreasing weight gain in a mammal.

Another embodiment of the present invention provides the use of a compound of Formula I, or a pharmaceutically acceptable salt thereof, in the manufacture of a medicament for treating or preventing type 2 diabetes mellitus in a mammal.

Another embodiment of the present invention provides the use of a compound of Formula I, or a pharmaceutically acceptable salt thereof, in the manufacture of a medicament for treating or preventing diabetic complications.

Another embodiment of the present invention provides the use of a compound of Formula I, or a pharmaceutically acceptable salt thereof, in the manufacture of a medicament for treating or preventing symptoms of diabetes.

Another embodiment of the present invention provides the use of a compound of Formula I, or a pharmaceutically acceptable salt thereof, in the manufacture of a medicament for treating or preventing metabolic syndrome in a mammal.

Another embodiment of the present invention provides the use of a compound of Formula I, or a pharmaceutically acceptable salt thereof, in the manufacture of a medicament for treating or preventing obesity in a mammal.

Another embodiment of the present invention provides the use of a compound of Formula I, or a pharmaceutically acceptable salt thereof, in the manufacture of a medicament for treating or preventing dyslipidemia or dyslipoproteinemia.

Another embodiment of the present invention provides the use of a compound of Formula I, or a pharmaceutically acceptable salt thereof, in the manufacture of a medicament for treating neurological disorders in a mammal.

Another embodiment of the present invention provides the use of a compound of Formula I, or a pharmaceutically acceptable salt thereof, in the manufacture of a medicament for inducing satiety in a mammal.

Another embodiment of the present invention provides the use of a compound of Formula I, or a pharmaceutically acceptable salt thereof, in the manufacture of a medicament for decreasing food intake in a mammal.

Another embodiment of the present invention provides the use of a compound of Formula I, or a pharmaceutically acceptable salt thereof, in the manufacture of a medicament for controlling or decreasing weight gain of a mammal.

In one embodiment, the compound of Formula I is selected from any one of the compounds of Examples 1-166 or a pharmaceutically acceptable salt thereof. In one embodiment, the pharmaceutically acceptable salt is a trifluoroacetate salt or a hydrochloride salt.

EXAMPLES

The following examples illustrate the invention. In the examples described below, unless otherwise indicated all temperatures are set forth in degrees Celsius. Reagents were purchased from commercial suppliers such as Aldrich Chemical Company, Lancaster, Alfa, Aesar, TCI, Maybridge, or other suitable suppliers, and were used without further purification unless otherwise indicated. THF, DCM, toluene, DMF) and dioxane were purchased from Aldrich in Sure/Seal™ bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried or dried under a stream of dry nitrogen.

Column chromatography was done on a Biotage system (Manufacturer: Dyax Corporation) having a silica gel or C-18 reverse phase column, or on a silica SepPak cartridge (Waters), or using conventional flash column chromatography on silica gel, unless otherwise specified.

Abbreviations used herein have the following meanings:

| | |
|---|---|
| ACN | acetonitrile |
| APCI | Atmospheric Pressure Chemical Ionization |
| BINAP | 2,2'-bis(diphenylphosphino)-1,1'-binaphthyl |
| Boc | tert-butoxycarbonyl |
| $CDCl_3$ | Deuterated Chloroform |
| DCC | N,N'-dicyclohexylcarbodiimide |
| DCM | Dichloromethane |
| DIEA | Diisopropylethylamine |
| DIPHOS | 1,2-Bis(Diphenylphosphino)ethane |
| DME | 1,2-dimethoxyethane |
| DMF | N,N-Dimethylformamide |
| DMSO | dimethylsulfoxide |
| HPLC | High pressure liquid chromatography |
| $NaBH(OAc)_3$ | Sodium triacetoxyborohydride |
| NMP | N-methylpyrrolidine |

-continued

| | |
|---|---|
| Pd(PPh$_3$)$_4$ | Tetrakis(triphenylphosphine)palladium(0) |
| PdCl$_2$(dppf)*dcm | 1,1'-Bis(diphenylphosphino)ferrocene-palladium(II)dichloride dichloromethane complex |
| Pd$_2$dba$_3$ | Tris(dibenzylideneacetone)dipalladium(0) |
| TFA | Trifluoroacetic acid |
| THF | Tetrahydrofuran |
| TLC | Thin layer chromatography |
| XPHOS | 2-Dicyclohexylphosphino-2',4',6'-triisopropylbiphenyl |

Biological Assay

Example A cAMP Production Assay

The assay utilized HEK-293 cells that stably express a modified version of the GPR119 receptor (94% identity to human receptor), under the control of a CMV promoter containing a tet-on element for tetracycline-inducible expression. GPR119 agonist-induced cyclic AMP (cAMP) production was measured in this cell line using the LANCE cAMP kit (Perkin Elmer, Waltham, Mass.). To generate a working stock of cells for the assay, cells were treated overnight with 1 µg/mL doxycycline at 37° C. in the presence of 5% CO$_2$ to induce receptor expression. Cells were then harvested by enzymatic dissociation with 0.05% trypsin, resuspended in freezing medium (DMEM growth medium with 10% each of fetal bovine serum and DMSO), aliquoted and frozen at −80° C. On the day of the assay, frozen cells were thawed, washed 1× in PBS and resuspended in Hank's buffered salt solution (HBSS) containing 5 mM HEPES, 0.1% BSA and Alexa Fluor 647-conjugated anti-cAMP antibody (diluted 1:100). The cell suspension was then transferred to a Proxiplate Plus white 384-well assay plate (Perkin-Elmer) at 2000 cells/well. Test compounds at final concentrations ranging from 0.2 nM to 10 µM were added to the assay plate, followed by a one-hour incubation at ambient temperature (volume=10 µL/well). DMSO concentration was held constant at 0.5%. After incubation with test compounds, 10 µL of a detergent buffer containing a biotinylated cAMP/Europium-conjugated streptavidin complex (Europium-labeled cAMP tracer) were added to each well on the assay plate, followed by a 2-hour incubation at ambient temperature. During this incubation cAMP released from lysed cells competes with the Europium-labeled cAMP tracer for binding to the Alexa Fluor 647-conjugated antibody. Agonist-induced cellular cAMP production resulted in increased competition with the Europium-labeled cAMP tracer, leading to a proportional decrease in the time-resolved fluorescence resonance energy transfer (TR-FRET) signal detected by the Perkin-Elmer Envision plate reader. Cellular cAMP levels were then determined by interpolation of raw signal data using a cAMP standard curve. Compounds were determined to have agonist activity if they stimulated a 1.5-fold or greater increase in cAMP relative to basal levels. Results for the compounds of Examples 1-165 are shown in Table A.

TABLE A

| Ex # | cAMP production in HEK-293 cells (nMol) | Fold over baseline |
|---|---|---|
| 1 | 23.5 | 3.9 |
| 2 | 27.9 | 4.8 |
| 3 | 23.2 | 5.0 |
| 4 | 27.3 | 4.1 |
| 5 | 12.3 | 2.2 |
| 6 | 9.2 | 1.8 |
| 7 | 7.7 | 2.4 |
| 8 | 8.6 | 2.5 |
| 9 | 13.5 | 2.3 |
| 10 | 6.5 | 2.1 |
| 11 | 27.1 | 3.4 |
| 12 | 23.4 | 3.8 |
| 13 | 24.8 | 4.4 |
| 14 | 32.3 | 5.5 |
| 15 | 24.2 | 4.2 |
| 16 | 21.4 | 4.0 |
| 17 | 107.3 | 5.3 |
| 18 | 7.7 | 1.8 |
| 19 | 9.9 | 2.1 |
| 20 | 24.4 | 6.5 |
| 21 | 6.6 | 1.9 |
| 22 | 32.7 | 5.6 |
| 23 | 13.6 | 3.0 |
| 24 | 24.8 | 2.9 |
| 25 | 11.6 | 2.9 |
| 26 | 19.1 | 4.2 |
| 27A | 12.9 | 2.9 |
| 27B | 7.5 | 2.2 |
| 28 | 39.4 | 4.0 |
| 29 | 11.5 | 2.1 |
| 30 | 6.6 | 2.0 |
| 31 | 14.5 | 2.9 |
| 32 | 10.9 | 2.4 |
| 33 | 15.9 | 3.3 |
| 34 | 11.4 | 2.8 |
| 35 | 14.5 | 4.1 |
| 36 | 17.4 | 3.2 |
| 37 | 23.4 | 3.4 |
| 38 | 9.5 | 2.4 |
| 39 | 20.6 | 3.7 |
| 40 | 12.4 | 2.2 |
| 41 | 7.4 | 1.7 |
| 42 | 5.7 | 2.1 |
| 43 | 6.9 | 1.7 |
| 44 | 20.4 | 4.1 |
| 45 | 13.3 | 2.3 |
| 46 | 10.7 | 2.2 |
| 47 | 9.3 | 2.0 |
| 48 | 16.9 | 3.0 |
| 49 | 10.6 | 2.2 |
| 50 | 11.4 | 2.3 |
| 51 | 8.8 | 2.7 |
| 52 | 19.6 | 4.6 |
| 53 | 15.8 | 3.7 |
| 54 | 7.3 | 2.3 |
| 55 | 9.3 | 2.6 |
| 56 | 18.0 | 2.4 |
| 57 | 22.8 | 3.3 |
| 58 | 13.2 | 2.4 |
| 59 | 22.6 | 3.4 |
| 60 | 27.4 | 4.4 |
| 61 | 19.6 | 3.1 |
| 62 | 9.8 | 2.9 |
| 63 | 16.2 | 3.4 |
| 64 | 7.4 | 2.0 |
| 65 | 21.0 | 3.4 |
| 66 | 4.9 | 1.6 |
| 67 | 15.6 | 2.9 |
| 68 | 8.8 | 1.9 |
| 69 | 21.3 | 3.2 |
| 70 | 6.1 | 1.8 |
| 71 | 17.6 | 5.6 |
| 72 | 7.5 | 2.8 |
| 73 | 14.4 | 3.0 |
| 74 | 8.6 | 2.2 |
| 75 | 9.1 | 2.5 |
| 76 | 5.9 | 1.9 |
| 77 | 21.3 | 2.5 |
| 78 | 13.6 | 3.4 |
| 79 | 18.0 | 3.8 |
| 80 | 18.3 | 3.7 |

TABLE A-continued

| Ex # | cAMP production in HEK-293 cells (nMol) | Fold over baseline |
|---|---|---|
| 81 | 22.7 | 5.0 |
| 82 | 18.5 | 4.0 |
| 83 | 13.0 | 2.9 |
| 84 | 6.3 | 1.8 |
| 85 | 6.5 | 1.9 |
| 86 | 5.9 | 1.9 |
| 87 | 5.5 | 1.8 |
| 88 | 9.1 | 2.4 |
| 89 | 23.1 | 4.8 |
| 90 | 11.7 | 2.7 |
| 91 | 38.0 | 3.9 |
| 92 | 16.6 | 3.0 |
| 93 | 11.1 | 2.2 |
| 94 | 6.9 | 2.0 |
| 95 | 9.0 | 2.3 |
| 96 | 31.7 | 3.5 |
| 97 | 15.3 | 2.2 |
| 98 | 31.2 | 3.5 |
| 99 | 12.4 | 3.5 |
| 100 | 8.4 | 2.6 |
| 101 | 6.6 | 2.0 |
| 102 | 15.5 | 3.4 |
| 103 | 15.4 | 2.7 |
| 104 | 13.5 | 2.8 |
| 105 | 11.5 | 1.6 |
| 106 | 17.8 | 3.0 |
| 107 | 20.9 | 3.2 |
| 108 | 15.8 | 2.6 |
| 109 | 15.8 | 2.9 |
| 110 | 29.3 | 2.3 |
| 111 | 37.9 | 3.0 |
| 112 | 22.5 | 1.7 |
| 113 | 29.1 | 2.1 |
| 114 | 17.7 | 3.8 |
| 115 | 15.4 | 3.8 |
| 116 | 10.2 | 2.1 |
| 117 | 31.1 | 4.0 |
| 118 | 40.6 | 3.4 |
| 119 | 16.3 | 3.3 |
| 120 | 18.6 | 3.8 |
| 121 | 10.6 | 2.5 |
| 122 | 6.5 | 1.5 |
| 123 | 15.8 | 3.5 |
| 124 | 14.1 | 3.6 |
| 125 | 9.0 | 2.0 |
| 126 | 10.4 | 2.4 |
| 127 | 13.0 | 2.7 |
| 128 | 16.6 | 3.4 |
| 129 | 28.4 | 2.1 |
| 130 | 26.8 | 3.5 |
| 131 | 24.8 | 3.8 |
| 132 | 9.1 | 1.5 |
| 133 | 27.9 | 2.2 |
| 134 | 35.7 | 2.7 |
| 135 | 31.0 | 6.6 |
| 136 | 36.5 | 3.0 |
| 137 | 31.7 | 6.5 |
| 138 | 38.6 | 6.7 |
| 139 | 26.6 | 5.0 |
| 140 | 12.2 | 2.7 |
| 141 | 15.5 | 3.7 |
| 142 | 21.7 | 8.3 |
| 143 | 13.3 | 4.3 |
| 144 | 19.6 | 2.9 |
| 145 | 28.3 | 2.1 |
| 146 | 34.6 | 2.6 |
| 147 | 46.4 | 3.6 |
| 148 | 14.4 | 2.4 |
| 149 | 6.8 | 1.5 |
| 150 | 17.1 | 3.4 |
| 151 | 35.8 | 4.7 |
| 152 | 26.6 | 3.3 |
| 153 | 14.3 | 3.1 |
| 154 | 14.6 | 3.1 |
| 155 | 13.4 | 2.5 |
| 156 | 17.3 | 2.3 |
| 157 | 8.3 | 3.1 |
| 158 | 12.5 | 3.2 |
| 159 | 8.0 | 2.0 |
| 160 | 22.3 | 3.9 |
| 161 | 13.8 | 3.6 |
| 162 | 16.2 | 2.8 |
| 163 | 18.3 | 3.9 |
| 164 | 21.6 | 4.3 |
| 165 | 16.0 | 3.2 |
| 166 | 15.3 | 3.6 |

Preparation A 1-(5-ethylpyrimidin-2-yl)piperidin-4-amine

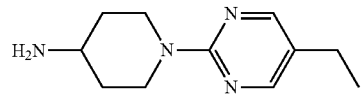

Step A: To a solution of tert-butyl piperidin-4-ylcarbamate (5.0 g, 25 mmol) and DIEA (13.0 mL, 74.9 mmol) in DMF (50 mL) was added 2-chloro-5-ethylpyrimidine (4.3 g, 30 mmol). This mixture stirred at 100° C. for 18 hours in a sealed tube. The mixture was poured into water (500 mL) and extracted into EtOAc (3×100 mL). The combined organic layers were washed with brine, dried over MgSO$_4$, filtered and concentrated in vacuo. The residue was purified over silica gel (100% EtOAc) to yield tert-butyl 1-(5-ethylpyrimidin-2-yl)piperidin-4-ylcarbamate (3.2 g, 10 mmol, 42%).

Step B: A solution of tert-butyl 1-(5-ethylpyrimidin-2-yl)piperidin-4-ylcarbamate (3.2 g, 10 mmol) in 50% TFA/CH$_2$Cl$_2$ (30 mL) was stirred at ambient temperature for 1 hour. The mixture was concentrated in vacuo. The residue was dissolved in EtOAc (200 mL) and washed with saturated sodium carbonate (200 mL) then brine. The combined organic layers were dried over MgSO$_4$, filtered and concentrated in vacuo to yield (1-(5-ethylpyrimidin-2-yl)piperidin-4-amine (2.2 g, 11 mmol, 100%). Mass spectrum (apci) m/z=207.1 (M+H).

Preparation B 1-bromo-2-fluoro-5-methyl-4-(methylsulfonyl)benzene

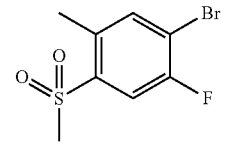

Step A: 4-Bromo-5-fluoro-2-methylaniline (5 g, 24.5 mmol) was dissolved in 1,2-dimethyldisulfane (35 mL, 394 mmol) and heated to 75° C. under nitrogen. Isoamyl nitrite (8.52 mL, 63.7 mmol) was added dropwise to the reaction via an addition funnel through a reflux condenser (~1 drop/sec). (NOTE—a large exotherm may occur if addition is too fast.) After addition was complete, the reaction was heated to 95°

C. for 1 hour and allowed to cool to ambient temperature. The reaction was concentrated and purified over silica gel (100% hexanes) to afford (4-bromo-5-fluoro-2-methylphenyl)(methyl)sulfane (4.9 g, 20.8 mmol, 85.0% yield) as an orange solid.

Step B: (4-Bromo-5-fluoro-2-methylphenyl)(methyl)sulfane (4.9 g, 21 mmol) was dissolved in $CH_2Cl_2$ (200 mL) and cooled in an ice bath. 70% MCPBA (11 g, 46 mmol) was added and the reaction was allowed to stir at 0° C. for 15 minutes and then warmed to ambient temperature. The reaction was stirred at ambient temperature for 2 hours, filtered and concentrated. The crude mixture was purified over silica gel (30% EtOAc in hexanes) to afford 1-bromo-2-fluoro-5-methyl-4-(methylsulfonyl)benzene (5.4 g, 20 mmol, 97% yield) as a white solid.

Preparation C 1,2,4-trifluoro-5-(methylsulfonyl)benzene

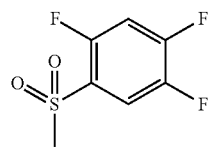

Step A: To a solution of sodium sulfite (153 g, 1214 mmol) in 1000 mL water was added a solution of 2,4,5-trifluorobenzene-1-sulfonyl chloride (40 g, 173 mmol) in dioxane (300 mL) dropwise. After the complete addition of sulfonyl chloride, the reaction was basified to about pH 14 by the addition of 1 N NaOH, and the reaction mixture was stirred overnight. The reaction mixture was cooled in ice bath and acidified using ~100 mL concentrated $H_2SO_4$ to pH about 1. The mixture was extracted with EtOAc and $CH_2Cl_2$ and the combined organic layers were dried over $Na_2SO_4$, filtered and concentrated to afford 2,4,5-trifluorobenzenesulfinic acid (34 g, 100%).

Step B: To a solution of 2,4,5-trifluorobenzenesulfinic acid (34 g, 173 mmol), in DMF (200 mL), was added iodomethane (21.6 mL, 347 mmol), and N-ethyl-N-isopropylpropan-2-amine (60.5 mL, 347 mmol). The reaction mixture was stirred overnight at ambient temperature. The reaction was concentrated and partitioned between water and ethyl acetate and extracted with $CH_2Cl_2$. The combined organic layers were concentrated and purified over silica gel (15-100% EtOAc in hexanes) to afford 1,2,4-trifluoro-5-(methylsulfonyl)benzene (25.8 g, 123 mmol, 71% yield) as yellow solid.

The following compounds in Table 1 were also prepared according to Preparation C.

TABLE 1

| Compound # | Structure | Name |
|---|---|---|
| 1 | 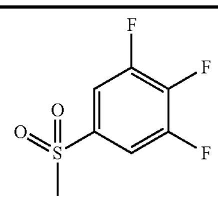 | 1,2,3-trifluoro-5-(methylsulfonyl)benzene |
| 2 | | 1-chloro-4,5-difluoro-2-(methylsulfonyl)benzene |

Preparation D (R)-tert-butyl 4-(3-(methylsulfonyloxy)-2-oxopyrrolidin-1-yl)piperidine-1-carboxylate

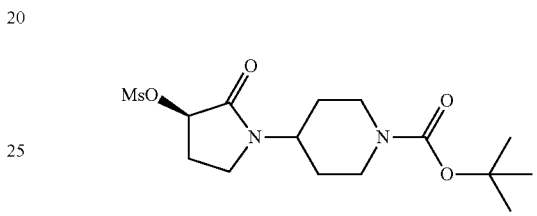

Step A: (R)-2-(2,2-Dimethyl-5-oxo-1,3-dioxolan-4-yl)acetic acid (25 g, 144 mmol) was dissolved in $CH_2Cl_2$ (500 mL) and cooled in an ice bath. Ethanethiol (21.2 mL, 287 mmol) and N,N-dimethylpyridin-4-amine (0.351 g, 2.87 mmol) were added followed by DCC (35.5 g, 172 mmol). This mixture was stirred in ice bath for 1 hour, and then 2 hours at ambient temperature. Acetic acid (45 mL) was added and then stirred the mixture for 10 minutes. The reaction mixture was then poured into vigorously stirred ether (400 mL) and filtered. The filtrate was washed with 10% sodium carbonate, water, 0.5 N HCl, water and brine. The organic layer was dried over $Na_2SO_4$, filtered and concentrated. The residue was purified over silica gel (1-5-10% EtOAc in hexanes) to afford (R)—S-ethyl 2-(2,2-dimethyl-5-oxo-1,3-dioxolan-4-yl)ethanethioate (22.5 g, 103 mmol, 71.8% yield) as a clear colorless oil that solidified to a white solid.

Step B: (R)—S-Ethyl 2-(2,2-dimethyl-5-oxo-1,3-dioxolan-4-yl)ethanethioate (22.5 g, 103 mmol) was dissolved in $CH_2Cl_2$ (500 mL), purged with nitrogen and 10% palladium on carbon (2.19 g, 2.06 mmol) was added and triethylsilane (24.7 mL, 155 mmol) was dissolved in $CH_2Cl_2$ (20 mL) and added dropwise through an addition funnel over 30 minutes and stirred at ambient temperature overnight under nitrogen. The reaction was filtered through celite, concentrated and purified over silica gel (10 to 40% EtOAc in hexanes) to afford (R)-2-(2,2-dimethyl-5-oxo-1,3-dioxolan-4-yl)acetaldehyde (16 g, 101 mmol, 98.1% yield) as a clear colorless oil.

Step C: (R)-2-(2,2-Dimethyl-5-oxo-1,3-dioxolan-4-yl)acetaldehyde (16 g, 101 mmol) was dissolved in $ClCH_2CH_2Cl$ (500 mL) and tert-butyl 4-aminopiperidine-1-carboxylate (40.5 g, 202 mmol) and acetic acid (6.94 mL, 121 mmol) were added and stirred at ambient temperature for 15 minutes. $NaBH(OAc)_3$ (64.3 g, 304 mmol) was added in 3 portions and the reaction stirred at ambient temperature overnight. The reaction was carefully quenched with saturated aqueous $NaHCO_3$. The reaction was partitioned between aqueous $NaHCO_3$ and $CH_2Cl_2$, extracted, washed with 10% citric acid, brine, dried over $Na_2SO_4$, filtered and concentrated. The solids were purified over silica gel (5 to 10% methanol in EtOAc) to afford (R)-tert-butyl 4-(3-hydroxy-2-oxopyrrolidin-1-yl)piperidine-1-carboxylate (20.5 g, 72.1 mmol, 71.3% yield) as a white solid.

Step D: (R)-tert-Butyl 4-(3-hydroxy-2-oxopyrrolidin-1-yl)piperidine-1-carboxylate (20.5 g, 72.1 mmol) was dissolved in THF (500 mL) and triethylamine (20.1 mL, 144 mmol) and methanesulfonyl chloride (6.74 mL, 86.5 mmol) were added to the reaction and stirred at ambient temperature for 1 hour. The reaction was partitioned between saturated aqueous $NaHCO_3$ and EtOAc, dried over $Na_2SO_4$, filtered and concentrated. The residue was purified over silica gel to afford (R)-tert-butyl 4-(3-(methylsulfonyloxy)-2-oxopyrrolidin-1-yl)piperidine-1-carboxylate (Preparation D; 25.5 g, 70.4 mmol, 98% yield) as a white solid. $^1$H NMR $CDCl_3$ 5.2 ppm (t, 1H), 4.3 ppm (m, 2H), 4.1 ppm (m, 1H), 3.4 ppm (m, 1H), 3.3 ppm (m, 1H), 3.3 ppm (s, 3H), 2.8 ppm (m, 2H), 2.6 ppm (m, 1H), 2.3 ppm (m, 1H), 1.7 ppm (m, 2H, 1.6 ppm (m, 2H), 1.5 ppm (s, 9H).

Preparation E

S-3-(2-fluoro-4-(methylsulfonyl)phenylamino)-1-(piperidin-4-yl)pyrrolidin-2-one

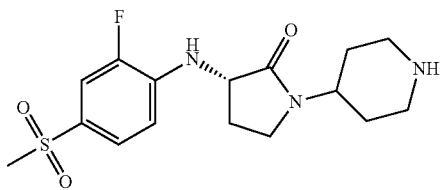 [SMILES: CS(=O)(=O)c1ccc(N[C@H]2CCN(C3CCNCC3)C2=O)c(F)c1]

Step A: A solution of HBTU (8.1 g, 21 mmol), (S)-2-(tert-butoxycarbonylamino)-4-(methylthio)butanoic acid (5.3 g, 21 mmol) and DIEA (8.2 mL, 47 mmol) in DMF (50 mL) was stirred at ambient temperature for 30 minutes. Benzyl 4-aminopiperidine-1-carboxylate (5.0 g, 21 mmol) was added and the mixture was stirred at ambient temperature for 18 hours. The mixture was poured into 1N NaOH (500 mL) and the combined organic layers were extracted into EtOAc (500 mL). The combined organic layers were washed with 1N HCl (500 mL) and brine (500 mL). The combined organic layers were dried over $MgSO_4$, filtered and concentrated in vacuo to yield (S)-benzyl 4-(2-(tert-butoxycarbonylamino)-4-(methylthio)butanamido)piperidine-1-carboxylate (10 g, 21 mmol, 100%).

Step B: A solution of (S)-benzyl 4-(2-(tert-butoxycarbonylamino)-4-(methylthio)butanamido)piperidine-1-carboxylate (10 g, 21.5 mmol) in neat MeI (40.2 mL, 640 mmol) was stirred at ambient temperature for 4 hours. The reaction was evaporated to dryness to yield (S)-benzyl 4-(3-(2-fluoro-4-(methylsulfonyl)phenylamino)-2-oxopyrrolidin-1-yl)piperidine-1-carboxylate methiodide salt (10 g, 17 mmol, 79%).

Step C: The (S)-Benzyl 4-(3-(2-fluoro-4-(methylsulfonyl)phenylamino)-2-oxopyrrolidin-1-yl)piperidine-1-carboxylate methiodide salt (10 g, 17 mmol) was dissolved in dry THF (100 mL) and cooled to 0° C. Lithium bis(trimethylsilyl) amide (21 mL, 21 mmol) was added and the mixture was warmed to ambient temperature and stirred for 2 hours. The mixture was poured into saturated ammonium chloride (100 mL) and extracted into EtOAc (3×100 mL). The combined organic layers were washed with brine, dried over $MgSO_4$, filtered and concentrated in vacuo to yield (S)-benzyl 4-(3-(tert-butoxycarbonylamino)-2-oxopyrrolidin-1-yl)piperidine-1-carboxylate (7 g, 17 mmol, 100%).

Step D: A solution of (S)-benzyl 4-(3-(tert-butoxycarbonylamino)-2-oxopyrrolidin-1-yl)piperidine-1-carboxylate (7 g, 17 mmol) in 50% $TFA/CH_2Cl_2$ (50 mL) was stirred at ambient temperature for 1 hour. The mixture was concentrated in vacuo. The residue was dissolved in EtOAc (200 mL) and washed with saturated sodium carbonate (200 mL) and brine. The combined organic layers were dried over $MgSO_4$, filtered and concentrated in vacuo to yield (S)-benzyl 4-(3-amino-2-oxopyrrolidin-1-yl)piperidine-1-carboxylate (3.4 g, 11 mmol, 64%).

Step E: A solution of (S)-benzyl 4-(3-amino-2-oxopyrrolidin-1-yl)piperidine-1-carboxylate (2.0 g, 6.3 mmol), 1,2-difluoro-4-(methylsulfonyl)benzene (1.2 g, 6.3 mmol), and $Na_2CO_3$ (3.3 g, 32 mmol) in DMSO (20 mL) was stirred at 120° C. for 48 hours. The reaction mixture was poured into water (200 mL) and extracted with EtOAc (3×100 mL). The combined organic layers were washed with brine and dried over $MgSO_4$, filtered then concentrated in vacuo. The material was purified over silica gel (100% EtOAc) to yield (S)-benzyl 4-(3-(2-fluoro-4-(methylsulfonyl)phenylamino)-2-oxopyrrolidin-1-yl)piperidine-1-carboxylate (1.3 g, 2.7 mmol, 42%).

Step F: A solution of (S)-benzyl 4-(3-(2-fluoro-4-(methylsulfonyl)phenylamino)-2-oxopyrrolidin-1-yl)piperidine-1-carboxylate (1.3 g, 27 mmol) in ethanol (20 mL) and concentrated HCl (300 μL) was hydrogenated at 40 PSI with 10% Degussa type Pd/C (650 mg) for 18 hours. The mixture was filtered through celite and the solids were washed with MeOH (200 mL) and water (200 mL). The methanol in the filtrate was removed in vacuo. The water layer was extracted with EtOAc (3×100 mL). The combined organic layers were washed with brine, dried over $MgSO_4$, filtered and concentrated in vacuo to yield (S)-3-(2-fluoro-4-(methylsulfonyl) phenylamino)-1-(piperidin-4-yl)pyrrolidin-2-one (600 mg, 1.7 mmol, 64%). Mass spectrum (apci) m/z=356.1 (M+H).

The following compounds in Table 2 were also prepared according to the method of Preparation E.

TABLE 2

| Compound # | Structure | Name | Mass spectrum |
|---|---|---|---|
| E-1 | ![structure] | (S)-3-(2,5-difluoro-4-(methylsulfonyl)phenyl amino)-1-(piperidin-4-yl)pyrrolidin-2-one | (apci) m/z = 374.2 (M + H). |

TABLE 2-continued

| Compound # | Structure | Name | Mass spectrum |
|---|---|---|---|
| E-2 | 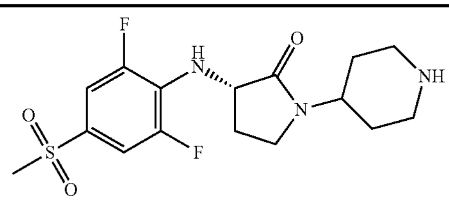 | (S)-3-(2,6-difluoro-4-(methylsulfonyl)phenyl amino)-1-(piperidin-4-yl)pyrrolidin-2-one | (apci) m/z = 374.2 (M + H). |

Preparation F (S)-3-(2-fluoro-4-(methylsulfonyl)phenoxy)-1-(piperidin-4-yl)pyrrolidin-2-one hydrochloride

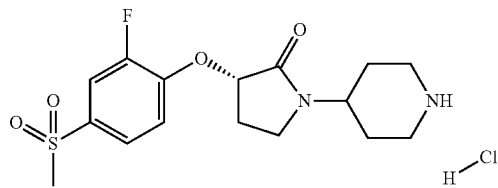

Step A: (R)-tert-Butyl 4-(3-(methylsulfonyloxy)-2-oxopyrrolidin-1-yl)piperidine-1-carboxylate (Preparation D; 1.7 g, 4.7 mmol) was dissolved in dry DMSO (30 mL) and 4-bromo-2-fluorophenol (1.1 g, 5.6 mmol) and $K_2CO_3$ (0.78 g, 5.6 mmol) was added and the reaction heated to 70° C. under nitrogen. The reaction became purple then black. The reaction was cooled to ambient temperature after 3 hours and partitioned between water and EtOAc, extracted with EtOAc, washed with brine, dried over $Na_2SO_4$, filtered and concentrated. The residue was purified over silica gel (40% EtOAc in hexanes) to afford (S)-tert-butyl 4-(3-(4-bromo-2-fluorophenoxy)-2-oxopyrrolidin-1-yl)piperidine-1-carboxylate (1.8 g, 3.9 mmol, 84% yield) as a white solid.

Step B: (S)-tert-Butyl 4-(3-(4-bromo-2-fluorophenoxy)-2-oxopyrrolidin-1-yl)piperidine-1-carboxylate (1.8 g, 3.9 mmol) was dissolved in DMSO (30 mL) and purged with nitrogen. Sodium methanesulfinate (0.60 g, 5.9 mmol) and trans-cyclohexane-1,2-diamine (0.19 mL, 1.6 mmol) were added followed by Cu(I) triflate benzene complex (0.20 g, 0.39 mmol). The reaction was plunged into a 110° C. oil bath under nitrogen and stirred overnight. The reaction was cooled to ambient temperature, partitioned between water and EtOAc, extracted with EtOAc, washed with brine, dried over $Na_2SO_4$, filtered and concentrated. The residue was purified over silica gel (100% EtOAc) to afford (S)-tert-butyl 4-(3-(2-fluoro-4-(methylsulfonyl)phenoxy)-2-oxopyrrolidin-1-yl)piperidine-1-carboxylate (1.6 g, 3.5 mmol, 89% yield) as a white solid.

Step C: (S)-tert-Butyl 4-(3-(2-fluoro-4-(methylsulfonyl)phenoxy)-2-oxopyrrolidin-1-yl)piperidine-1-carboxylate (1.6 g, 3.5 mmol) was dissolved in $CH_2Cl_2$ (20 mL) and 4N HCl in dioxane (~15 mL) was added and stirred at ambient temperature overnight. The reaction was concentrated to afford (S)-3-(2-fluoro-4-(methylsulfonyl)phenoxy)-1-(piperidin-4-yl)pyrrolidin-2-one hydrochloride (1.5 g, 3.8 mmol, 109% yield) as a white solid. Mass spectrum (apci) m/z=357.2 (M+H).

The following compounds in Table 3 were also prepared according to the procedure of Preparation F.

TABLE 3

| Cmpd. # | Structure | Name | Mass spectrum |
|---|---|---|---|
| F-1 | 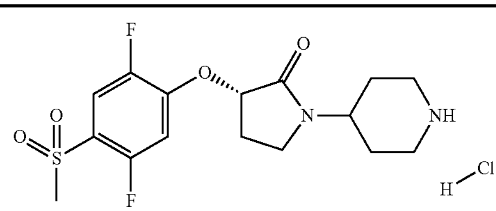 | (S)-3-(2,5-difluoro-4-(methylsulfonyl)phenoxy)-1-(piperidin-4-yl)pyrrolidin-2-one hydrochloride | (apci) m/z = 375.1 (M + H). |
| F-2 | 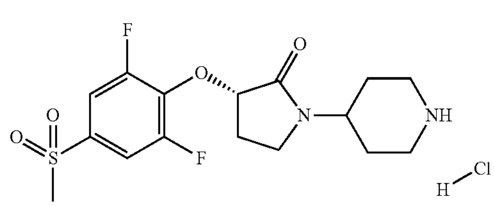 | (S)-3-(2,6-difluoro-4-(methylsulfonyl)phenoxy)-1-(piperidin-4-yl)pyrrolidin-2-one hydrochloride | (apci) m/z = 375.1 (M + H). |

Preparation G (S)-3-(2,5-difluoro-4-(methylsulfonyl)phenoxy)-[1,4'-bipiperidin]-2-one

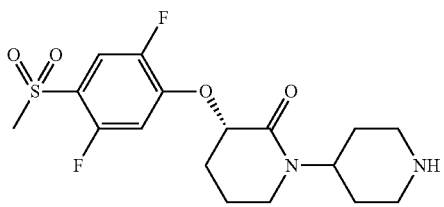 [SMILES: CS(=O)(=O)c1cc(F)c(O[C@H]2CCCN(C3CCNCC3)C2=O)cc1F]

Step A: (Conditions modified from Duttone, F. E., et. al., *J. Med. Chem.* 2003, 46, 2057) To a stirred solution of (methoxymethyl)triphenylphosphonium chloride (1.19 g, 3.48 mmol) in anhydrous ether (50 mL) at −10° C. under nitrogen was added phenyllithium (1.93 mL, 3.48 mmol) 1.8 M solution in diethyl ether, over 1 minute using a syringe. The mixture was stirred at 0° C. for 30 minutes and then cooled to −78° C. A solution of (R)-2-(2,2-dimethyl-5-oxo-1,3-dioxolan-4-yl)acetaldehyde (Preparation D, Step B; 0.500 g, 3.16 mmol) in ether/THF 1:1 (50 mL) was introduced via addition funnel, and the reaction mixture was stirred at −78° C. for 1 hour and then warmed to ambient temperature and stirred for 4 hours. The crude was filtered and the residue was purified over silica gel (5-50% EtOAc in hexanes) to afford (R)-5-(3-methoxyallyl)-2,2-dimethyl-1,3-dioxolan-4-one (0.355 g, 1.90 mmol, 60% yield) as a clear, colorless oil (mixture of (E)- and (Z)-isomers).

Step B: (Conditions modified from Duttone, F. E., et. al., *J. Med. Chem.* 2003, 46, 2057). A solution of (R)-5-(3-methoxyallyl)-2,2-dimethyl-1,3-dioxolan-4-one (600 mg, 3.22 mmol) in acetone (32.2 mL, 3.22 mmol) and $H_2SO_4$ (1 drop) at ambient temperature was stirred for 70 minutes. Saturated aqueous $NaHCO_3$ (4-5 drops) was added and the mixture was concentrated in vacuo at ambient temperature. The residue was diluted with ether, washed with water, dried ($Na_2SO_4$), and concentrated in vacuo to afford (R)-3-(2,2-dimethyl-5-oxo-1,3-dioxolan-4-yl)propanal (407 mg, 0.938 mmol, 58% yield) as a yellow oil (2:1 mixture of aldehyde to dimethyl acetal).

Step C: To a stirred solution of (R)-3-(2,2-dimethyl-5-oxo-1,3-dioxolan-4-yl)propanal (2.0 g, 8.71 mmol) in THF (120 mL) at 0° C. was added tert-butyl 4-aminopiperidine-1-carboxylate (1.92 g, 9.58 mmol). Sodium triacetoxyborohydride (2.77 g, 13.1 mmol) was added portionwise such that the internal temperature did not exceed 5° C. The mixture was stirred overnight while warming to ambient temperature. The reaction mixture was diluted with EtOAc and washed with brine. The aqueous layer was extracted twice with EtOAc, and the combined extracts were washed with brine, dried over magnesium sulfate and concentrated in vacuo. The residue was purified by reverse phase chromatography on C18 (0-60% ACN in water), to afford (R)-tert-butyl 3-hydroxy-2-oxo-[1,4'-bipiperidine]-1'-carboxylate as a light, white solid (1.55 g, 4.94 mmol, 57% yield). Mass spectrum (apci) m/z=199.1 (M+H-Boc).

Step D: To a stirred solution of (R)-tert-butyl 3-hydroxy-2-oxo-1,4'-bipiperidine-1'-carboxylate (151 mg, 0.506 mmol) in THF (10 mL) at 8° C. was added N-ethyl-N-isopropylpropan-2-amine (0.176 µL, 1.01 mmol) in one portion. Methanesulfonyl chloride (47.3 µL, 0.607 mmol) was added such that the internal temperature did not exceed 5° C. After 45 minutes additional methanesulfonyl chloride (22 µL, 0.31 mmol) was added and stirring was continued for 15 minutes. To the reaction mixture was added 25 mL of EtOAc, followed by aqueous saturated $NaHCO_3$ (35 mL) via syringe such that the internal temperature did not exceed 5° C. The mixture was extracted with EtOAc, washed with, brine, dried ($MgSO_4$) and concentrated in vacuo. The residue was purified over silica gel (50-100% EtOAc in hexanes) to give (R)-tert-butyl 3-(methylsulfonyloxy)-2-oxo-1,4'-bipiperidine-1'-carboxylate (105 mg, 0.273 mmol, 54% yield). $^1$H NMR $CDCl_3$ δ 4.90 (m, 1H), 4.45 (m, 1H), 4.13 (m, 2H), 3.18 (s, 3H), 3.11 (m, 2H), 2.69 (m, 2H), 2.15 (m, 1H), 1.99 (m, 1H), 1.75 (m, 4H), 1.36 (s, 9H).

Step E: To a stirred mixture of (R)-tert-butyl 3-(methylsulfonyloxy)-2-oxo-1,4'-bipiperidine-1'-carboxylate (1.10 g, 2.92 mmol) and potassium carbonate (485 mg, 3.51 mmol, 300 mesh, powdered) in THF (75 mL) was added 4-bromo-2,5-difluorophenol (733 mg, 3.51 mmol) and the reaction mixture was heated to reflux for 18 hours under nitrogen. The mixture was concentrated in vacuo and purified over silica gel (1:1 hexane/EtOAc) to afford (S)-tert-butyl 3-(4-bromo-2,5-difluorophenoxy)-2-oxo-1,4'-bipiperidine-1'-carboxylate obtained as a white solid (987 mg, 1.96 mmol, 67% yield). Mass spectrum (apci) m/z=389 (M+H-Boc). Chiral HPLC-analysis indicated this material was about 81% ee.

Normal Phase Chiral Method Conditions: Column: CHIRALPAK ADH (4.6×150 mm; 5 µm, Part #19324); UV: 222 nm; Sample preparation: 0.5 mg/mL methanol; Injection volume: 10 µL; Approximate retention times: (R)-enantiomer: 9.2 minutes; (S)-enantiomer: 9.8 minutes.

Gradient:

| Time (mins.) | Flow (mL/min) | Mobile phase A: hexanes (%) | Mobile phase B: ethanol (200 proof) (%) |
|---|---|---|---|
| 0 | 0.8 | 90 | 10 |
| 1 | 0.8 | 90 | 10 |
| 20 | 0.8 | 5 | 95 |
| 30 | 0.8 | 5 | 95 |

Step F: A suspension of (S)-tert-butyl 3-(4-bromo-2,5-difluorophenoxy)-2-oxo-1,4'-bipiperidine-1'-carboxylate (700 mg, 1.39 mmol), and sodium methanesulfinate (219 mg, 2.08 mmol) in DMSO (5.55 mL), was deoxygenated and purged with nitrogen. Cu(I) triflate benzene complex (77.6 mg, 0.139 mmol) and (1S,2S)-cyclohexane-1,2-diamine (63.4 mg, 0.555 mmol) were introduced and the heterogeneous mixture was sealed and heated to 110° C. in an oil bath and stirred for 18 hours. The mixture was cooled to ambient temperature, diluted with EtOAc (75 mL), washed with water (30 mL) and brine (three 50 mL washes), dried ($Na_2SO_4$), filtered and concentrated in vacuo. The residue was purified over silica gel (EtOAc) to afford (S)-tert-butyl 3-(2,5-difluoro-4-(methylsulfonyl)phenoxy)-2-oxo-1,4'-bipiperidine-1'-carboxylate (305 mg, 0.606 mmol, 44% yield) as a light yellow oil that solidified. Mass spectrum (apci) m/z=389.1 (M+H-Boc).

Step G: To a stirred solution of (S)-tert-butyl 3-(2,5-difluoro-4-(methylsulfonyl)phenoxy)-2-oxo-1,4'-bipiperidine-1'-carboxylate (370 mg, 0.757 mmol) in methanol (5 mL) was added, 5 M HCl in IPA (1.51 mL, 7.57 mmol) and the mixture was stirred at ambient temperature for 6 hours and concentrated in vacuo. The residue was stirred in 1M NaOH (20 mL) and DCM (25 mL). The organic layers were combined, dried ($Na_2SO_4$), filtered and concentrated in vacuo to give (S)-3-

(2,5-difluoro-4-(methylsulfonyl)phenoxy)-[1,4'-bipiperidin]-2-one as light brown foam (282 mg, 0.726 mmol, 96% yield). Mass spectrum (apci) m/z=389.1 (M+H).

Example 1

(S)-1-(1-(5-chloropyrazin-2-yl)piperidin-4-yl)-3-(2-fluoro-5-methyl-4-(methylsulfonyl)phenylamino)pyrrolidin-2-one

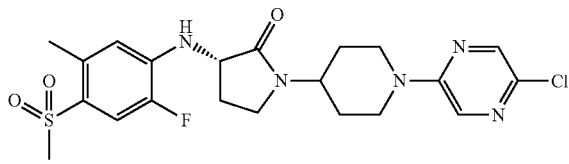 [SMILES: Cc1cc(N[C@H]2CCN(C3CCN(c4cnc(Cl)cn4)CC3)C2=O)c(F)cc1S(C)(=O)=O]

Step A: (S)-Benzyl 4-(3-amino-2-oxopyrrolidin-1-yl)piperidine-1-carboxylate (750 mg, 2.36 mmol) (Preparation E, Step D) was dissolved in toluene (20 mL). Racemic Binap (147 mg, 0.236 mmol), 1-bromo-2-fluoro-5-methyl-4-(methylsulfonyl)benzene (947 mg, 3.54 mmol) and $Cs_2CO_3$ (924 mg, 2.84 mmol) were added and the reaction was bubbled through with nitrogen for 5 minutes. $Pd_2dba_3$ (108 mg, 0.118 mmol) was added and the reaction plunged into 95° C. oil bath overnight. The reaction was cooled to ambient temperature, filtered and concentrated. The residue was purified over silica gel (50 to 100% EtOAc in hexanes) to afford (S)-benzyl 4-(3-(2-fluoro-5-methyl-4-(methylsulfonyl)phenylamino)-2-oxopyrrolidin-1-yl)piperidine-1-carboxylate (906 mg, 1.80 mmol, 76.1% yield) as a tan solid.

Step B: (S)-Benzyl 4-(3-(2-fluoro-5-methyl-4-(methylsulfonyl)phenylamino)-2-oxopyrrolidin-1-yl)piperidine-1-carboxylate (906 mg, 1.80 mmol) was dissolved in EtOH (15 mL) and 10% Pd/C was added and stirred under balloon pressure of hydrogen overnight. The reaction was filtered and concentrated to afford (S)-3-(2-fluoro-5-methyl-4-(methylsulfonyl)phenylamino)-1-(piperidin-4-yl)pyrrolidin-2-one (680 mg, 1.84 mmol, 102% yield).

Step C: (S)-3-(2-Fluoro-5-methyl-4-(methylsulfonyl)phenylamino)-1-(piperidin-4-yl)pyrrolidin-2-one (420 mg, 1.14 mmol) was dissolved in DMSO (10 mL) and 2,5-dichloropyrazine (203 mg, 1.36 mmol) and N-ethyl-N-isopropylpropan-2-amine (297 µL, 1.71 mmol) were added and the reaction heated to 110° C. overnight. The reaction was cooled to ambient temperature, water (60 mL) was added and the solids filtered. The solids were dissolved in $CH_2Cl_2$, washed with brine, dried over $Na_2SO_4$, filtered and concentrated. The residue was purified over silica gel (70 to 100% EtOAc in hexanes) to afford (S)-1-(1-(5-chloropyrazin-2-yl)piperidin-4-yl)-3-(2-fluoro-5-methyl-4-(methylsulfonyl)phenylamino)pyrrolidin-2-one (330 mg, 0.685 mmol, 60.2% yield) as a pale yellow solid. Mass spectrum (apci) m/z=482.2 (M+H).

Example 2

(S)-1-(1-(5-ethylpyrazin-2-yl)piperidin-4-yl)-3-(2-fluoro-5-methyl-4-(methylsulfonyl)phenylamino)pyrrolidin-2-one

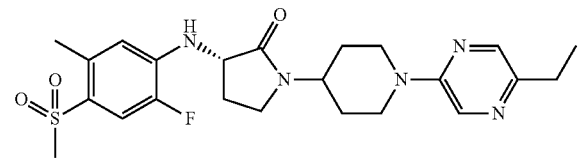 [SMILES: CCc1cnc(N2CCC(N3CC[C@H](Nc4cc(C)c(S(C)(=O)=O)cc4F)C3=O)CC2)cn1]

(S)-1-(1-(5-Chloropyrazin-2-yl)piperidin-4-yl)-3-(2-fluoro-5-methyl-4-(methylsulfonyl)phenylamino)pyrrolidin-2-one (Example 1; 320 mg, 0.664 mmol) was dissolved in THF (6 mL) and $K_2CO_3$ (275 mg, 1.99 mmol) and $PdCl_2$(dppf)*$CH_2Cl_2$ (54.2 mg, 0.0664 mmol) were added and purged with nitrogen. Diethylzinc (1 M in THF; 797 µL, 0.797 mmol) was added and the reaction heated to 60° C. for 1 hour. The reaction was cooled to ambient temperature, partitioned between water and EtOAc, dried over $Na_2SO_4$, filtered and concentrated in vacuo. The residue was purified over silica gel (100% EtOAc) to afford (S)-1-(1-(5-ethylpyrazin-2-yl)piperidin-4-yl)-3-(2-fluoro-5-methyl-4-(methylsulfonyl)phenylamino)pyrrolidin-2-one (175 mg, 0.368 mmol, 55.4% yield) as a tan solid. Mass spectrum (apci) m/z=476.3 (M+H).

Example 3

(S)-1-(1-(5-chloropyrazin-2-yl)piperidin-4-yl)-3-(2,5-difluoro-4-(methylsulfonyl)phenylamino)pyrrolidin-2-one

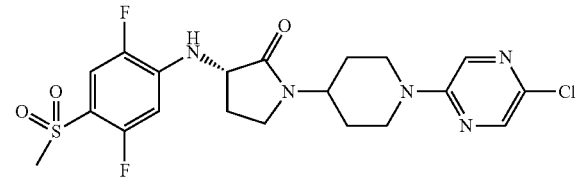 [SMILES: CS(=O)(=O)c1cc(F)c(N[C@H]2CCN(C3CCN(c4cnc(Cl)cn4)CC3)C2=O)cc1F]

Step A: A solution of (S)-benzyl 4-(3-amino-2-oxopyrrolidin-1-yl)piperidine-1-carboxylate (2.5, 7.9 mmol) (Preparation E, Step D), 1,2,4-trifluoro-5-(methylsulfonyl)benzene (3.3 g, 16 mmol), and $Na_2CO_3$ (2.5 g, 24 mmol) in DMSO (20 mL) was degassed using nitrogen and was stirred at 130° C. for 18 hours in a sealed tube. The reaction mixture was poured into water (200 mL) and extracted with EtOAc (3×100 mL). The combined organic layers were washed with brine and dried over $MgSO_4$, filtered then concentrated in vacuo. The material was purified over silica gel (100% EtOAc) to yield (S)-benzyl 4-(3-(2,5-difluoro-4-(methylsulfonyl)phenylamino)-2-oxopyrrolidin-1-yl)piperidine-1-carboxylate (2.6 g, 5.1 mmol, 65%).

Step B: A solution of (S)-benzyl 4-(3-(2,5-difluoro-4-(methylsulfonyl)phenylamino)-2-oxopyrrolidin-1-yl)piperidine-1-carboxylate (2.6 g, 5.1 mmol) in ethanol (20 mL) was hydrogenated using a double balloon of hydrogen with 10% Degussa type Pd/C (650 mg) for 18 hours. The mixture was filtered through celite and the solids were washed with MeOH (200 mL) The combined organic layers were concentrated in vacuo to yield (S)-3-(2,5-difluoro-4-(methylsulfonyl)phenylamino)-1-(piperidin-4-yl)pyrrolidin-2-one (2.0 g, 5.4 mmol, >95%). Mass spectrum (apci) m/z=374.2 (M+H).

Step C: To a solution of (S)-3-(2,5-difluoro-4-(methylsulfonyl)phenylamino)-1-(piperidin-4-yl)pyrrolidin-2-one (Table 2, compound 1; 1.5 g, 4.02 mmol) and DIEA (3.50 mL, 20.1 mmol) in DMF (15 mL) was added 2,5-dichloropyrazine (1.20 g, 8.03 mmol). This mixture was heated to 100° C. for 3 hours under nitrogen. The mixture was poured into brine (150 mL) and extracted into ethyl acetate (3×500 mL). The combined organic layers were dried over MgSO$_4$, filtered and concentrated in vacuo to give an oil. Ether (100 mL) was added and a precipitate formed overnight. The ether was decanted and the solid was triturated using ethanol (100 mL) at reflux with stirring for 5 minutes. The material was purified by column chromatography using 50% to 100% ethyl acetate/hexane. The resulting solid was dried over the weekend under high vacuum to provide the title compound (0.83 g, 39% yield). Mass spectrum (apci) m/z=486.1 (M+H).

Example 4

(S)-1-(1-(5-chloropyrazin-2-yl)piperidin-4-yl)-3-(2-fluoro-4-(methylsulfonyl)phenylamino)pyrrolidin-2-one

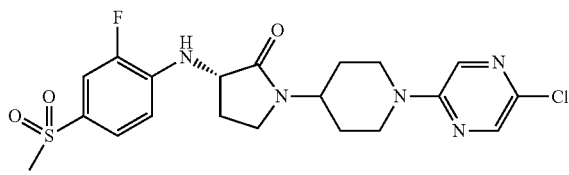 [SMILES: CS(=O)(=O)c1ccc(N[C@H]2CCN(C3CCN(c4cnc(Cl)cn4)CC3)C2=O)c(F)c1]

To a solution of (S)-3-(2-fluoro-4-(methylsulfonyl)phenylamino)-1-(piperidin-4-yl)pyrrolidin-2-one (Preparation E; 3 g, 8.44 mmol) and DIEA (7.35 mL, 42.2 mmol) in DMF (30 mL) was added 2,5-dichloropyrazine (2.51 g, 16.9 mmol). This mixture was degassed with nitrogen for 30 minutes then stirred at 100° C. for 4 hours under nitrogen. The mixture was poured into brine (500 mL) and extracted into ethyl acetate (3×100 mL). The combined organic layers were dried over MgSO$_4$, filtered and concentrated in vacuo to give an oil. Diethyl ether (200 mL) was added and a precipitate formed overnight. The ether was decanted and the solid was triturated using ethanol (100 mL) at reflux with stirring for 5 minutes. The suspension was filtered and the solid was washed using ethanol to give a solid crystal. This solid was dried over the weekend under high vacuum to provide the title compound (2.9 g, 73% yield). Mass spectrum (apci) m/z=468.1 (M+H).

The following compounds were also prepared according to Example 4.

| Ex. # | Structure | Name | Mass spectrum |
|---|---|---|---|
| 5 | 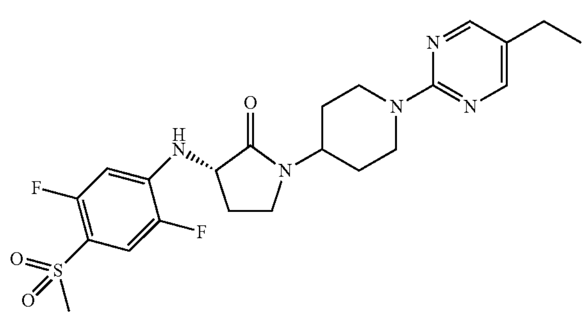 [SMILES: CCc1cnc(N2CCC(N3CC[C@H](Nc4cc(F)c(S(C)(=O)=O)cc4F)C3=O)CC2)nc1] | (S)-3-(2,5-difluoro-4-(methylsulfonyl)phenylamino)-1-(1-(5-ethylpyrimidin-2-yl)piperidin-4-yl)pyrrolidin-2-one | (apci) m/z = 480.2 (M + H) |
| 6 | 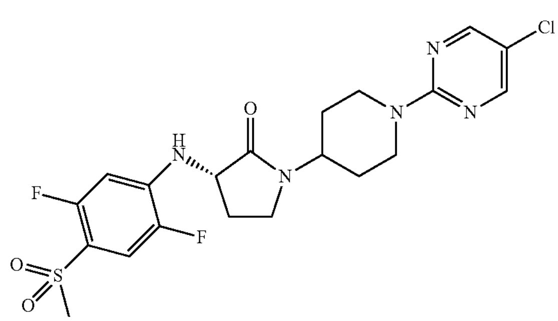 [SMILES: CS(=O)(=O)c1cc(F)c(N[C@H]2CCN(C3CCN(c4ncc(Cl)cn4)CC3)C2=O)cc1F] | (S)-3-(2,5-difluoro-4-(methylsulfonyl)phenylamino)-1-(1-(5-chloropyrimidin-2-yl)piperidin-4-yl)pyrrolidin-2-one | (apci) m/z = 486.3 (M + H) |

-continued

| Ex. # | Structure | Name | Mass spectrum |
|---|---|---|---|
| 7 | 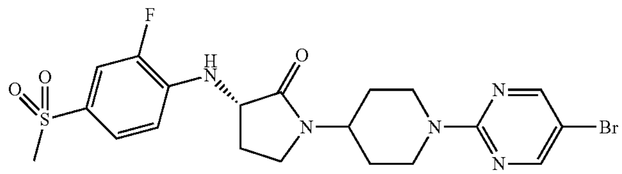 [SMILES: CS(=O)(=O)c1ccc(N[C@H]2CCN(C3CCN(c4ncc(Br)cn4)CC3)C2=O)c(F)c1] | (S)-1-(1-(5-bromopyrimidin-2-yl)piperidin-4-yl)-3-(2-fluoro-4-(methylsulfonyl)phenylamino)pyrrolidin-2-one | (apci) m/z = 512.1, 514.1 (M + H) |
| 8 | 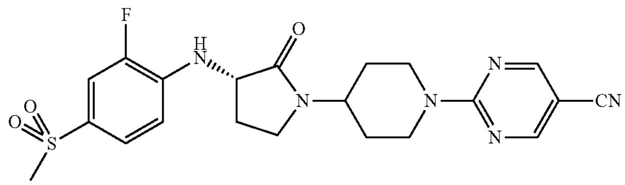 [SMILES: CS(=O)(=O)c1ccc(N[C@H]2CCN(C3CCN(c4ncc(C#N)cn4)CC3)C2=O)c(F)c1] | (S)-2-(4-(3-(2-fluoro-4-(methylsulfonyl)phenylamino)-2-oxopyrrolidin-1-yl)piperidin-1-yl)pyrimidine-5-carbonitrile | (apci) m/z = 459.2 (M + H) |
| 9 | 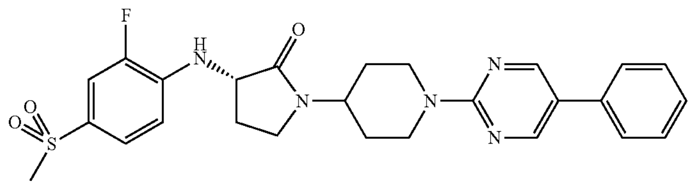 [SMILES: CS(=O)(=O)c1ccc(N[C@H]2CCN(C3CCN(c4ncc(-c5ccccc5)cn4)CC3)C2=O)c(F)c1] | (S)-3-(2-fluoro-4-(methylsulfonyl)phenylamino)-1-(1-(5-phenylpyrimidin-2-yl)piperidin-4-yl)pyrrolidin-2-one | (apci) m/z = 510.3 (M + H − TFA) |
| 10 | 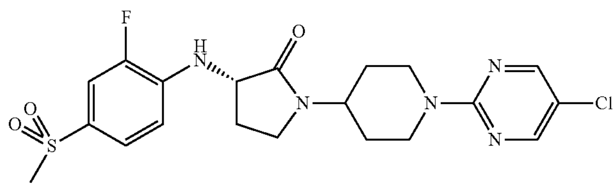 [SMILES: CS(=O)(=O)c1ccc(N[C@H]2CCN(C3CCN(c4ncc(Cl)cn4)CC3)C2=O)c(F)c1] | (S)-1-(1-(5-chloropyrimidin-2-yl)piperidin-4-yl)-3-(2-fluoro-4-(methylsulfonyl)phenylamino)pyrrolidin-2-one | (apci) m/z = 468.2 (M + H) |
| 11 | 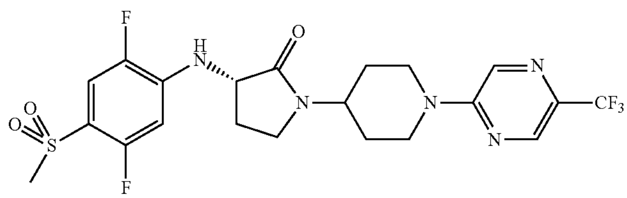 [SMILES: CS(=O)(=O)c1cc(F)c(N[C@H]2CCN(C3CCN(c4cnc(C(F)(F)F)cn4)CC3)C2=O)cc1F] | (S)-3-(2,5-difluoro-4-(methylsulfonyl)phenylamino)-1-(1-(5-(trifluoromethyl)pyrazin-2-yl)piperidin-4-yl)pyrrolidin-2-one | (apci) m/z = 520 (M + H) |
| 12 | 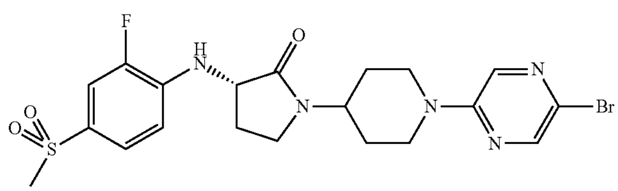 [SMILES: CS(=O)(=O)c1ccc(N[C@H]2CCN(C3CCN(c4cnc(Br)cn4)CC3)C2=O)c(F)c1] | (S)-1-(1-(5-bromopyrazin-2-yl)piperidin-4-yl)-3-(2-fluoro-4-(methylsulfonyl)phenylamino)pyrrolidin-2-one | (apci) m/z = 512, 514 (M + H) |
| 13 | 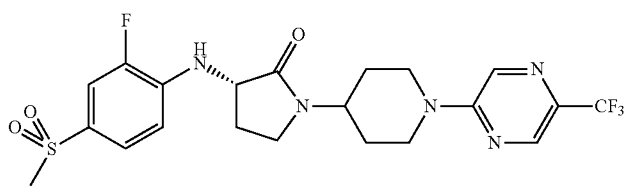 [SMILES: CS(=O)(=O)c1ccc(N[C@H]2CCN(C3CCN(c4cnc(C(F)(F)F)cn4)CC3)C2=O)c(F)c1] | (S)-3-(2-fluoro-4-(methylsulfonyl)phenylamino)-1-(1-(5-(trifluoromethyl)pyrazin-2-yl)piperidin-4-yl)pyrrolidin-2-one | (apci) m/z = 502 (M + H) |
| 14 | 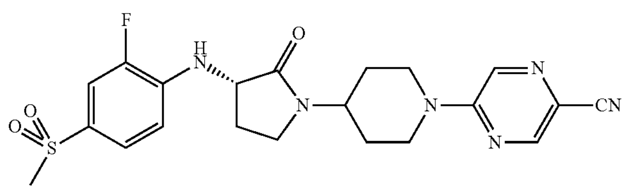 [SMILES: CS(=O)(=O)c1ccc(N[C@H]2CCN(C3CCN(c4cnc(C#N)cn4)CC3)C2=O)c(F)c1] | (S)-5-(4-(3-(2-fluoro-4-(methylsulfonyl)phenylamino)-2-oxopyrrolidin-1-yl)piperidin-1-yl)pyrazine-2-carbonitrile | (apci) m/z = 459 (M + H) |

-continued

| Ex. # | Structure | Name | Mass spectrum |
|---|---|---|---|
| 15 | 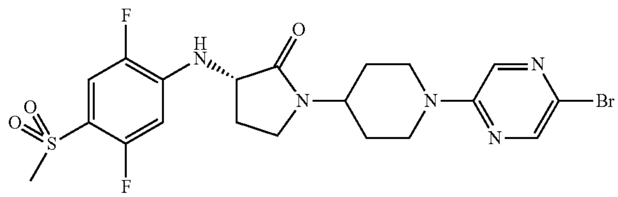 [SMILES: CS(=O)(=O)c1cc(F)c(N[C@H]2CCN(C3CCN(c4cnc(Br)cn4)CC3)C2=O)cc1F] | (S)-1-(1-(5-bromopyrazin-2-yl)piperidin-4-yl)-3-(2,5-difluoro-4-(methylsulfonyl)phenylamino)pyrrolidin-2-one | (apci) m/z = 530, 532 (M + H) |
| 16 | 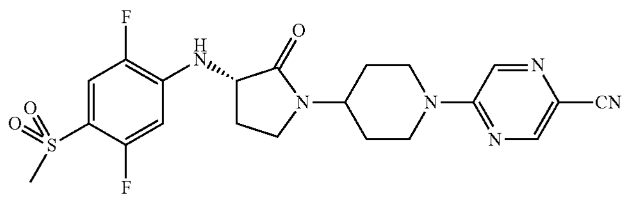 [SMILES: CS(=O)(=O)c1cc(F)c(N[C@H]2CCN(C3CCN(c4cnc(C#N)cn4)CC3)C2=O)cc1F] | (S)-5-(4-(3-(2,5-difluoro-4-(methylsulfonyl)phenylamino)-2-oxopyrrolidin-1-yl)piperidin-1-yl)pyrazine-2-carbonitrile | (apci) m/z = 477 (M + H) |
| 17 | 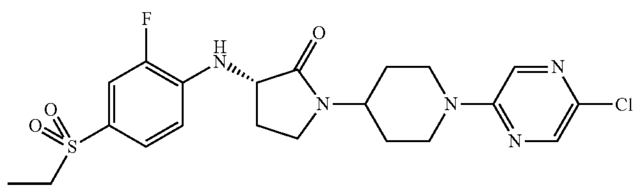 [SMILES: CCS(=O)(=O)c1ccc(N[C@H]2CCN(C3CCN(c4cnc(Cl)cn4)CC3)C2=O)c(F)c1] | (S)-1-(1-(5-chloropyrazin-2-yl)piperidin-4-yl)-3-(4-(ethylsulfonyl)-2-fluorophenylamino)pyrrolidin-2-one | (apci) m/z = 482 (M + H) |
| 18 | 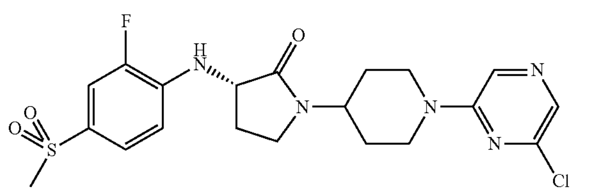 [SMILES: CS(=O)(=O)c1ccc(N[C@H]2CCN(C3CCN(c4cncc(Cl)n4)CC3)C2=O)c(F)c1] | (S)-1-(1-(6-chloropyrazin-2-yl)piperidin-4-yl)-3-(2-fluoro-4-(methylsulfonyl)phenylamino)pyrrolidin-2-one | (apci) m/z = 468 (M + H) |
| 19 | 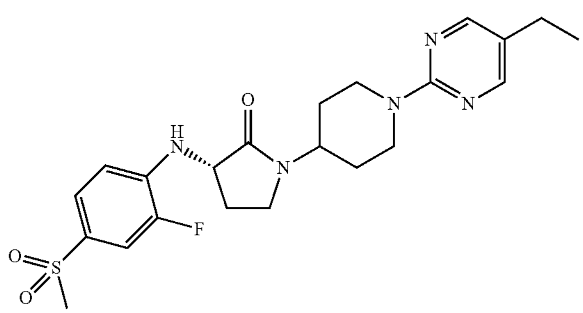 [SMILES: CCc1cnc(N2CCC(N3CC[C@H](Nc4ccc(S(C)(=O)=O)cc4F)C3=O)CC2)nc1] | (S)-1-(1-(5-ethylpyrimidin-2-yl)piperidin-4-yl)-3-(2-fluoro-4-(methylsulfonyl)phenylamino)pyrrolidin-2-one | (apci) m/z = 462.3 (M + H) |
| 20 | 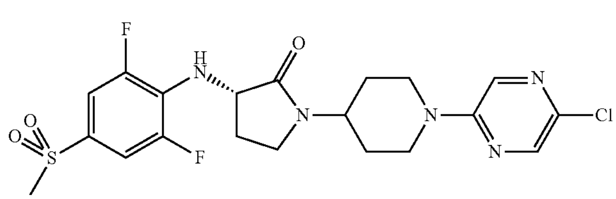 [SMILES: CS(=O)(=O)c1cc(F)c(N[C@H]2CCN(C3CCN(c4cnc(Cl)cn4)CC3)C2=O)c(F)c1] | (S)-1-(1-(5-chloropyrazin-2-yl)piperidin-4-yl)-3-(2,6-difluoro-4-(methylsulfonyl)phenylamino)pyrrolidin-2-one | (apci) m/z = 486 (M + H) |

| Ex. # | Structure | Name | Mass spectrum |
|---|---|---|---|
| 21 | 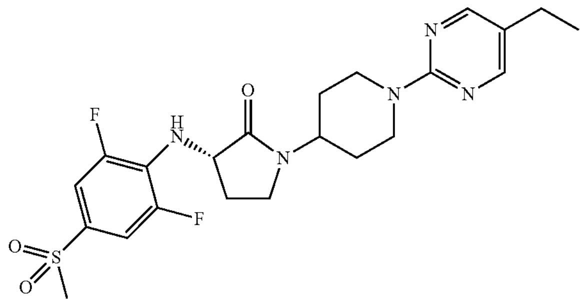 [SMILES: CCc1cnc(N2CCC(N3CC[C@H](Nc4c(F)cc(S(C)(=O)=O)cc4F)C3=O)CC2)nc1] | (S)-3-(2,6-difluoro-4-(methylsulfonyl)phenylamino)-1-(1-(5-ethylpyrimidin-2-yl)piperidin-4-yl)pyrrolidin-2-one | (apci) m/z = 480.3 (M + H) |
| 22 | 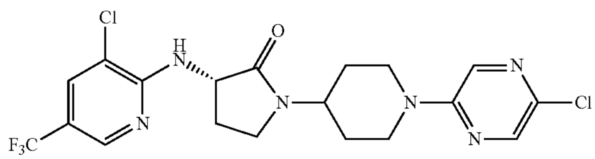 [SMILES: O=C1[C@@H](Nc2ncc(C(F)(F)F)cc2Cl)CCN1C1CCN(c2cnc(Cl)cn2)CC1] | (S)-3-(3-chloro-5-(trifluoromethyl)pyridin-2-ylamino)-1-(1-(5-chloropyrazin-2-yl)piperidin-4-yl)pyrrolidin-2-one | (apci) m/z = 475 (M + H) |
| 23 | 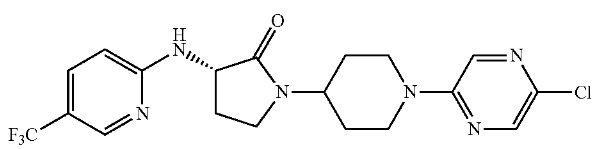 [SMILES: O=C1[C@@H](Nc2ccc(C(F)(F)F)cn2)CCN1C1CCN(c2cnc(Cl)cn2)CC1] | (S)-1-(1-(5-chloropyrazin-2-yl)piperidin-4-yl)-3-(5-(trifluoromethyl)pyridin-2-ylamino)pyrrolidin-2-one | (apci) m/z = 441 (M + H) |

Example 24

1-(1-(5-ethylpyridin-2-yl)piperidin-4-yl)-3-(2-fluoro-4-(methylsulfonyl)phenylamino)pyrrolidin-2-one

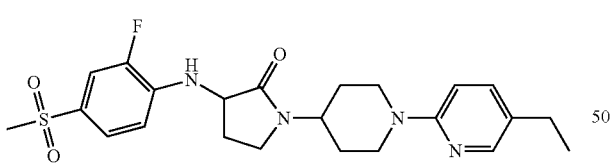

To a nitrogen purged vessel was added Pd₂dba₃ (0.0386 g, 0.0422 mmol), NaOtBu (0.169 g, 1.76 mmol), 2,8,9-triisobutyl-2,5,8,9-tetraaza-1-phosphabicyclo[3.3.3]undecane (0.0600 mL, 0.169 mmol), 2-chloro-5-ethylpyridine (0.100 g, 0.703 mmol) and (S)-3-(2-fluoro-4-(methylsulfonyl)phenylamino)-1-(piperidin-4-yl)pyrrolidin-2-one (Preparation E; 0.300 g, 0.844 mmol). Toluene (4 mL, purged with nitrogen) was added and the reaction was heated at 100° C. overnight. The mixture was cooled to ambient temperature, diluted with EtOAc, and washed with water. The organics were dried over Na₂SO₄, concentrated and purified on silica eluting with 100% EtOAc to give 1-(1-(5-ethylpyridin-2-yl)piperidin-4-yl)-3-(2-fluoro-4-(methylsulfonyl)phenylamino)pyrrolidin-2-one (0.177 g, 54% yield) as white solids. Mass spectrum (apci) m/z=461.3 (M+H).

Example 25

3-(2-fluoro-4-(methylsulfonyl)phenylamino)-1-(1-(5-phenylpyridin-2-yl)piperidin-4-yl)pyrrolidin-2-one

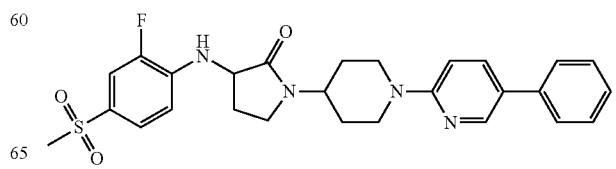

Prepared according to the method of Example 24. Mass spectrum (apci) m/z=509.3 (M+H).

Example 26

3-(2,5-difluoro-4-(methylsulfonyl)phenoxy)-1'-(5-ethylpyrimidin-2-yl)-1,4'-bipiperidin-2-one

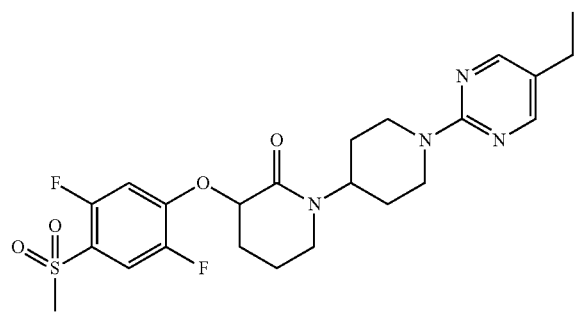 [SMILES: CCc1cnc(N2CCC(N3CCCC(Oc4cc(F)c(S(C)(=O)=O)cc4F)C3=O)CC2)nc1]

Step A: To a 3 neck flask equipped with an addition funnel and reflux condenser was added red phosphorus (1.85 g, 60 mmol) and valerolactone (12.0 g, 120 mmol). The reaction was cooled to 0° C. with an ice bath and bromine (42.1 g, 264 mmol) added dropwise (Caution: very exothermic). After the addition was complete, the dark slurry was heated with an oil bath at 50° C. for 12 hours. The reaction was cooled to ambient temperature and transferred to a fresh round bottom for distillation. The 2,5-dibromopentanoyl bromide (17.5 g, 45%) was distilled under a vacuum of 0.5 mm mercury at 83-85° C. and isolated as a clear liquid. The crude material was used in the next step without further purification.

Step B: To a solution of crude 2,5-dibromopentanoyl bromide (6.50 g, 20 mmol) and triethylamine (3.06 g, 30.2 mmol) in $CH_2Cl_2$ (40 mL) cooled to 0° C. was added tert-butyl-4-aminopiperidine-1-carboxylate (4.23 g, 21.1 mmol) in one portion. The reaction was allowed to stir for 4 hours at which point the reaction was quenched by the addition of saturated aqueous $NaHCO_3$ (5 mL) and $CH_2Cl_2$ (10 mL). The organic layer was separated and the aqueous layer washed with additional $CH_2Cl_2$ (3×15 mL). The combined organic layers were dried with $MgSO_4$ and concentrated. The crude material was purified over silica gel (3:1 hexanes/EtOAc) to give tert-butyl 4-(2,5-dibromopentanamido)piperidine-1-carboxylate (8.00 g, 90%) as a white solid.

Step C: To a solution of tert-butyl 4-(2,5-dibromopentanamido)piperidine-1-carboxylate (2.21 g, 5.00 mmol) dissolved in DMF (10 mL) was added 60% sodium hydride (0.220 g, 5.5 mmol). The reaction was allowed to stir for 2 hours and then concentrated under vacuum. The resulting material was diluted with water and EtOAc. The organic layer was separated and the aqueous layer washed with EtOAc. The combined organic layers were dried with $MgSO_4$ and concentrated. The residue was purified over silica gel (2:1 hexanes:EtOAc) to give tert-butyl 3-bromo-2-oxo-1,4'-bipiperidine-1'carboxylate (1.35 g, 75%) as a white solid.

Step D: To a solution of tert-butyl 3-bromo-2-oxo-1,4'-bipiperidine-1'carboxylate (723 mg, 2.00 mmol) in DMF (5 mL) was added $K_2CO_3$ (553 mg, 4.00 mmol) and 4-bromo-2,5-difluorophenol (460 mg, 2.20 mmol). The reaction was heated at 60° C. overnight. The reaction was cooled and diluted with water and EtOAc. The organic layer was separated and the aqueous washed with EtOAc. The combined organic layers were dried with $MgSO_4$ and concentrated. The crude residue was purified over silica gel (2:1 hexanes/EtOAc) to give tert-butyl 3-(4-bromo-2,5-difluorophenoxy)-2-oxo-1,4'-bipiperidine-1'-carboxylate (710 mg, 73%) as a white solid.

Step E: To a solution of tert-butyl 3-(4-bromo-2,5-difluorophenoxy)-2-oxo-1,4'-bipiperidine-1'-carboxylate (710 mg, 1.45 mmol) in DMSO (4 mL) was added Cu(I) triflate benzene complex (73 mg, 0.145 mmol), sodium methanesulfinate (222 mg, 2.18 mmol) and trans-cyclohexane-1,2-diamine (66.3 mg, 0.580 mmol). The reaction was heated at 110° C. overnight. The reaction was cooled to ambient temperature and diluted with water (5 mL) and EtOAc (5 mL). The organic layer was separated and the aqueous washed with EtOAc (2×10 mL). The combined organic layers were dried with $MgSO_4$ and concentrated. The crude residue was purified over silica gel (2:1 hexanes/EtOAc) to give a clear oil. This material was then dissolved in $CH_2Cl_2$ (10 mL) and excess 2 N HCl in ether (5 mL) added. The reaction was allowed to stir overnight and then concentrated under vacuum to give 3-(2,5-difluoro-4-(methylsulfonyl)phenoxy)-1,4'-bipiperidin-2-one HCl salt (238 mg, 89%) was an off white solid.

Step F: To a solution of 3-(2,5-difluoro-4-(methylsulfonyl)phenoxy)-1,4'-bipiperidin-2-one HCl salt (64 mg, 0.15 mmol) and DIEA (0.080 mL, 0.45 mmol) in DMSO (2 mL) was added 2-chloro-5-ethylpyrimidine (26 mg, 0.18 mmol). The reaction was heated at 120° C. overnight. The reaction was cooled to ambient temperature and diluted with water (2 mL) and EtOAc (5 mL). The organic layer was separated and the aqueous washed with EtOAc. The combined organic layers were dried with $MgSO_4$ and concentrated. The crude residue was purified by reverse phase HPLC (5 to 95% acetonitrile in water with 0.1% TFA). The combined fractions were concentrated to remove $CH_3CN$ and the pH adjusted to neutral by the addition of $NaHCO_3$. The aqueous layer was extracted with EtOAc. The combined organic layers were dried with $MgSO_4$ and concentrated to give 3-(2,5-difluoro-4-(methylsulfonyl)phenoxy)-1'-(5-ethylpyrimidine-2-yl)-1,4'-bipiperidine-2-one (15 mg, 20%) as an off white solid. Mass spectrum (apci) m/z=495.2 (M+H).

Example 27A and 27B (S)-1-(1-(5-ethylpyridin-2-yl)piperidin-4-yl)-3-(2-fluoro-4-(methylsulfonyl)phenylamino)pyrrolidin-2-one and (R)-1-(1-(5-ethylpyridin-2-yl)piperidin-4-yl)-3-(2-fluoro-4-(methylsulfonyl)phenylamino)pyrrolidin-2-one

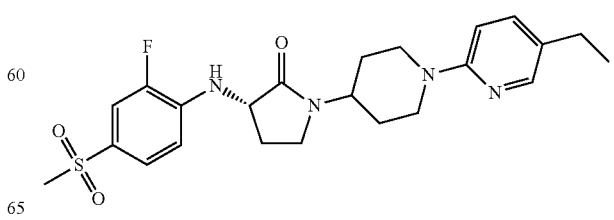

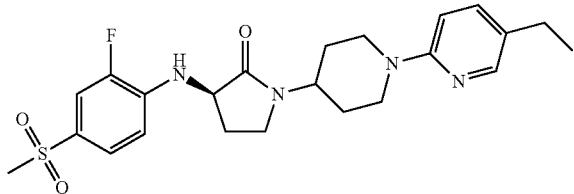

(S)-1-(1-(5-Ethylpyridin-2-yl)piperidin-4-yl)-3-(2-fluoro-4-(methylsulfonyl)phenylamino)pyrrolidin-2-one (Example 27A) and (R)-1-(1-(5-ethylpyridin-2-yl)piperidin-4-yl)-3-(2-fluoro-4-(methylsulfonyl)phenylamino)pyrrolidin-2-one (Example 27B) were isolated by purification of 1-(1-(5-ethylpyridin-2-yl)piperidin-4-yl)-3-(2-fluoro-4-(methylsulfonyl)phenylamino)pyrrolidin-2-one (Example 24) via chiral preparative HPLC. Mass spectrum (apci) m/z=461.3 (M+H).

Example 28

1-(1-(5-ethyl-3-methylpyridin-2-yl)piperidin-4-yl)-3-(2-fluoro-4-(methylsulfonyl)phenylamino)pyrrolidin-2-one

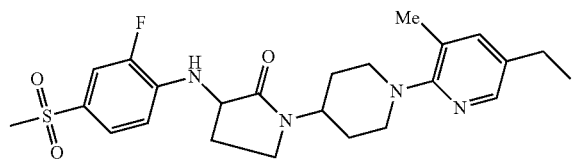 [SMILES: CCc1cnc(N2CCC(N3CCC(Nc4ccc(S(C)(=O)=O)cc4F)C3=O)CC2)c(C)c1]

To a nitrogen purged reaction vessel was added Pd$_2$ dba$_3$ (0.0129 g, 0.0141 mmol), Cs$_2$CO$_3$ (0.229 g, 0.703 mmol), Binap-rac (0.035 g, 0.0563 mmol), 2-chloro-5-ethyl-3-methylpyridine (0.037 g, 0.234 mmol) and (S)-3-(2-fluoro-4-(methylsulfonyl)phenylamino)-1-(piperidin-4-yl)pyrrolidin-2-one (Preparation E; 0.100 g, 0.281 mmol). Toluene (3 mL, purged with nitrogen) was added and the reaction was heated at 110° C. overnight. The reaction was cooled to ambient temperature, diluted with EtOAc and washed with water. The combined organic layers were dried over Na$_2$SO$_4$ and purified by preparative HPLC (Parallex Flex) to give 1-(1-(5-ethyl-3-methylpyridin-2-yl)piperidin-4-yl)-3-(2-fluoro-4-(methylsulfonyl)phenylamino)pyrrolidin-2-one (0.026 g, 23% yield) as white solids. Mass spectrum (apci) m/z=475.3 (M+H).

Example 29

(S)-3-(2-fluoro-4-(methylsulfonyl)phenylamino)-1-(1-(5-isopropylpyrimidin-2-yl)piperidin-4-yl)pyrrolidin-2-one trifluoroacetate

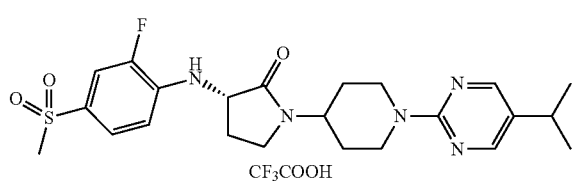

To a solution of (S)-1-(1-(5-bromopyrimidin-2-yl)piperidin-4-yl)-3-(2-fluoro-4-(methylsulfonyl)phenylamino)pyrrolidin-2-one (Example 7; 0.30 g, 0.59 mmol) in dioxane (15 mL) was bubbled nitrogen directly into the solution for 30 minutes, followed by addition of diisopropylzinc (2.3 mL, 2.3 mmol, 1 M solution in THF) and PdCl$_2$(dppf)*CH$_2$Cl$_2$ (0.096 g, 0.12 mmol) and the reaction stirred at 100° C. for 3 hours. The reaction was poured into water and extracted into EtOAc. The combined organic layers were washed with water, brine, dried over MgSO$_4$, filtered and concentrated in vacuo. The material was taken up in acetonitrile and filtered, and the solution purified by reverse phase HPLC (5 to 95% acetonitrile in water with 0.1% TFA) to yield (S)-3-(2-fluoro-4-(methylsulfonyl)phenylamino)-1-(1-(5-isopropylpyrimidin-2-yl)piperidin-4-yl)pyrrolidin-2-one trifluoroacetate (0.027 g, 0.057 mmol, 9.7% yield). Mass Spectrum (apci) m/z=476.3 (M+H).

Example 30

(S)-3-(2-fluoro-4-(methylsulfonyl)phenylamino)-1-(1-(5-(methylthio)pyrimidin-2-yl)piperidin-4-yl)pyrrolidin-2-one

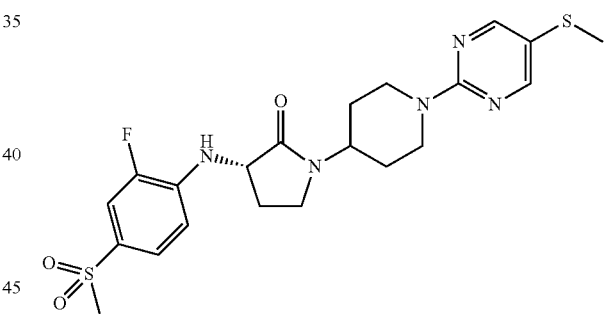

(S)-1-(1-(5-Bromopyrimidin-2-yl)piperidin-4-yl)-3-(2-fluoro-4-(methylsulfonyl)phenylamino)pyrrolidin-2-one (Example 7; 0.10 g, 0.20 mmol), Xantphos (0.056 g, 0.098 mmol), K$_3$PO$_4$ (0.11 g, 0.51 mmol), and Pd$_2$ dba$_3$ (0.045 g, 0.049 mmol) were diluted in degassed toluene (3 mL). Sodium methanethiolate (0.032 g, 0.45 mmol) was added and the reaction was stirred at 100° C. overnight. The material was cooled to ambient temperature and flash chromatographed to give (S)-3-(2-fluoro-4-(methylsulfonyl)phenylamino)-1-(1-(5-(methylthio)pyrimidin-2-yl)piperidin-4-yl)pyrrolidin-2-one (0.011 g, 0.023 mmol, 12% yield) as a white solid. Mass spectrum (apci) m/z=480.1 (M+H).

Example 31

(S)-1-(1-(5-(1H-pyrazol-4-yl)pyrimidin-2-yl)piperidin-4-yl)-3-(2-fluoro-4-(methylsulfonyl)phenylamino)pyrrolidin-2-one

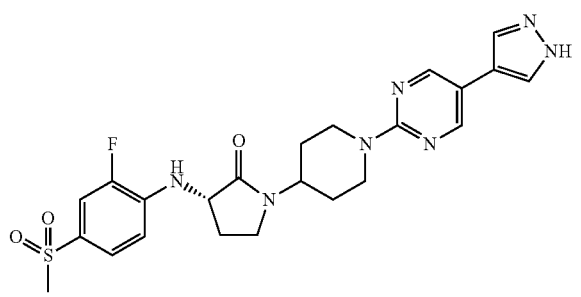 [SMILES: CS(=O)(=O)c1ccc(N[C@H]2CCN(C3CCN(c4ncc(-c5cn[nH]c5)cn4)CC3)C2=O)c(F)c1]

(S)-1-(1-(5-Bromopyrimidin-2-yl)piperidin-4-yl)-3-(2-fluoro-4-(methylsulfonyl)phenylamino)pyrrolidin-2-one (Example 7; 0.090 g, 0.17 mmol), tert-butyl 4-(4,4,5,5-tetramethyl-1,3,2-dioxaborolan-2-yl)-1H-pyrazole-1-carboxylate (0.057 g, 0.19 mmol), Pd(PPh$_3$)$_4$ (0.020 g, 0.018 mmol) and Na$_2$CO$_3$ (0.44 mL, 0.88 mmol) were suspended in dioxane in a sealed tube and stirred at 110° C. overnight. The material was cooled and filtered through silica gel (10% MeOH/EtOAc). The material was purified by reverse phase HPLC purification (5 to 95% acetonitrile in water) to give (S)-1-(1-(5-(1H-pyrazol-4-yl)pyrimidin-2-yl)piperidin-4-yl)-3-(2-fluoro-4-(methylsulfonyl)phenylamino)pyrrolidin-2-one (0.037 g, 42% yield) as a white solid. Mass spectrum (apci) m/z=500.3 (M+H).

The following compounds were prepared according to the method of Example 31.

| Ex. # | Structure | Name | Mass spectrum |
|---|---|---|---|
| 32 | 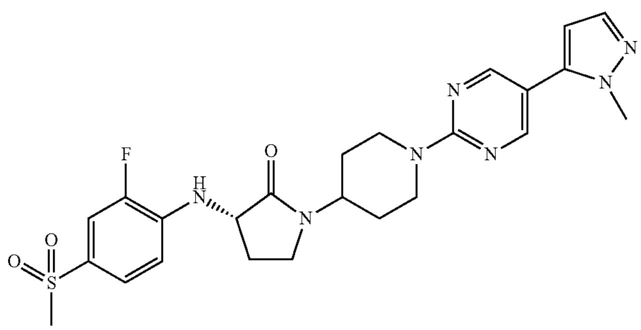 [SMILES: Cn1nccc1-c1cnc(N2CCC(N3CC[C@H](Nc4ccc(S(C)(=O)=O)cc4F)C3=O)CC2)nc1] | (S)-3-(2-fluoro-4-(methylsulfonyl)phenylamino)-1-(1-(5-(1-methyl-1H-pyrazol-5-yl)pyrimidin-2-yl)piperidin-4-yl)pyrrolidin-2-one | (apci) m/z = 514.3 (M + H). |
| 33 | 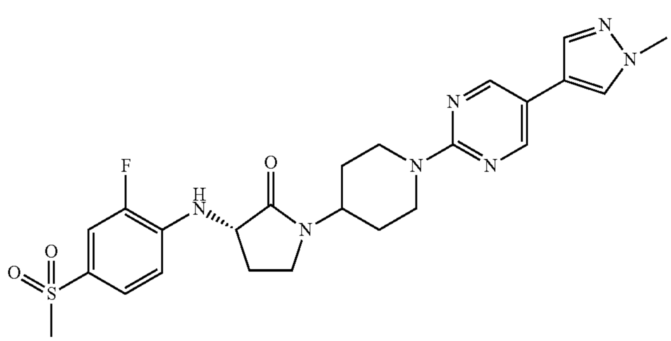 [SMILES: Cn1cc(-c2cnc(N3CCC(N4CC[C@H](Nc5ccc(S(C)(=O)=O)cc5F)C4=O)CC3)nc2)cn1] | (S)-3-(2-fluoro-4-(methylsulfonyl)phenylamino)-1-(1-(5-(1-methyl-1H-pyrazol-4-yl)pyrimidin-2-yl)piperidin-4-yl)pyrrolidin-2-one | (apci) m/z = 514.3 (M + H). |

Example 34

(S)-1-(1-(5-ethylpyrimidin-2-yl)piperidin-4-yl)-3-(4-(ethylsulfonyl)-2-fluorophenylamino)pyrrolidin-2-one

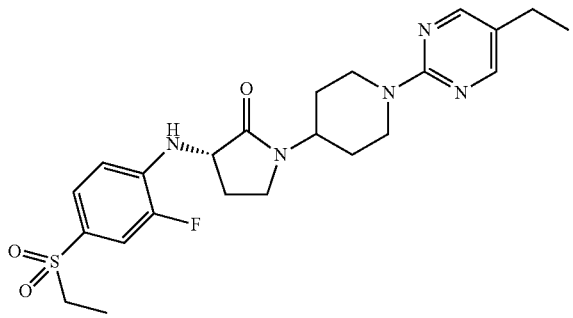 [SMILES: CCc1cnc(N2CCC(N3CC[C@H](Nc4ccc(S(=O)(=O)CC)cc4F)C3=O)CC2)nc1]

Step A: A solution of 1-((dimethylamino)(dimethyliminio)methyl)-1H-benzo[d][1,2,3]triazole 3-oxide hexafluorophosphate(V) (4.0 g, 11 mmol) (S)-2-(tert-butoxycarbonylamino)-4-(methylthio)butanoic acid (2.7 g, 11 mmol), and DIEA (4.1 mL, 23 mmol) in DMF (20 mL) was stirred at ambient temperature for 30 minutes. 1-(5-Ethylpyrimidin-2-yl)piperidin-4-amine (Preparation A; 2.2 g, 11 mmol) was added and the mixture was stirred at ambient temperature for 18 hours. The mixture was poured into 1N NaOH (500 mL) and the combined organic layers were extracted into EtOAc (500 mL). The combined organic layers were washed with 1 N HCl (500 mL) and brine (500 mL). The combined organic layers were dried over MgSO$_4$, filtered and concentrated in vacuo to yield (S)-tert-butyl 1-(1-(5-ethylpyrimidin-2-yl)piperidin-4-ylamino)-4-(methylthio)-1-oxobutan-2-ylcarbamate (4.4 g, 10 mmol, 96%).

Step B: A solution of (S)-tert-butyl 1-(1-(5-ethylpyrimidin-2-yl)piperidin-4-ylamino)-4-(methylthio)-1-oxobutan-2-ylcarbamate (4.4 g, 10 mmol) in neat methyl iodide (22 mL, 340 mmol) stirred at ambient temperature for 18 hours. The reaction was evaporated to dryness to yield (S)-tert-butyl 1-(1-(5-ethylpyrimidin-2-yl)piperidin-4-ylamino)-4-(methylthio)-1-oxobutan-2-ylcarbamate methyliodide (7 g, 12 mmol, >95%).

Step C: To a solution of (S)-tert-butyl 1-(1-(5-ethylpyrimidin-2-yl)piperidin-4-ylamino)-4-(methylthio)-1-oxobutan-2-ylcarbamate methyliodide (7 g, 12 mmol) in CH$_2$Cl$_2$ (70 mL) was added 60% NaH in oil (580 mg, 14 mmol). After 5 minutes, DMF (7 mL) was added and the mixture stirred at ambient temperature for 1 hour. The mixture was poured into saturated ammonium chloride (70 mL) and the solution was extracted with CH$_2$Cl$_2$ (3×100 mL). The combined organic layers were washed with brine, dried over MgSO$_4$, filtered and concentrated in vacuo. The resulting oil was triturated with ether (100 mL) and the ether layer was washed with brine. The combined organic layers were dried over MgSO$_4$, filtered and concentrated in vacuo to yield (S)-tert-butyl 1-(1-(5-ethylpyrimidin-2-yl)piperidin-4-yl)-2-oxopyrrolidin-3-ylcarbamate (3.2 g, 8.2 mmol, 68%).

Step D: A solution of (S)-tert-butyl 1-(1-(5-ethylpyrimidin-2-yl)piperidin-4-yl)-2-oxopyrrolidin-3-ylcarbamate (1 g, 2.6 mmol) in 50% TFA/CH$_2$Cl$_2$ (10 mL) was stirred at ambient temperature for 1 hour. The mixture was concentrated in vacuo. The residue was dissolved in CH$_2$Cl$_2$ (100 mL) and washed with 1N NaOH (100 mL) and brine. The combined organic layers were dried over MgSO$_4$, filtered and concentrated in vacuo to yield (S)-3-amino-1-(1-(5-ethylpyrimidin-2-yl)piperidin-4-yl)pyrrolidin-2-one (0.75 g, 2.6 mmol, 100%)

Step E: A solution of ((S)-3-amino-1-(1-(5-ethylpyrimidin-2-yl)piperidin-4-yl)pyrrolidin-2-one (100 mg, 0.35 mmol), 1,2-difluoro-4-(ethylsulfonyl)benzene (0.2 g, 1.0 mmol), and Na$_2$CO$_3$ (110 mg, 1.0 mmol) in DMSO (2 mL) was stirred at 130° C. for 18 hours. The reaction mixture was poured into water (100 mL) and extracted with EtOAc (3×100 mL). The combined organic layers were washed with brine and dried over MgSO$_4$, filtered and concentrated in vacuo. The crude material was purified over silica gel (10% methanol in EtOAc) to yield (S)-1-(1-(5-ethylpyrimidin-2-yl)piperidin-4-yl)-3-(4-(ethylsulfonyl)-2-fluorophenylamino)pyrrolidin-2-one (50 mg, 0.11 mmol, 30%). Mass spectrum (apci) m/z=476.3 (M+H).

Example 35

(S)-1-(1-(5-ethylpyrimidin-2-yl)piperidin-4-yl)-3-(2-fluoro-5-methyl-4-(methylsulfonyl)phenylamino)pyrrolidin-2-one

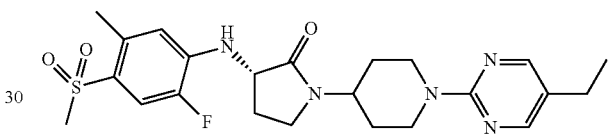

(S)-3-Amino-1-(1-(5-ethylpyrimidin-2-yl)piperidin-4-yl)pyrrolidin-2-one (Example 34, Steps A-D; 152 mg, 0.525 mmol) was dissolved in toluene (5 mL). 2,2'-Bis(diphenylphosphino)-1,1'-binaphthyl (32.7 mg, 0.0525 mmol), 1-bromo-2-fluoro-5-methyl-4-(methylsulfonyl)benzene (Preparation B; 281 mg, 1.05 mmol) and Cs$_2$CO$_3$ (205 mg, 0.630 mmol) were added and nitrogen bubbled through for 5 minutes. Pd$_2$dba$_3$ (24.0 mg, 0.0263 mmol) was added and the reaction plunged into a 95° C. oil bath and stirred under nitrogen overnight. The reaction was cooled, concentrated, dissolved in small amount of CH$_2$Cl$_2$, solids filtered away and filtrate purified over silica gel (90% EtOAc in hexanes) to afford (S)-1-(1-(5-ethylpyrimidin-2-yl)piperidin-4-yl)-3-(2-fluoro-5-methyl-4-(methylsulfonyl)phenylamino)pyrrolidin-2-one (59.3 mg, 0.125 mmol, 24% yield) as a tan solid. Mass spectrum (apci) m/z=476.3.

Example 36

S-3-6-chloro-4-oxochroman-7-ylamino)-1-(1-5-ethylpyrimidin-2-yl)piperidin-4-yl)pyrrolidin-2-one

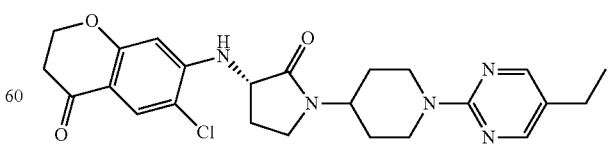

(S)-3-Amino-1-(1-(5-ethylpyrimidin-2-yl)piperidin-4-yl)pyrrolidin-2-one (Example 34, Steps A-D; 120 mg, 0.42 mmol) was dissolved in toluene (3 mL). 2,2'-Bis(diphenylphosphino)-1,1'-binaphthyl (26 mg, 0.042 mmol), 6-chloro-4-oxochroman-7-yl trifluoromethanesulfonate (206 mg, 0.62 mmol) and Cs₂CO₃ (162 mg, 0.498 mmol) were added and the reaction was bubbled through with nitrogen for 5 minutes. Pd₂dba₃ (19.0 mg, 0.021 mmol) was added and the reaction plunged into 95° C. oil bath overnight. The reaction was cooled to ambient temperature, partitioned between water and EtOAc, dried over Na₂SO₄, filtered and concentrated. The residue was purified over silica gel (75 to 100% EtOAc in hexanes) to afford a mixture. The mixture was further purified by reverse phase chromatography (25 to 95% ACN in water) to afford (S)-3-(6-chloro-4-oxochroman-7-ylamino)-1-(1-(5-ethylpyrimidin-2-yl)piperidin-4-yl)pyrrolidin-2-one (10 mg, 0.022 mmol, 5% yield. Mass spectrum (apci) m/z=470.3 (M+H).

Example 37

(S)-3-((2,5-difluoro-4-(methylsulfonyl)phenyl)(methyl)amino)-1-(1-(5-ethylpyrimidin-2-yl)piperidin-4-yl)pyrrolidin-2-one trifluoroacetate

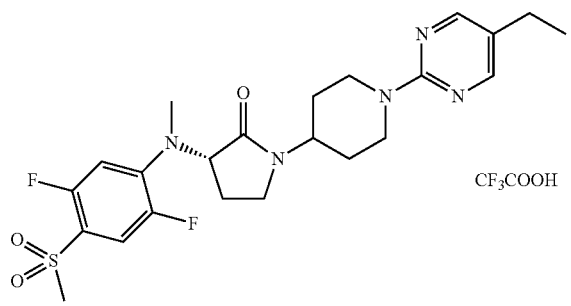 [SMILES: CCc1cnc(N2CCC(N3CC[C@H](N(C)c4cc(F)c(S(C)(=O)=O)cc4F)C3=O)CC2)nc1 ; "CF3COOH"]

Step A: To a solution of (S)-tert-butyl 1-(1-(5-ethylpyrimidin-2-yl)piperidin-4-yl)-2-oxopyrrolidin-3-ylcarbamate (Example 34, Steps A-C, 0.30 g, 0.77 mmol) in DMF (5 mL) was added NaH (0.040 g, 0.92 mmol). This mixture stirred at ambient temperature for 10 minutes and then iodomethane (0.13 g, 0.92 mmol) was added. After 30 minutes, saturated sodium carbonate (50 mL) was added and the product was extracted into EtOAc (3×50 mL). The combined organic layers were washed with brine, dried over MgSO₄, filtered and concentrated in vacuo to yield (S)-tert-butyl 1-(1-(5-ethylpyrimidin-2-yl)piperidin-4-yl)-2-oxopyrrolidin-3-ylmethyl)carbamate (0.3 g, 0.7 mmol, 100%).

Step B: A solution of (S)-tert-butyl 1-(1-(5-ethylpyrimidin-2-yl)piperidin-4-yl)-2-oxopyrrolidin-3-ylmethyl)carbamate (0.3 g, 0.7 mmol) in 50% TFA/CH₂Cl₂ (10 mL) was stirred at ambient temperature for 1 hour. The mixture was concentrated in vacuo. The residue was dissolved in CH₂Cl₂ (100 mL) and washed with 1N NaOH (100 mL) then brine. The combined organic layers were dried over MgSO₄, filtered and concentrated in vacuo to yield (S)-1-(1-(5-ethylpyrimidin-2-yl)piperidin-4-yl)-3-(methylamino)pyrrolidin-2-one (220 mg, 0.72 mmol, 97%).

Step C: (S)-1-(1-(5-Ethylpyrimidin-2-yl)piperidin-4-yl)-3-(methylamino) pyrrolidin-2-one (0.10 g, 0.33 mmol) was dissolved in DMSO (2 mL). 1,2,4-Trifluoro-5-(methylsulfonyl)benzene (Preparation C, 0.21 g, 0.99 mmol) and powdered Na₂CO₃ (0.11 g, 0.99 mmol) were added. This mixture was stirred at 130° C. for 18 hours in a sealed tube. The reaction mixture was partitioned between brine (100 mL) and EtOAc (100 mL). The combined organic layers were washed with brine and dried over MgSO₄. After concentration in vacuo the material was purified using reverse phase HPLC (5 to 95% acetonitrile in water with 0.1% TFA) to give (S)-3-((2,5-difluoro-4-(methylsulfonyl)phenyl)(methyl)amino)-1-(1-(5-ethylpyrimidin-2-yl)piperidin-4-yl)pyrrolidin-2-one trifluoroacetate (40 mg, 80 mmol, 25%). Mass spectrum (apci) m/z=494.3 (M+H).

Example 38

(S)-3-((2,5-difluoro-4-(methylsulfonyl)phenyl)(methyl)amino)-1-(1-(5-ethylpyrimidin-2-yl)piperidin-4-yl)pyrrolidin-2-one

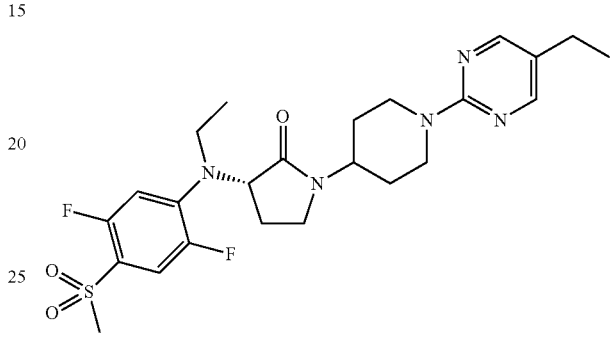

Prepared according to the method of Example 37. Mass spectrum (apci) m/z=552.2 (M+2Na).

Example 39

(3S,4S)-1-(1-(5-chloropyrazin-2-yl)piperidin-4-yl)-3-(2-fluoro-4-(methylsulfonyl)phenoxy)-4-hydroxypyrrolidin-2-one

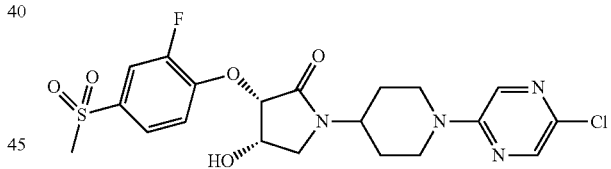

Step A: (2R,3R)-Diethyl 2-(benzyloxy)-3-hydroxysuccinate (15 g, 50.6 mmol) was dissolved in 30% aqueous THF (250 mL) and lithium hydroxide hydrate (4.25 g, 101 mmol) was added and the reaction stirred at ambient temperature overnight. The reaction was then partitioned between aqueous citric acid and EtOAc, dried over Na₂SO₄, filtered and concentrated to afford (2R,3R)-2-(benzyloxy)-3-hydroxysuccinic acid (11.5 g, 47.9 mmol, 94.6% yield) as a clear colorless oil.

Step B: (2R,3R)-2-(Benzyloxy)-3-hydroxysuccinic acid (11.1 g, 46.2 mmol) was dissolved in 2,2-dimethoxypropane (46 mL, 374 mmol) and 4-methylbenzenesulfonic acid hydrate (0.0879 g, 0.462 mmol) was added and the reaction was stirred at ambient temperature for 4 hours. Water (30 mL) and NaHCO₃ (0.0388 g, 0.462 mmol) were added and extracted with CH₂Cl₂, dried over Na₂SO₄, filtered and concentrated to provide (R)-2-(benzyloxy)-2-((R)-2,2-dimethyl-5-oxo-1,3-dioxolan-4-yl)acetic acid. The crude product was taken on to next step without further purification.

Step C: Crude (R)-2-(benzyloxy)-2-((R)-2,2-dimethyl-5-oxo-1,3-dioxolan-4-yl)acetic acid (13 g, 46 mmol) was dissolved in CH$_2$Cl$_2$ (150 mL) and cooled in an ice bath. Ethanethiol (6.9 mL, 93 mmol) and N,N-dimethylpyridin-4-amine (0.11 g, 0.93 mmol) were added followed by DCC (11 g, 56 mmol). This mixture was stirred in ice bath and allowed to slowly warm to ambient temperature overnight. Acetic acid (15 mL) was added and the reaction was stirred for 10 minutes. The reaction mixture was poured into vigorously stirring ether (400 mL) and then filtered. The filtrate was washed with 10% sodium carbonate, water, 0.5 N HCl, water, brine. The organic layer was dried over Na$_2$SO$_4$, filtered and concentrated. The crude material was purified over silica gel (1-5% EtOAc in hexanes) to afford (R)—S-ethyl 2-(benzyloxy)-2-((R)-2,2-dimethyl-5-oxo-1,3-dioxolan-4-yl)ethanethioate (2.3 g, 7.1 mmol, 15% yield) as a yellow oil.

Step D: (R)—S-Ethyl 2-(benzyloxy)-2-((R)-2,2-dimethyl-5-oxo-1,3-dioxolan-4-yl)ethanethioate (2.3 g, 7.09 mmol) was dissolved in CH$_2$Cl$_2$ (50 mL) and 10% palladium on carbon (0.377 g, 0.355 mmol) was added and stirred under nitrogen. Triethylsilane (1.70 mL, 10.6 mmol) was dissolved in CH$_2$Cl$_2$ (5 mL) and added dropwise. The reaction was allowed to stir overnight. The reaction was filtered, concentrated and purified over silica gel (5 to 10% EtOAc in hexanes) to afford a small amount of product and a large amount of starting material. The isolated starting material was subjected to the conditions described above and combined with the product isolated from the first batch to afford (R)-2-(benzyloxy)-2-((R)-2,2-dimethyl-5-oxo-1,3-dioxolan-4-yl)acetaldehyde (750 mg, 2.84 mmol, 40% yield).

Step E: (R)-2-(Benzyloxy)-2-((R)-2,2-dimethyl-5-oxo-1,3-dioxolan-4-yl)acetaldehyde (750 mg, 2.84 mmol) was dissolved in ClCH$_2$CH$_2$Cl (20 mL) and tert-butyl 4-aminopiperidine-1-carboxylate (1137 mg, 5.68 mmol) and acetic acid (195 µL, 3.41 mmol) were added and the reaction mixture was stirred at ambient temperature for 15 minutes. Na(OAc)$_3$BH (1804 mg, 8.51 mmol) was added and the reaction stirred at ambient temperature for 2 hours. The reaction was carefully quenched with saturated aqueous NaHCO$_3$. The reaction was partitioned between aqueous NaHCO$_3$ and CH$_2$Cl$_2$, extracted, washed with 10% citric acid, brine, dried over Na$_2$SO$_4$, filtered and concentrated. The resulting solids were purified over silica gel (5% methanol in EtOAc) to afford tert-butyl 4-((3R,4S)-4-(benzyloxy)-3-hydroxy-2-oxopyrrolidin-1-yl)piperidine-1-carboxylate (525 mg, 1.34 mmol, 47.4% yield).

Step F: tert-Butyl 4-((3R,4S)-4-(benzyloxy)-3-hydroxy-2-oxopyrrolidin-1-yl)piperidine-1-carboxylate (525 mg, 1.34 mmol) was dissolved in THF (10 mL) and triethylamine (375 µL, 2.69 mmol) and methanesulfonyl chloride (126 µL, 1.61 mmol) were added to the reaction and stirred for 1 hour. The reaction was partitioned between saturated aqueous NaHCO$_3$ and EtOAc, dried over Na$_2$SO$_4$, filtered and concentrated to afford tert-butyl 4-((3R,4S)-4-(benzyloxy)-3-(methylsulfonyloxy)-2-oxopyrrolidin-1-yl)piperidine-1-carboxylate (623 mg, 1.33 mmol, 98.9% yield) as a white solid.

Step G: Tert-butyl 4-((3R,4S)-4-(benzyloxy)-3-(methylsulfonyloxy)-2-oxopyrrolidin-1-yl)piperidine-1-carboxylate (620 mg, 1.32 mmol) was dissolved in dry DMSO (10 mL) and 4-bromo-2-fluorophenol (303 mg, 1.59 mmol) and K$_2$CO$_3$ (219 mg, 1.59 mmol) were added and the reaction heated to 70° C. under nitrogen overnight. The reaction was partitioned between water and EtOAc, extracted, dried over Na$_2$SO$_4$ and concentrated. The residue was purified over silica gel (50 to 75% EtOAc in hexane) to afford tert-butyl 4-((3S,4S)-4-(benzyloxy)-3-(4-bromo-2-fluorophenoxy)-2-oxopyrrolidin-1-yl)piperidine-1-carboxylate (300 mg, 0.532 mmol, 40.2% yield) as a crude material, which was taken forward without further purification.

Step H: Tert-butyl 4-((3S,4S)-4-(benzyloxy)-3-(4-bromo-2-fluorophenoxy)-2-oxopyrrolidin-1-yl)piperidine-1-carboxylate (300 mg, 0.532 mmol) was dissolved in DMSO (5 mL) and degassed for 10 minutes. Sodium methanesulfinate (81.5 mg, 0.799 mmol) and trans-cyclohexane-1,2-diamine (25.6 µL, 0.213 mmol) were added, followed by Cu(I) triflate benzene complex (26.8 mg, 0.0532 mmol) and the reaction was heated to 110° C. overnight. The reaction was cooled, partitioned between water and EtOAc, extracted with EtOAc, washed with brine, dried over Na$_2$SO$_4$, filtered and concentrated. The residue was purified over silica gel (100% EtOAc) to afford tert-butyl 4-((3S,4S)-4-(benzyloxy)-3-(2-fluoro-4-(methylsulfonyl)phenoxy)-2-oxopyrrolidin-1-yl)piperidine-1-carboxylate (160 mg, 0.284 mmol, 53.4% yield).

Step I: Tert-butyl 4-((3S,4S)-4-(benzyloxy)-3-(2-fluoro-4-(methylsulfonyl)phenoxy)-2-oxopyrrolidin-1-yl)piperidine-1-carboxylate (160 mg, 0.284 mmol) was dissolved in EtOH (3 mL) and 100 mg 10% Pd/C was added and stirred under balloon pressure of hydrogen overnight. The reaction was filtered and concentrated to afford tert-butyl 4-((3S,4S)-3-(2-fluoro-4-(methylsulfonyl)phenoxy)-4-hydroxy-2-oxopyrrolidin-1-yl)piperidine-1-carboxylate (80 mg, 0.169 mmol, 59.5% yield).

Step J: tert-butyl 4-((3S,4S)-3-(2-fluoro-4-(methylsulfonyl)phenoxy)-4-hydroxy-2-oxopyrrolidin-1-yl)piperidine-1-carboxylate (80 mg, 0.169 mmol) was dissolved in CH$_2$Cl$_2$ (1 mL) and 4N HCl in dioxane (1 mL) was added and stirred at ambient temperature for 6 hours. The reaction was concentrated to afford crude (3S,4S)-3-(2-fluoro-4-(methylsulfonyl)phenoxy)-4-hydroxy-1-(piperidin-4-yl)pyrrolidin-2-one hydrochloride (80 mg).

Step K: (3S,4S)-3-(2-fluoro-4-(methylsulfonyl)phenoxy)-4-hydroxy-1-(piperidin-4-yl)pyrrolidin-2-one hydrochloride (0.03 g, 0.073 mmol) was dissolved in DMF (2 mL) and 2,5-dichloropyrazine (0.012 g, 0.081 mmol) and Hunig's base (0.040 mL, 0.22 mmol) were added. The reaction was heated at 100° C. for 4 hours. The reaction was cooled and concentrated. The residue was purified by reverse phase chromatography (5 to 95% ACN in water) to afford (3S,4S)-1-(1-(5-chloropyrazin-2-yl)piperidin-4-yl)-3-(2-fluoro-4-(methylsulfonyl)phenoxy)-4-hydroxypyrrolidin-2-one (0.0027 g, 0.0056 mmol, 7.6% yield). Mass spectrum (apci) m/z=485.2 (M+H).

Example 40

(S)-1'-(5-ethylpyrimidin-2-yl)-3-(2-fluoro-4-(methylsulfonyl)phenylamino)-[1,4'-bipiperidin]-2-one

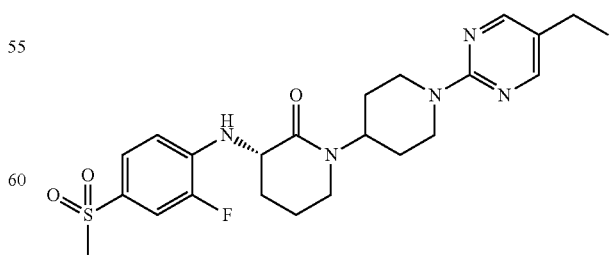

(S)-3-(2-fluoro-4-(methylsulfonyl)phenylamino)-1,4'-bipiperidin-2-one hydrochloride (prepared according to the method of Example 45) (0.35 g, 0.862 mmol), 2-chloro-5- ethylpyrimidine (0.123 g, 0.862 mmol) and DIEA (0.334 g, 2.59 mmol) were dissolved in DMF (5 mL) and The reaction was stirred at 100° C. overnight. The reaction was cooled to ambient temperature and concentrated. The residue was purified over silica gel (50-100% EtOAc in hexanes) to afford (S)-1'-(5-ethylpyrimidin-2-yl)-3-(2-fluoro-4-(methylsulfonyl)phenylamino)-1,4'-bipiperidin-2-one (0.142 g, 0.299 mmol, 34.6% yield) as a yellow solid. Mass spectrum (apci) m/z=476.2 (M+H).

The following compounds were also prepared according to the method of Example 40.

| Ex. # | Structure | Name | Mass spectrum |
|---|---|---|---|
| 41 | 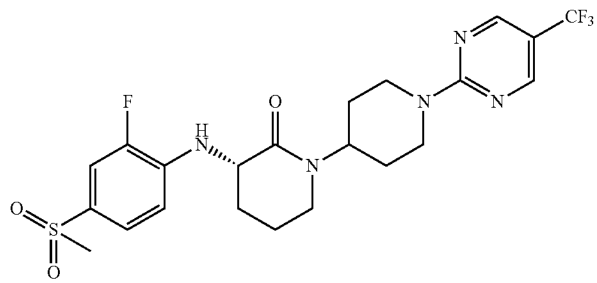 [SMILES: CS(=O)(=O)c1ccc(N[C@H]2CCCN(C3CCN(c4ncc(C(F)(F)F)cn4)CC3)C2=O)c(F)c1] | (S)-3-(2-fluoro-4-(methylsulfonyl)phenylamino)-1'-(5-(trifluoromethyl)pyrimidin-2-yl)-1,4'-bipiperidin-2-one | (apci) m/z = 516.2 (M + H). |
| 42 | 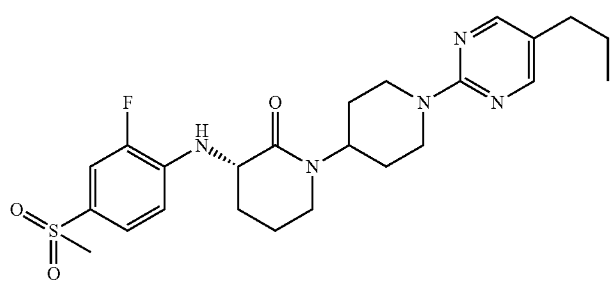 [SMILES: CCCc1cnc(N2CCC(N3CCC[C@H](Nc4ccc(S(C)(=O)=O)cc4F)C3=O)CC2)nc1] | (S)-3-(2-fluoro-4-(methylsulfonyl)phenylamino)-1'-(5-propylpyrimidin-2-yl)-[1,4'-bipiperidin]-2-one | (apci) m/z = 490.2 (M + H). |
| 43 | 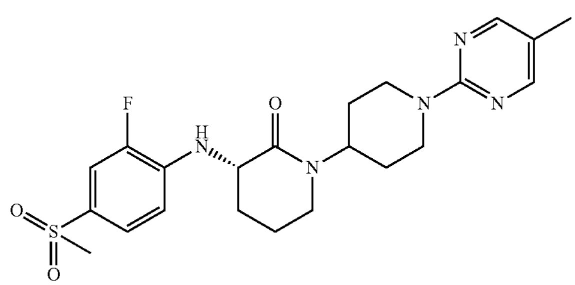 [SMILES: Cc1cnc(N2CCC(N3CCC[C@H](Nc4ccc(S(C)(=O)=O)cc4F)C3=O)CC2)nc1] | (S)-3-(2-fluoro-4-(methylsulfonyl)phenylamino)-1'-(5-methylpyrimidin-2-yl)-[1,4'-bipiperidin]-2-one | (apci) m/z = 462.2 (M + H). |
| 44 | 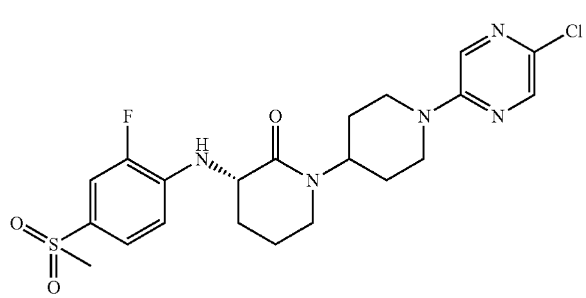 [SMILES: CS(=O)(=O)c1ccc(N[C@H]2CCCN(C3CCN(c4cnc(Cl)cn4)CC3)C2=O)c(F)c1] | (S)-1'-(5-chloropyrazin-2-yl)-3-(2-fluoro-4-(methylsulfonyl)phenylamino)-[1,4'-bipiperidin]-2-one | (apci) m/z = 482.2 (M + H) |

Example 45

(S)-3-(2,5-difluoro-4-(methylsulfonyl)phenylamino)-1'-(5-ethylpyrimidin-2-yl)-[1,4'-bipiperidin]-2-one

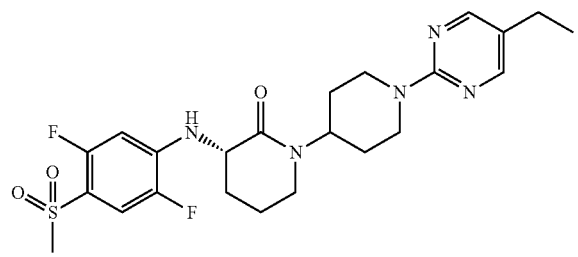 [SMILES: CCc1cnc(N2CCC(N3CCC[C@H](Nc4cc(F)c(S(C)(=O)=O)cc4F)C3=O)CC2)nc1]

Step A: (S)-5-amino-2-(benzyloxycarbonylamino)pentanoic acid (50 g, 188 mmol) was dissolved in THF (800 mL) and water (100 mL). Tert-butyl 4-oxopiperidine-1-carboxylate (37 g, 188 mmol) was added and the reaction was stirred for 1 hour. The reaction was cooled to 0° C. and sodium cyanoborohydride (12 g, 188 mmol) was added and the reaction stirred at ambient temperature overnight. The reaction was concentrated to provide (S)-2-(benzyloxycarbonylamino)-5-(1-(tert-butoxycarbonyl)piperidin-4-ylamino)pentanoic acid, which was used directly in the next step.

Step B: Crude (S)-2-(benzyloxycarbonylamino)-5-(1-(tert-butoxycarbonyl)piperidin-4-ylamino)pentanoic acid (84 g, 187 mmol) was dissolved in DMF (600 mL), and cooled to 0° C. N1-((ethylimino)methylene)-N3,N3-dimethylpropane-1,3-diamine hydrochloride (35.8 g, 187 mmol) and N-ethyl-N-isopropylpropan-2-amine (32.5 mL, 187 mmol) were added and the reaction stirred at ambient temperature overnight. The reaction was concentrated and dissolved in EtOAc (1000 mL), washed with 1N HCl, saturated aqueous NaHCO₃ and brine, dried over Na₂SO₄, filtered and concentrated. The residue was purified over silica gel (50% EtOAc in hexanes) to afford (S)-tert-butyl 3-(benzyloxycarbonylamino)-2-oxo-1,4'-bipiperidine-1'-carboxylate (49 g, 114 mmol, 60.8% yield) as white solid.

Step C: (S)-tert-butyl 3-(benzyloxycarbonylamino)-2-oxo-1,4'-bipiperidine-1'-carboxylate (20.9 g, 48.4 mmol) was dissolved in methanol (250 mL). 10% Pd/C (500 mg) was added and stirred under balloon pressure hydrogen overnight. The reaction was filtered through celite and concentrated. The residue was purified over silica gel (50-100% EtOAc in hexanes followed by 5% ammoniated methanol in CH₂Cl₂) to afford (S)-tert-butyl 3-amino-2-oxo-1,4'-bipiperidine-1'-carboxylate (11.2 g, 37.7 mmol, 77.8% yield) as white solid.

Step D: (S)-tert-butyl 3-amino-2-oxo-1,4'-bipiperidine-1'-carboxylate (4.0 g, 13 mmol), 1,2,4-trifluoro-5-(methylsulfonyl)benzene (Preparation C, 4.2 g, 20 mmol) and Na₂CO₃ (2.9 g, 27 mmol) were dissolved in DMF (30 mL) and heated at 130° C. overnight. The reaction was concentrated and purified over silica gel (25-75% EtOAc in hexanes) to afford (S)-tert-butyl 3-(2,5-difluoro-4-(methylsulfonyl)phenylamino)-2-oxo-1,4'-bipiperidine-1'-carboxylate (4.6 g, 9.4 mmol, 70% yield) as yellow solid.

Step E: (S)-tert-butyl 3-(2,5-difluoro-4-(methylsulfonyl)phenylamino)-2-oxo-1,4'-bipiperidine-1'-carboxylate (4.6 g, 9.4 mmol) was dissolved in CH₂Cl₂ (100 mL) and methanol (10 mL). 4N HCl in dioxane (24 mL, 94 mmol) was added and the reaction stirred at ambient temperature overnight. The reaction was concentrated to provide (S)-3-(2,5-difluoro-4-(methylsulfonyl)phenylamino)-1,4'-bipiperidin-2-one hydrochloride, which was used directly in the next step without purification.

Step F: (S)-3-(2,5-difluoro-4-(methylsulfonyl)phenylamino)-1,4'-bipiperidin-2-one hydrochloride (2.6 g, 6.1 mmol) was dissolved in DMF (30 mL) and DIEA (3.2 mL, 18 mmol) and 2-chloro-5-ethylpyrimidine (1.1 g, 8.0 mmol) were added and heated at 100° C. overnight. The reaction was concentrated and purified over silica gel (25-100% EtOAc in hexanes) to afford (S)-3-(2,5-difluoro-4-(methylsulfonyl)phenylamino)-1'-(5-ethylpyrimidin-2-yl)-1,4'-bipiperidin-2-one (1.5 g, 3.1 mmol, 51% yield) as a white solid. Mass spectrum (apci) m/z=494.3 (M+H).

The following compounds were prepared according to the method of Example 45.

| Ex. # | Structure | Name | Mass spectrum |
|---|---|---|---|
| 46 | 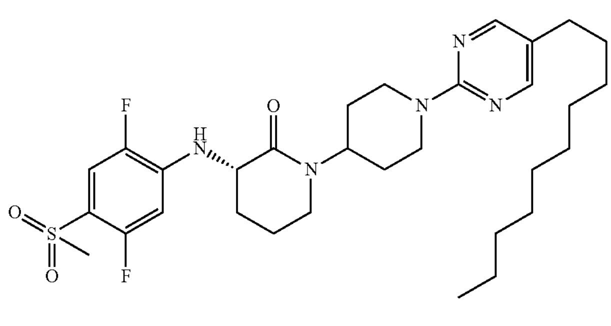 [SMILES: CCCCCCCCCCc1cnc(N2CCC(N3CCC[C@H](Nc4cc(F)c(S(C)(=O)=O)cc4F)C3=O)CC2)nc1] | (S)-1'-(5-decylpyrimidin-2-yl)-3-(2,5-difluoro-4-(methylsulfonyl)phenylamino)-[1,4'-bipiperidin]-2-one | (apci) m/z = 606.4 (M + H). |

-continued

| Ex. # | Structure | Name | Mass spectrum |
|---|---|---|---|
| 47 | 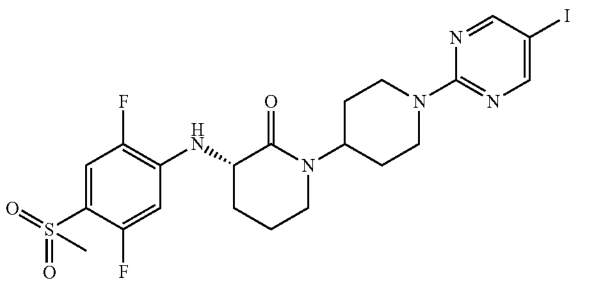 [SMILES: CS(=O)(=O)c1cc(F)c(N[C@H]2CCCN(C3CCN(c4ncc(I)cn4)CC3)C2=O)cc1F] | (S)-3-(2,5-difluoro-4-(methylsulfonyl)phenylamino)-1'-(5-iodopyrimidin-2-yl)-[1,4'-bipiperidin]-2-one | (apci) m/z = 592.1 (M + H). |
| 48 | 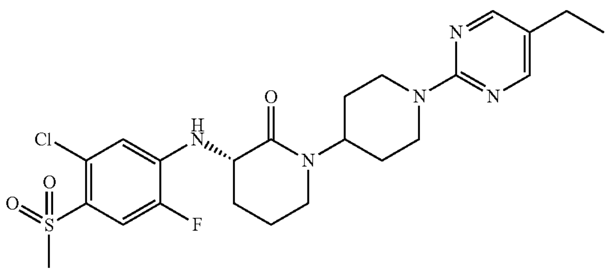 [SMILES: CCc1cnc(N2CCC(N3CCC[C@H](Nc4cc(Cl)c(S(C)(=O)=O)cc4F)C3=O)CC2)nc1] | (S)-3-(5-chloro-2-fluoro-4-(methylsulfonyl)phenylamino)-1'-(5-ethylpyrimidin-2-yl)-[1,4'-bipiperidin]-2-one | (apci) m/z = 510.2 (M + H). |
| 49 | 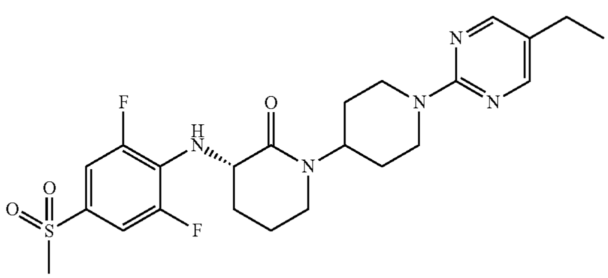 [SMILES: CCc1cnc(N2CCC(N3CCC[C@H](Nc4c(F)cc(S(C)(=O)=O)cc4F)C3=O)CC2)nc1] | (S)-3-(2,6-difluoro-4-(methylsulfonyl)phenylamino)-1'-(5-ethylpyrimidin-2-yl)-[1,4'-bipiperidin]-2-one | (apci) m/z = 494.3 (M + H). |
| 50 | 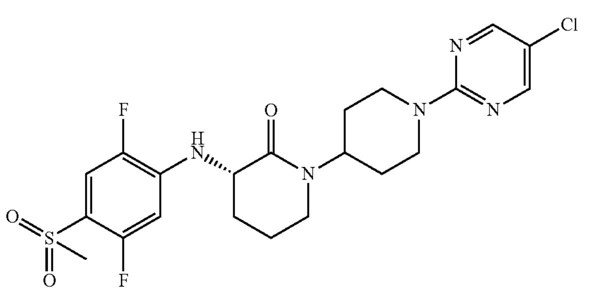 [SMILES: CS(=O)(=O)c1cc(F)c(N[C@H]2CCCN(C3CCN(c4ncc(Cl)cn4)CC3)C2=O)cc1F] | (S)-1'-(5-chloropyrimidin-2-yl)-3-(2,5-difluoro-4-(methylsulfonyl)phenylamino)-[1,4'-bipiperidin]-2-one | (apci) m/z = 500.2 (M + H). |
| 51 | 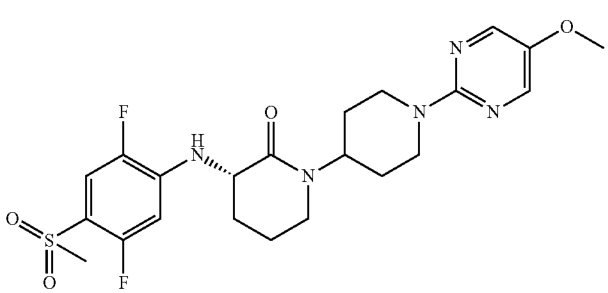 | (S)-2-(3-(2,5-difluoro-4-(methylsulfonyl)phenylamino)-2-oxo-[1,4'-bipiperidin]-1'-yl)pyrimidine-5-carbonitrile | (apci) m/z = 491.2 (M + H). |

| Ex. # | Name | Mass spectrum |
|---|---|---|
| 52 | (S)-1'-(6-chloropyridazin-3-yl)-3-(2,5-difluoro-4-(methylsulfonyl)phenylamino)-[1,4'-bipiperidin]-2-one | (apci) m/z = 500.3 (M + H). |
| 53 | (S)-1'-(5-chloropyrazin-2-yl)-3-(2,5-difluoro-4-(methylsulfonyl)phenylamino)-[1,4'-bipiperidin]-2-one | (apci) m/z = 500.2 (M + H). |
| 53 | (R)-3-(2,5-difluoro-4-(methylsulfonyl)phenylamino)-1'-(5-ethylpyrimidin-2-yl)-[1,4'-bipiperidin]-2-one | (apci) m/z = 494.2 (M + H). |
| 54 | (S)-3-(2,5-difluoro-4-(methylsulfonyl)phenylamino)-1'-(5-(trifluoromethyl)pyridin-2-yl)-[1,4'-bipiperidin]-2-one | (apci) m/z = 533.2 (M + H). |
| 55 | (S)-1'-(5-ethylpyrimidin-2-yl)-3-(4-(methylsulfonyl)-2-(trifluoromethyl)phenylamino)-[1,4'-bipiperidin]-2-one | (apci) m/z = 526.2 (M + H). |

| Ex. # | Structure | Name | Mass spectrum |
|---|---|---|---|
| 56 | 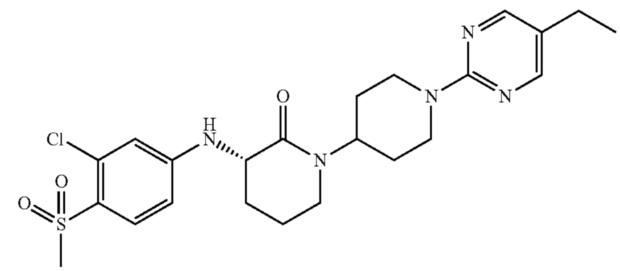 | (S)-3-(3-chloro-4-(methylsulfonyl)phenylamino)-1'-(5-ethylpyrimidin-2-yl)-[1,4'-bipiperidin]-2-one | (apci) m/z = 492.2 (M + H). |

Example 57

(S)-1'-(5-chloropyrazin-2-yl)-3-(2,5-difluoro-4-(methylsulfonyl)phenylamino)-[1,4'-bipiperidin]-2-one

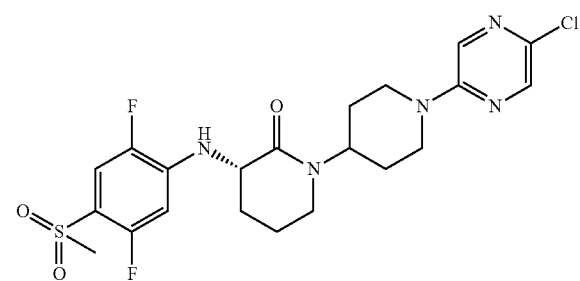 [SMILES: CS(=O)(=O)c1cc(F)c(N[C@H]2CCCN(C3CCN(c4ccc(Cl)nn4)CC3)C2=O)cc1F]

Step A: (S)-5-amino-2-(benzyloxycarbonylamino)pentanoic acid (50 g, 188 mmol) was dissolved in THF (800 mL) and water (100 mL). Tert-butyl 4-oxopiperidine-1-carboxylate (37 g, 188 mmol) was added and the reaction was stirred for 1 hour. The reaction was cooled to 0° C. and sodium cyanoborohydride (12 g, 188 mmol) was added and the reaction stirred at ambient temperature overnight. The reaction was concentrated to provide (S)-2-(benzyloxycarbonylamino)-5-(1-(tert-butoxycarbonyl)piperidin-4-ylamino)pentanoic acid, which was used directly in the next step.

Step B: Crude (S)-2-(benzyloxycarbonylamino)-5-(1-(tert-butoxycarbonyl)piperidin-4-ylamino)pentanoic acid (84 g, 187 mmol) was dissolved in DMF (600 mL), and cooled to 0° C. N1-((ethylimino)methylene)-N3,N3-dimethylpropane-1,3-diamine hydrochloride (35.8 g, 187 mmol) and N-ethyl-N-isopropylpropan-2-amine (32.5 mL, 187 mmol) were added and the reaction stirred at ambient temperature overnight. The reaction was concentrated and dissolved in EtOAc (1000 mL), washed with 1N HCl, saturated aqueous NaHCO₃ and brine, dried over Na₂SO₄, filtered and concentrated. The residue was purified over silica gel (50% EtOAc in hexanes) to afford (S)-tert-butyl 3-(benzyloxycarbonylamino)-2-oxo-1,4'-bipiperidine-1'-carboxylate (49 g, 114 mmol, 60.8% yield) as white solid.

Step C: (S)-tert-butyl 3-(benzyloxycarbonylamino)-2-oxo-1,4'-bipiperidine-1'-carboxylate (20.9 g, 48.4 mmol) was dissolved in methanol (250 mL). 10% Pd/C (500 mg) was added and stirred under balloon pressure hydrogen overnight. The reaction was filtered through celite and concentrated. The residue was purified over silica gel (50-100% EtOAc in hexanes followed by 5% ammoniated methanol in CH₂Cl₂) to afford (S)-tert-butyl 3-amino-2-oxo-1,4'-bipiperidine-1'-carboxylate (11.2 g, 37.7 mmol, 77.8% yield) as white solid.

Step D: (S)-tert-butyl 3-amino-2-oxo-1,4'-bipiperidine-1'-carboxylate (4.0 g, 13 mmol), 1,2,4-trifluoro-5-(methylsulfonyl)benzene (Preparation C, 4.2 g, 20 mmol) and Na₂CO₃ (2.9 g, 27 mmol) were dissolved in DMF (30 mL) and heated at 130° C. overnight. The reaction was concentrated and purified over silica gel (25-75% EtOAc in hexanes) to afford (S)-tert-butyl 3-(2,5-difluoro-4-(methylsulfonyl)phenylamino)-2-oxo-1,4'-bipiperidine-1'-carboxylate (4.6 g, 9.4 mmol, 70% yield) as yellow solid.

Step E: (S)-tert-butyl 3-(2,5-difluoro-4-(methylsulfonyl)phenylamino)-2-oxo-1,4'-bipiperidine-1'-carboxylate (4.6 g, 9.4 mmol) was dissolved in CH₂Cl₂ (100 mL) and methanol (10 mL). 4N HCl in dioxane (24 mL, 94 mmol) was added and the reaction stirred at ambient temperature overnight. The reaction was concentrated to provide (S)-3-(2,5-difluoro-4-(methylsulfonyl)phenylamino)-1,4'-bipiperidin-2-one hydrochloride, which was used directly in the next step without purification.

Step F: To a solution of 3-(2,5-difluoro-4-(methylsulfonyl)phenoxy)-1,4'-bipiperidin-2-one HCl salt (500 mg, 1.2 mmol) and DIEA (0.52 mL, 3.0 mmol) in DMF (6 mL) was added 2,5-dichloropyrazine (264 mg, 1.8 mmol). The reaction was heated at 120° C. overnight. The reaction was cooled to ambient temperature and partitioned between water and ethyl acetate. The organic layer was separated and the aqueous washed with EtOAc. The combined organic layers were dried with MgSO₄ and concentrated. The crude residue was purified by column chromatography to give (S)-1'-(5-chloropyrazin-2-yl)-3-(2,5-difluoro-4-(methylsulfonyl)phenylamino)-1,4'-bipiperidin-2-one (0.37 g, 0.73 mmol, 62%) Mass spectrum (apci) m/z=500.2 (M+H).

Example 58

(S)-1'-(5-ethylpyrimidin-2-yl)-3-(2-fluoro-5-methyl-4-(methylsulfonyl)phenylamino)-[1,4'-bipiperidin]-2-one

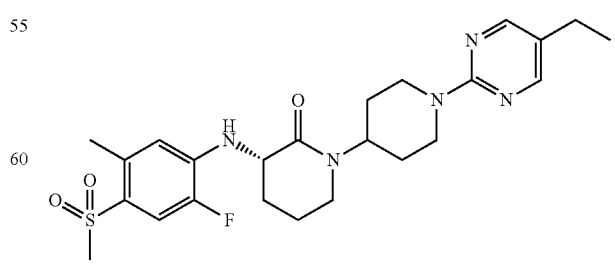

Step A: A flask was charged with (S)-tert-butyl 3-(benzyloxycarbonylamino)-2-oxo-1,4'-bipiperidine-1'-carboxylate (Example 39, Steps A-B; 5.0 g, 12 mmol), CH$_2$Cl$_2$ (50 mL), and methanol (5 mL), 4N HCl in dioxane (29 mL, 116 mmol) was added and the reaction stirred overnight. The reaction was concentrated to afford crude (S)-benzyl 2-oxo-1,4'-bipiperidin-3-ylcarbamate hydrochloride (4.3 g, 100%) which was taken forward without further purification.

Step B: A flask was charged with (S)-benzyl 2-oxo-1,4'-bipiperidin-3-ylcarbamate hydrochloride (4.1 g, 11 mmol), 2-chloro-5-ethylpyrimidine (1.7 g, 12 mmol), DIEA (3.9 mL, 22 mmol), and DMF (30 mL). The reaction was heated to 100° C. overnight. The reaction was cooled to ambient temperature, concentrated and purified over silica gel (25-75% EtOAc in hexanes) to afford (S)-benzyl 1'-(5-ethylpyrimidin-2-yl)-2-oxo-1,4'-bipiperidin-3-ylcarbamate (2.8 g, 57% yield).

Step C: (S)-benzyl 1'-(5-ethylpyrimidin-2-yl)-2-oxo-1,4'-bipiperidin-3-ylcarbamate (275 mg, 0.629 mmol) was dissolved in 1:1 EtOH/EtOAc and 10% Pd/C (50 mg) was added, and the reaction was stirred under a balloon pressure of hydrogen for 1.5 hours. The reaction was filtered through celite and concentrated to afford crude (S)-3-amino-1'-(5-ethylpyrimidin-2-yl)-1,4'-bipiperidin-2-one (220 mg, 0.725 mmol, 115% yield) as an oil.

Step D: (S)-3-amino-1'-(5-ethylpyrimidin-2-yl)-1,4'-bipiperidin-2-one (220 mg, 0.725 mmol) was dissolved in toluene (7 mL) and BINAP (45.2 mg, 0.0725 mmol), 1-bromo-2-fluoro-5-methyl-4-(methylsulfonyl)benzene (Preparation B; 291 mg, 1.09 mmol) and Cs$_2$CO$_3$ (284 mg, 0.870 mmol) were added. The reaction was bubbled through with nitrogen for 5 minutes. Pd$_2$dba$_3$ (33.2 mg, 0.0363 mmol) was added and the reaction heated to 90° C. overnight. The reaction was cooled to ambient temperature, filtered and concentrated. The residue was purified over silica gel (90% EtOAc in hexanes) to afford a mixture. The mixture was then purified on reverse phase chromatography (15 to 95% ACN in water) to afford (S)-1'-(5-ethylpyrimidin-2-yl)-3-(2-fluoro-5-methyl-4-(methylsulfonyl)phenylamino)-1,4'-bipiperidin-2-one (178 mg, 0.364 mmol, 50.1% yield) as a white solid. Mass spectrum (apci) m/z=490.3 (M+H).

Example 59

(S)-3-(2,5-difluoro-4-(methylsulfonyl)phenylamino)-1'-(5-ethylpyrazin-2-yl)-[1,4'-bipiperidin]-2-one

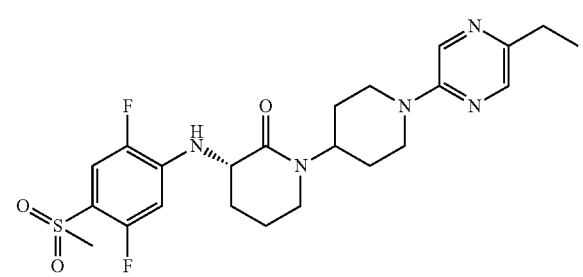 [SMILES: CCc1cnc(N2CCC(N3CCC[C@H](Nc4cc(F)c(S(C)(=O)=O)cc4F)C3=O)CC2)cn1]

(S)-1'-(5-chloropyrazin-2-yl)-3-(2,5-difluoro-4-(methylsulfonyl)phenylamino)-1,4'-bipiperidin-2-one (prepared according to the procedure of Example 45) (50 mg, 0.100 mmol) was dissolved in THF (2 mL) and K$_2$CO$_3$ (41.5 mg, 0.300 mmol) and PdCl$_2$(dppf)*CH$_2$Cl$_2$ (8.17 mg, 0.0100 mmol) were added and purged with nitrogen. 1M diethylzinc (110 µL, 0.110 mmol) was added and the reaction was heated to 60° C. for 3 hours. The reaction was cooled to ambient temperature, concentrated in vacuo and purified over silica gel (70 to 90% EtOAc in hexanes) to afford (S)-3-(2,5-difluoro-4-(methylsulfonyl)phenylamino)-1'-(5-ethylpyrazin-2-yl)-1,4'-bipiperidin-2-one (26.8 mg, 0.0543 mmol, 54.3% yield) as a tan solid. Mass spectrum (apci) m/z=494.3 (M+H).

Example 60

(S)-3-(2,5-difluoro-4-(methylsulfonyl)phenylamino)-1'-(5-isopropylpyrazin-2-yl)-[1,4'-bipiperidin]-2-one

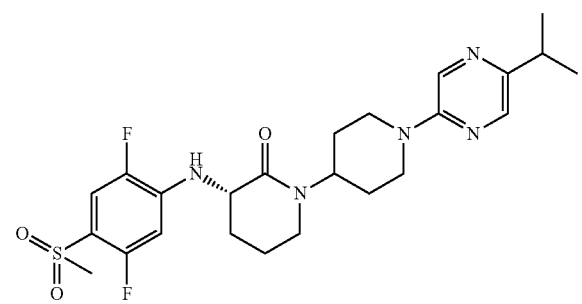 [SMILES: CC(C)c1cnc(N2CCC(N3CCC[C@H](Nc4cc(F)c(S(C)(=O)=O)cc4F)C3=O)CC2)cn1]

Prepared from (S)-1'-(5-chloropyrazin-2-yl)-3-(2,5-difluoro-4-(methylsulfonyl)phenylamino)-1,4'-bipiperidin-2-one (Example 57) according to the method of Example 59. Mass spectrum (apci) m/z=508.3 (M+H).

Example 61

(S)-3-(2,5-difluoro-4-(methylsulfonyl)phenylamino)-1'-(5-o-tolylpyrazin-2-yl)-[1,4'-bipiperidin]-2-one

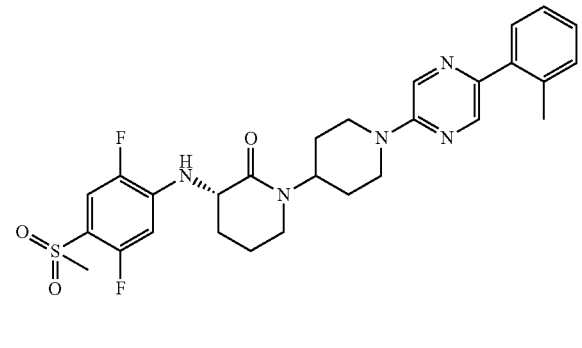 [SMILES: Cc1ccccc1-c1cnc(N2CCC(N3CCC[C@H](Nc4cc(F)c(S(C)(=O)=O)cc4F)C3=O)CC2)cn1]

(S)-1'-(5-chloropyrazin-2-yl)-3-(2,5-difluoro-4-(methylsulfonyl)phenylamino)-1,4'-bipiperidin-2-one (Example 57; 50 mg, 0.100 mmol) was dissolved in dioxane (2 mL) and purged with nitrogen. 2M Na$_2$CO$_3$ (200 µL, 0.400 mmol), o-tolylboronic acid (20.4 mg, 0.150 mmol) and Pd(PPh$_3$)$_4$ (11.6 mg, 0.0100 mmol) were added and the reaction heated to 95° C. under nitrogen for 8 hours. The reaction was allowed to cool overnight, filtered and concentrated. The residue was purified over silica gel twice (80% EtOAc in hexanes) to afford (S)-3-(2,5-difluoro-4-(methylsulfonyl)phenylamino)-

1'-(5-O—  tolylpyrazin-2-yl)-1,4'-bipiperidin-2-one (42.6 mg, 0.0767 mmol, 76.7% yield) as a tan solid. Mass spectrum (apci) m/z=556.3 (M+H).

Example 62

1'-(5-ethylpyrimidin-2-yl)-3-(2-fluoro-4-(methylsulfonyl)phenylamino)-[1,4'-bipiperidin]-2-one

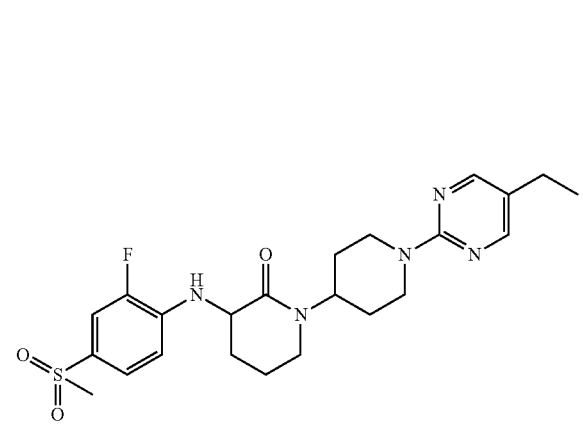 [SMILES: CCc1cnc(N2CCC(N3CCCC(Nc4ccc(S(C)(=O)=O)cc4F)C3=O)CC2)nc1]

Step A: (S)-tert-Butyl 3-amino-2-oxo-1,4'-bipiperidine-1'-carboxylate (Example 39, Steps A-C, 5.0 g, 17 mmol), 2,2'-bis(diphenylphosphino)-1,1'-binaphthyl (1.0 g, 1.7 mmol), 1-bromo-2-fluoro-4-(methylsulfonyl)benzene (6.4 g, 25 mmol) and NaOtBu (1.9 g, 20 mmol) were dissolved in degassed toluene (100 mL). $Pd_2 dba_3$ (0.77 g, 0.84 mmol) was added and the reaction heated in an 80° C. oil bath for 5 hours. The reaction was concentrated and purified over silica gel (50-100% EtOAc in hexanes followed by 5% ammoniated methanol in $CH_2Cl_2$) to afford tert-butyl 3-(2-fluoro-4-(methylsulfonyl)phenylamino)-2-oxo-1,4'-bipiperidine-1'-carboxylate (8.4 g, 18 mmol, 106% yield) as yellow solid.

Step B: Tert-butyl 3-(2-fluoro-4-(methylsulfonyl)phenylamino)-2-oxo-1,4'-bipiperidine-1'-carboxylate (7.9 g, 17 mmol) was dissolved in $CH_2Cl_2$ (100 mL) and MeOH (10 mL). 4N HCl in dioxane (29 mL, 118 mmol) was added and the reaction stirred at ambient temperature for 3 hours. The reaction was concentrated and purified over silica gel (50-100% EtOAc in hexanes followed by 5% ammoniated methanol in $CH_2Cl_2$) to afford 3-(2-fluoro-4-(methylsulfonyl)phenylamino)-1,4'-bipiperidin-2-one (6.2 g, 17 mmol, 100% yield) as yellow solid.

Step C: 3-(2-Fluoro-4-(methylsulfonyl)phenylamino)-1,4'-bipiperidin-2-one (0.300 g, 0.812 mmol), 2-chloro-5-ethylpyrimidine (0.116 g, 0.812 mmol) and DIEA (0.210 g, 1.62 mmol) were dissolved in DMF (5 mL) and heated at 100° C. overnight. The reaction was concentrated and purified over silica gel (50-100% EtOAc in hexanes) to provide 1'-(5-ethylpyrimidin-2-yl)-3-(2-fluoro-4-(methylsulfonyl)phenylamino)-1,4'-bipiperidin-2-one (0.198 g, 0.416 mmol, 51.3% yield) as white solid. Mass spectrum (apci) m/z=476.2 (M+H).

Example 63

1'-(5-ethylpyrimidin-2-yl)-3-(3-fluoro-4-(methylsulfonyl)phenylamino)-[1,4'-bipiperidin]-2-one

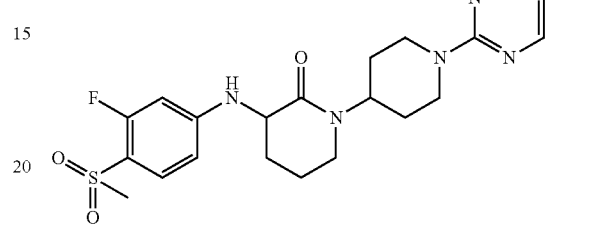

Prepared according to the method of Example 62. Mass spectrum (apci) m/z=476.2 (M+H).

Example 64

(3S)-3-(2,5-difluoro-4-(methylsulfonyl)phenylamino)-1'-(5-(1-hydroxyethyl)pyrimidin-2-yl)-[1,4'-bipiperidin]-2-one

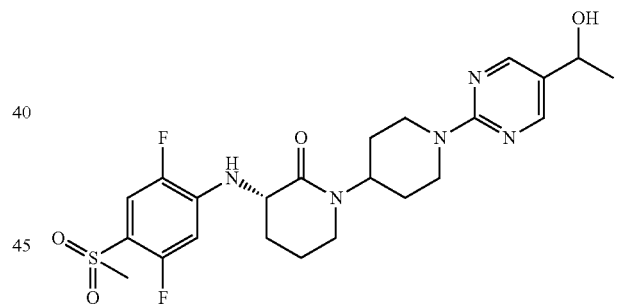

Step A: (S)-3-(2,5-difluoro-4-(methylsulfonyl)phenylamino)-1,4'-bipiperidin-2-one hydrochloride (Example 45, Steps A-E; 0.4 g, 0.944 mmol), 1-(6-chloropyridin-3-yl)ethanone (0.220 g, 1.42 mmol) and DIEA (0.523 mL, 2.83 mmol) were dissolved in DMF (5 mL) and heated at 100° C. overnight. The reaction was concentrated and purified over silica gel (50-100% EtOAc in hexanes) to afford (S)-1'-(5-acetylpyridin-2-yl)-3-(2,5-difluoro-4-(methylsulfonyl)phenylamino)-1,4'-bipiperidin-2-one (0.328 g, 0.647 mmol, 68.6% yield) as yellow solid.

Step B: (S)-1'-(5-acetylpyridin-2-yl)-3-(2,5-difluoro-4-(methylsulfonyl)phenylamino)-1,4'-bipiperidin-2-one (0.310 g, 0.612 mmol) was dissolved in methanol (5 mL). $NaBH_4$ (0.0232 g, 0.612 mmol) was added slowly and stirred at ambient temperature for 1 hour. The reaction was concentrated and purified over silica gel (50-100% EtOAc in hexanes) to afford (3S)-3-(2,5-difluoro-4-(methylsulfonyl)phenylamino)-1'-(5-(1-hydroxyethyl)pyridin-2-yl)-1,4'- bipiperidin-2-one (0.265 g, 0.469 mmol, 76.6% yield). Mass spectrum (apci) m/z=509.2 (M+H).

Example 65

(S)-1'-(5-chloropyrazin-2-yl)-3-(2,6-difluoro-4-(methylsulfonyl)phenylamino)-[1,4'-bipiperidin]-2-one

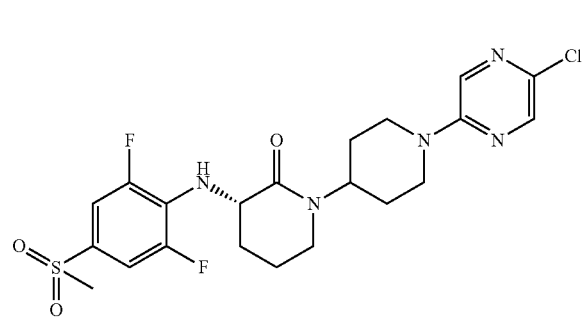 [SMILES: CS(=O)(=O)c1cc(F)c(N[C@H]2CCCN(C3CCN(c4cnc(Cl)cn4)CC3)C2=O)c(F)c1]

Step A: A flask was charged with (S)-tert-butyl 3-amino-2-oxo-1,4'-bipiperidine-1'-carboxylate (Example 39, Steps A-C, 1.2 g, 4.0 mmol), 1,2,3-trifluoro-5-(methylsulfonyl)benzene (Table 1, compound 1; 1.3 g, 6.1 mmol), Na$_2$CO$_3$ (0.86 g, 8.1 mmol), and DMF (10 mL). The reaction mixture was stirred at 130° C. overnight. The organic solvents were removed under reduced pressure. The reaction mixture was purified using silica gel column chromatography with 50% ethyl acetate in hexanes to provide (S)-tert-butyl 3-(2,6-difluoro-4-(methylsulfonyl)phenylamino)-2-oxo-1,4'-bipiperidine-1'-carboxylate (1.2 g, 2.5 mmol, 61% yield) as light yellow solid. Mass spectrum (apci) m/z=488.2 (M+H).

Step B: A flask was charged with (S)-tert-butyl 3-(2,6-difluoro-4-(methylsulfonyl)phenylamino)-2-oxo-1,4'-bipiperidine-1'-carboxylate (1.2 g, 2.46 mmol), HCl (6.15 mL, 24.6 mmol), DCM (25 mL), and methanol (1 mL). The reaction mixture was stirred at ambient temperature overnight. The organic solvents were removed under reduced pressure to afford (S)-3-(2,6-difluoro-4-(methylsulfonyl)phenylamino)-[1,4'-bipiperidin]-2-one hydrochloride (0.986 g, 94.5% yield). Mass spectrum (apci) m/z=388.2 (M+H).

Step C: A flask was charged with (S)-3-(2,6-difluoro-4-(methylsulfonyl)phenylamino)-1,4'-bipiperidin-2-one hydrochloride (0.250 g, 0.590 mmol), 2,5-dichloropyrazine (0.105 g, 0.708 mmol), Hunig's base (0.309 mL, 1.77 mmol), and DMF (5 mL). The reaction mixture was stirred at 100° C. overnight. The organic solvents were removed under reduced pressure. The residue was purified using silica gel column chromatography eluting with ethyl acetate to provide (S)-1'-(5-chloropyrazin-2-yl)-3-(2,6-difluoro-4-(methylsulfonyl)phenylamino)-[1,4'-bipiperidin]-2-one (0.102 g, 0.204 mmol, 34.6% yield) as light yellow solid. Mass spectrum (apci) m/z=500.1 (M+H).

Example 66

3-(6-(1H-tetrazol-1-yl)pyridin-3-yloxy)-1-(1-(5-ethylpyrimidin-2-yl)piperidin-4-yl)pyrrolidin-2-one

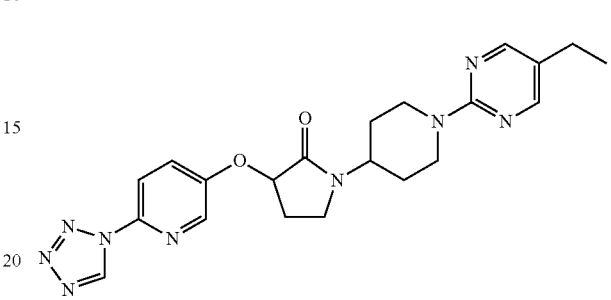

Step A: To a solution of sodium azide (2.90 g, 44 mmol) in triethylorthoformate (8 mL) and AcOH (50 mL) was added 6-amino-pyridine-3-ol (3.5 g, 32 mmol). The reaction was heated to 100° C. for 6 hours and then cooled to ambient temperature and allowed to stir overnight. The solids were filtered, washed with EtOAc and dried in vacuo to give the 6-(1H-tetrazol-1-yl)pyridin-3-ol (4.20 g, 81%) as a beige solid.

Step B: To a solution of tert-butyl 4(3-bromo-2-oxopyrrolidine-1-yl)piperidine-1-carboxylate (1.04 g, 3.0 mmol) and 6-(1H-tetrazol-1-yl)pyridin-3-ol (538 mg, 3.3 mmol) in DMSO (10 mL) was added K$_2$CO$_3$ (1.04 g, 7.5 mmol). The reaction was heated to 70° C. for 12 hours. The reaction was cooled to ambient temperature and diluted with water (10 mL) and EtOAc (20 mL). The organic layer was separated and the aqueous layer extracted with EtOAc. The combined organic layers were dried with MgSO$_4$ and concentrated in vacuo. The material was purified by silica gel chromatography eluting with 3:1 hexanes/EtOAc to yield tert-butyl 4-(3-(6-(1H-tetrazol-1-yl)pyridine-3-yloxy-2-oxopyrrolidin-1-yl)piperidine-1-carboxylate (978 mg, 76%) as an off white solid.

Step C: To a solution of tert-butyl 4-(3-(6-(1H-tetrazol-1-yl)pyridine-3-yloxy-2-oxopyrrolidin-1-yl)piperidine-1-carboxylate (978 mg, 2.28 mmol) in DCM (10 mL) was added excess 4N HCl in dioxane (3 mL). The reaction was stirred for 4 hours at which point it was concentrated in vacuo to yield 3-(6-(1H-tetrazol-1-yl)pyridin-3-yloxy)-1-(piperidin-4-yl)pyrrolidin-2-one bishydrochloride salt (796 mg, 87%) as an off white solid, which was used without any further purification.

Step D: To a solution of 3-(6-(1H-tetrazol-1-yl)pyridin-3-yloxy)-1-(piperidin-4-yl)pyrrolidin-2-one bishydrochloride salt (101 mg, 0.25 mmol) and DIEA (0.30 mL, 1.75 mmol) in DMF (3 mL) was added 2-chloro-5-ethylpyrimidine (71 mg, 0.50 mmol). The reaction was heated at 100° C. for 6 hours. The reaction was cooled to ambient temperature and diluted by the addition of water (5 mL). The aqueous layer was extracted with EtOAc (3×10 mL). The combined organic layers were washed with brine, dried over MgSO$_4$, filtered and concentrated in vacuo. The material was purified by silica gel chromatography eluting with a gradient of 2:1 hexanes/EtOAc up to 100% EtOAc to yield 3-(6-(1H-tetrazol-1-yl)pyridin-3-yloxy)-1-(1-(5-ethylpyrimidin-2-yl)piperidin-4- yl)pyrrolidin-2-one (52 mg, 48%) as an off white solid. Mass spectrum (apci) m/z=383.2 (M-N₃CH+3H).

The following compounds were also prepared according to the method of Example 66.

| Ex. # | Structure | Name | Mass spectrum |
|---|---|---|---|
| 67 | 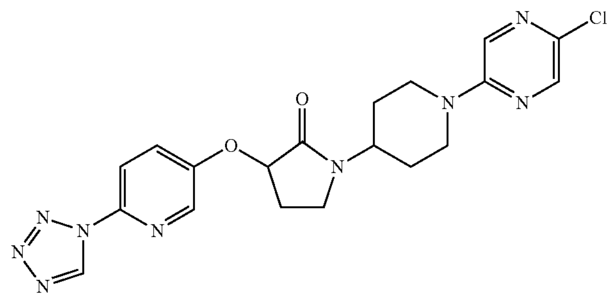 [SMILES: O=C1C(Oc2ccc(-n3cnnn3)nc2)CCN1C1CCN(c2cnc(Cl)cn2)CC1] | 3-(6-(1H-tetrazol-1-yl)pyridin-3-yloxy)-1-(1-(5-chloropyrazin-2-yl)piperidin-4-yl)pyrrolidin-2-one | (apci) m/z = 389.2 (M − N₃CH + 3H). |
| 68 | 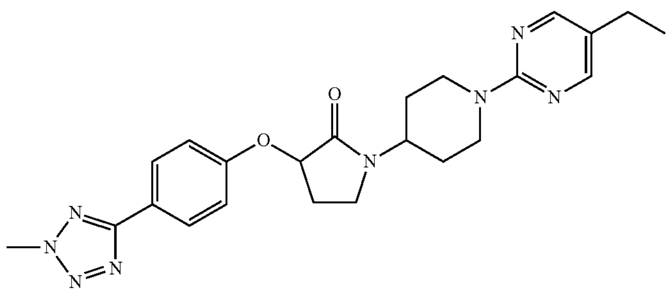 [SMILES: CCc1cnc(N2CCC(N3CCC(Oc4ccc(-c5nnn(C)n5)cc4)C3=O)CC2)nc1] | 1-(1-(5-ethylpyrimidin-2-yl)piperidin-4-yl)-3-(4-(2-methyl-2H-tetrazol-5-yl)phenoxy)pyrrolidin-2-one | (apci) m/z = 449.2 (M + H). |

Example 69

(S)-1-(1-(5-chloropyrazin-2-yl)piperidin-4-yl)-3-(6-(methylsulfonyl)pyridin-3-yloxy)pyrrolidin-2-one

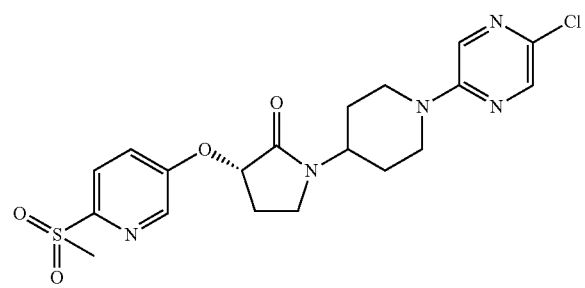 [SMILES: CS(=O)(=O)c1ccc(O[C@H]2CCN(C3CCN(c4cnc(Cl)cn4)CC3)C2=O)cn1]

Step A: To a suspension of (R)-3-hydroxydihydrofuran-2(3H)-one (500 mg, 4.9 mmol) in toluene (15 mL) was added triphenylphosphine (1.54 g, 5.88 mmol) and 6-bromopyridin-3-ol (1.02 g, 5.88 mmol). The solution was cooled to 0° C. and degassed with nitrogen bubble for 10 minutes. Di-tert-butyl diazene-1,2-dicarboxylate was dissolved in toluene (5 mL) and added over a 5 minute period. The reaction was allowed to stir for 12 hours with warming to ambient temperature. The reaction was concentrated in vacuo and the resulting material purified by silica gel chromatography eluting 1:1 hexanes/EtOAc to yield (S)-3-(6-bromopyridin-3-yloxy)dihydrofuran-2(3H)-one (1.0 g, 79%) as an off white solid.

Step B: To a solution of tert-butyl 4-aminopiperidine-1-carboxylate (0.93 g, 4.65 mmol) in DCM (15 mL) was added dropwise 2M trimethylaluminum (2.8 mL, 5.7 mmol) in toluene. The resulting mixture was stirred for 15 minutes, and (S)-3-(6-bromopyridin-3-yloxy)dihydrofuran-2(3H)-one (1.0 g, 3.87 mmol) in DCM (10 mL) was added slowly over 5 minutes and the reaction stirred at ambient temperature for 2 hours. The reaction was slowly quenched by the addition of 5% tartaric acid (5 mL), saturated NaHCO₃ (5 mL) and DCM (10 mL). The organic layer was separated, dried over MgSO₄, filtered and concentrated in vacuo to provide (S)-tert-butyl 4-(2-(6-bromopyridin-3-yloxy)-4-hydroxybutanamido)piperidine-1-carboxylate. The crude material was taken on without a further purification.

Step C: A solution of (S)-tert-butyl 4-(2-(6-bromopyridin-3-yloxy)-4-hydroxybutanamido)piperidine-1-carboxylate (1.30 g, 2.84 mmol) and tributylphosphine (689 mg, 3.40 mmol) in toluene (15 mL) was degassed with nitrogen bubble for 10 minutes and then cooled to 0° C. Di-tert-butyl diazene-1,2-dicarboxylate (784 mg, 3.4 mmol) dissolved in toluene (5 mL) and was added over a 5 minute period. The reaction was allowed to warm to ambient temperature over 12 hours. The reaction was concentrated in vacuo and purified by silica gel chromatography eluting with 1:1 hexanes/EtOAc to yield (S)-tert-butyl-4-(3-(6-bromopyridin-3-yloxy)-2-oxopyrrolidin-1-yl)piperidine-1-carboxylate (934 mg, 75%) as an off-white solid.

Step D: A solution of (S)-tert-butyl-4-(3-(6-bromopyridin-3-yloxy)-2-oxopyrrolidin-1-yl)piperidine-1-carboxylate (315 mg, 0.714 mmol) in degassed DMSO (5 mL) was added sodium ethanesulfinate (117 mg, 1.15 mmol), trans-cyclohexane-1,2-diamine (33 mg, 0.286 mmol) and Cu(I) triflate benzene complex (54 mg, 0.107 mmol). The reaction was heated to 110° C. for 12 hours at which point the reaction was cooled to ambient temperature and partitioned between water (5 mL) and EtOAc (10 mL). The organic layer was separated and the aqueous layer extracted with EtOAc (2×5 mL). The combined organic layers were dried over MgSO₄, filtered and concentrated in vacuo. The resulting material was purified by silica gel chromatography eluting with 1:1 hexanes/EtOAc to yield (S)-tert-butyl-4-(3-(6-(methylsulfonyl)pyridine-3-yloxy)-2-oxopyrrolidin-1-yl)piperidine-1-carboxylate (315 mg, 94%) as a white solid.

Step E: To a solution of (S)-tert-butyl-4-(3-(6-(methylsulfonyl)pyridine-3-yloxy)-2-oxopyrrolidin-1-yl)piperidine-1-carboxylate (259 mg, 0.59 mmol) in DCM (10 mL) was added excess 4N HCl in dioxane (3 mL). The reaction was stirred for 4 hours, then concentrated in vacuo to yield (S)-3-(6-(methylsulfonyl)pyridin-3-yloxy)-1-(piperidin-4-yl)pyrrolidin-2-one hydrochloride salt (210 mg, 94%) as an off white solid, which was used without any further purification.

Step F: To a solution of (S)-3-(6-(methylsulfonyl)pyridin-3-yloxy)-1-(piperidin-4-yl)pyrrolidin-2-one hydrochloride salt (100 mg, 0.26 mmol) and DIEA (0.324 mL, 1.86 mmol) in DMF (3 mL) was added 2-chloro-5-ethylpyrimidine (76 mg, 0.532 mmol). The reaction was heated to 100° C. for 4 hours at which point the reaction was poured into water (10 mL) and EtOAc (10 mL). The organic layer was separated and the aqueous layer extracted with EtOAc (2×5 mL). The combined organic layers were dried with MgSO$_4$ and concentrated in vacuo. The resulting material was purified by silica gel chromatography eluting with 1:1 hexanes/EtOAc to EtOAc to yield (S)-1-(1-(5-ethylpyrimidin-2-yl)piperidine-4-yl)-3-(6-(methylsulfonyl)pyridine-3-yloxy)pyrrolidin-2-one (35 mg, 30%) as an off white solid. Mass spectrum (apci) m/z=452.2 (M+H).

Example 70

(S)-1-(1-(5-ethylpyrimidin-2-yl)piperidin-4-yl)-3-(4-(5-methyl-1H-tetrazol-1-yl)phenoxy)pyrrolidin-2-one

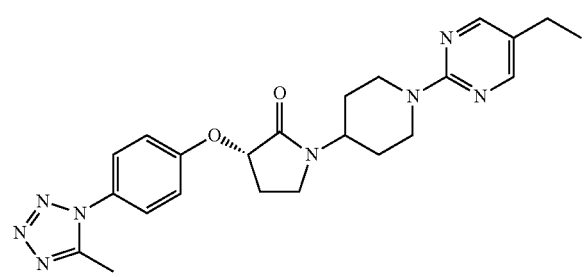 [SMILES: CCc1cnc(N2CCC(N3CC[C@H](Oc4ccc(-n5nnnc5C)cc4)C3=O)CC2)nc1]

Step A: To a solution of (R)-tert-butyl-4-(3-(methylsulfonyloxy)-2-oxopyrrolidin-1-yl)piperidine-1-carboxylate (Preparation D; 1.03 g, 2.84 mmol) and 4-(5-methyl-1H-tetrazol-1-yl)phenol (500 mg, 2.84 mmol) in DMSO (10 mL) was added K$_2$CO$_3$ (1.18 g, 8.51 mmol). The reaction was heated to 70° C. for 12 hours and then diluted with water (10 mL) and EtOAc (10 mL). The organic layer was separated and the aqueous layer extracted with EtOAc (2×15 mL). The combined organic layers were dried with MgSO$_4$ and concentrated in vacuo. The material was purified by silica gel chromatography eluting with 1:1 hexanes/EtOAc to EtOAc to yield tert-butyl-4-(3-(4-(5-methyl-1H-tetrazol-1-yl)phenoxy)-2-oxopyrrolidin-1-yl)piperidine-1-carboxylate (621 mg, 52%) as an off white solid.

Step B: To a solution of tert-butyl-4-(3-(4-(5-methyl-1H-tetrazol-1-yl)phenoxy)-2-oxopyrrolidin-1-yl)piperidine-1-carboxylate (621 mg, 1.4 mmol) in DCM (15 mL) was added excess 4N HCl in dioxane (5 mL). The reaction was stirred for 4 hours and then concentrated in vacuo to yield (S)-3-(4-(5-methyl-1H-tetrazol-1-yl)phenoxy)-1-(piperidin-4-yl)pyrrolidin-2-one hydrochloride salt (501 mg, 94%) as an off white solid, which was used without any further purification.

Step C: To a solution of (S)-3-(4-(5-methyl-1H-tetrazol-1-yl)phenoxy)-1-(piperidin-4-yl)pyrrolidin-2-one hydrochloride salt (128 mg, 0.198 mmol) and DIEA (0.173 mL, 0.99 mmol) in DMF (3 mL) was added 2-chloro-5-ethylpyrimidine (85 mg, 0.532 mmol). The reaction was heated to 100° C. for 4 hours and then poured into water (10 mL) and EtOAc (10 mL). The organic layer was separated and the aqueous layer extracted with EtOAc (2×5 mL). The combined organic layers were dried with MgSO$_4$ and concentrated in vacuo. The resulting material was purified by silica gel chromatography eluting with a gradient of 1:1 hexanes/EtOAc to EtOAc to yield (S)-1-(1-(5-ethylpyrimidin-2-yl)piperidin-4-yl)-3-(4-(5-methyl-1H-tetrazol-1-yl)phenoxy)pyrrolidin-2-one (15 mg, 17%) as an off white solid. Mass spectrum (apci) m/z=449.2 (M+H).

Example 71

(S)-1-(1-(5-chloropyrazin-2-yl)piperidin-4-yl)-3-(2-fluoro-4-(5-methyl-1,3,4-oxadiazol-2-yl)phenoxy)pyrrolidin-2-one

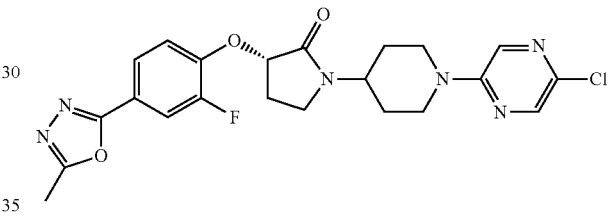

Step A: (R)-tert-butyl 4-(3-(methylsulfonyloxy)-2-oxopyrrolidin-1-yl)piperidine-1-carboxylate (Preparation D; 1.0 g, 2.8 mmol) was dissolved in dry DMSO (15 mL) and methyl 3-fluoro-4-hydroxybenzoate (0.56 g, 3.3 mmol) and K$_2$CO$_3$ (0.46 g, 3.3 mmol) were added and the reaction heated to 70° C. under nitrogen. The reaction became purple and then black. The reaction was cooled to ambient temperature after 3 hours, stirred at ambient temperature overnight, partitioned between water and EtOAc, extracted with EtOAc, washed with brine, dried over Na$_2$SO$_4$, filtered and concentrated. The residue was purified over silica gel (60% EtOAc in hexanes) to afford (S)-tert-butyl 4-(3-(2-fluoro-4-(methoxycarbonyl)phenoxy)-2-oxopyrrolidin-1-yl)piperidine-1-carboxylate (1.2 g, 2.7 mmol, 100% yield) as a white solid.

Step B: (S)-tert-butyl 4-(3-(2-fluoro-4-(methoxycarbonyl)phenoxy)-2-oxopyrrolidin-1-yl)piperidine-1-carboxylate (900 mg, 2.06 mmol) was dissolved in THF (20 mL) and potassium trimethylsilanolate (529 mg, 4.12 mmol) was added and the reaction stirred at ambient temperature. After 2 hours, additional potassium trimethylsilanolate (529 mg, 4.12 mmol) was added and stirred for 3 hours, the reaction was poured into 1N HCl and extracted with EtOAc, dried over Na$_2$SO$_4$, filtered and concentrated to afford (S)-4-(1-(1-(tert-butoxycarbonyl)piperidin-4-yl)-2-oxopyrrolidin-3-yloxy)-3-fluorobenzoic acid (834 mg, 1.97 mmol, 95.7% yield) as a white solid.

Step C: (S)-4-(1-(1-(tert-butoxycarbonyl)piperidin-4-yl)-2-oxopyrrolidin-3-yloxy)-3-fluorobenzoic acid (834 mg, 1.97 mmol), acetohydrazide (219 mg, 2.96 mmol) and N-ethyl-N-isopropylpropan-2-amine (1375 μL, 7.90 mmol) were dissolved in CH$_2$Cl$_2$ (20 mL) and bis(2-oxooxazolidin- 3-yl)phosphinic chloride (2010 mg, 7.90 mmol) was added and stirred at ambient temperature for 3 hours. The reaction was poured into water, extracted with EtOAc, washed with brine, dried over $Na_2SO_4$, filtered and concentrated to afford crude (S)-tert-butyl 4-(3-(4-(2-acetylhydrazinecarbonyl)-2-fluorophenoxy)-2-oxopyrrolidin-1-yl)piperidine-1-carboxylate (960 mg, 2.01 mmol, 102% yield) which was taken forward without further purification.

Step D: (S)-tert-butyl 4-(3-(4-(2-acetylhydrazinecarbonyl)-2-fluorophenoxy)-2-oxopyrrolidin-1-yl)piperidine-1-carboxylate (960 mg, 2.01 mmol) was dissolved in $CH_2Cl_2$ (20 mL) and cooled to 0° C. under nitrogen. 1H-imidazole (341 mg, 5.02 mmol), triphenylphosphine (1158 mg, 4.41 mmol) and perbromomethane (1464 mg, 4.41 mmol) were added and the reaction was allowed to warm to ambient temperature overnight. The reaction was partitioned between water and EtOAc, dried over $Na_2SO_4$, filtered and concentrated. The residue was purified over silica gel (100% EtOAc) to afford (S)-tert-butyl 4-(3-(2-fluoro-4-(5-methyl-1,3,4-oxadiazol-2-yl)phenoxy)-2-oxopyrrolidin-1-yl)piperidine-1-carboxylate (680 mg, 1.48 mmol, 73.6% yield).

Step E: (S)-tert-butyl 4-(3-(2-fluoro-4-(5-methyl-1,3,4-oxadiazol-2-yl)phenoxy)-2-oxopyrrolidin-1-yl)piperidine-1-carboxylate (680 mg, 1.48 mmol) was dissolved in $CH_2Cl_2$ (10 mL) and TFA (4 mL) was added and stirred at ambient temperature for 1 hour and then concentrated in vacuo to afford crude (S)-3-(2-fluoro-4-(5-methyl-1,3,4-oxadiazol-2-yl)phenoxy)-1-(piperidin-4-yl)pyrrolidin-2-one 2,2,2-trifluoroacetate as an oil which was taken forward without further purification.

Step F: (S)-3-(2-fluoro-4-(5-methyl-1,3,4-oxadiazol-2-yl)phenoxy)-1-(piperidin-4-yl)pyrrolidin-2-one 2,2,2-trifluoroacetate (150 mg, 0.316 mmol) was dissolved in DMSO (3 mL) and 2,5-dichloropyrazine (70.7 mg, 0.474 mmol) and N-ethyl-N-isopropylpropan-2-amine (138 µL, 0.790 mmol) were added and the reaction heated to 100° C. overnight. The reaction was cooled and diluted with water, extracted with EtOAc, washed with brine, dried over $Na_2SO_4$, filtered and concentrated. The residue was purified twice over silica gel (100% EtOAc) to afford (S)-1-(1-(5-chloropyrazin-2-yl)piperidin-4-yl)-3-(2-fluoro-4-(5-methyl-1,3,4-oxadiazol-2-yl)phenoxy)pyrrolidin-2-one (15.2 mg, 0.0321 mmol, 10.2% yield) as a red solid. Mass spectrum (apci) m/z=473.1 (M+H).

Example 72

(S)-1-(1-(5-chloropyrimidin-2-yl)piperidin-4-yl)-3-(2-fluoro-4-(5-methyl-1,3,4-oxadiazol-2-yl)Phenoxy)pyrrolidin-2-one

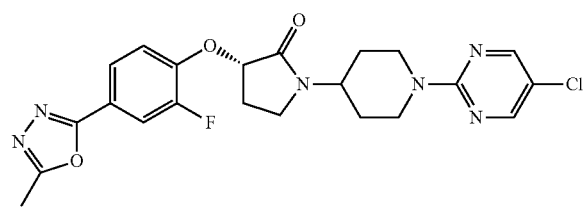 [SMILES: Cc1nnc(-c2ccc(O[C@H]3CCN(C4CCN(c5ncc(Cl)cn5)CC4)C3=O)c(F)c2)o1]

Prepared according to the procedure of Example 71. Mass spectrum (apci) m/z=473.1 (M+H).

Example 73

(S)-1'-(5-ethylpyrimidin-2-yl)-3-((6-fluoro-1,1-dioxido-2,3-dihydrobenzo[b]thiophen-5-yl)amino)-[1,4'-bipiperidin]-2-one

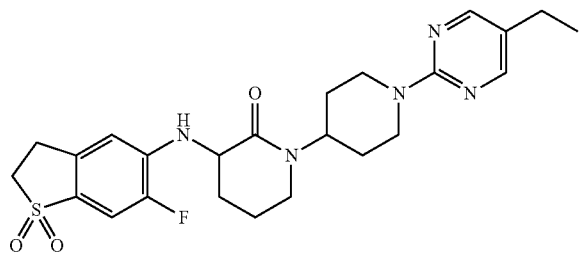 [SMILES: CCc1cnc(N2CCC(N3CCCC(Nc4cc5c(cc4F)S(=O)(=O)CC5)C3=O)CC2)nc1]

Step A: A flask was charged with (S)-tert-butyl 3-(benzyloxycarbonylamino)-2-oxo-1,4'-bipiperidine-1'-carboxylate (Example 39, Steps A-B; 10.0 g, 23.2 mmol), DCM (60 mL), methanol (6 mL), HCl (57.9 mL, 232 mmol) and the reaction was stirred overnight. The organic solvents were removed under reduced pressure to provide (S)-benzyl 2-oxo-[1,4'-bipiperidin]-3-ylcarbamate hydrochloride (8.52 g, 100% yield). Mass spectrum (apci) m/z=332.2 (M+H).

Step B: (S)-Benzyl 2-oxo-[1,4'-bipiperidin]-3-ylcarbamate hydrochloride (8.52 g, 23.2 mmol), Hunig's base (12.0 g, 92.6 mmol), and 2-chloro-5-ethylpyrimidine (6.60 g, 46.3 mmol) were combined and charged with DMF (120 mL). The solution was stirred at 100° C. for 2 hours. The solution was cooled and diluted with water, extracted with EtOAc, dried, and concentrated. Flash chromatography gave 3.66 g of crude material which was impure. This crude material was purified on a Horizon reverse phase HPLC system to give (S)-benzyl-1'-(5-ethylpyrimidin-2-yl)-2-oxo-[1,4'-bipiperidin]-3-ylcarbamate (2.17 g, 4.96 mmol, 21.4% yield) as a white solid. Mass spectrum (apci) m/z=438.2 (M+H).

Step C: (S)-benzyl-1'-(5-ethylpyrimidin-2-yl)-2-oxo-[1,4'-bipiperidin]-3-ylcarbamate (2.176 g, 4.973 mmol) was dissolved in MeOH and 10% Pd/C (1 g) was added and stirred in a parr shaker at 30 psi overnight. The reaction was filtered through GF/F paper and separated on the reverse phase Horizon system to give (S)-3-amino-1'-(5-ethylpyrimidin-2-yl)-[1,4'-bipiperidin]-2-one (0.280 g, 0.9229 mmol, 18.56% yield) as a clear oil. Mass spectrum (apci) m/z=304.2 (M+H).

Step D: To a suspension of 1-bromo-2,4-difluorobenzene (11.7 mL, 104 mmol) in 96 mL concentrated $H_2SO_4$ at 0° C. was added concentrated $HNO_3$ (85 mL) dropwise maintaining the temperature below 20° C. The resulting mixture was stirred for 10 minutes at 0° C., then poured into a mixture of ether and ice water with vigorous stirring. The aqueous phase was separated and extracted with ether. The combined organic phases were washed with aqueous $NaHCO_3$ and brine, dried and concentrated. The residue was purified using silica gel column chromatography with 15% acetone in hexanes to provide 1-bromo-2,4-difluoro-5-nitrobenzene (23 g, 96.6 mmol, 93.3% yield) as yellow oil.

Step E: A mixture of $Pd_2dba_3$ (1.924 g, 2.101 mmol), and $PPh_3$ (2.204 g, 8.404 mmol) was dissolved in toluene (200 mL), degassed and then stirred 10 minutes at ambient temperature. A solution of 1-bromo-2,4-difluoro-5-nitrobenzene (10 g, 42.02 mmol) in toluene (200 mL) was then added to the above solution, followed by tributyl(vinyl)stannane (18.40 mL, 63.03 mmol). The mixture was refluxed for 2 hours, then poured into a mixture of aqueous NaF and diethyl ether. The residue was purified using silica gel column chromatography with 5-10-20% acetone in hexanes to provide 1,5-difluoro-2-nitro-4-vinylbenzene (6 g, 32.41 mmol, 77.13% yield) as yellow oil.

Step F: A flask was charged with triphenylsilanethiol (12 g, 41 mmol), and 1,5-difluoro-2-nitro-4-vinylbenzene (5 g, 27 mmol) in benzene (80 mL), and then (E)-2,2'-(diazene-1,2-diyl)bis(2-methylpropanenitrile) (1.3 g, 8.1 mmol) was added. The mixture was refluxed for 1 hour, then cooled to ambient temperature and concentrated. The residue was purified using silica gel column chromatography with 10% acetone in hexanes to provide (2,4-difluoro-5-nitrophenethylthio)triphenylsilane (13 g, 27 mmol, 100% yield).

Step G: A solution of (2,4-difluoro-5-nitrophenethylthio)triphenylsilane (12 g, 25 mmol) in ethanol (400 mL), and THF (800 mL) was cooled in an ice bath, and then treated with potassium hydroxide (4.7 mL, 38 mmol). The resulting mixture was stirred for 15 minutes, then quenched with 6N HCl (5 mL), and concentrated. The residue was partitioned between 1M HCl and diethyl ether. The organic layer was dried and concentrated to provide 6-fluoro-5-nitro-2,3-dihydrobenzo[b]thiophene (2.1 g, 11 mmol, 42% yield) as yellow solid.

Step H: To a solution of 6-fluoro-5-nitro-2,3-dihydrobenzo[b]thiophene (2.1 g, 10.5 mmol) in ethanol (80 mL), THF (40 mL), and aqueous NH₄Cl (20 mL) was added Fe (O) (3.53 g, 63.3 mmol). The mixture was refluxed for 2 hours, then filtered through celite and washed with ethyl acetate. The residue was purified using silica gel column chromatography with 50% ethyl acetate in hexanes to provide 6-fluoro-2,3-dihydrobenzo[b]thiophen-5-amine (1.68 g, 94.2% yield).

Step I:

A flask was charged with 6-fluoro-2,3-dihydrobenzo[b]thiophen-5-amine (1.17 g, 6.91 mmol), copper(II) bromide (1.85 g, 8.30 mmol), and acetonitrile (100 mL). To the above mixture was added tert-butyl nitrite (1.37 mL, 10.4 mmol) under nitrogen and then heated to 65° C. for 30 minutes. The organic solvent was removed under reduced pressure. DCM was added to the residue and was washed with brine. The organic layers were dried over sodium sulphate, concentrated, and the residue was purified using silica gel column chromatography with hexanes followed by 25% ethyl acetate in hexanes to provide 5-bromo-6-fluoro-2,3-dihydrobenzo[b]thiophene (0.4 g, 24.8% yield).

Step J: A flask was charged with 5-bromo-6-fluoro-2,3-dihydrobenzo[b]thiophene (0.4 g, 1.7 mmol), 3-chlorobenzoperoxoic acid (1.48 g, 8.58 mmol), and acetic acid (10 mL). The reaction was stirred at ambient temperature for 3 days. The organic solvent was removed under reduced pressure and saturated sodium bicarbonate solution was added. The solution was extracted with ethyl acetate and DCM. The organic layers were combined, dried, and concentrated. The residue was purified using silica gel column chromatography with 25%-50% ethyl acetate in hexanes followed by 2N NaOH wash to provide 5-bromo-6-fluoro-2,3-dihydrobenzo[b]thiophene 1,1-dioxide (0.45 g, 1.70 mmol, 98.9% yield) as white solid.

Step K: A flask was charged with 5-bromo-6-fluoro-2,3-dihydrobenzo[b]thiophene 1,1-dioxide (0.070 g, 0.26 mmol), (S)-3-amino-1'-(5-ethylpyrimidin-2-yl)-[1,4'-bipiperidin]-2-one (Steps A-C, 0.05 g, 0.16 mmol), Pd₂ dba₃ (0.0075 g, 0.0082 mmol), Binap-rac (0.0010 g, 0.0016 mmol), sodium t-butoxide (0.033 g, 0.35 mmol), and degassed toluene (3 mL). The reaction was stirred at 90° C. for 4 hours. The organic solvent was removed under reduced pressure. The residue was purified using silica gel column chromatography with 50-100% ethyl acetate, followed by preparative TLC using 2% methanol in ethyl acetate to provide (S)-1'-(5-ethylpyrimidin-2-yl)-3-((6-fluoro-1,1-dioxido-2,3-dihydrobenzo[b]thiophen-5-yl)amino)-[1,4'-bipiperidin]-2-one (0.025 g, 0.051 mmol, 31% yield) as off white solid. Mass spectrum (apci) m/z=488.3 (M+H).

Example 74

(S)-3-(1H-indazol-5-yloxy)-1-(1-(5-chloropyrazin-2-yl)piperidin-4-yl)pyrrolidin-2-one

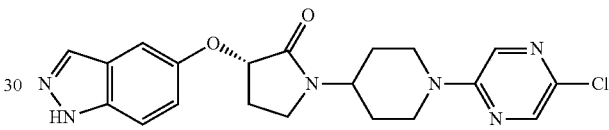

Step A: A flask was charged with 1H-indazol-5-ol (0.89 g, 0.66 mmol), (R)-tert-butyl 4-(3-(methylsulfonyloxy)-2-oxopyrrolidin-1-yl)piperidine-1-carboxylate (Preparation D; 0.2 g, 0.55 mmol), K₂CO₃ (0.092 g, 0.66 mmol), and DMSO (4 mL). The reaction was stirred at 130° C. overnight. Added water and extracted with ethyl acetate. The organic layers were combined, dried, filtered and concentrated. The residue was purified using silica gel column chromatography with 50-100% ethyl acetate in hexanes to provide (S)-tert-butyl 4-(3-(1H-indazol-5-yloxy)-2-oxopyrrolidin-1-yl)piperidine-1-carboxylate (0.198 g, 90% yield).

Step B: A flask was charged with (S)-tert-butyl 4-(3-(1H-indazol-5-yloxy)-2-oxopyrrolidin-1-yl)piperidine-1-carboxylate (0.300 g, 0.749 mmol), HCl in dioxane (1.87 mL, 7.49 mmol), DCM (10 mL), and methanol (1 mL). The reaction was stirred at ambient temperature for 2 hours. The organic solvents were removed under reduced pressure. The residue was purified using silica gel column chromatography using 50-100% ethyl acetate in hexanes, then 5% ammoniated methanol in DCM, and then 30% ammoniated methanol in ethyl acetate to provide (S)-3-(1H-indazol-5-yloxy)-1-(piperidin-4-yl)pyrrolidin-2-one (0.225 g, 100% yield).

Step C: A flask was charged with (S)-3-(1H-indazol-5-yloxy)-1-(piperidin-4-yl)pyrrolidin-2-one (0.120 g, 0.400 mmol), 2,5-dichloropyrazine (0.0655 g, 0.439 mmol), DIEA (d 0.742) (0.0696 mL, 0.400 mmol), and DMF (3 mL). The reaction was stirred at 100° C. overnight. The organic solvents were removed under reduced pressure. The residue was purified using preparative TLC with 10% methanol in ethyl acetate to provide (S)-3-(1H-indazol-5-yloxy)-1-(1-(5-chloropyrazin-2-yl)piperidin-4-yl)pyrrolidin-2-one (0.0047 g, 0.0114 mmol, 2.85% yield). Mass spectrum (apci) m/z=413.2 (M+H).

Example 75

(S)-3-(3-chloro-5-(trifluoromethyl)pyridin-2-ylamino)-1'-(5-chloropyrazin-2-yl)-[1,4'-bipiperidin]-2-one

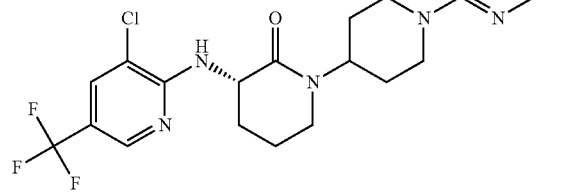

Step A: A flask was charged with 2,3-dichloro-5-(trifluoromethyl)pyridine (0.2919 mL, 2.093 mmol), (S)-tert-butyl 3-amino-2-oxo-1,4'-bipiperidine-1'-carboxylate (0.415 g, 1.395 mmol), $Na_2CO_3$ (0.2958 g, 2.791 mmol), and DMSO (5 mL). The reaction mixture was stirred at 130° C. overnight. Water was added and the reaction mixture was extracted with ethyl acetate. The organic layers were combined, dried, filtered, concentrated. The residue was purified using silica gel column chromatography with 30% ethyl acetate in hexanes to provide (S)-tert-butyl 3-(3-chloro-5-(trifluoromethyl)pyridin-2-ylamino)-2-oxo-1,4'-bipiperidine-1'-carboxylate (0.51 g, 76.63% yield). Mass spectrum (apci) m/z=377.2 (M+H-Boc).

Step B: A flask was charged with (S)-tert-butyl 3-(3-chloro-5-(trifluoromethyl)pyridin-2-ylamino)-2-oxo-1,4'-bipiperidine-1'-carboxylate (0.51 g, 1.1 mmol), DCM (10 mL), methanol (1 mL), and HCl (2.7 mL, 11 mmol) (in dioxane). The reaction mixture was stirred at ambient temperature overnight. The organic solvents were removed under reduced pressure to provide (S)-3-(3-chloro-5-(trifluoromethyl)pyridin-2-ylamino)-[1,4'-bipiperidin]-2-one hydrochloride (0.40 g, 91% yield). Mass spectrum (apci) m/z=377.2 (M+H).

Step D: A flask was charged with (S)-3-(3-chloro-5-(trifluoromethyl)pyridin-2-ylamino)-1,4'-bipiperidin-2-one hydrochloride (0.075 g, 0.18 mmol), 2,5-dichloropyrazine (0.030 g, 0.20 mmol), Hunig's base (0.095 mL, 0.54 mmol), and DMF (3 mL). The reaction was stirred at 100° C. overnight. The organic solvents were removed under reduced pressure. The residue was purified using silica gel column chromatography with 50-100% ethyl acetate in hexanes to provide (S)-3-(3-chloro-5-(trifluoromethyl)pyridin-2-ylamino)-1'-(5-chloropyrazin-2-yl)-[1,4'-bipiperidin]-2-one (0.037 g, 0.076 mmol, 42% yield) as yellow solid. Mass spectrum (apci) m/z=489.2 (M+H).

Example 76

(S)-3-(3-chloro-5-(trifluoromethyl)pyridin-2-ylamino)-1'-(5-ethylpyrimidin-2-yl)-[1,4'-bipiperidin]-2-one

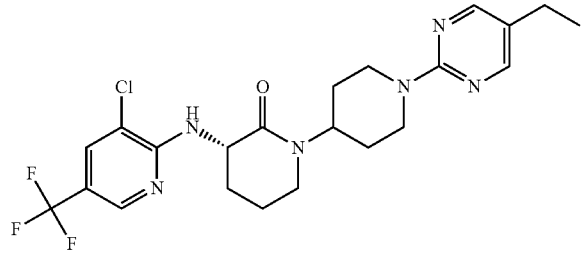 [SMILES: CCc1cnc(N2CCC(N3CCC[C@H](Nc4ncc(C(F)(F)F)cc4Cl)C3=O)CC2)nc1]

Prepared according to the procedure of Example 75. Mass spectrum (apci) m/z=489.2 (M+H).

Example 77

1'-(5-ethyl-3-methylpyridin-2-yl)-3-(2-fluoro-4-(methylsulfonyl)phenylamino)-[1,4'-bipiperidin]-2-one

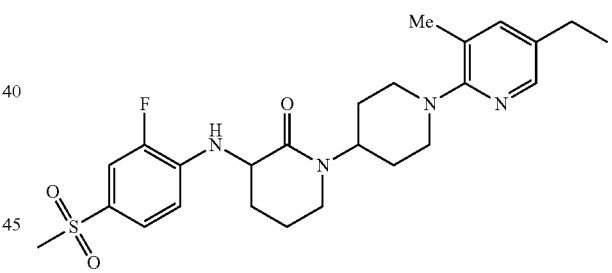

To a solution of (S)-3-(2-fluoro-4-(methylsulfonyl)phenylamino)-1,4'-bipiperidin-2-one hydrochloride (prepared according to the method of Example 45) (0.100 g, 0.246 mmol) in 5 mL MeOH was added KOH (0.014 g, 0.246 mmol). The mixture was stirred for 30 minutes at ambient temperature, cooled in an ice bath and filtered through a syringe filter, and the filtrate was concentrated and used directly. To the obtained residue was added 2-chloro-5-ethyl-3-methylpyridine (0.0460 g, 0.296 mmol), toluene (5 mL), $Pd(OAc)_2$ (0.00830 g, 0.0370 mmol), 2'-(dicyclohexylphosphino)-N,N-dimethylbiphenyl-2-amine (also known as "DavePhos") (0.0291 g, 0.0739 mmol), and NaOtBu (0.0710 g, 0.739 mmol) and the mixture was heated at 110° C. overnight. The reaction was cooled to ambient temperature, diluted with water and extracted with $CH_2Cl_2$. The organic layers were combined, dried over $Na_2SO_4$ and purified on silica gel eluting with 100% EtOAc to give 1'-(5-ethyl-3-methylpyridin-2-yl)-3-(2-fluoro-4-(methylsulfonyl)phenylamino)-1,4'-bipiperidin-2-one (0.080 g, 66.5% yield) as a white solid. Mass spectrum (apci) m/z=489.3 (M+H).

Example 78

(S)-3-((2,5-difluoro-4-(methylsulfonyl)phenyl)(methyl)amino)-1'-(5-ethylpyrimidin-2-yl)-[1,4'-bipiperidin]-2-one

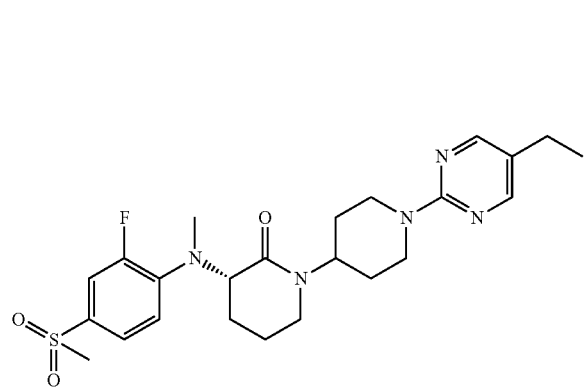

Step A: (S)-benzyl 1'-(5-ethylpyrimidin-2-yl)-2-oxo-1,4'-bipiperidin-3-ylcarbamate (Example 58, Steps A-B; 0.250 g, 0.571 mmol) was dissolved in DMF (5 mL). 60% NaH (0.0274 g, 0.686 mmol) was added and stirred for 5 minutes. Iodomethane (0.071 mL, 1.1 mmol) was added and stirred at ambient temperature overnight. The reaction was concentrated and purified over silica gel (25-100% EtOAc in hexanes) to afford (S)-benzyl 1'-(5-ethylpyrimidin-2-yl)-2-oxo-1,4'-bipiperidin-3-yl(methyl)carbamate (100 mg, 0.22 mmol, 39% yield).

Step B: (S)-benzyl 1'-(5-ethylpyrimidin-2-yl)-2-oxo-1,4'-bipiperidin-3-yl(methyl)carbamate (0.100 g, 0.22 mmol) was dissolved in methanol (5 mL). 10% Pd/C (10 mg) was added and the reaction mixture was stirred under hydrogen balloon pressure overnight. The reaction was filtered and concentrated and purified over silica gel (100% EtOAc) to afford (S)-1'-(5-ethylpyrimidin-2-yl)-3-(methylamino)-1,4'-bipiperidin-2-one (40 mg, 0.13 mmol, 57% yield).

Step C: (S)-1'-(5-ethylpyrimidin-2-yl)-3-(methylamino)-1,4'-bipiperidin-2-one (0.040 g, 0.13 mmol), 1,2,4-trifluoro-5-(methylsulfonyl)benzene (Preparation C, 0.053 g, 0.25 mmol) and Na$_2$CO$_3$ (0.040 g, 0.38 mmol) were dissolved in DMF (1 mL) and heated at 130° C. overnight. The reaction was concentrated and the residue was purified using preparative TLC (100% EtOAc) to afford (S)-3-((2,5-difluoro-4-(methylsulfonyl)phenyl)(methyl)amino)-1'-(5-ethylpyrimidin-2-yl)-1,4'-bipiperidin-2-one (0.018 g, 0.035 mmol, 28% yield) as yellow solid. Mass spectrum (apci) m/z=508.3 (M+H).

Example 79

(S)-1-(1-(5-ethylpyrimidin-2-yl)piperidin-4-O-3-(2-fluoro-4-(methylsulfonyl)phenylamino)azepan-2-one hydrochloride

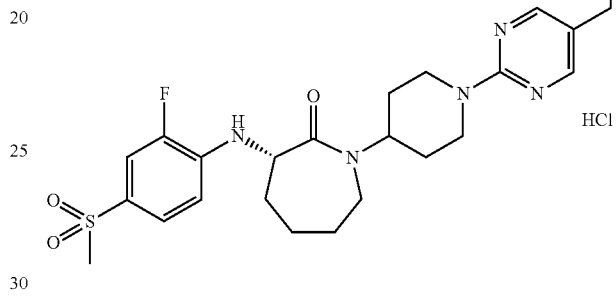

Step A: (S)-tert-butyl 4-(3-(2-fluoro-4-(methylsulfonyl)phenylamino)-2-oxoazepan-1-yl)piperidine-1-carboxylate was synthesized following the procedure for Example 45, substituting (S)-6-amino-2-(benzyloxycarbonylamino)hexanoic acid for (S)-2-(benzyloxycarbonylamino)-5-(1-(tert-butoxycarbonyl)piperidin-4-ylamino)pentanoic acid in Step A.

Step B: A solution of (S)-tert-butyl 4-(3-(2-fluoro-4-(methylsulfonyl)phenylamino)-2-oxoazepan-1-yl)piperidine-1-carboxylate (1.0 g, 2.0 mmol) in 50% TFA/DCM was stirred a ambient temperature for 1 hour. The mixture was concentrated in vacuo. 1N NaOH (100 mL) was added to the residue and the product was extracted into DCM (2×50 mL). The combined organic layers were dried over MgSO$_4$, filtered and concentrated in vacuo to give (S)-3-(2-fluoro-4-(methylsulfonyl)phenylamino)-1-(piperidin-4-yl)azepan-2-one (0.4 g, 1 mmol, 50%).

Step C: To a solution of (S)-3-(2-fluoro-4-(methylsulfonyl)phenylamino)-1-(piperidin-4-yl)azepan-2-one (0.10 g, 0.26 mmol) and DIEA (0.14 mL, 0.78 mmol) in DMF (2 mL) was added 2-chloro-5-ethylpyrimidine (0.11 g, 0.78 mmol). This mixture stirred at 100° C. for 4 hours in a sealed tube. The mixture was poured into water (50 mL) and extracted into ethyl acetate (3×50 mL). The combined organic layers were washed with brine, dried over MgSO$_4$, filtered and concentrated in vacuo. The material was purified by column chromatography using 50% to 100% hexanes/ethyl acetate. The HCl salt was made using HCl in ether to give (S)-1-(1-(5-ethylpyrimidin-2-yl)piperidin-4-yl)-3-(2-fluoro-4-(methylsulfonyl)phenylamino)azepan-2-one hydrochloride (0.055 g, 0.11 mmol, 43%) (APCI POS 490 M+H).

The following compounds were also prepared according to the procedure of Example 79.

| Ex. # | Structure | Name | Mass Spectrum |
|---|---|---|---|
| 80 | 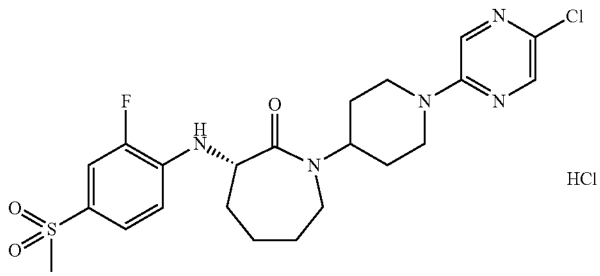 [SMILES: CS(=O)(=O)c1ccc(N[C@H]2CCCCN(C3CCN(c4cnc(Cl)cn4)CC3)C2=O)c(F)c1 ; Cl] | (S)-1-(1-(5-chloropyrazin-2-yl)piperidin-4-yl)-3-(2-fluoro-4-(methylsulfonyl) phenylamino)azepan-2-one hydrochloride | (apci) m/z = 496 (M + H). |
| 81 | 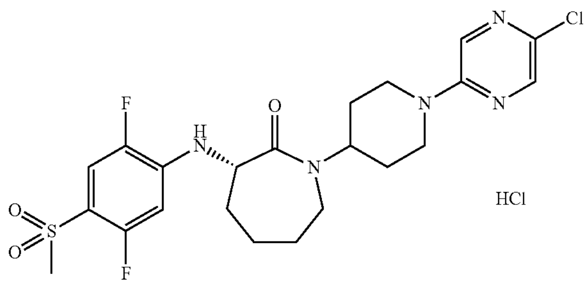 [SMILES: CS(=O)(=O)c1cc(F)c(N[C@H]2CCCCN(C3CCN(c4cnc(Cl)cn4)CC3)C2=O)cc1F ; Cl] | (S)-1-(1-(5-chloropyrazin-2-yl)piperidin-4-yl)-3-(2,5-difluoro-4-(methylsulfonyl) phenylamino)azepan-2-one hydrochloride | (apci) m/z = 514 (M + H). |
| 82 | 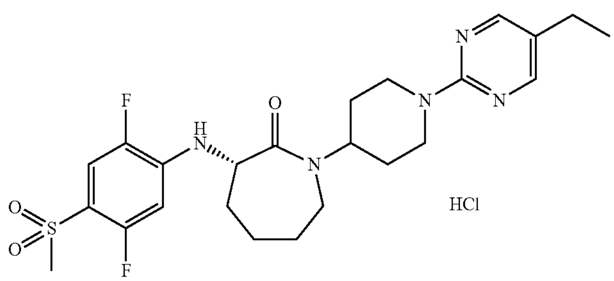 [SMILES: CCc1cnc(N2CCC(N3CCCC[C@H](Nc4cc(F)c(S(C)(=O)=O)cc4F)C3=O)CC2)nc1 ; Cl] | (S)-3-(2,5-difluoro-4-(methylsulfonyl)phenylamino)-1-(1-(5-ethylpyrimidin-2-yl)piperidin-4-yl)azepan-2-one hydrochloride | (apci) m/z = 508 (M + H). |
| 83 | 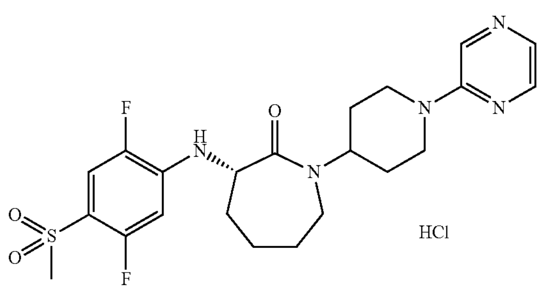 [SMILES: CS(=O)(=O)c1cc(F)c(N[C@H]2CCCCN(C3CCN(c4cnccn4)CC3)C2=O)cc1F ; Cl] | (S)-3-(2,5-difluoro-4-(methylsulfonyl)phenylamino)-1-(1-(pyrazin-2-yl)piperidin-4-yl)azepan-2-one hydrochloride | (apci) m/z = 480 (M + H). |
| 84 | 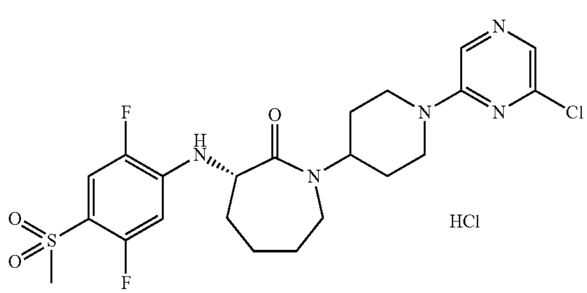 [SMILES: CS(=O)(=O)c1cc(F)c(N[C@H]2CCCCN(C3CCN(c4cncc(Cl)n4)CC3)C2=O)cc1F ; Cl] | (S)-1-(1-(6-chloropyrazin-2-yl)piperidin-4-yl)-3-(2,5-difluoro-4-(methylsulfonyl) phenylamino)azepan-2-one hydrochloride | (apci) m/z = 514 (M + H). |

| Ex. # | Structure | Name | Mass Spectrum |
|---|---|---|---|
| 85 | [structure] | (S)-3-(4-(3-(2,5-difluoro-4-(methylsulfonyl)phenylamino)-2-oxoazepan-1-yl)piperidin-1-yl)pyrazine-2-carbonitrile hydrochloride | (apci) m/z = 505 (M + H). |

Example 86

3-(2,5-difluoro-4-(methylsulfonyl)phenoxy)-1-(1-(5-isopropylpyrimidin-2-yl)piperidin-4-yl)pyrrolidin-2-one

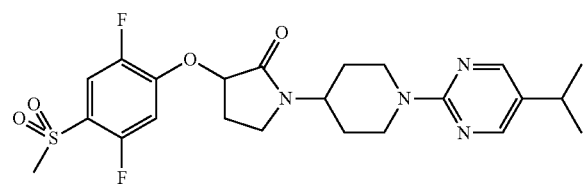 [SMILES: CC(C)c1cnc(N2CCC(N3CCC(Oc4cc(F)c(S(C)(=O)=O)cc4F)C3=O)CC2)nc1]

Step A: To a solution of 3-(2,5-difluoro-4-(methylsulfonyl)phenoxy)-1-(piperidin-4-yl)pyrrolidin-2-one (Table 2, compound 1; 0.35 g, 0.93 mmol) in dimethylformamide (5 mL) was added 5-bromo-2-chloropyrimidine (0.54 g, 2.8 mmol) and N-ethyl-N-isopropylpropan-2-amine (0.36 g, 2.8 mmol) and the reaction heated to 100° C. for 3 hours. The reaction was poured into water and extracted into EtOAc. The combined organic layers were washed with water, brine, dried over MgSO$_4$, filtered and concentrated in vacuo. The solid that formed was triturated with ether to give 1-(1-(5-bromopyrimidin-2-yl)piperidin-4-yl)-3-(2,5-difluoro-4-(methylsulfonyl)phenoxy)pyrrolidin-2-one (0.35 g, 70%).

Step B: To a solution of 1-(1-(5-bromopyrimidin-2-yl)piperidin-4-yl)-3-(2,5-difluoro-4-(methylsulfonyl)phenoxy)pyrrolidin-2-one (0.35 g, 0.659 mmol) in dioxane (10 mL) purged with nitrogen was added 1M diisopropylzinc (2.63 mL, 2.63 mmol) and PdCl$_2$(dppf)*CH$_2$Cl$_2$ (0.0538 g, 0.0659 mmol) and the reaction heated to 100° C. for 3 hours. The reaction was poured into water and extracted into EtOAc. The combined organic layers were washed with water, brine, dried over MgSO$_4$, filtered and concentrated in vacuo. The material was purified over silica gel (100% EtOAc) to yield crude product, which was further purified by reverse phase HPLC (5 to 95% acetonitrile in water with 0.1% TFA) to yield 3-(2,5-difluoro-4-(methylsulfonyl)phenoxy)-1-(1-(5-isopropylpyrimidin-2-yl)piperidin-4-yl)pyrrolidin-2-one trifluoroacetate (0.0664 g, 0.134 mmol, 20.4% yield). Mass Spectrum (apci) m/z=495.3 (M+H).

The following compounds were also prepared according to the method of Example 86, Step A.

| Ex. # | Structure | Name | Mass spectrum |
|---|---|---|---|
| 87 | [structure] | 3-(2,5-difluoro-4-(methylsulfonyl)phenoxy)-1-(1-(5-ethylpyrimidin-2-yl)piperidin-4-yl)pyrrolidin-2-one trifluoroactetate | (apci) m/z = 481.2 (M + H − TFA). |
| 88 | [structure] | 3-(2,5-difluoro-4-(methylsulfonyl)phenoxy)-1-(1-(5-phenylpyrimidin-2-yl)piperidin-4-yl)pyrrolidin-2-one trifluoroactetate | (apci) m/z = 529.2 (M + H). |

| Ex. # | Structure | Name | Mass spectrum |
|---|---|---|---|
| 89 | 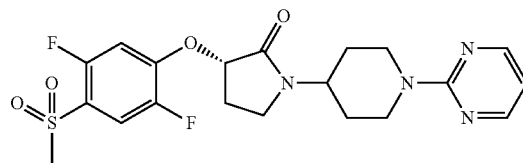 CF₃COOH | (S)-1-(1-(5-ethylpyrazin-2-yl)piperidin-4-yl)-3-(2-fluoro-4-(methylsulfonyl)phenylamino)pyrrolidin-2-one trifluoroactetate | (apci) m/z = 462 (M + H). |

Example 90

(S)-1-(1-(5-bromopyrimidin-2-yl)piperidin-4-yl)-3-(2,5-difluoro-4-(methylsulfonyl)phenoxy)pyrrolidin-2-one

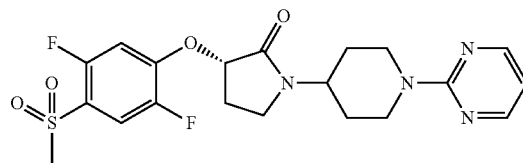

(S)-3-(2,5-difluoro-4-(methylsulfonyl)phenoxy)-1-(piperidin-4-yl)pyrrolidin-2-one (Table 2, compound 1; 432 mg, 1.15 mmol) was dissolved in DMF (6 mL) and N-ethyl-N-isopropylpropan-2-amine (301 µL, 1.73 mmol) and 5-bromo-2-chloropyrimidine (268 mg, 1.38 mmol) were added and the reaction heated to 100° C. under nitrogen for 1.5 hours. The reaction was poured into water and the solids filtered, purified over silica gel (70 to 90% EtOAc in hexanes) to afford (S)-1-(1-(5-bromopyrimidin-2-yl)piperidin-4-yl)-3-(2,5-difluoro-4-(methylsulfonyl)phenoxy)pyrrolidin-2-one (430 mg, 0.809 mmol, 70.1% yield) as a white solid. Mass spectrum (apci) m/z=531.1, 533.1 (M+H).

Example 91

(S)-1-(1-(5-chloropyrazin-2-yl)piperidin-4-yl)-3-(2-fluoro-4-(methylsulfonyl)phenoxy)pyrrolidin-2-one

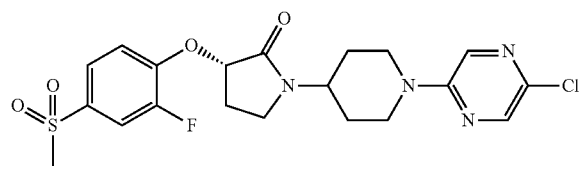 [SMILES: CS(=O)(=O)c1ccc(O[C@H]2CCN(C3CCN(c4cnc(Cl)cn4)CC3)C2=O)c(F)c1]

Prepared according to the method of Example 90. Mass spectrum (apci) m/z=469 (M+H).

Example 92

S-3-(2,5-difluoro-4-(methylsulfonyl)phenoxy)-1-(1-(5-phenylpyrimidin-2-yl)piperidin-4-yl)pyrrolidin-2-one

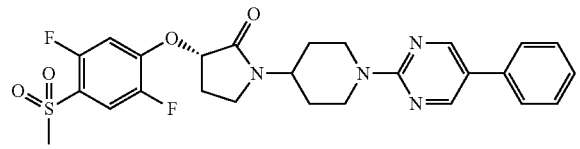 [SMILES: CS(=O)(=O)c1cc(F)c(O[C@H]2CCN(C3CCN(c4ncc(-c5ccccc5)cn4)CC3)C2=O)cc1F]

(S)-1-(1-(5-bromopyrimidin-2-yl)piperidin-4-yl)-3-(2,5-difluoro-4-(methylsulfonyl)phenoxy)pyrrolidin-2-one (Example 90; 80 mg, 0.15 mmol) was dissolved in dioxane (2 mL) and phenylboronic acid (28 mg, 0.23 mmol), 2M Na₂CO₃ (301 µL, 0.60 mmol) and Pd(PPh₃)₄ (17 mg, 0.015 mmol) were added and the reaction heated to 95° C. under nitrogen for 2 hours. The reaction was cooled to ambient temperature and partitioned between water and CH₂Cl₂, and the organic layers were dried over Na₂SO₄, filtered and concentrated. The residue was purified over silica gel (70% EtOAc in hexanes) to afford impure material. The material was then purified on C18 reverse phase chromatography (20 to 95% ACN in water) to afford (S)-3-(2,5-difluoro-4-(methylsulfonyl)phenoxy)-1-(1-(5-phenylpyrimidin-2-yl)piperidin-4-yl)pyrrolidin-2-one (51 mg, 0.096 mmol, 64% yield) as a white solid. Mass spectrum (apci) m/z=529.3 (M+H).

Example 93

(S)-3-(2,5-difluoro-4-(methylsulfonyl)phenoxy)-1-(1-(5-o-tolylpyrimidin-2-yl)piperidin-4-yl)pyrrolidin-2-one

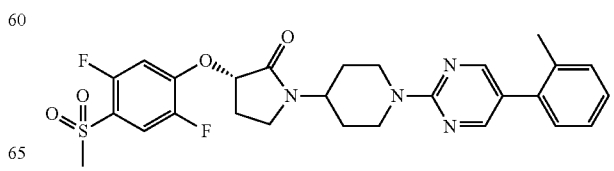

Prepared according to the method of Example 92. Mass spectrum (apci) m/z=543.2 (M+H).

Example 94

(S)-3-(2,5-difluoro-4-(methylsulfonyl)phenoxy)-1-(1-(5-(pyridin-2-yl)pyrimidin-2-yl)piperidin-4-yl)pyrrolidin-2-one

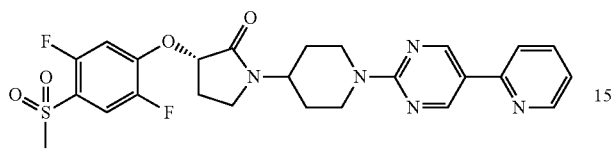

Pyridin-2-yl zinc(II) bromide (0.5M; 632 µL, 0.316 mmol) was added to a nitrogen purged flask. Pd(PPh₃)₄ (17.4 mg, 0.0151 mmol) was added followed by (S)-1-(1-(5-bromopyrimidin-2-yl)piperidin-4-yl)-3-(2,5-difluoro-4-(methylsulfonyl)phenoxy)pyrrolidin-2-one (Example 90; 80 mg, 0.151 mmol) dissolved in THF (1 mL). The reaction was stirred at ambient temperature for 1 hour and 55° C. for 6 hours. Additional zinc reagent and palladium were added and the reaction stirred at 55° C. overnight. The reaction was partitioned between aqueous NH₄Cl and CH₂Cl₂, dried over Na₂SO₄, filtered and concentrated. The residue was purified over silica gel (95% EtOAc in hexanes) to afford (S)-3-(2,5-difluoro-4-(methylsulfonyl)phenoxy)-1-(1-(5-(pyridin-2-yl)pyrimidin-2-yl)piperidin-4-yl)pyrrolidin-2-one (44.9 mg, 0.0848 mmol, 56.3% yield) as a pale yellow solid. Mass spectrum (apci) m/z=530.2 (M+H).

Example 95

(S)-1-(1-(2,5'-bipyrimidin-2'-yl)piperidin-4-yl)-3-(2,5-difluoro-4-(methylsulfonyl)phenoxy)pyrrolidin-2-one

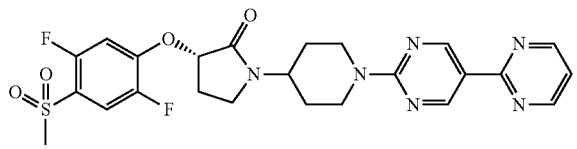 [SMILES: CS(=O)(=O)c1cc(F)c(O[C@H]2CCN(C3CCN(c4ncc(-c5ncccn5)cn4)CC3)C2=O)cc1F]

Step A: A mixture of (S)-1-(1-(5-bromopyrimidin-2-yl)piperidin-4-yl)-3-(2,5-difluoro-4-(methylsulfonyl)phenoxy)pyrrolidin-2-one (Example 90; 170 mg, 0.320 mmol), 4,4,4',4',5,5,5',5'-octamethyl-2,2'-bi(1,3,2-dioxaborolane) (89.4 mg, 0.352 mmol), potassium acetate (94.2 mg, 0.960 mmol) and PdCl₂(dppf)*CH₂Cl₂ (26.1 mg, 0.0320 mmol) in DMF (3 mL) was stirred at 80° C. under nitrogen overnight. The reaction was cooled, filtered through celite and concentrated. The residue was purified over silica gel to afford (S)-3-(2,5-difluoro-4-(methylsulfonyl)phenoxy)-1-(1-(5-(4,4,5,5-tetramethyl-1,3,2-dioxaborolan-2-yl)pyrimidin-2-yl)piperidin-4-yl)pyrrolidin-2-one (173 mg, 0.299 mmol, 93.5% yield).

Step B: (S)-3-(2,5-difluoro-4-(methylsulfonyl)phenoxy)-1-(1-(5-(4,4,5,5-tetramethyl-1,3,2-dioxaborolan-2-yl)pyrimidin-4-yl)pyrrolidin-2-one (173 mg, 0.299 mmol), 2-chloropyrimidine (41.1 mg, 0.359 mmol) and 2M Na₂CO₃ (748 µL, 1.50 mmol) were dissolved in dioxane (3 mL) and purged with nitrogen. Pd(PPh₃)₄ (34.6 mg, 0.0299 mmol) was added and the reaction was heated to 80° C. for 3 hours. The reaction was cooled to ambient temperature, partitioned between water and CH₂Cl₂, extracted twice, dried over Na₂SO₄, filtered and concentrated. The residue was purified over silica gel (eluting with 90 to 100% EtOAc in hexanes) to afford (S)-1-(1-(2,5'-bipyrimidin-2'-yl)piperidin-4-yl)-3-(2,5-difluoro-4-(methylsulfonyl)phenoxy)pyrrolidin-2-one (76 mg, 0.143 mmol, 47.9% yield) as a white solid. Mass spectrum (apci) m/z=531.2 (M+H).

Example 96

(S)-1-(1-(5-ethylpyrimidin-2-yl)piperidin-4-yl)-3-(2-fluoro-5-methyl-4-(methylsulfonyl)phenoxy)pyrrolidin-2-one

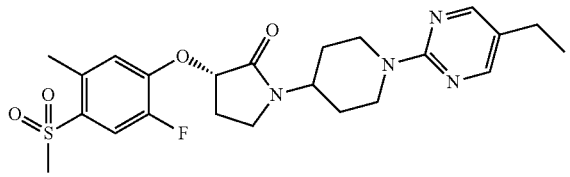 [SMILES: CCc1cnc(N2CCC(N3CC[C@H](Oc4cc(C)c(S(C)(=O)=O)cc4F)C3=O)CC2)nc1]

Step A: 2-Fluoro-5-methylphenol (5.0 g, 40 mmol) was dissolved in chloroform (200 mL). Tetrabutylammonium tribromide (19 g, 40 mmol) was added and the reaction stirred at ambient temperature for 30 minutes. The reaction was concentrated and purified over silica gel (20% EtOAc in hexanes) to afford 4-bromo-2-fluoro-5-methylphenol (7.8 g, 38 mmol, 96% yield) as an amber oil.

Step B: (R)-3-hydroxydihydrofuran-2(3H)-one (2.0 g, 20 mmol) was suspended in Toluene (150 mL) and triphenylphosphine (6.2 g, 24 mmol) and 4-bromo-2-fluoro-5-methylphenol (4.8 g, 24 mmol) were added and cooled to 0° C. The solution was degassed with nitrogen bubble for 10 minutes. Di-tert-butyl diazene-1,2-dicarboxylate (5.4 g, 24 mmol) was dissolved in toluene (40 mL) and added to the reaction over 5 minutes. The reaction was allowed to slowly warm to ambient temperature overnight. The toluene was removed and the oily residue was purified over silica gel (20 to 40% EtOAc in hexanes) to afford (S)-3-(4-bromo-2-fluoro-5-methylphenoxy)dihydrofuran-2(3H)-one (2.9 g, 10 mmol, 51% yield).

Step C: To a stirred solution of tert-butyl 4-aminopiperidine-1-carboxylate (2.4 g, 12 mmol) in CH₂Cl₂ (30 mL) was added trimethylaluminum (6.0 mL, 12 mmol) dropwise. The resulting mixture was stirred for 15 minutes, then (S)-3-(4-bromo-2-fluoro-5-methylphenoxy)dihydrofuran-2(3H)-one (2.9 g, 10 mmol) in CH₂Cl₂ (30 mL) was added slowly and stirred at ambient temperature for 1 hour. The reaction was slowly quenched with 5% tartaric acid, neutralized with aqueous NaHCO₃ and filtered through celite. The filtrate was extracted with CH₂Cl₂, dried over Na₂SO₄, filtered and concentrated. The residue was purified over silica gel (100% EtOAc) to afford (S)-tert-butyl 4-(2-(4-bromo-2-fluoro-5-methylphenoxy)-4-hydroxybutanamido)piperidine-1-carboxylate (3.2 g, 6.5 mmol, 65% yield).

Step D: Tributylphosphine (2.0 mL, 7.8 mmol) was added slowly to a degassed solution of di-tert-butyl diazene-1,2-dicarboxylate (1.8 g, 7.8 mmol) in dry THF (30 mL) at ambient temperature. The resulting mixture was stirred for 5 minutes, then added dropwise to a 0° C. solution of (S)-tert-butyl 4-(2-(4-bromo-2-fluoro-5-methylphenoxy)-4-hydroxybutanamido)piperidine-1-carboxylate (3.2 g, 6.5 mmol) in THF (30 mL). The reaction was allowed to stir at ambient temperature overnight. Another 1.2 equivalents of reagents (tributylphosphine, tert-butyl diazene-1,2-dicarboxylate, and THF, prepared in same fashion) was added to the reaction mixture, and the reaction was stirred overnight. The reaction was concentrated and purified over silica gel (35 to 50% EtOAc in hexanes) to afford (S)-tert-butyl 4-(3-(4-bromo-2-fluoro-5-methylphenoxy)-2-oxopyrrolidin-1-yl)piperidine-1-carboxylate (2.3 g, 4.9 mmol, 75% yield) as a white solid.

Step E: (S)-tert-butyl 4-(3-(4-bromo-2-fluoro-5-methylphenoxy)-2-oxopyrrolidin-1-yl)piperidine-1-carboxylate (2.3 g, 4.9 mmol) was dissolved in $CH_2Cl_2$:MeOH (9:1, 50 mL). 4N HCl in dioxane (10 mL) was added and the reaction stirred at ambient temperature overnight. The reaction was concentrated to afford crude (S)-3-(4-bromo-2-fluoro-5-methylphenoxy)-1-(piperidin-4-yl)pyrrolidin-2-one hydrochloride (2.0 g, 4.9 mmol, 101% yield) which was used without further purification.

Step F: (S)-3-(4-bromo-2-fluoro-5-methylphenoxy)-1-(piperidin-4-yl)pyrrolidin-2-one hydrochloride (600 mg, 1.47 mmol) was dissolved in DMSO (10 mL) and N-ethyl-N-isopropylpropan-2-amine (641 µl, 3.68 mmol) and 2-chloro-5-ethylpyrimidine (252 mg, 1.77 mmol) were added and the reaction heated to 110° C. overnight. The reaction was cooled to ambient temperature, poured into water and extracted with EtOAc, dried over $Na_2SO_4$, filtered and concentrated. The residue was purified over silica gel (60% EtOAc in hexanes) to afford (S)-3-(4-bromo-2-fluoro-5-methylphenoxy)-1-(1-(5-ethylpyrimidin-2-yl)piperidin-4-yl)pyrrolidin-2-one (420 mg, 0.880 mmol, 59.8% yield) as a tan solid.

Step G: (S)-3-(4-bromo-2-fluoro-5-methylphenoxy)-1-(1-(5-ethylpyrimidin-2-yl)piperidin-4-yl)pyrrolidin-2-one (200 mg, 0.42 mmol), trans-cyclohexane-1,2-diamine (20 µL, 0.17 mmol), sodium methanesulfinate (64 mg, 0.63 mmol) was dissolved in DMSO (3 mL) and nitrogen bubbled through for 15 minutes. Cu(I) triflate benzene-complex (21 mg, 0.04 mmol) was added and the reaction was plunged into 110° C. oil bath and stirred under nitrogen overnight. Additional trans-cyclohexane-1,2-diamine (20 µL, 0.17 mmol), sodium methanesulfinate (64 mg, 0.63 mmol) and Cu(I) triflate benzene-complex (21 mg, 0.04 mmol) were added and stirred for another 4 hours at 110° C. The reaction was cooled to ambient temperature, partitioned between water and EtOAc, extracted with EtOAc, washed with brine, dried over $Na_2SO_4$, filtered and concentrated. The residue was purified over silica gel (100% EtOAc) to afford (S)-1-(1-(5-ethylpyrimidin-2-yl)piperidin-4-yl)-3-(2-fluoro-5-methyl-4-(methylsulfonyl)phenoxy)pyrrolidin-2-one (119.8 mg, 0.25 mmol, 60% yield) as a white solid. Mass spectrum (apci) m/z=477.3 (M+H).

Example 97

(S)-3-(4-bromo-2-fluoro-5-methylphenoxy)-1-(1-(5-ethylpyrimidin-2-yl)piperidin-4-yl)pyrrolidin-2-one

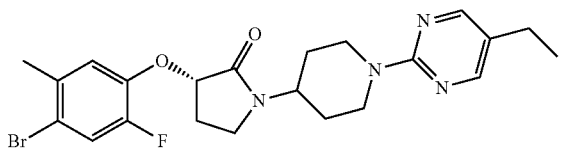 [SMILES: CCc1cnc(N2CCC(N3CC[C@H](Oc4cc(C)c(Br)cc4F)C3=O)CC2)nc1]

Prepared according to the method of Example 96, steps A-C. Mass spectrum (apci) m/z=477.1, 479.1 (M+H).

Example 98

(S)-4-(1-(1-(5-ethylpyrimidin-2-yl)piperidin-4-yl)-2-oxopyrrolidin-3-yloxy)-5-fluoro-2-methylbenzonitrile

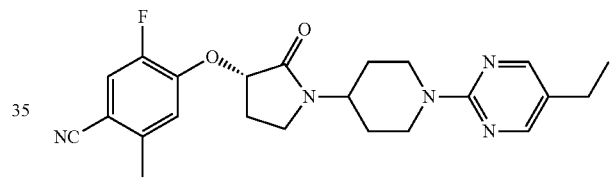

(S)-3-(4-bromo-2-fluoro-5-methylphenoxy)-1-(1-(5-ethylpyrimidin-2-yl)piperidin-4-yl)pyrrolidin-2-one (Example 96, Steps A-F; 200 mg, 0.419 mmol) was dissolved in NMP (1 mL) and cyanocopper (150 mg, 1.68 mmol) was added and heated to 160° C. overnight. The reaction was partitioned between dilute sodium bicarbonate and EtOAc, dried, filtered and concentrated. The residue was purified on 25M biotage (90% EtOAc/hexane) to afford (S)-4-(1-(1-(5-ethylpyrimidin-2-yl)piperidin-4-yl)-2-oxopyrrolidin-3-yloxy)-5-fluoro-2-methylbenzonitrile (99.6 mg, 0.235 mmol, 56.1% yield) as a pale yellow solid. Mass spectrum (apci) m/z=424 (M+H).

The following compounds were made according to the method of Example 3.

| Ex. # | Structure | Name | Data |
|---|---|---|---|
| 99 | ![structure] | (S)-3-(2-fluoro-4-(methylsulfonyl)phenylamino)-1-(1-(5-(trifluoromethyl)pyridin-2-yl)piperidin-4-yl)pyrrolidin-2-one | Mass spectrum (apci) m/z = 501.1 (M + H). |

-continued

| Ex. # | Structure | Name | Data |
|---|---|---|---|
| 100 | 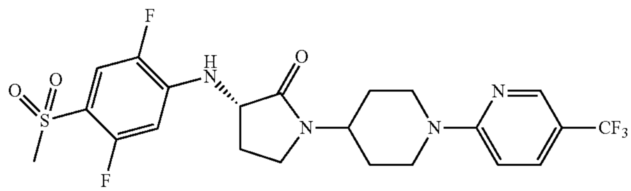 [SMILES: CS(=O)(=O)c1cc(F)c(N[C@H]2CCN(C3CCN(c4ccc(C(F)(F)F)cn4)CC3)C2=O)cc1F] | (S)-3-(2,5-difluoro-4-(methylsulfonyl)phenylamino)-1-(1-(5-(trifluoromethyl)pyridin-2-yl)piperidin-4-yl)pyrrolidin-2-one | Mass spectrum (apci) m/z = 519.2 (M + H). |
| 101 | 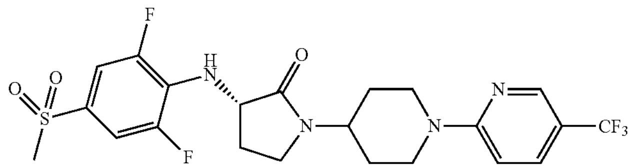 [SMILES: CS(=O)(=O)c1cc(F)c(N[C@H]2CCN(C3CCN(c4ccc(C(F)(F)F)cn4)CC3)C2=O)c(F)c1] | (S)-3-(2,6-difluoro-4-(methylsulfonyl)phenylamino)-1-(1-(5-(trifluoromethyl)pyridin-2-yl)piperidin-4-yl)pyrrolidin-2-one | Mass spectrum (apci) m/z = 519.2 (M + H). |
| 102 | 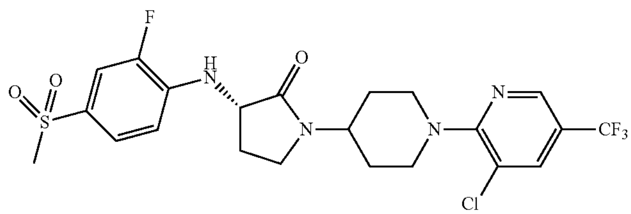 [SMILES: CS(=O)(=O)c1ccc(N[C@H]2CCN(C3CCN(c4ncc(C(F)(F)F)cc4Cl)CC3)C2=O)c(F)c1] | (S)-1-(1-(3-chloro-5-(trifluoromethyl)pyridin-2-yl)piperidin-4-yl)-3-(2-fluoro-4-(methylsulfonyl)phenylamino)pyrrolidin-2-one | Mass spectrum (apci) m/z = 535.1, 537.3 (M + H). |

The following compounds were prepared according to the method of Example 4.

| Ex. # | Structure | Name | Mass spectrum |
|---|---|---|---|
| 103 | 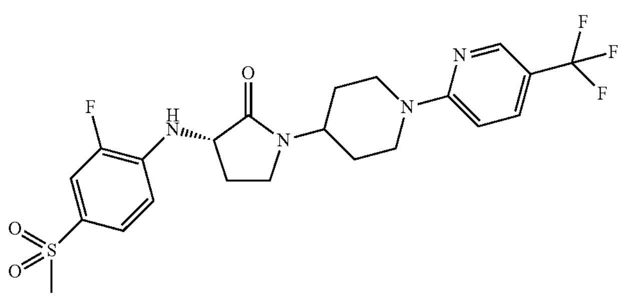 [SMILES: CS(=O)(=O)c1ccc(N[C@H]2CCN(C3CCN(c4ccc(C(F)(F)F)cn4)CC3)C2=O)c(F)c1] | (S)-3-(2-fluoro-4-(methylsulfonyl)phenylamino)-1-(1-(5-(trifluoromethyl)pyridin-2-yl)piperidin-4-yl)pyrrolidin-2-one | (apci) m/z = 501.1 (M + H) |
| 104 | 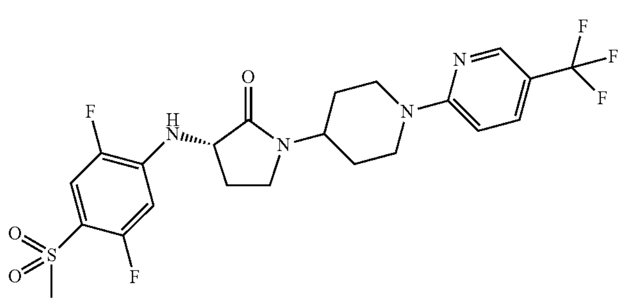 [SMILES: CS(=O)(=O)c1cc(F)c(N[C@H]2CCN(C3CCN(c4ccc(C(F)(F)F)cn4)CC3)C2=O)cc1F] | (S)-3-(2,5-difluoro-4-(methylsulfonyl)phenylamino)-1-(1-(5-(trifluoromethyl)pyridin-2-yl)piperidin-4-yl)pyrrolidin-2-one | (apci) m/z = 519.2 (M + H) |

-continued

| Ex. # | Structure | Name | Mass spectrum |
|---|---|---|---|
| 105 | 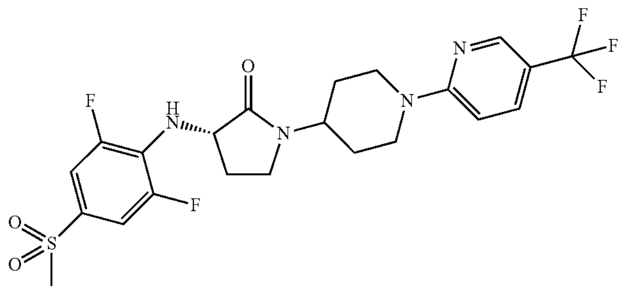 [SMILES: CS(=O)(=O)c1cc(F)c(N[C@H]2CCN(C3CCN(c4ccc(C(F)(F)F)cn4)CC3)C2=O)c(F)c1] | (S)-3-(2,6-difluoro-4-(methylsulfonyl)phenyl-amino)-1-(1-(5-(trifluoromethyl)pyridin-2-yl)piperidin-4-yl)pyrrolidin-2-one | (apci) m/z = 519.2 (M + H) |
| 106 | 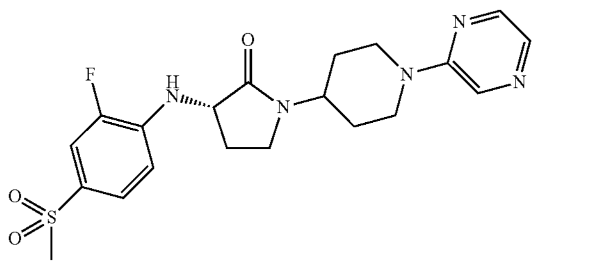 [SMILES: CS(=O)(=O)c1ccc(N[C@H]2CCN(C3CCN(c4cnccn4)CC3)C2=O)c(F)c1] | (S)-3-(2-fluoro-4-(methylsulfonyl)phenyl-amino)-1-(1-(pyrazin-2-yl)piperidin-4-yl)pyrrolidin-2-one | (apci) m/z = 434.2 (M + H) |
| 107 | 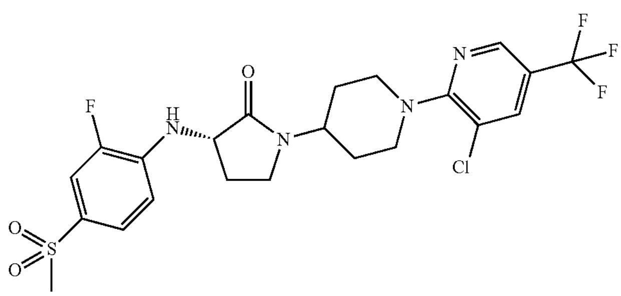 [SMILES: CS(=O)(=O)c1ccc(N[C@H]2CCN(C3CCN(c4ncc(C(F)(F)F)cc4Cl)CC3)C2=O)c(F)c1] | (S)-1-(1-(3-chloro-5-(trifluoromethyl)pyridin-2-yl)piperidin-4-yl)-3-(2-fluoro-4-(methylsulfonyl)phenylamino)pyrrolidin-2-one | (apci) m/z = 535.1 (M + H) |
| 108 | 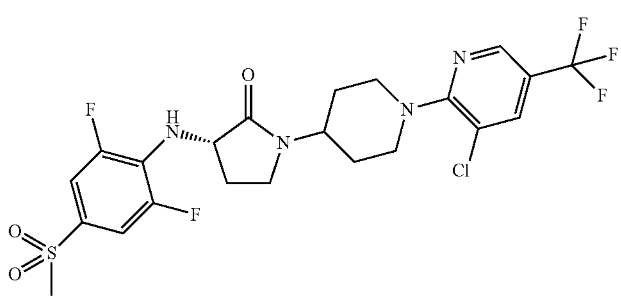 [SMILES: CS(=O)(=O)c1cc(F)c(N[C@H]2CCN(C3CCN(c4ncc(C(F)(F)F)cc4Cl)CC3)C2=O)c(F)c1] | (S)-1-(1-(3-chloro-5-(trifluoromethyl)pyridin-2-yl)piperidin-4-yl)-3-(2,6-difluoro-4-(methylsulfonyl)phenyl-amino)pyrrolidin-2-one | (apci) m/z = 553.0 (M + H) |
| 109 | 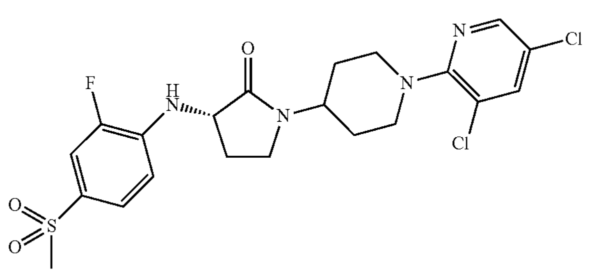 | (S)-1-(1-(3,5-dichloropyridin-2-yl)piperidin-4-yl)-3-(2-fluoro-4-(methylsulfonyl)phenyl-amino)pyrrolidin-2-one | (apci) m/z = 501.0 (M + H) |

-continued

| Ex. # | Structure | Name | Mass spectrum |
|---|---|---|---|
| 110 | 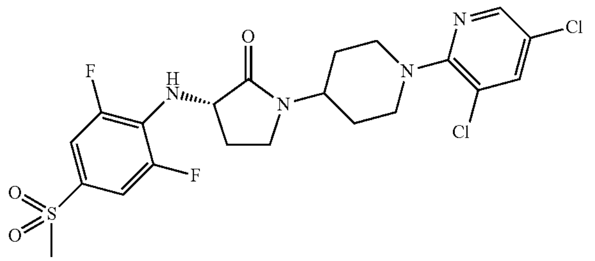 [SMILES: CS(=O)(=O)c1cc(F)c(N[C@H]2CCN(C3CCN(c4ncc(Cl)cc4Cl)CC3)C2=O)c(F)c1] | (S)-1-(1-(3,5-dichloropyridin-2-yl)piperidin-4-yl)-3-(2,6-difluoro-4-(methylsulfonyl)phenyl-amino)pyrrolidin-2-one | (apci) m/z = 519.2 (M + H) |
| 111 | 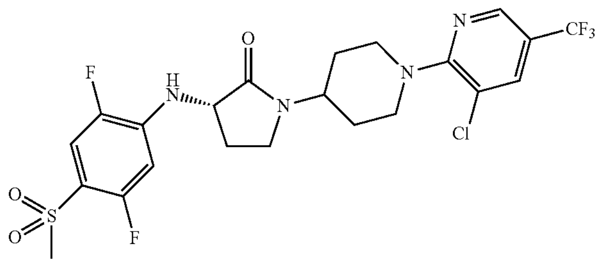 [SMILES: CS(=O)(=O)c1cc(F)c(N[C@H]2CCN(C3CCN(c4ncc(C(F)(F)F)cc4Cl)CC3)C2=O)cc1F] | (S)-1-(1-(3-chloro-5-(trifluoromethyl)pyridin-2-yl)piperidin-4-yl)-3-(2,5-difluoro-4-(methylsulfonyl)phenyl-amino)pyrrolidin-2-one | (apci) m/z = 553.2 (M + H) |
| 112 | 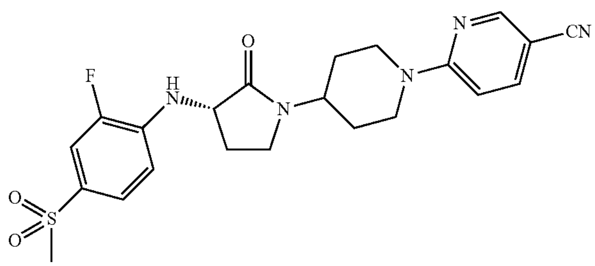 [SMILES: CS(=O)(=O)c1ccc(N[C@H]2CCN(C3CCN(c4ccc(C#N)cn4)CC3)C2=O)c(F)c1] | (S)-6-(4-(3-(2-fluoro-4-(methylsulfonyl)phenyl-amino)-2-oxopyrrolidin-1-yl)piperidin-1-yl)nicotinonitrile | (apci) m/z = 458.2 (M + H) |
| 113 | 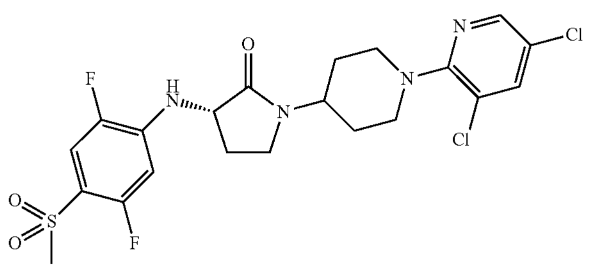 [SMILES: CS(=O)(=O)c1cc(F)c(N[C@H]2CCN(C3CCN(c4ncc(Cl)cc4Cl)CC3)C2=O)cc1F] | (S)-1-(1-(3,5-dichloropyridin-2-yl)piperidin-4-yl)-3-(2,5-difluoro-4-(methylsulfonyl)phenyl-amino)pyrrolidin-2-one | (apci) m/z = 521.1 (M + H) |
| 114 | 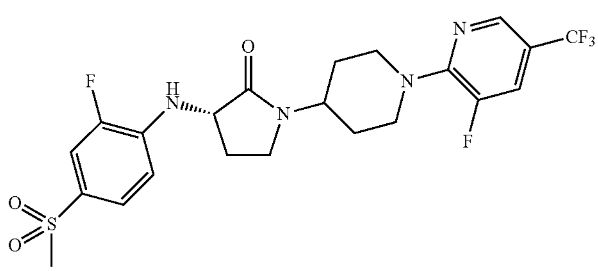 [SMILES: CS(=O)(=O)c1ccc(N[C@H]2CCN(C3CCN(c4ncc(C(F)(F)F)cc4F)CC3)C2=O)c(F)c1] | (S)-3-(2-fluoro-4-(methylsulfonyl)phenyl-amino)-1-(1-(3-fluoro-5-(trifluoromethyl)pyridin-2-yl)piperidin-4-yl)pyrrolidin-2-one | (apci) m/z = 519.2 (M + H) |

| Ex. # | Structure | Name | Mass spectrum |
|---|---|---|---|
| 115 | 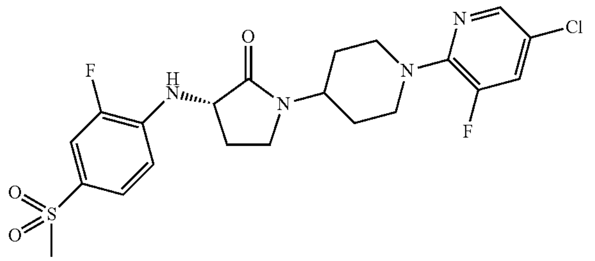 [SMILES: CS(=O)(=O)c1ccc(N[C@H]2CCN(C3CCN(c4ncc(Cl)cc4F)CC3)C2=O)c(F)c1] | (S)-1-(1-(5-chloro-3-fluoropyridin-2-yl)piperidin-4-yl)-3-(2-fluoro-4-(methylsulfonyl)phenyl-amino)pyrrolidin-2-one | (apci) m/z = 485.0 (M + H) |
| 116 | 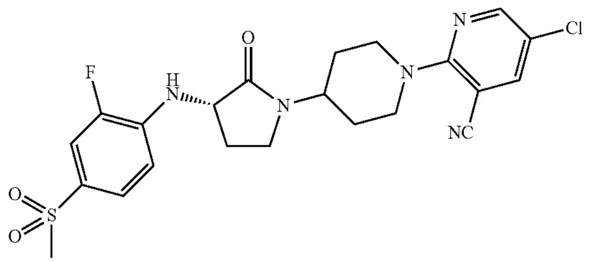 [SMILES: CS(=O)(=O)c1ccc(N[C@H]2CCN(C3CCN(c4ncc(Cl)cc4C#N)CC3)C2=O)c(F)c1] | (S)-5-chloro-2-(4-(3-(2-fluoro-4-(methylsulfonyl)phenyl-amino)-2-oxopyrrolidin-1-yl)piperidin-1-yl)nicotinonitrile | (apci) m/z = 491.9 (M + H) |
| 117 | 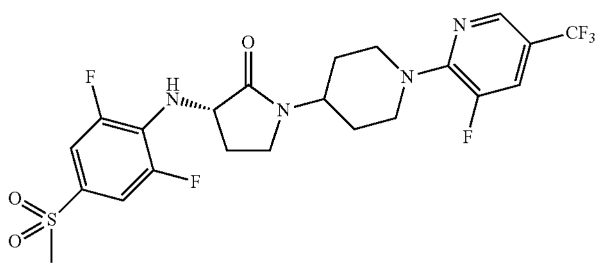 [SMILES: CS(=O)(=O)c1cc(F)c(N[C@H]2CCN(C3CCN(c4ncc(C(F)(F)F)cc4F)CC3)C2=O)c(F)c1] | (S)-3-(2,6-difluoro-4-(methylsulfonyl)phenyl-amino)-1-(1-(3-fluoro-5-(trifluoromethyl)pyridin-2-yl)piperidin-4-yl)pyrrolidin-2-one | (apci) m/z = 537.0 (M + H ) |
| 118 | 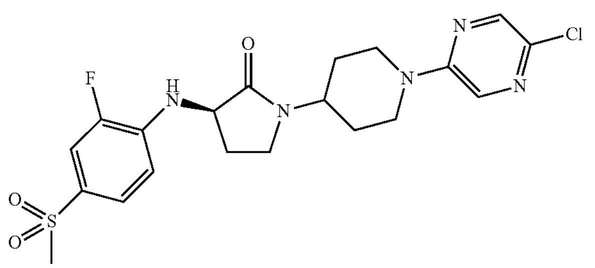 [SMILES: CS(=O)(=O)c1ccc(N[C@@H]2CCN(C3CCN(c4cnc(Cl)cn4)CC3)C2=O)c(F)c1] | (R)-1-(1-(5-chloropyrazin-2-yl)piperidin-4-yl)-3-(2-fluoro-4-(methylsulfonyl)phenyl-amino)pyrrolidin-2-one | (apci) m/z = 468.2 (M + H) |

The following compounds were prepared according to Example 4. The optical purity for the compounds of Examples 119-130 was not determined.

| Ex. # | Structure | Name | Mass spectrum |
|---|---|---|---|
| 119 | 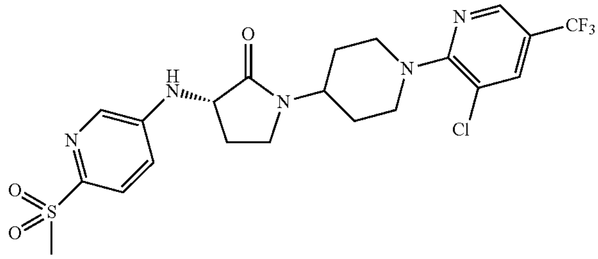 [SMILES: CS(=O)(=O)c1ccc(N[C@H]2CCN(C3CCN(c4ncc(C(F)(F)F)cc4Cl)CC3)C2=O)cn1] | (S)-1-(1-(3-chloro-5-(trifluoromethyl)pyridin-2-yl)piperidin-4-yl)-3-(6-(methylsulfonyl)pyridin-3-ylamino)pyrrolidin-2-one | (apci) m/z = 518.0 (M + H) |

| Ex. # | Structure | Name | Mass spectrum |
|---|---|---|---|
| 120 | 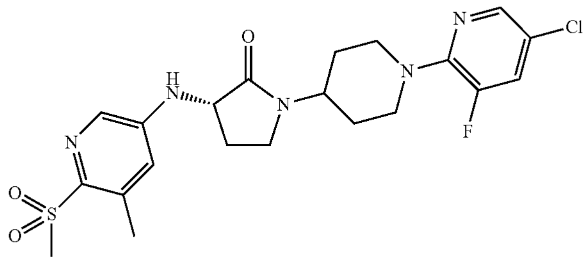 [SMILES: Cc1cc(N[C@H]2CCN(C3CCN(c4ncc(Cl)cc4F)CC3)C2=O)cnc1S(C)(=O)=O] | (S)-1-(1-(5-chloro-3-fluoropyridin-2-yl)piperidin-4-yl)-3-(5-methyl-6-(methylsulfonyl)pyridin-3-ylamino)pyrrolidin-2-one | (apci) m/z = 482.0 (M + H) |
| 121 | 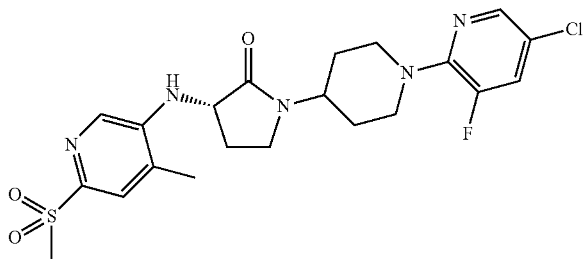 [SMILES: Cc1cc(S(C)(=O)=O)ncc1N[C@H]1CCN(C2CCN(c3ncc(Cl)cc3F)CC2)C1=O] | (S)-1-(1-(5-chloro-3-fluoropyridin-2-yl)piperidin-4-yl)-3-(4-methyl-6-(methylsulfonyl)pyridin-3-ylamino)pyrrolidin-2-one | (apci) m/z = 482.0 (M + H) |
| 122 | 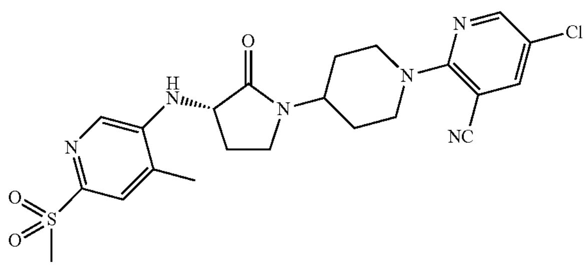 [SMILES: Cc1cc(S(C)(=O)=O)ncc1N[C@H]1CCN(C2CCN(c3ncc(Cl)cc3C#N)CC2)C1=O] | (S)-5-chloro-2-(4-(3-(4-methyl-6-(methylsulfonyl)pyridin-3-ylamino)-2-oxopyrrolidin-1-yl)piperidin-1-yl)icotinonitrile | (apci) m/z = 489.0 (M + H) |
| 123 | 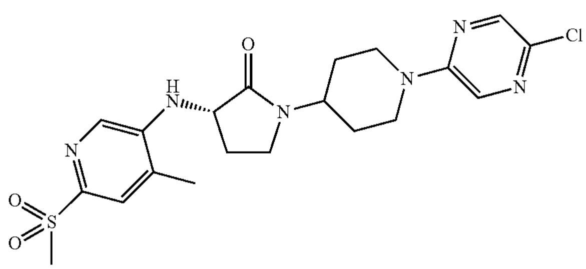 [SMILES: Cc1cc(S(C)(=O)=O)ncc1N[C@H]1CCN(C2CCN(c3cnc(Cl)cn3)CC2)C1=O] | (S)-1-(1-(5-chloropyrazin-2-yl)piperidin-4-yl)-3-(4-methyl-6-(methylsulfonyl)pyridin-3-ylamino)pyrrolidin-2-one | (apci) m/z = 465.0 (M + H) |
| 124 | 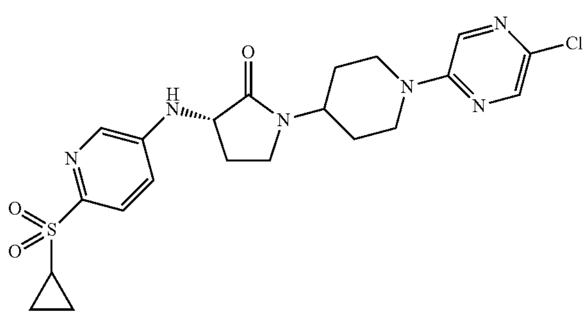 [SMILES: O=C1[C@@H](Nc2ccc(S(=O)(=O)C3CC3)nc2)CCN1C1CCN(c2cnc(Cl)cn2)CC1] | (S)-1-(1-(5-chloropyrazin-2-yl)piperidin-4-yl)-3-(6-(cyclopropylsulfonyl)pyridin-3-ylamino)pyrrolidin-2-one | (apci) m/z = 477.0 (M + H) |

-continued

| Ex. # | Structure | Name | Mass spectrum |
|---|---|---|---|
| 125 | 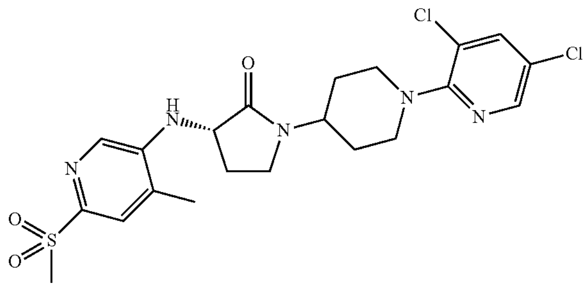 [SMILES: Cc1cc(S(C)(=O)=O)ncc1N[C@H]1CCN(C2CCN(c3ncc(Cl)cc3Cl)CC2)C1=O] | (S)-1-(1-(3,5-dichloro-pyridin-2-yl)piperidin-4-yl)-3-(4-methyl-6-(methylsulfonyl)pyridin-3-ylamino)pyrrolidin-2-one | (apci) m/z = 497.9 (M + H) |
| 126 | 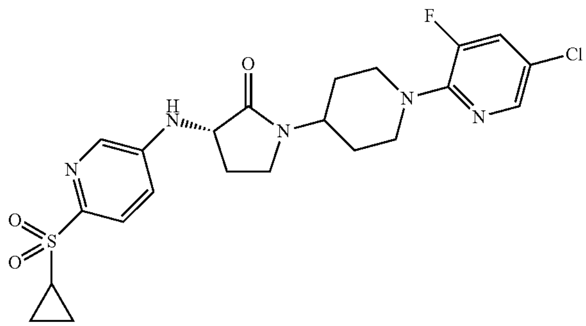 [SMILES: O=C1[C@@H](Nc2ccc(S(=O)(=O)C3CC3)nc2)CCN1C1CCN(c2ncc(Cl)cc2F)CC1] | (S)-1-(1-(5-chloro-3-fluoropyridin-2-yl)piperidin-4-yl)-3-(6-(cyclopropylsulfonyl)pyridin-3-ylamino)pyrrolidin-2-one | (apci) m/z = 494.0 (M + H) |
| 127 | 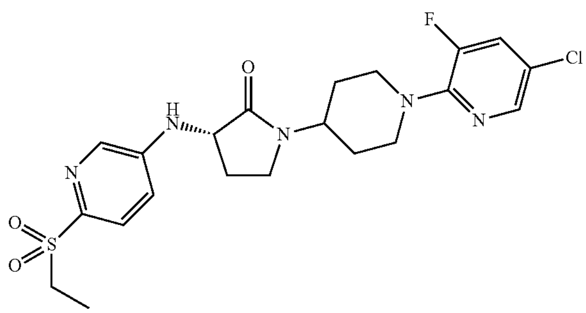 [SMILES: CCS(=O)(=O)c1ccc(N[C@H]2CCN(C3CCN(c4ncc(Cl)cc4F)CC3)C2=O)cn1] | (S)-1-(1-(5-chloro-3-fluoropyridin-2-yl)piperidin-4-yl)-3-(6-(ethylsulfonyl)pyridin-3-ylamino)pyrrolidin-2-one | (apci) m/z = 482.0 (M + H) |
| 128 | 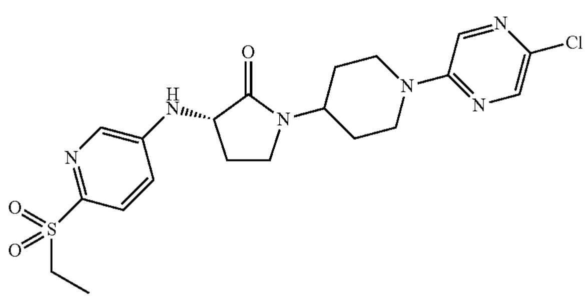 [SMILES: CCS(=O)(=O)c1ccc(N[C@H]2CCN(C3CCN(c4cnc(Cl)cn4)CC3)C2=O)cn1] | (S)-1-(1-(5-chloropyrazin-2-yl)piperidin-4-yl)-3-(6-(ethylsulfonyl)pyridin-3-ylamino)pyrrolidin-2-one | (apci) m/z = 464.9 (M + H) |
| 129 | 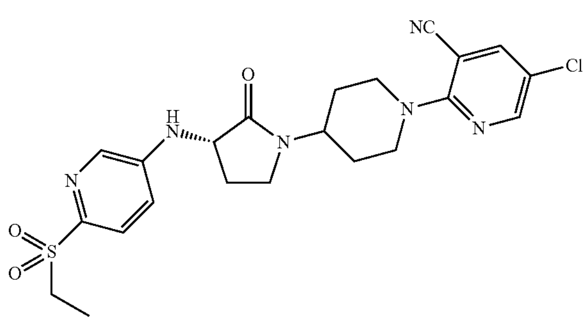 [SMILES: CCS(=O)(=O)c1ccc(N[C@H]2CCN(C3CCN(c4ncc(Cl)cc4C#N)CC3)C2=O)cn1] | (S)-5-chloro-2-(4-(3-(6-(ethylsulfonyl)pyridin-3-ylamino)-2-oxopyrrolidin-1-yl)piperidin-1-yl)nicotinonitrile | (apci) m/z = 489.0 (M + H) |

| Ex. # | Structure | Name | Mass spectrum |
|---|---|---|---|
| 130 | 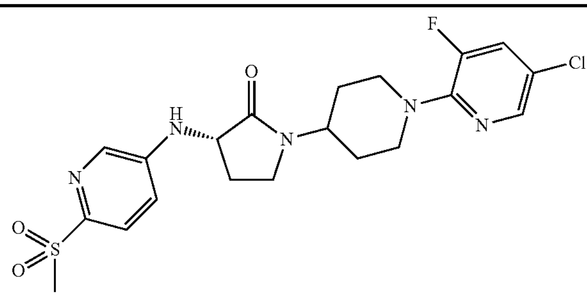 | (S)-1-(1-(5-chloro-3-fluoropyridin-2-yl)piperidin-4-yl)-3-(6-(methylsulfonyl)pyridin-3-ylamino)pyrrolidin-2-one | (apci) m/z = 468.0 (M + H) |

The following compounds were prepared according to Example 4, substituting NMP for DMF. The optical purity for compounds of Examples 131-135 was not determined.

| Ex. # | Structure | Name | Mass spectrum |
|---|---|---|---|
| 131 | 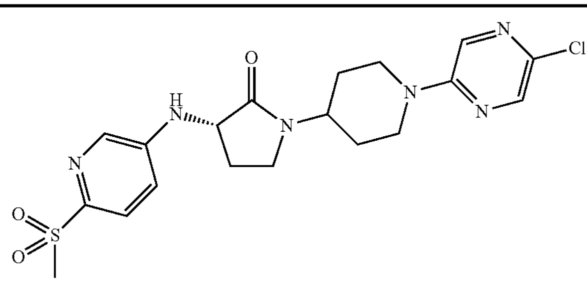 | (S)-1-(1-(5-chloropyrazin-2-yl)piperidin-4-yl)-3-(6-(methylsulfonyl)pyridin-3-ylamino)pyrrolidin-2-one | (apci) m/z = 451.2 (M + H) |
| 132 | 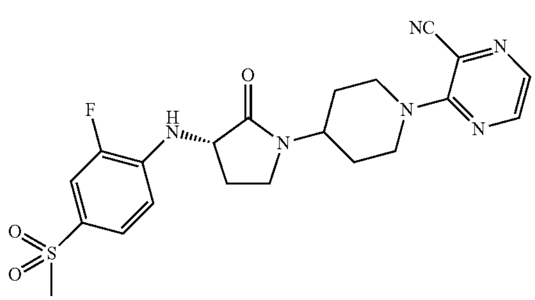 [SMILES: CS(=O)(=O)c1ccc(N[C@H]2CCN(C3CCN(c4nccnc4C#N)CC3)C2=O)c(F)c1] | (S)-3-(4-(3-(2-fluoro-4-(methylsulfonyl)phenylamino)-2-oxopyrrolidin-1-yl)piperidin-1-yl)pyrazine-2-carbonitrile | (apci) m/z = 459.1 (M + H) |
| 133 | 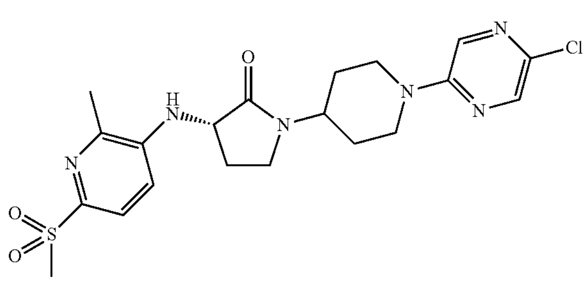 [SMILES: Cc1nc(S(C)(=O)=O)ccc1N[C@H]1CCN(C2CCN(c3cnc(Cl)cn3)CC2)C1=O] | (S)-1-(1-(5-chloropyrazin-2-yl)piperidin-4-yl)-3-(2-methyl-6-(methylsulfonyl)pyridin-3-ylamino)pyrrolidin-2-one | (apci) m/z = 465.3 (M + H) |

-continued

| Ex. # | Structure | Name | Mass spectrum |
|---|---|---|---|
| 134 | 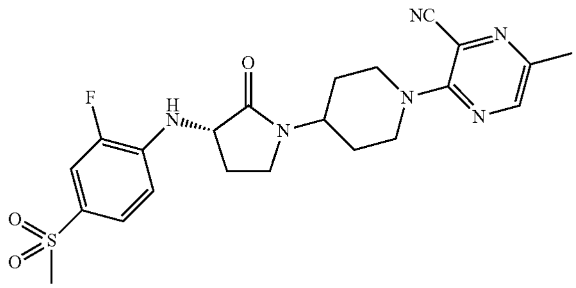 [SMILES: Cc1cnc(N2CCC(N3CC[C@H](Nc4ccc(S(C)(=O)=O)cc4F)C3=O)CC2)c(C#N)n1] | (S)-3-(4-(3-(2-fluoro-4-(methylsulfonyl)phenyl-amino)-2-oxopyrrolidin-1-yl)piperidin-1-yl)-6-methylpyrazine-2-carbonitrile | (apci) m/z = 473.2 (M + H) |
| 135 | 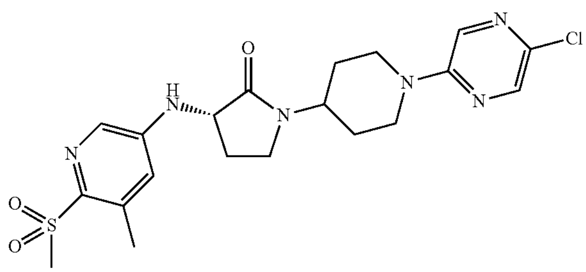 [SMILES: Cc1cc(N[C@H]2CCN(C3CCN(c4cnc(Cl)cn4)CC3)C2=O)cnc1S(C)(=O)=O] | 1-(1-(5-chloropyrazin-2-yl)piperidin-4-yl)-3-(5-methyl-6-(methylsulfonyl)pyridin-3-ylamino)pyrrolidin-2-one | (apci) m/z = 465.0 (M + H) |

The following compounds were prepared according to the method described in Example 90.

| Ex. # | Structure | Name | Mass spectrum |
|---|---|---|---|
| 136 | 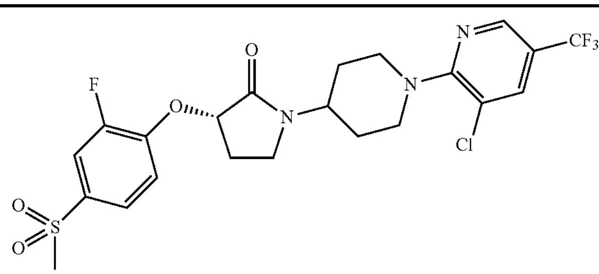 | (S)-1-(1-(3-chloro-5-(trifluoromethyl)pyridin-2-yl)piperidin-4-yl)-3-(2-fluoro-4-(methyl-sulfonyl)phenoxy)pyrrol-idin-2-one | (apci) m/z = 536.0 (M + H) |
| 137 | 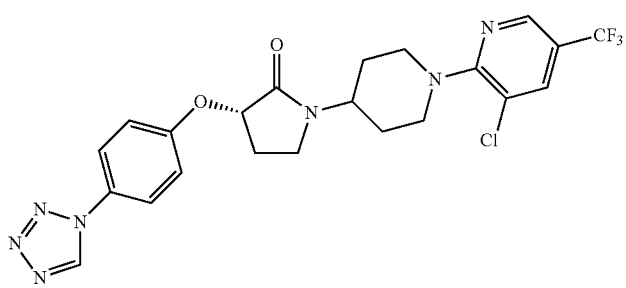 | (S)-3-(4-(1H-tetrazol-1-yl)phenoxy)-1-(1-(3-chloro-5-(trifluoro-methyl)pyridin-2-yl)piperidin-4-yl)pyrrolidin-2-one | (apci) m/z = 507.0 (M + H) |
| 138 | 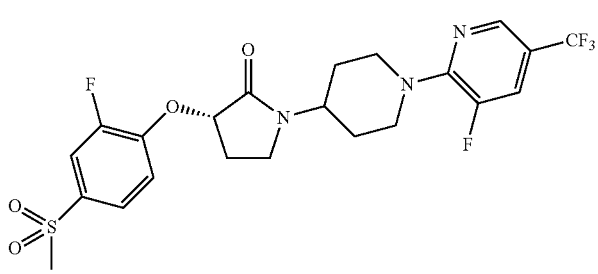 | (S)-3-(2-fluoro-4-(methyl-sulfonyl)phenoxy)-1-(1-(3-fluoro-5-(trifluoro-methyl)pyridin-2-yl)piperidin-4-yl)pyrrolidin-2-one | (apci) m/z = 520.0 (M + H) |

| Ex. # | Name | Mass spectrum |
|---|---|---|
| 139 | (S)-1-(1-(5-chloro-3-fluoropyridin-2-yl)piperidin-4-yl)-3-(2-fluoro-4-(methylsulfonyl)phenoxy)pyrrolidin-2-one | (apci) m/z = 485.9 (M + H) |
| 140 | (S)-methyl 4-(1-(1-(3-chloro-5-(trifluoromethyl)pyridin-2-yl)piperidin-4-yl)-2-oxopyrrolidin-3-yloxy)-3-fluorobenzoate | (apci) m/z = 515.9 (M + H) |
| 141 | (S)-3-(4-(1H-1,2,4-triazol-1-yl)phenoxy)-1-(1-(3-chloro-5-(trifluoromethyl)pyridin-2-yl)piperidin-4-yl)pyrrolidin-2-one | (apci) m/z = 507.0 (M + H) |
| 142 | (S)-1-(1-(3-fluoro-5-(trifluoromethyl)pyridin-2-yl)piperidin-4-yl)-3-(6-(methylsulfonyl)pyridin-3-yloxy)pyrrolidin-2-one | (apci) m/z = 503.0 (M + H) |
| 143 | (S)-1-(1-(3-chloro-5-(trifluoromethyl)pyridin-2-yl)piperidin-4-yl)-3-(6-(methylsulfonyl)pyridin-3-yloxy)pyrrolidin-2-one | (apci) m/z = 518.9 (M + H) |

| Ex. # | Structure | Name | Mass spectrum |
|---|---|---|---|
| 144 | 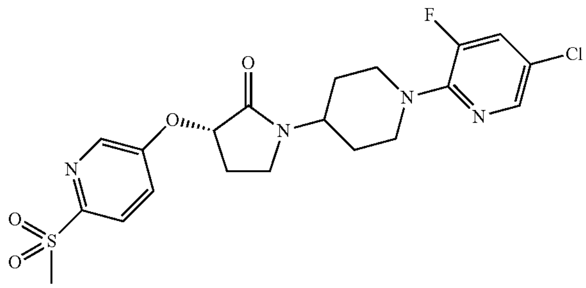 [SMILES: CS(=O)(=O)c1ccc(O[C@H]2CCN(C3CCN(c4ncc(Cl)cc4F)CC3)C2=O)cn1] | (S)-1-(1-(5-chloro-3-fluoropyridin-2-yl)piperidin-4-yl)-3-(6-(methylsulfonyl)pyridin-3-yloxy)pyrrolidin-2-one | (apci) m/z = 468.9 (M + H) |

The following compounds were prepared according to the method described in Example 45.

| Ex. # | Structure | Name | Mass spectrum |
|---|---|---|---|
| 145 | 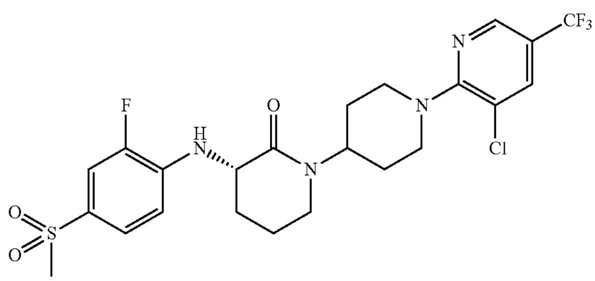 [SMILES: CS(=O)(=O)c1ccc(N[C@H]2CCCN(C3CCN(c4ncc(C(F)(F)F)cc4Cl)CC3)C2=O)c(F)c1] | (S)-1'-(3-chloro-5-(trifluoromethyl)pyridin-2-yl)-3-(2-fluoro-4-(methylsulfonyl)phenylamino)-1,4'-bipiperidin-2-one | (apci) m/z = 549.1 (M + H) |
| 146 | 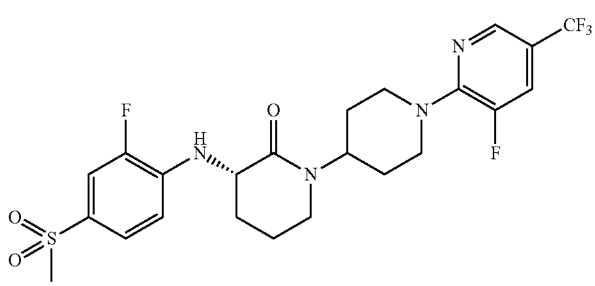 [SMILES: CS(=O)(=O)c1ccc(N[C@H]2CCCN(C3CCN(c4ncc(C(F)(F)F)cc4F)CC3)C2=O)c(F)c1] | (S)-3-(2-fluoro-4-(methylsulfonyl)phenylamino)-1'-(3-fluoro-5-(trifluoromethyl)pyridin-2-yl)-1,4'-bipiperidin-2-one | (apci) m/z = 533.0 (M + H) |

Example 147

(S)-1-(1-(3,5-dichloropyrazin-2-yl)piperidin-4-yl)-3-(2-fluoro-4-(methylsulfonyl)phenylamino)pyrrolidin-2-one

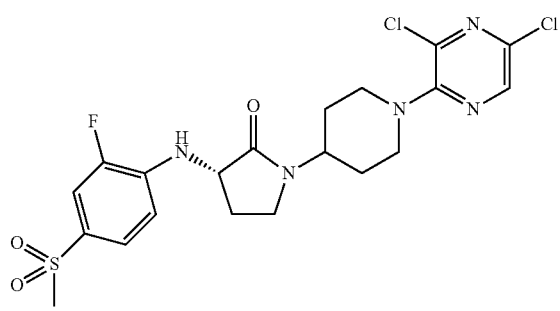 [SMILES: CS(=O)(=O)c1ccc(N[C@H]2CCN(C3CCN(c4ncc(Cl)nc4Cl)CC3)C2=O)c(F)c1]

N-Chlorosuccinimide (0.016 g, 0.12 mmol) was added to a mixture of (S)-1-(1-(5-chloropyrazin-2-yl)piperidin-4-yl)-3-(2-fluoro-4-(methylsulfonyl)phenylamino)pyrrolidin-2-one (Example 4; 0.042 g, 0.090 mmol) in AcOH (0.3 mL). The mixture was stirred at 50° C. for 1.5 hour and then cooled to ambient temperature. The volatiles were removed by a stream of flowing nitrogen and the resulting residue was stirred in a mixture of saturated aqueous Na$_2$SO$_3$ (1.5 mL) and EtOAc (1.5 mL) for 15 minutes. The mixture was then partitioned between saturated aqueous NaHCO$_3$ (20 mL) and EtOAc (40 mL). The organic phase was washed successively with water (20 mL), water (20 mL) and brine (20 mL). The combined organic phases were dried over MgSO$_4$, filtered and concentrated. The residue was purified on silica (eluting with 2:1 EtOAc/hexanes) to afford (S)-1-(1-(3,5-dichloropyrazin-2-yl)piperidin-4-yl)-3-(2-fluoro-4-(methylsulfonyl)phenylamino)pyrrolidin-2-one (0.024 g, 0.048 mmol, 53%) as a white solid. Mass spectrum (apci) m/z=502 (M+H).

Example 148

(S)-1-(1-(5-chloro-3-fluoropyridin-2-yl)piperidin-4-yl)-3-(6-(pyrrolidine-1-carbonyl)pyridin-3-yloxy)pyrrolidin-2-one

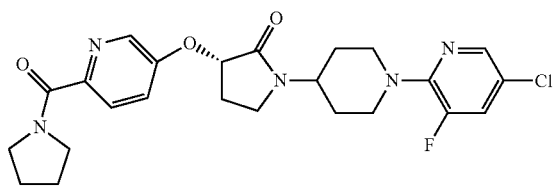 [SMILES: O=C(c1ccc(O[C@H]2CCN(C3CCN(c4ncc(Cl)cc4F)CC3)C2=O)cn1)N1CCCC1]

Step A: (R)-tert-Butyl 4-(3-(methylsulfonyloxy)-2-oxopyrrolidin-1-yl)piperidine-1-carboxylate (Preparation D; 0.20 g, 0.55 mmol) was added to a mixture of methyl 5-hydroxypicolinate (0.10 g, 0.66 mmol), and potassium carbonate (0.099 g, 0.72 mmol) in DMF (1.6 mL). The mixture was stirred at 60° C. overnight and then cooled to ambient temperature. The mixture was partitioned between saturated aqueous NH$_4$Cl (40 mL) and EtOAc (100 mL). The organic phase was washed successively with water (40 mL), water (40 mL) and brine (40 mL). The combined organic phases were dried over MgSO$_4$, filtered and concentrated. The residue was purified on silica (eluting with EtOAc) to afford (S)-methyl 5-(1-(1-(tert-butoxycarbonyl)piperidin-4-yl)-2-oxopyrrolidin-3-yloxy)picolinate (0.19 g, 0.45 mmol, 81%).

Step B: Concentrated aqueous HCl (2 mL) was added to a suspension of (S)-methyl 5-(1-(1-(tert-butoxycarbonyl)piperidin-4-yl)-2-oxopyrrolidin-3-yloxy)picolinate (0.19 g, 0.45 mmol) in MeOH (4 mL). The mixture was stirred at ambient temperature overnight and then concentrated. The residue was concentrated from MeOH twice to afford (S)-methyl 5-(2-oxo-1-(piperidin-4-yl)pyrrolidin-3-yloxy)picolinate hydrochloride (0.19 g, 0.44 mmol, 98%).

Step C: 5-Chloro-2,3-difluoropyridine (0.20 g, 1.3 mmol) was added to a mixture of (S)-methyl 5-(2-oxo-1-(piperidin-4-yl)pyrrolidin-3-yloxy)picolinate hydrochloride (0.17 g, 0.44 mmol) and DIEA (0.38 mL, 2.2 mmol) in DMF (1.5 mL). The mixture was stirred at 100° C. overnight and then cooled to ambient temperature. The mixture was partitioned between saturated aqueous NH$_4$Cl (20 mL) and EtOAc (50 mL). The organic phase was washed successively with water (20 mL), water (20 mL) and then brine (20 mL). The combined organic phases were dried over MgSO$_4$, filtered and concentrated. The residue was purified on silica (eluting with EtOAc) to afford (S)-methyl 5-(1-(1-(5-chloro-3-fluoropyridin-2-yl)piperidin-4-yl)-2-oxopyrrolidin-3-yloxy)picolinate (0.17 g, 0.38 mmol, 86%).

Step D: Aqueous 1 M LiOH (1.5 mL, 1.5 mmol) was added to a solution of (S)-methyl 5-(1-(1-(5-chloro-3-fluoropyridin-2-yl)piperidin-4-yl)-2-oxopyrrolidin-3-yloxy)picolinate (0.17 g, 0.38 mmol) in THF (2 mL). The mixture was stirred overnight at ambient temperature. The THF was removed under vacuum and the resulting aqueous solution was adjusted to pH 1 via the addition of aqueous 1 M HCl. The resulting solids were collected by filtration and air-dried to afford (S)-5-(1-(1-(5-chloro-3-fluoropyridin-2-yl)piperidin-4-yl)-2-oxopyrrolidin-3-yloxy)picolinic acid hydrochloride (0.13 g, 0.28 mmol, 74%).

Step E: (S)-5-(1-(1-(5-Chloro-3-fluoropyridin-2-yl)piperidin-4-yl)-2-oxopyrrolidin-3-yloxy)picolinic acid hydrochloride (0.027 g, 0.062 mmol), hydroxybenzotriazole hydrate (0.013 g, 0.084 mmol), EDCI (0.016 g, 0.084 mmol), and DIEA (0.016 mL, 0.093 mmol) were stirred in CH$_2$Cl$_2$ (0.5 mL) for five minutes. Pyrrolidine (0.010 mL, 0.12 mmol) was added and the solution was stirred overnight at ambient temperature. The mixture was partitioned between saturated aqueous NH$_4$Cl (20 mL) and EtOAc (40 mL). The organic phase was washed successively with saturated aqueous NaHCO$_3$ (20 mL) and brine (20 mL). The organics were dried over MgSO$_4$, filtered and concentrated. The residue was purified on silica (eluting with 1:24 MeOH/EtOAc) to afford (S)-1-(1-(5-chloro-3-fluoropyridin-2-yl)piperidin-4-yl)-3-(6-(pyrrolidine-1-carbonyl)pyridin-3-yloxy)pyrrolidin-2- one (24 mg, 0.049 mmol, 79%) as a colorless solid. Mass spectrum (apci) m/z=488 (M+H).

Example 149

(S)-5-(1-(1-(5-chloro-3-fluoropyridin-2-yl)piperidin-4-yl)-2-oxopyrrolidin-3-yloxy)-N,N-dimethylpicolinamide

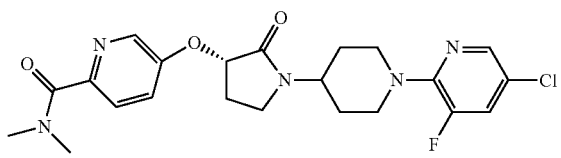 [SMILES: CN(C)C(=O)c1ccc(O[C@H]2CCN(C3CCN(c4ncc(Cl)cc4F)CC3)C2=O)cn1]

(S)-5-(1-(1-(5-Chloro-3-fluoropyridin-2-yl)piperidin-4-yl)-2-oxopyrrolidin-3-yloxy)-N,N-dimethylpicolinamide (18 mg, 0.039 mmol, 63%) was synthesized following the procedure in Example 148, substituting dimethylamine (2 M in THF) for pyrrolidine in Step E. Mass spectrum (apci) m/z=462 (M+H).

Example 150

(S)-6-(1-(1-(3-chloro-5-(trifluoromethyl)pyridin-2-yl)piperidin-4-yl)-2-oxopyrrolidin-3-ylamino)pyridazine-3-carbonitrile Step A: To a solution of (S)-benzyl 4-(3-(tert-butoxycarbonylamino)-2-oxopyrrolidin-1-yl)piperidine-1-carboxylate (Preparation E, Step C, 7.0 g, 17 mmol) in methanol (300 mL) purged with nitrogen was added Pd/C (10%, 2 g) and the reaction was stirred overnight at ambient temperature under a balloon of hydrogen gas. The reaction was next purged with nitrogen and filtered through Celite®, and the filter cake was washed with methanol (about 100 mL). The combined organic phases were concentrated under vacuum to yield (S)-tert-butyl 2-oxo-1-(piperidin-4-yl)pyrrolidin-3-ylcarbamate (4.0 g, 83%)

Step B: To a solution of (S)-tert-butyl 2-oxo-1-(piperidin-4-yl)pyrrolidin-3-ylcarbamate (4.0 g, 14 mmol) in DMF (50 mL) was added N-ethyl-N-isopropylpropan-2-amine (5.5 g, 42 mmol) and 2,3-dichloro-5-(trifluoromethyl)pyridine (9.1 g, 42 mmol) and the reaction was stirred overnight at ambient temperature. The reaction was diluted with EtOAc (about 200 mL) and the organic layer was washed with water (100 mL), and brine (50 mL), dried over MgSO$_4$, and concentrated under vacuum. The crude material was purified on silica using a gradient of DCM to 5% EtOAc/DCM as eluent to give (S)-tert-butyl 1-(1-(3-chloro-5-(trifluoromethyl)pyridin-2-yl)piperidin-4-yl)-2-oxopyrrolidin-3-ylcarbamate (4.0 g, 61%).

Step C: To a solution of (S)-tert-butyl 1-(1-(3-chloro-5-(trifluoromethyl)pyridin-2-yl)piperidin-4-yl)-2-oxopyrrolidin-3-ylcarbamate (4 g, 8.6 mmol) in EtOAc (20 mL) was added HCl in isopropanol (5-6 M, 16 mL) and the reaction was stirred overnight at ambient temperature. The reaction was concentrated under vacuum and the material dissolved in water (about 20 mL). The aqueous layer was basified to about pH 12 using NaOH (1 N) and the aqueous layer extracted with DCM (150 mL). The organic layer was washed with brine (30 mL), dried over MgSO$_4$, filtered and concentrated under vacuum to give (S)-3-amino-1-(1-(3-chloro-5-(trifluoromethyl)pyridin-2-yl)piperidin-4-yl)pyrrolidin-2-one (3.1 g, 100%).

Step D: To a solution of (S)-3-amino-1-(1-(3-chloro-5-(trifluoromethyl)pyridin-2-yl)piperidin-4-yl)pyrrolidin-2-one (0.15 g, 0.41 mmol) in DMF (10 mL) was added N-ethyl-N-isopropylpropan-2-amine (0.160 g, 1.24 mmol) and 6-chloropyridazine-3-carbonitrile (0.173 g, 1.24 mmol) and the reaction was heated to 90° C. overnight. The reaction was diluted with EtOAc (150 mL) and washed with water (100 mL), and brine (10 mL), dried over MgSO$_4$, filtered and concentrated under vacuum. The material was purified on silica, using 1:1 EtOAc:DCM as eluent to yield a solid, which was further triturated with diethyl ether to yield (S)-6-(1-(1-(3-chloro-5-(trifluoromethyl)pyridin-2-yl)piperidin-4-yl)-2-oxopyrrolidin-3-ylamino)pyridazine-3-carbonitrile (0.028 g, 0.060 mmol, 14% yield). Mass spectrum (apci) m/z=466.0, 467.9 (M+H).

Example 151

S)-1-(1-(3-chloro-5-(trifluoromethyl)pyridin-2-yl)piperidin-4-yl)-3-(2-fluoro-4-(pyrrolidine-1-carbonyl)phenoxy)pyrrolidin-2-one

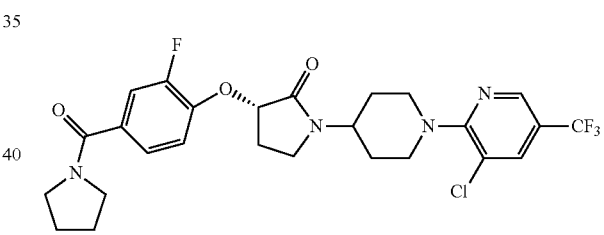

(Step A: To a solution of (R)-tert-butyl 4-(3-(methylsulfonyloxy)-2-oxopyrrolidin-1-yl)piperidine-1-carboxylate (Preparation D; 2 g, 5.5 mmol) in DMF (20 mL) was added potassium carbonate (0.99 g, 7.2 mmol) and methyl 3-fluoro-4-hydroxybenzoate (1.1 g, 6.6 mmol) and the reaction was heated to 60° C. overnight. The reaction was diluted with water (100 mL) and extracted with EtOAc (100 mL). The organic layer was washed with 1 N NaOH (20 mL), and brine (20 mL), dried over MgSO$_4$, filtered and concentrated under vacuum to give (S)-tert-butyl 4-(3-(2-fluoro-4-(methoxycarbonyl)phenoxy)-2-oxopyrrolidin-1-yl)piperidine-1-carboxylate (2 g, 83%).

Step B: To a solution of (S)-tert-butyl 4-(3-(2-fluoro-4-(methoxycarbonyl)phenoxy)-2-oxopyrrolidin-1-yl)piperidine-1-carboxylate (2 g, 4.6 mmol) in EtOAc (20 mL) was added hydrogen chloride in isopropanol (5-6 M) (9.2 mL, 46 mmol) and the reaction was stirred overnight at ambient temperature. The reaction was concentrated under vacuum to give (S)-methyl 3-fluoro-4-(2-oxo-1-(piperidin-4-yl)pyrrolidin-3-yloxy)benzoate hydrochloride (1.5 g, 100%), which was used crude in the next reaction Step C: To a solution of (S)-methyl 3-fluoro-4-(2-oxo-1-(piperidin-4-yl)pyrrolidin-3-yloxy)benzoate hydrochloride (0.1 g, 0.29 mmol) in DMF (10 mL) was added N-ethyl-N-isopropylpropan-2-amine (0.543 mL, 2.97 mmol) and 2,3-dichloro-5-(trifluoromethyl)pyridine (0.193 g, 0.892 mmol) and the reaction was stirred overnight at ambient temperature. The reaction was diluted with EtOAc (50 mL) and washed with water (20 mL), and brine (20 mL), dried over MgSO$_4$, filtered and concentrated under vacuum. The material was purified on silica, using a gradient of DCM to 10% EtOAc/DCM as eluent to yield (S)-methyl 4-(1-(1-(3-chloro-5-(trifluoromethyl)pyridin-2-yl)piperidin-4-yl)-2-oxopyrrolidin-3-yloxy)-3-fluorobenzoate (0.10 g, 63% yield).

Step D: To a solution of (S)-methyl 4-(1-(1-(3-chloro-5-(trifluoromethyl)pyridin-2-yl)piperidin-4-yl)-2-oxopyrrolidin-3-yloxy)-3-fluorobenzoate (0.1 g, 0.19 mmol) in THF (2 mL) was added LiOH (3 M, 2 mL) and the reaction was stirred overnight at ambient temperature. The THF was removed with a stream of nitrogen. The aqueous layer was acidified with 1 N HCl to about pH 1 and the solid that formed was filtered and washed with water. The solid was dried under vacuum to yield (S)-4-(1-(1-(3-chloro-5-(trifluoromethyl)pyridin-2-yl)piperidin-4-yl)-2-oxopyrrolidin-3-yloxy)-3-fluorobenzoic acid (0.040 g, 0.081 mmol, 42% yield).

Step E: To a solution of (S)-4-(1-(1-(3-chloro-5-(trifluoromethyl)pyridin-2-yl)piperidin-4-yl)-2-oxopyrrolidin-3-yloxy)-3-fluorobenzoic acid (0.040 g, 0.080 mmol) and pyrrolidine (0.028 g, 0.40 mmol) in DMF (1 mL) was added HTBU (0.060 g, 0.16 mmol) and the reaction was stirred overnight at ambient temperature. The reaction was diluted with EtOAc (20 mL) and washed with 1 N HCl (5 mL), 1 N NaOH (5 mL), and brine (5 mL), and the combined organic phases were dried over MgSO$_4$, and concentrated under vacuum. The material was purified on silica, using EtOAc as eluent to yield (S)-1-(1-(3-chloro-5-(trifluoromethyl)pyridin-2-yl)piperidin-4-yl)-3-(2-fluoro-4-(pyrrolidine-1-carbonyl)phenoxy)pyrrolidin-2-one (0.0026 g, 0.005 mmol, 6% yield). Mass spectrum (apci) m/z=555.0 (M+H).

Example 152

(S)-4-(1-(1-(3-chloro-5-(trifluoromethyl)pyridin-2-yl)piperidin-4-yl)-2-oxopyrrolidin-3-ylamino)-3-fluorobenzonitrile

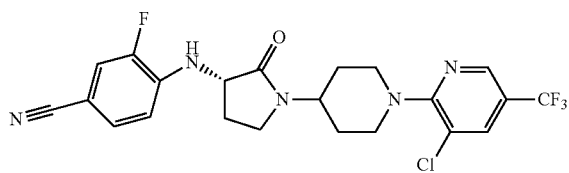 [SMILES: N#Cc1ccc(N[C@H]2CCN(C3CCN(c4ncc(C(F)(F)F)cc4Cl)CC3)C2=O)c(F)c1]

To a solution of (S)-3-amino-1-(1-(3-chloro-5-(trifluoromethyl)pyridin-2-yl)piperidin-4-yl)pyrrolidin-2-one (Example 150, Step C; 0.30 g, 0.83 mmol) in DMSO (3 mL) was added 3,4-difluorobenzonitrile (0.35 g, 2.5 mmol) and potassium carbonate (0.34 g, 2.5 mmol) and the reaction was heated to 130° C. for 6 hours. The reaction was diluted with EtOAc (20 mL) and washed with water (20 mL), and brine (20 mL), and the combined organic phases were dried over MgSO$_4$, filtered and concentrated under vacuum. The crude material was purified on silica using a gradient of 1:9 to 1:4 EtOAc:DCM as eluent to give a solid, which was further triturated with DCM to give (S)-4-(1-(1-(3-chloro-5-(trifluoromethyl)pyridin-2-yl)piperidin-4-yl)-2-oxopyrrolidin-3-ylamino)-3-fluorobenzonitrile (0.006 g, 0.012 mmol, 2% yield). Mass spectrum (apci) m/z=482.0, 483.9 (M+H).

Example 153

(S)-1-(1-(5-chloro-3-fluoropyridin-2-yl)piperidin-4-yl)-3-(2-fluoro-4-((S)-3-hydroxypyrrolidine-1-carbonyl)phenoxy)pyrrolidin-2-one

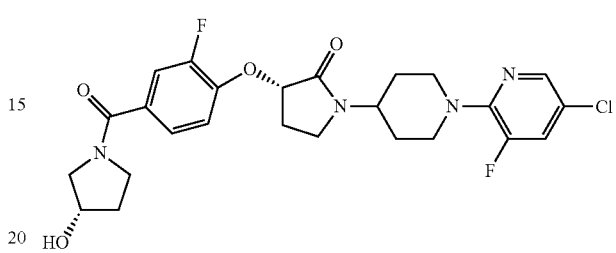

Step A: To a solution of (S)-methyl 3-fluoro-4-(2-oxo-1-(piperidin-4-yl)pyrrolidin-3-yloxy)benzoate hydrochloride (Example 151, Step B; 2.0 g, 5.9 mmol) in DMF (3 mL) was added N-ethyl-N-isopropylpropan-2-amine (3.8 g, 30 mmol) and 5-chloro-2,3-difluoropyridine (2.7 g, 18 mmol) and the reaction was heated to 60° C. overnight. The reaction was next diluted with EtOAc (30 mL) and washed with water (30 mL), and brine (30 mL), and the combined organic phases were dried over MgSO$_4$, filtered and concentrated under vacuum. The crude material was purified on silica using a gradient of DCM to 1:19 EtOAc:DCM as eluent to yield (S)-methyl 4-(1-(1-(5-chloro-3-fluoropyridin-2-yl)piperidin-4-yl)-2-oxopyrrolidin-3-yloxy)-3-fluorobenzoate (1.5 g, 54%)

Step B: To a solution of (S)-methyl 4-(1-(1-(5-chloro-3-fluoropyridin-2-yl)piperidin-4-yl)-2-oxopyrrolidin-3-yloxy)-3-fluorobenzoate (1.5 g, 3.2 mmol) in THF (30 mL) was added 3 N lithium hydroxide (4.3 mL, 13 mmol) and the reaction was stirred overnight at ambient temperature. Additional 3 N LiOH (4.3 mL, 13 mmol) was added, and the reaction was stirred for an additional 3 hours. The THF was removed with a stream of nitrogen. The aqueous layer was acidified by addition of HCl (1 N) and the solid that formed was filtered and washed with water. The solid was dried under vacuum to yield (S)-4-(1-(1-(5-chloro-3-fluoropyridin-2-yl)piperidin-4-yl)-2-oxopyrrolidin-3-yloxy)-3-fluorobenzoic acid (1.3 g, 2.9 mmol, 89% yield).

Step C: To a solution of (S)-4-(1-(1-(5-chloro-3-fluoropyridin-2-yl)piperidin-4-yl)-2-oxopyrrolidin-3-yloxy)-3-fluorobenzoic acid (0.10 g, 0.22 mmol) in DMF (2 mL) was added HATU (0.17 g, 0.44 mmol) and N-ethyl-N-isopropylpropan-2-amine (0.12 mL, 0.66 mmol) and the reaction was stirred for 20 minutes at ambient temperature. (S)-Pyrrolidin-3-ol (0.058 g, 0.66 mmol) was added, and the reaction was stirred for 2 hours at ambient temperature. The reaction was diluted with EtOAc (30 mL) and washed with HCl (1 N, 10 mL), NaOH (1 N, 10 mL), water (10 mL), and brine (10 mL), and the combined organic phases were dried over MgSO$_4$, filtered and concentrated under vacuum. The crude material was purified by reverse preparative HPLC. The combined fractions were diluted with EtOAc (50 mL) and washed with 1N NaOH (10 mL), water (10 mL), and brine (10 mL), and the combined organic phases were dried over MgSO$_4$, filtered and concentrated under vacuum to give (S)-1-(1-(5-chloro-3-fluoropyridin-2-yl)piperidin-4-yl)-3-(2-fluoro-4-((S)-3-hydroxypyrrolidine-1-carbonyl)phenoxy)pyrrolidin-2-one (0.0353 g, 0.0678 mmol, 30.6% yield). Mass spectrum (apci) m/z=521.0 (M+H).

Example 154

(S)-4-(1-(1-(5-chloro-3-fluoropyridin-2-yl)piperidin-4-yl)-2-oxopyrrolidin-3-yloxy)-3-fluoro-N-(2-hydroxyethyl)-N-methylbenzamide

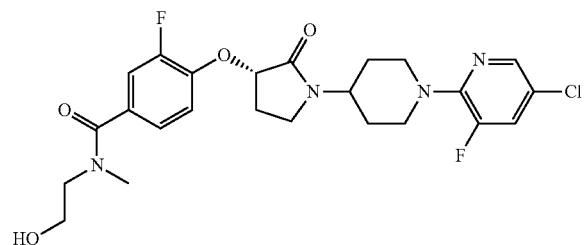 [SMILES: CN(CCO)C(=O)c1ccc(O[C@H]2CCN(C3CCN(c4ncc(Cl)cc4F)CC3)C2=O)c(F)c1]

To a solution of (S)-4-(1-(1-(5-chloro-3-fluoropyridin-2-yl)piperidin-4-yl)-2-oxopyrrolidin-3-yloxy)-3-fluorobenzoic acid (Example 153, Step B; 0.1 g, 0.22 mmol) in DMF (2 mL) was added HATU (0.17 g, 0.44 mmol) and N-ethyl-N-isopropylpropan-2-amine (0.12 mL, 0.66 mmol) and the reaction was stirred for 20 minutes at ambient temperature. 2-(Methylamino)ethanol (0.050 g, 0.66 mmol) was added, and the reaction was stirred for 2 hours at ambient temperature. The reaction was diluted with EtOAc (30 mL) and washed with HCl (1 N, 10 mL), NaOH (1 N, 10 mL), water (10 mL), and brine (10 mL), and the combined organic phases were dried over MgSO$_4$, filtered and concentrated under vacuum. The crude material was purified by reverse phase HPLC. The combined fractions were diluted with EtOAc (50 mL) and washed with 1 N NaOH (10 mL), water (10 mL), and brine (10 mL), and the combined organic phases were dried over MgSO$_4$, filtered and concentrated under vacuum to give (S)-4-(1-(1-(5-chloro-3-fluoropyridin-2-yl)piperidin-4-yl)-2-oxopyrrolidin-3-yloxy)-3-fluoro-N-(2-hydroxyethyl)-N-methylbenzamide (0.033 g, 0.064 mmol, 29% yield). Mass spectrum (apci) m/z=509.0 (M+H).

Example 155

(S)-1-(1-(5-chloro-3-fluoropyridin-2-yl)piperidin-4-yl)-3-(2-fluoro-4-((R)-3-hydroxypyrrolidine-1-carbonyl)phenoxy)pyrrolidin-2-one

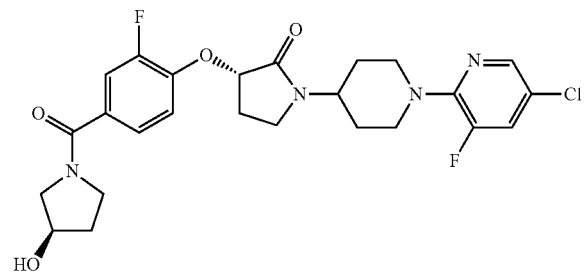 [SMILES: O=C(c1ccc(O[C@H]2CCN(C3CCN(c4ncc(Cl)cc4F)CC3)C2=O)c(F)c1)N1CC[C@@H](O)C1]

To a solution of (S)-4-(1-(1-(5-chloro-3-fluoropyridin-2-yl)piperidin-4-yl)-2-oxopyrrolidin-3-yloxy)-3-fluorobenzoic acid (Example 153, Step B; 0.10 g, 0.22 mmol) in DMF (2 mL) was added HATU (0.17 g, 0.44 mmol) and N-ethyl-N-isopropylpropan-2-amine (0.12 mL, 0.66 mmol) and the reaction was stirred for 20 minutes at ambient temperature. (R)-pyrrolidin-3-ol hydrochloride (0.058 g, 0.66 mmol) was added and the reaction was stirred for 2 hours at ambient temperature. The reaction was diluted with EtOAc (30 mL), washed with HCl (1N, 10 mL), NaOH (1N, 10 mL), water (10 mL), and brine (10 mL), dried over MgSO$_4$, filtered and concentrated under vacuum. The crude material was purified by reverse phase HPLC. The combined fractions were diluted with EtOAc (50 mL) and washed with 1 N NaOH (10 mL), water (10 mL), and brine (10 mL), dried over MgSO$_4$, filtered and concentrated under vacuum to give (S)-1-(1-(5-chloro-3-fluoropyridin-2-yl)piperidin-4-yl)-3-(2-fluoro-4-((R)-3-hydroxypyrrolidine-1-carbonyl)phenoxy)pyrrolidin-2-one (0.038 g, 0.072 mmol, 33% yield). Mass spectrum (apci) m/z=521.0 (M+H).

Example 156

(S)-1-(1-(3-chloro-5-(hydroxymethyl)pyridin-2-yl)piperidin-4-yl)-3-(2-fluoro-4-(methylsulfonyl)phenylamino)pyrrolidin-2-one

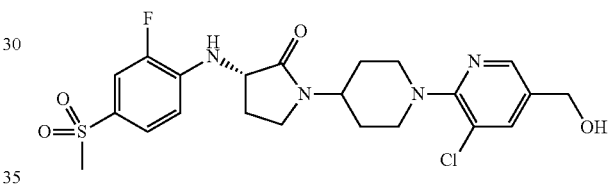

Step A: To a solution of (S)-3-(2-fluoro-4-(methylsulfonyl)phenylamino)-1-(piperidin-4-yl)pyrrolidin-2-one (Preparation E; 1.0 g, 2.8 mmol) in DMF (30 mL) was added N-ethyl-N-isopropylpropan-2-amine (1.1 g, 8.4 mmol) and methyl 5,6-dichloronicotinate (1.7 g, 8.4 mmol) and the reaction was stirred overnight at ambient temperature. The reaction was diluted with EtOAc (250 mL) and washed with water (100 mL), and brine (50 mL), and the combined organic phases were dried over MgSO$_4$, filtered and concentrated under vacuum. The crude material was purified on silica using a gradient of 1:9 to 1:4 EtOAc:DCM as eluent to yield a solid, which was further precipitated from using isopropanol to give (S)-methyl 5-chloro-6-(4-(3-(2-fluoro-4-(methylsulfonyl)phenylamino)-2-oxopyrrolidin-1-yl)piperidin-1-yl)nicotinate (0.70 g, 47% yield).

Step B: To a solution of (S)-methyl 5-chloro-6-(4-(3-(2-fluoro-4-(methylsulfonyl)phenylamino)-2-oxopyrrolidin-1-yl)piperidin-1-yl)nicotinate (0.20 g, 0.38 mmol) in THF (20 mL) was added LiBH$_4$ (2 M in THF, 0.19 mL, 0.38 mmol) and the reaction was stirred overnight at ambient temperature. The reaction was diluted with DCM (50 mL) and the organic layer was washed with water (20 mL), 1 N HCl (10 mL), 1 N NaOH (10 mL) and brine (10 mL), and the combined organic phases were dried over MgSO$_4$, filtered and concentrated under vacuum. The crude material was purified on silica using EtOAc as eluent to yield a solid, which was further triturated with isopropanol/hexanes to give (S)-1-(1-(3-chloro-5-(hydroxymethyl)pyridin-2-yl)piperidin-4-yl)-3-(2-fluoro-4-

(methylsulfonyl)phenylamino)pyrrolidin-2-one (0.021 g, 0.043 mmol, 11% yield). Mass spectrum (apci) m/z=497.0 (M+H$^+$).

Example 157

(S)-5-chloro-6-(4-(3-(2-fluoro-4-(methylsulfonyl)phenylamino)-2-oxopyrrolidin-1-yl)piperidin-1-yl)-N,N-dimethylnicotinamide

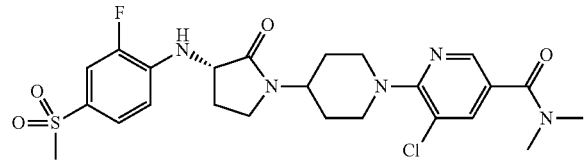 [SMILES: CN(C)C(=O)c1cnc(N2CCC(N3CC[C@H](Nc4ccc(S(C)(=O)=O)cc4F)C3=O)CC2)c(Cl)c1]

Step A: To a solution of (S)-methyl 5-chloro-6-(4-(3-(2-fluoro-4-(methylsulfonyl)phenylamino)-2-oxopyrrolidin-1-yl)piperidin-1-yl)nicotinate (Example 156, Step A; 0.50 g, 0.95 mmol) in THF (20 mL) was added a 3 M solution of LiOH (3 mL) and the reaction was stirred overnight at ambient temperature. The THF was removed with a stream of nitrogen. The aqueous layer was acidified to pH 1 by the addition of 1 N HCl. The solids that formed were filtered, washed with water and dried under vacuum to give (S)-5-chloro-6-(4-(3-(2-fluoro-4-(methylsulfonyl)phenylamino)-2-oxopyrrolidin-1-yl)piperidin-1-yl)nicotinic acid (0.40 g, 82% yield).

Step B: To a solution of (S)-5-chloro-6-(4-(3-(2-fluoro-4-(methylsulfonyl)phenylamino)-2-oxopyrrolidin-1-yl)piperidin-1-yl)nicotinic acid (0.40 g, 0.38 mmol) in DCM (20 mL) was added sulfurous dichloride (0.28 g, 2.3 mmol) and DMF (1 drop) and the reaction was stirred at ambient temperature for 3 hours. The reaction was concentrated under vacuum to give (S)-5-chloro-6-(4-(3-(2-fluoro-4-(methylsulfonyl)phenylamino)-2-oxopyrrolidin-1-yl)piperidin-1-yl)nicotinoyl chloride (0.41 g, 100%). The material was used directly in the next step without purification.

Step C: To a solution of (S)-5-chloro-6-(4-(3-(2-fluoro-4-(methylsulfonyl)phenylamino)-2-oxopyrrolidin-1-yl)piperidin-1-yl)nicotinoyl chloride (0.15 g, 0.28 mmol) in 5 mL of DMF/ACN/THF (1:1:1) was added dimethylamine (2 M solution in THF, 1.4 mL, 2.8 mmol) and the reaction was stirred at ambient temperature for 4 hours. The reaction was diluted with EtOAc (100 mL) and the organic layer was washed with water (20 mL) and brine (20 mL), and the organic layer was dried over MgSO$_4$, and concentrated under vacuum. The material was triturated with isopropanol (about 6 mL) to give (S)-5-chloro-6-(4-(3-(2-fluoro-4-(methylsulfonyl)phenylamino)-2-oxopyrrolidin-1-yl)piperidin-1-yl)-N,N-dimethylnicotinamide (0.059 g, 0.11 mmol, 38% yield). Mass spectrum (apci) m/z=538.0 (M+H).

Example 158

(S)-3-(2-fluoro-4-(methylsulfonyl)phenylamino)-1-(1-(2-(trifluoromethyl)pyrimidin-5-yl)piperidin-4-yl)pyrrolidin-2-one

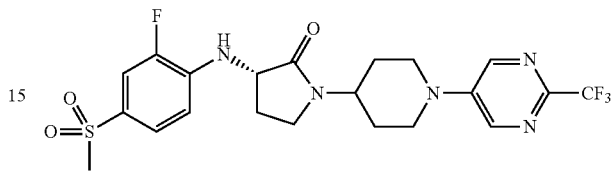

A mixture of (S)-3-(2-fluoro-4-(methylsulfonyl)phenylamino)-1-(piperidin-4-yl)pyrrolidin-2-one (Preparation E; 0.20 g, 0.56 mmol), 5-bromo-2-(trifluoromethyl)pyrimidine (0.15 g, 0.68 mmol), (S)-(−)-2,2'-bis(di-p-tolylphosphino)-1,1'-binaphthyl (0.076 g, 0.11 mmol), Pd(OAc)$_2$ (0.025 g, 0.11 mmol), and Cs$_2$CO$_3$ (0.92 g, 2.8 mmol) were combined in degassed toluene (6 mL) and stirred in a sealed tube at 110° C. overnight. The solution was cooled, quenched with water, extracted with EtOAc, dried over MgSO$_4$, and concentrated. Flash chromatography of the crude product on silica followed by trituration of the isolated material with 9:1 hexanes:DCM gave a white solid that was filtered and dried. The material was characterized as (S)-3-(2-fluoro-4-(methylsulfonyl)phenylamino)-1-(1-(2-(trifluoromethyl)pyrimidin-5-yl)piperidin-4-yl)pyrrolidin-2-one (0.064 g, 0.13 mmol, 23% yield). Mass spectrum (apci) m/z=502.1 (M+H). Optical purity was not determined.

Example 159

(S)-1-(1-(2-ethylpyrimidin-5-yl)piperidin-4-yl)-3-(2-fluoro-4-(methylsulfonyl)phenylamino)pyrrolidin-2-one

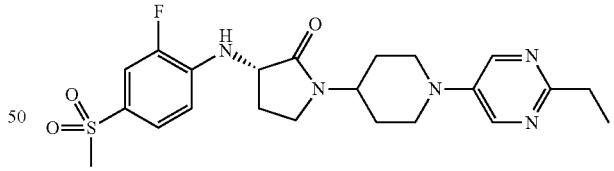

A mixture of (S)-3-(2-fluoro-4-(methylsulfonyl)phenylamino)-1-(piperidin-4-yl)pyrrolidin-2-one (Preparation E; 0.20 g, 0.56 mmol), 5-bromo-2-ethylpyrimidine (0.13 g, 0.68 mmol), Binap-rac (0.035 g, 0.056 mmol), Pd(OAc)$_2$ (0.013 g, 0.056 mmol), and Cs$_2$CO$_3$ (0.92 g, 2.8 mmol) were combined in degassed toluene (6 mL) and stirred in a sealed tube at 110° C. overnight. The solution was cooled, quenched with water, extracted with EtOAc, dried over MgSO$_4$, and concentrated. Flash chromatography (2% MeOH in EtOAc) of the crude material, followed by trituration of the crude product with 9:1 hexanes:DCM gave a white solid that was filtered and dried. The material was characterized as (S)-1-(1-(2-ethylpyrimidin-5-yl)piperidin-4-yl)-3-(2-fluoro-4-(methylsulfonyl)phenylamino)pyrrolidin-2-one (0.010 g, 0.023 mmol, 4% yield).

¹H NMR (400 MHz, CDCl₃) δ 1.20 (t, 3H), 1.61-1.92 (m, 5H), 2.47 (q, 2H), 2.60-2.70 (m, 1H), 2.90-3.03 (m, 2H), 3.03 (s, 3H), 3.30-3.47 (m, 2H), 4.10-4.17 (m, 1H), 4.25-4.38 (m, 1H), 4.83-4.92 (m, 2H), 5.10 (s, 1H), 6.80 (t, 1H), 7.55 (d, 1H), 7.60 (d, 1H), 7.70 (s, 2H). Optical purity was not determined.

Example 160

(S)-3-(2-fluoro-4-(methylsulfonyl)phenylamino)-1-(1-(5-methoxypyrazin-2-yl)piperidin-4-yl)pyrrolidin-2-one

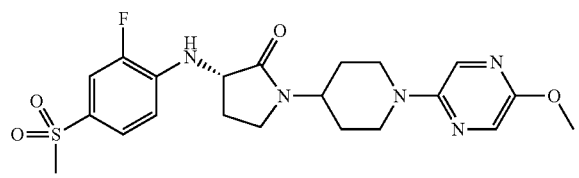 [SMILES: COc1cnc(N2CCC(N3CC[C@H](Nc4ccc(S(C)(=O)=O)cc4F)C3=O)CC2)cn1]

(S)-3-(2-Fluoro-4-(methylsulfonyl)phenylamino)-1-(piperidin-4-yl)pyrrolidin-2-one (Preparation E; 0.050 g, 0.14 mmol), 2-bromo-5-methoxypyrazine (0.032 g, 0.17 mmol), NaOtBu (0.041 g, 0.42 mmol), Pd(OAc)₂ (0.005 g, 0.02 mmol), and 2-dicyclohexylphosphino-2'-(N,N-dimethylamino)-biphenyl (DavePHOS) (0.017 g, 0.042 mmol) were added to an argon-filled sealable flask. Toluene (1.5 mL) was added and the mixture was purged with bubbling argon for 5 minutes. The vessel was sealed and the mixture was stirred at 110° C. overnight. The mixture was cooled to ambient temperature, diluted with THF (12 mL), and stirred for 15 minutes. The mixture was filtered through GF/F paper and concentrated. The residue was purified by silica chromatography (EtOAc) to afford (S)-3-(2-fluoro-4-(methylsulfonyl)phenylamino)-1-(1-(5-methoxypyrazin-2-yl)piperidin-4-yl)pyrrolidin-2-one (0.031 g, 0.067 mmol, 48% yield). Mass spectrum (apci) m/z=464.2 (M+H). Optical purity was not determined.

Example 161

(S)-1-(1-(3,5-dichloropyrazin-2-yl)piperidin-4-yl)-3-(6-(methylsulfonyl)pyridin-3-ylamino)pyrrolidin-2-one

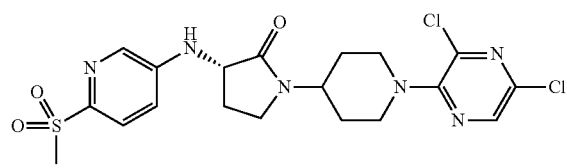 [SMILES: CS(=O)(=O)c1ccc(N[C@H]2CCN(C3CCN(c4ncc(Cl)nc4Cl)CC3)C2=O)cn1]

Step A: (S)-Benzyl 4-(3-amino-2-oxopyrrolidin-1-yl)piperidine-1-carboxylate (Preparation E, Step D; 0.26 g, 0.82 mmol), 5-bromo-2-(methylsulfonyl)pyridine (0.26 g, 1.10 mmol), Pd₂dba₃ (0.038 g, 0.041 mmol), Binap-rac (0.051 g, 0.082 mmol), and cesium carbonate (0.43 g, 1.30 mmol) were added to an argon-filled sealable flask. DMA (7.5 mL) was added and the system was purged with bubbling argon for 5 minutes. The system was sealed and stirred at 100° C. overnight. The mixture was cooled to ambient temperature and diluted with THF (60 mL) and stirred for 30 minutes. The mixture was filtered through GF/F paper and concentrated under vacuum. The residue was purified by silica chromatography (EtOAc) to afford (S)-benzyl 4-(3-(6-(methylsulfonyl)pyridin-3-ylamino)-2-oxopyrrolidin-1-yl)piperidine-1-carboxylate (0.23 g, 0.49 mmol, 51%).

Step B: (S)-Benzyl 4-(3-(6-(methylsulfonyl)pyridin-3-ylamino)-2-oxopyrrolidin-1-yl)piperidine-1-carboxylate (0.23 g, 0.49 mmol) was dissolved in MeOH (5 mL) and cooled to 0° C. The material was purged with N₂ by three vacuum pump/N₂ balloon cycles. Palladium on carbon (10 wt. % dry basis, wet, Degussa type, 0.053 g, 0.49 mmol) was added and the system was purged with 1 atm H₂ by three vacuum pump/H₂ balloon cycles. The reaction continued to stir under H₂ until the starting material was consumed. The mixture was filtered through GF/F paper and concentrated to give (S)-3-(6-(methylsulfonyl)pyridin-3-ylamino)-1-(piperidin-4-yl)pyrrolidin-2-one (0.17 g, 0.51 mmol, 100% yield).

Step C: (S)-3-(6-(Methylsulfonyl)pyridin-3-ylamino)-1-(piperidin-4-yl)pyrrolidin-2-one (0.076 g, 0.22 mmol) and 2,5-dichloropyrazine (0.054 g, 0.36 mmol) were dissolved in NMP (0.45 mL) and treated with DIEA (0.098 mL, 0.56 mmol). The mixture was stirred at 80° C. overnight and then cooled to ambient temperature. The reaction mixture was partitioned between EtOAc (40 mL) and H₂O (20 mL). The mixture was filtered through a 0.45 μm nylon membrane and the solids were washed with EtOAc and then dried under high vacuum to provide (S)-1-(1-(5-chloropyrazin-2-yl)piperidin-4-yl)-3-(6-(methylsulfonyl)pyridin-3-ylamino)pyrrolidin-2-one (0.030 g, 0.067 mmol, 30%).

Step D: N-Chlorosuccinimide (0.013 g, 0.098 mmol) was added to a suspension of (S)-1-(1-(5-chloropyrazin-2-yl)piperidin-4-yl)-3-(6-(methylsulfonyl)pyridin-3-ylamino)pyrrolidin-2-one (0.034 g, 0.075 mmol) in AcOH (0.3 mL). The mixture was stirred at ambient temperature for 1 hour and then at 50° C. for 1 hour. Acetic acid was removed with a stream of nitrogen. The residue was vigorously stirred in a mixture of 10% Na₂S₂O₃ (1 mL) and EtOAc (1 mL) for 40 minutes. The mixture was partitioned between EtOAc (30 mL) and saturated NaHCO₃ (20 mL). Solids which did not dissolve were collected by filtration of the suspension through a 0.45 μm nylon membrane to provide (S)-1-(1-(3,5-dichloropyrazin-2-yl)piperidin-4-yl)-3-(6-(methylsulfonyl)pyridin-3-ylamino)pyrrolidin-2-one (0.011 g, 0.023 mmol, 30%). Mass spectrum (apci) m/z=485.0 (M+H) 487.0. Optical purity of the product was not determined.

Example 162

(3S)-1-(1-(5-chloropyrazin-2-yl)-3,3-dimethylpiperidin-4-yl)-3-(2-fluoro-4-(methylsulfonyl)phenylamino)pyrrolidin-2-one

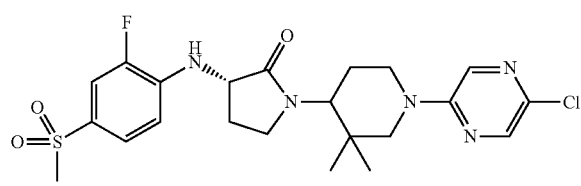 [SMILES: CC1(C)CN(c2cnc(Cl)cn2)CCC1N1CC[C@H](Nc2ccc(S(C)(=O)=O)cc2F)C1=O]

Step A: Sodium hydride (5.73 g, 143 mmol, 60% dispersion in mineral oil) was added to tert-butyl 4-oxopiperidine-1-carboxylate (13.6 g, 68.3 mmol) in THF (350 mL) at 0° C. and the reaction was stirred for 45 minutes. MeI (10.6 mL, 171 mmol) was added dropwise. The solution was stirred for 1 hour and then warmed to ambient temperature with overnight stirring. The solution was quenched with saturated ammonium chloride solution and extracted with EtOAc. The organic layer was washed with water, dried, and concentrated to give tert-butyl 3,3-dimethyl-4-oxopiperidine-1-carboxylate (7.96 g, 35.0 mmol, 51% yield) as a white solid.

Step B: To a 0° C. solution of tert-butyl 3,3-dimethyl-4-oxopiperidine-1-carboxylate (1.76 g, 7.74 mmol) and (S)-4-amino-2-(benzyloxycarbonylamino)butanoic acid (1.95 g, 7.74 mmol) in THF (20 mL) and water (3 mL) was added NaCNBH$_3$ (0.48 g, 7.7 mmol). This mixture was stirred at 60° C. for 2 days. The reaction was then evaporated to a solid to give the crude (2S)-2-(benzyloxycarbonylamino)-4-(1-(tert-butoxycarbonyl)-3,3-dimethylpiperidin-4-ylamino)butanoic acid. This material was taken on directly to the next step.

Step C: To a solution of (2S)-2-(benzyloxycarbonylamino)-4-(1-(tert-butoxycarbonyl)-3,3-dimethylpiperidin-4-ylamino)butanoic acid (3.59 g, 7.74 mmol) in DMF (20 mL) was added DIEA (4.1 mL, 23 mmol) and HBTU (3.5 g, 9.3 mmol). The mixture stirred at ambient temperature overnight. The mixture was poured into 1 N NaOH solution and extracted into ethyl acetate. The organic layer was washed with 1 N HCl solution and brine, dried over MgSO$_4$, filtered and concentrated under vacuum. Flash chromatography (7:3 EtOAc:hexanes) gave tert-butyl 4-((S)-3-(benzyloxycarbonylamino)-2-oxopyrrolidin-1-yl)-3,3-dimethylpiperidine-1-carboxylate (0.81 g, 1.8 mmol, 23%) as a white solid.

Step D: tert-Butyl 4-((S)-3-(benzyloxycarbonylamino)-2-oxopyrrolidin-1-yl)-3,3-dimethylpiperidine-1-carboxylate (0.81 g, 1.8 mmol) was dissolved in methanol (20 mL) and the mixture was purged with N$_2$ by three vacuum pump/N$_2$ balloon cycles. 10% Palladium on carbon (dry basis, wet, Degussa type, 0.5 g) was added and the system was purged with 1 atm H$_2$ by three vacuum pump/H$_2$ balloon cycles. The reaction was stirred under the H$_2$ atmosphere until the starting material was consumed. The mixture was filtered through Celite® and concentrated to afford tert-butyl 4-((S)-3-amino-2-oxopyrrolidin-1-yl)-3,3-dimethylpiperidine-1-carboxylate (0.59 g, 1.9 mmol, 100% yield) as a white solid.

Step E: tert-Butyl 4-((S)-3-amino-2-oxopyrrolidin-1-yl)-3,3-dimethylpiperidine-1-carboxylate (0.40 g, 1.3 mmol) was dissolved in DMSO (5 mL). 1,2-Difluoro-4-(methylsulfonyl)benzene (0.32 g, 1.7 mmol) and powdered Na$_2$CO$_3$ (0.18 g, 1.7 mmol) were added. The reaction mixture was bubbled under nitrogen for 15 minutes. The mixture stirred overnight at 120° C. The reaction mixture was cooled to ambient temperature and partitioned between brine and ethyl acetate. The organic layer was washed with brine, dried over MgSO$_4$, and concentrated. Flash chromatography of the crude material on silica gel followed by reverse phase HPLC purification gave tert-butyl 4-((S)-3-(2-fluoro-4-(methylsulfonyl)phenylamino)-2-oxopyrrolidin-1-yl)-3,3-dimethylpiperidine-1-carboxylate (0.10 g, 0.21 mmol, 16% yield) as a white solid.

Step F: tert-Butyl 4-((S)-3-(2-fluoro-4-(methylsulfonyl)phenylamino)-2-oxopyrrolidin-1-yl)-3,3-dimethylpiperidine-1-carboxylate (0.10 g, 0.21 mmol) was dissolved in DCM (5 mL). TFA (5 mL) was added and the reaction was stirred for 1 hour. The solution was concentrated, neutralized with saturated NaHCO$_3$ solution, and extracted with dichloromethane (3 times). The organic layers were combined, dried, filtered and concentrated to give (3S)-1-(3,3-dimethylpiperidin-4-yl)-3-(2-fluoro-4-(methylsulfonyl)phenylamino)pyrrolidin-2-one (0.020 g, 0.052 mmol, 25% yield) as a white solid.

Step G: To a solution of (3S)-1-(3,3-dimethylpiperidin-4-yl)-3-(2-fluoro-4-(methylsulfonyl)phenylamino)pyrrolidin-2-one (0.010 g, 0.026 mmol) in DMF (1 mL) was added 2,5-dichloropyrazine (0.0078 g, 0.052 mmol) and N-ethyl-N-isopropylpropan-2-amine (0.018 mL, 0.10 mmol) and the reaction was stirred for 3 hours at 100° C. The reaction was cooled, poured into brine and extracted into EtOAc. The organic layer was washed with water and brine, dried over MgSO$_4$, filtered and concentrated under vacuum. Reverse phase HPLC purification of the crude material gave (3S)-1-(1-(5-chloropyrazin-2-yl)-3,3-dimethylpiperidin-4-yl)-3-(2-fluoro-4-(methylsulfonyl)phenylamino)pyrrolidin-2-one (0.0023 g, 0.0046 mmol, 18% yield) as a white solid. $^1$H NMR (CDCl$_3$, 400 MHz) δ 1.02 (s, 3H), 1.03 (s, 3H), 1.81-1.91 (m 1H), 2.12-2.21 (m, 1H), 2.71-2.81 (m, 2H), 2.95-3.05 (m, 2H), 3.03 (m, 3H), 3.52 (dd, 2H), 3.97 (d, 1H), 4.15-4.23 (m, 2H), 4.47-4.51 (m, 1H), 5.12 (bs, 1H), 6.80 (t, 1H), 7.55 (d, 1H), 7.61 (d, 1H), 7.90 (s, 1H), 8.05 (s, 1H).

Example 163

(S)-3-(2,5-difluoro-4-(methylsulfonyl)phenoxy)-1'-(3-fluoro-5-(trifluoromethyl)pyridin-2-yl)-[1,4'-bipiperidin]-2-one

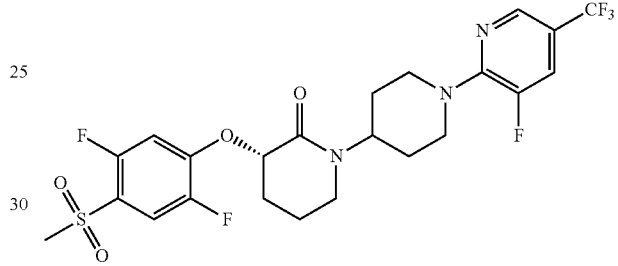

To a solution of (S)-3-(2,5-difluoro-4-(methylsulfonyl)phenoxy)-[1,4'-bipiperidin]-2-one (Preparation G; 30 mg, 0.077 mmol) in DMF was added 2,3-difluoro-5-(trifluoromethyl)pyridine (42 mg, 0.23 mmol) and DIEA (30 µL, 0.23 mmol) and the reaction was stirred at ambient temperature for 18 hours. The reaction was diluted with EtOAc and washed with brine, dried over Na$_2$SO$_4$ and concentrated in vacuo. The residue was purified by preparative TLC (EtOAc/DCM 4:1) to give (S)-3-(2,5-difluoro-4-(methyl-sulfonyl)phenoxy)-1'-(3-fluoro-5-(trifluoromethyl)pyridin-2-yl)-[1,4'-bipiperidin]-2-one as a white solid (20 mg, 0.035 mmol, 46% yield). Mass spectrum (apci) m/z=552.2 (M+H).

Example 164

(S)-1'-(5-chloropyrazin-2-yl)-3-(2,5-difluoro-4-(methylsulfonyl)phenoxy)-[1,4'-bipiperidin]-2-one

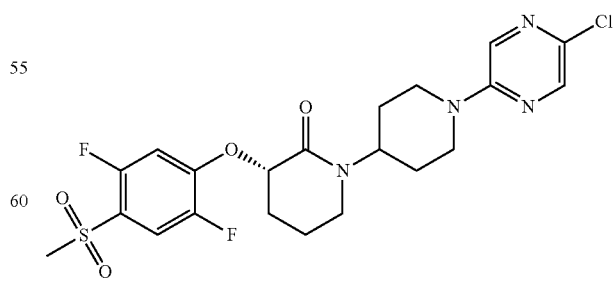

A stirred solution of (S)-3-(2,5-difluoro-4-(methylsulfonyl)phenoxy)-[1,4'-bipiperidin]-2-one (Preparation G; 40 mg, 0.103 mmol), DIEA (90 µL, 0.515 mmol), and 2,5- dichloropyrazine (30.7 mg, 0.206 mmol) in DMF (1 mL) was heated at 100° C. in a sealed tube for 2 hours. The mixture was cooled, diluted with EtOAc (25 mL), washed with brine, dried over Na$_2$SO$_4$ and concentrated in vacuo. The residue was purified by preparative TLC (EtOAc/DCM 4:1) to afford (S)-1'-(5-chloropyrazin-2-yl)-3-(2,5-difluoro-4-(methylsulfonyl)phenoxy)-[1,4'-bipiperidin]-2-one (2 mg, 0.004 mmol, 4% yield) as a white solid. Mass spectrum (apci) m/z=501.1 (M+H).

Example 165

(S)-3-(2,5-difluoro-4-(methylsulfonyl)phenoxy)-1'-(5-ethylpyrimidin-2-yl)-[1,4'-bipiperidin]-2-one

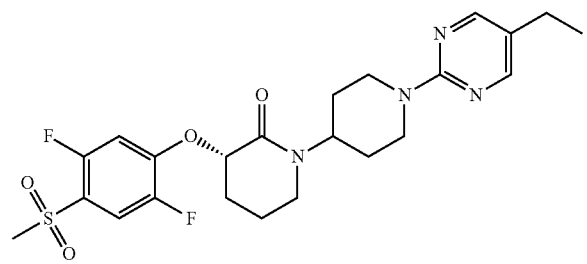 [SMILES: CCc1cnc(N2CCC(N3CCC[C@H](Oc4cc(F)c(S(C)(=O)=O)cc4F)C3=O)CC2)nc1]

A stirred solution of (S)-3-(2,5-difluoro-4-(methylsulfonyl)phenoxy)-[1,4'-bipiperidin]-2-one (Preparation G; 18 mg, 0.047 mmol), DIEA (24 μL mL, 0.14 mmol), and 2-chloro-5-ethylpyrimidine (20 mg, 0.14 mmol) in DMF (1 mL) was heated at 100° C. for 2 hours in a sealed tube. The mixture was cooled, diluted with EtOAc (25 mL), washed with brine, dried over Na$_2$SO$_4$ and concentrated in vacuo. The residue was purified by preparative TLC (EtOAc/DCM 4:1) to afford (S)-3-(2,5-difluoro-4-(methylsulfonyl)phenoxy)-1'-(5-ethylpyrimidin-2-yl)-[1,4'-bipiperidin]-2-one (9 mg, 0.018 mmol, 38% yield) as a white solid. Mass spectrum (apci) m/z=495.1.

Example 166

(S)-3-(2,5-difluoro-4-(methylsulfonyl)phenoxy)-1-(1-(3-fluoro-5-(trifluoromethyl)pyridin-2-yl)piperidin-4-yl)pyrrolidin-2-one

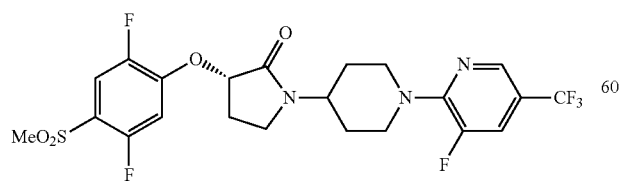

Prepared according to the method of Example 90. Mass spectrum (apci) m/z=538.2 (M+H).

What is claimed is:
1. A compound having the general formula I

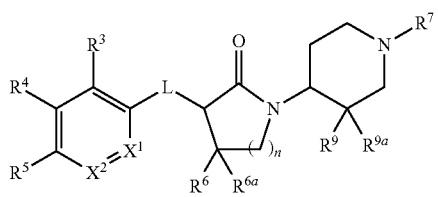

or a pharmaceutically acceptable salt or solvate thereof, wherein:
L is O, NH or N(1-3C)alkyl;
$X^1$ is N or $CR^1$ and $X^2$ is N or $CR^2$, wherein only one of $X^1$ and $X^2$ may be N;
$R^1$, $R^2$, $R^3$ and $R^4$ are independently selected from H, halogen, $CF_3$, (1-6C)alkyl and (1-6C)alkoxy;
$R^5$ is (1-3C)alkylsulfonyl, (3-6C)cycloalkylsulfonyl, (cyclopropylmethyl)sulfonyl, phenylsulfonyl, CN, Br, $CF_3$, triazolyl, (1-4C)alkoxycarbonyl, $R^xR^yNC(=O)—$, oxadiazolyl optionally substituted with (1-3C)alkyl, and tetrazolyl optionally substituted with (1-3C)alkyl;
or when $X^1$ is $CR^1$ and $X^2$ is $CR^2$, then $R^4$ and $R^5$ optionally together with the atoms to which they are attached form a 5-6 membered saturated heterocyclic ring having 1-2 ring heteroatoms independently selected from O and S and optionally substituted with an oxo group, wherein the S when present is optionally oxidized;
$R^x$ and $R^y$ are independently (1-4C)alkyl optionally substituted with OH, or
$R^x$ and $R^y$ together with the atom to which they are attached form a 5-6 membered saturated azacyclic ring optionally substituted with OH;
$R^6$ is H, OH or methyl;
$R^{6a}$ is H or methyl;
$R^7$ is a group having the structure

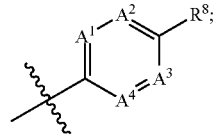

$A^1$ is N or $CR^a$;
$A^2$ is N or $CR^b$;
$A^3$ is N or $CR^c$;
$A^4$ is N or $CR^d$,
wherein at least one of $A^1$, $A^2$, $A^3$ and $A^4$ is N, and no more than two of $A^1$, $A^2$, $A^3$ and $A^4$ may be N;
$R^a$, $R^b$, $R^c$ and $R^d$ are independently H, $CF_3$, halogen, (1-4C)alkyl or CN;
$R^8$ is selected from hydrogen, halogen, $CF_3$, CN, (1-10C)alkyl, hydroxy(1-6C)alkyl, (1-6C)alkoxy, (1-6C alkyl)sulfanyl, phenyl, pyridyl, pyrimidyl, pyrazolyl, and di(1-3C)alkylcarbamyl, wherein each of said phenyl, pyridyl, pyrimidyl, and pyrazolyl is optionally substituted with one or more substituents independently selected from halogen, (1-4C)alkyl, (1-4C)alkoxy and $CF_3$;
$R^9$ and $R^{9a}$ are independently hydrogen or methyl; and
n is 1, 2 or 3.

2. The compound of claim 1, wherein:
L is O, NH or N(1-3C)alkyl;
$X^1$ is N or $CR^1$ and $X^2$ is N or $CR^2$, wherein only one of $X^1$ and $X^2$ may be N;
$R^1$, $R^2$, $R^3$ and $R^4$ are independently selected from H, halogen, $CF_3$, (1-6C)alkyl and (1-6C)alkoxy;
$R^5$ is (1-3C)alkylsulfonyl, (3-6C)cycloalkylsulfonyl, (cyclopropylmethyl)sulfonyl-, phenylsulfonyl-, CN, Br, $CF_3$, oxadiazolyl optionally substituted with (1-3C) alkyl, or tetrazolyl optionally substituted with (1-3C) alkyl;
or when $X^1$ is $CR^1$ and $X^2$ is $CR^2$, then $R^4$ and $R^5$ optionally together with the atoms to which they are attached form a 5-6 membered saturated heterocyclic ring having 1-2 ring heteroatoms independently selected from O and S and optionally substituted with an oxo group, wherein the S when present is optionally oxidized;
$R^6$ is H or OH;
$R^{6a}$ is H;
$R^7$ is a group having the structure:

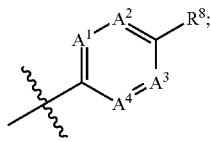

$A^1$ is N or $CR^a$;
$A^2$ is N or $CR^b$;
$A^3$ is N or $CR^c$;
$A^4$ is N or $CR^d$;
wherein at least one of $A^1$, $A^2$, $A^3$ and $A^4$ is N, and no more than two of $A^1$, $A^2$, $A^3$ and $A^4$ may be N;
$R^a$, $R^b$, $R^c$ and $R^d$ are independently H, $CF_3$, halogen, (1-4C)alkyl or CN;
$R^8$ is selected from hydrogen, halogen, $CF_3$, CN, (1-10C) alkyl, hydroxy(1-6C)alkyl-, (1-6C)alkoxy, (1-6C alkyl) sulfanyl, phenyl, pyridyl, pyrimidyl, and pyrazolyl, wherein each of said phenyl, pyridyl, pyrimidyl, and pyrazolyl is optionally substituted with one or more substituents independently selected from halogen, (1-4C)alkyl, (1-4C)alkoxy and $CF_3$;
$R^9$ and $R^{9a}$ are hydrogen; and
n is 1, 2 or 3.

3. A compound according to claim 1, wherein:
$X^1$ is N or $CR^1$ and $X^2$ is N or $CR^2$, wherein only one of $X^1$ and $X^2$ may be N;
$R^1$, $R^2$, $R^3$ and $R^4$ are independently selected from H, halogen, $CF_3$, (1-6C)alkyl and (1-6C)alkoxy; and
$R^5$ is (1-3C)alkylsulfonyl, (3-6C)cycloalkylsulfonyl, (cyclopropylmethyl)sulfonyl-, phenylsulfonyl-, CN, Br, $CF_3$, oxadiazolyl optionally substituted with (1-3C) alkyl, or tetrazolyl optionally substituted with (1-3C) alkyl.

4. The compound according to claim 1, wherein:
$X^1$ is $CR^1$;
$X^2$ is $CR^2$; and
$R^1$, $R^2$, $R^3$ and $R^4$ are independently selected from H, (1-6C)alkyl, $CF_3$ and halogen.

5. The compound of claim 4, wherein:
$R^1$ and $R^2$ are independently selected from H, F and Cl; and $R^3$ and $R^4$ are independently selected from H, Me, F, Cl and $CF_3$.

6. The compound of claim 4, wherein:
$R^1$ is H or F;
$R^2$ is H, F or Cl;
$R^3$ is H, F or $CF_3$; and
$R^4$ is H, Me, F or Cl.

7. The compound of claim 4, wherein:
$R^1$ and $R^4$ are H; and
$R^2$ and $R^3$ are F.

8. The compound of claim 4, wherein:
$R^1$, $R^2$ and $R^4$ are H; and
$R^3$ is F.

9. The compound according to claim 1, wherein:
$X^1$ is N; and
$X^2$ is $CR^2$.

10. The compound of claim 9, wherein $R^2$, $R^3$ and $R^4$ are independently selected from H, halogen, and (1-6C)alkyl.

11. The compound of claim 9, wherein $R^2$, $R^3$ and $R^4$ are each H.

12. The compound of claim 9, wherein $R^2$ and $R^4$ are H and $R^3$ is Cl.

13. The compound according to claim 1, wherein:
$X^1$ is $CR^1$; and
$X^2$ is N.

14. The compound according to claim 13, wherein $R^1$, $R^3$ and $R^4$ are independently selected from H, F, Cl and Me.

15. The compound according to claim 13, wherein each of $R^1$, $R^3$ and $R^4$ is H.

16. The compound according to claim 1, wherein $R^5$ is selected from (1-3C)alkylsulfonyl, (3-6C)cycloalkylsulfonyl-, (cyclopropylmethyl)sulfonyl, and phenylsulfonyl ($C_6H_5SO_2$—).

17. The compound according to claim 16, wherein $R^5$ is (1-3C)alkylsulfonyl.

18. The compound according to claim 17, wherein $R^5$ is methylsulfonyl.

19. The compound according to claim 1, wherein $R^5$ is selected from CN, Br and $CF_3$.

20. The compound according to claim 1, wherein $R^5$ is oxadiazolyl optionally substituted with (1-3C)alkyl.

21. The compound according to claim 1, wherein $R^5$ is tetrazolyl optionally substituted with (1-3C)alkyl.

22. The compound according to claim 1, wherein $X^1$ is $CR^1$, $X^2$ is $CR^2$, and $R^4$ and $R^5$ together with the atoms to which they are attached form a 5-6 membered saturated heterocyclic ring having 1-2 ring heteroatoms independently selected from O and S, wherein the heterocyclic ring is optionally substituted with an oxo group, and the S is optionally oxidized.

23. The compound according to claim 1, wherein $R^7$ is a group having the structure:

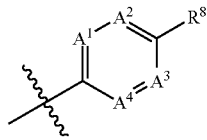

wherein
$A^1$ is $CR^a$,
$A^2$ is $CR^b$,
$A^3$ is $CR^c$,
$A^4$ is N; and
$R^a$, $R^b$ and $R^c$ are independently H, $CF_3$, halogen, (1-4C) alkyl or CN.

24. The compound of claim 23, wherein $R^a$, $R^b$ and $R^c$ are independently selected from hydrogen, Cl and (1-4C)alkyl.

25. The compound of claim 24, wherein two of $R^a$, $R^b$ and $R^c$ are hydrogen and the other is selected from hydrogen, Cl and methyl.

26. The compound of claim 25, wherein each of $R^a$, $R^b$ and $R^c$ is hydrogen.

27. The compound according to claim 1, wherein $R^7$ is a group having the structure:

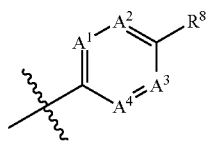

wherein:
- $A^1$ is N;
- $A^2$ is $CR^b$;
- $A^3$ is $CR^c$;
- $A^4$ is N; and
- $R^b$ and $R^c$ are independently H, $CF_3$, halogen, (1-4C)alkyl or CN.

28. The compound of claim 27, wherein one of $R^b$ and $R^c$ is hydrogen and the other is selected from hydrogen and (1-4C)alkyl.

29. The compound of claim 28, wherein $R^b$ and $R^c$ are both hydrogen.

30. The compound according to claim 1, wherein $R^7$ is a group having the structure:

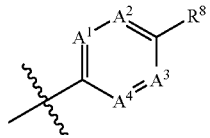

wherein
- $A^1$ is $CR^a$;
- $A^2$ is N;
- $A^3$ is $CR^c$;
- $A^4$ is N; and
- $R^a$ and $R^c$ are independently selected from H, $CF_3$, halogen, (1-4C)alkyl and CN.

31. The compound of claim 30, wherein one of $R^a$ and $R^c$ is hydrogen and the other is selected from hydrogen, halogen, CN and (1-4C)alkyl.

32. The compound of claim 31, wherein one of $R^a$ and $R^c$ is hydrogen and the other is selected from hydrogen, chloro, CN and methyl.

33. The compound of claim 32, wherein each of $R^a$ and $R^c$ is hydrogen.

34. The compound according to claim 1, wherein $R^7$ is a group having the structure:

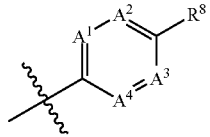

wherein:
- $A^1$ is $CR^a$;
- $A^2$ is $CR^b$;
- $A^3$ is N;
- $A^4$ is N; and
- $R^a$ and $R^b$ are independently selected from H, $CF_3$, halogen, (1-4C)alkyl and CN.

35. The compound of claim 34, wherein one of $R^a$ and $R^b$ is hydrogen and the other is selected from hydrogen and (1-4C)alkyl.

36. The compound of claim 35, wherein one of $R^a$ and $R^b$ is hydrogen and the other is selected from hydrogen and methyl.

37. The compound of claim 36, wherein each of $R^a$ and $R^b$ is hydrogen.

38. The compound according to claim 1, wherein $R^8$ is hydrogen.

39. The compound according to claim 1, wherein $R^8$ is halogen.

40. The compound according to claim 39, wherein $R^8$ is selected from Cl, Br and I.

41. The compound according to claim 40, wherein $R^8$ is Cl.

42. The compound according to claim 1, wherein $R^8$ is $CF_3$.

43. The compound according to claim 1, wherein $R^8$ is CN.

44. The compound according to claim 1, wherein $R^8$ is (1-10C)alkyl.

45. The compound according to claim 44, wherein $R^8$ is selected from methyl, ethyl, propyl, isopropyl, butyl, heptyl and decyl.

46. The compound according to claim 45, wherein $R^8$ is selected from methyl and ethyl.

47. The compound according to claim 46, wherein $R^8$ is methyl.

48. The compound according to claim 46, wherein $R^8$ is ethyl.

49. The compound according to claim 1, wherein $R^8$ is hydroxy(1-6C)alkyl-.

50. The compound according to claim 1, wherein $R^8$ is (1-6C)alkoxy.

51. The compound according to claim 1, wherein $R^8$ is (1-6C alkyl)sulfanyl.

52. The compound according to claim 1, wherein $R^8$ is phenyl optionally substituted with one or more substituents independently selected from halogen, (1-4C)alkyl, (1-4C)alkoxy and $CF_3$.

53. The compound according to claim 1, wherein $R^8$ is phenyl, pyrimidyl or pyrazolyl, each of which is optionally substituted with one or more substituents independently selected from (1-4C)alkyl.

54. The compound according to claim 53, wherein $R^8$ is pyridyl, pyrimidyl, or pyrazolyl, wherein each of said phenyl, pyridyl, pyrimidyl, and pyrazolyl are optionally substituted with one or more substituents independently selected from (1-4C)alkyl.

55. The compound according to claim 1, wherein L is O.

56. The compound according to claim 1, wherein L is NH or N(1-3C)alkyl.

57. The compound according to claim 56, wherein L is NH.

58. The compound according to claim 1, wherein n is 1 or 3.

59. The compound according to claim 1, wherein n is 1.

60. The compound according to claim 1, wherein n is 2.

61. The compound according to claim 1, wherein n is 2 and at least two of $R^1$, $R^2$, $R^3$ and $R^4$ is not H.

62. The compound according to claim 1, wherein n is 3.

63. The compound according to claim 1, wherein $R^6$ is H.

64. The compound according to claim 1, wherein $R^6$ is OH.

65. The compound according to claim 1, wherein $R^{6a}$ is H.

66. The compound according to claim 1, wherein $R^9$ and $R^{9a}$ are hydrogen.

67. The compound according to claim 1, wherein $R^9$ and $R^{9a}$ are methyl.

68. A compound of claim 1, selected from any one of Examples 1-73, or 75-166 or a pharmaceutically acceptable salt thereof.

69. A pharmaceutical composition, which comprises a compound of Formula I as defined in claim 1 or a pharmaceutically acceptable salt thereof, and a pharmaceutically acceptable diluent, carrier or excipient.

70. A method of treating type 2 diabetes in a mammal in need thereof, which comprises administering to said mammal a therapeutically effective amount of a compound of Formula I as defined in cliam 1 or a pharmaceutically acceptable salt thereof.

71. A process for the preparation of a compound of claim 1, which comprises:

(a) coupling a corresponding compound having the formula II

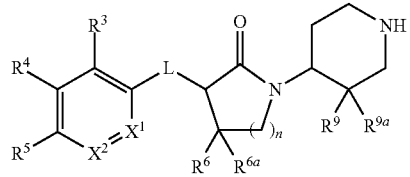

with a corresponding compound having the formula III

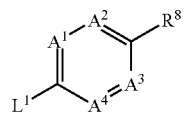

wherein $L^1$ is a leaving atom or group, in the presence of a base and optionally further in the presence of a metal catalyst and optionally in the presence of a ligand; or (b) coupling a corresponding compound having the formula IV

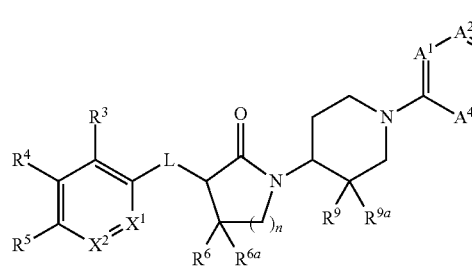

wherein $L^3$ is a leaving atom or group, with a compound having the formula $(R^8)_2Zn$ or $R^8ZnBr$ in the presence of a metal catalyst and a base; or (c) for a compound of Formula I wherein L is NH or N(1-3C)alkyl, coupling a corresponding compound having the formula V

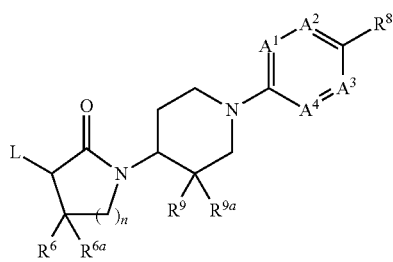

with a corresponding compound having the formula VI

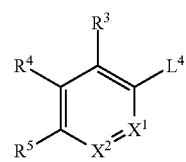

wherein $L^4$ is a leaving atom or group, in the presence of a base and optionally further in the presence of a metal catalyst; or (d) for a compound of Formula I wherein $R^5$ is a group having the $R^{5a}SO_2$— where $R^{5a}$ is (1-3C) alkyl, (3-6C) cycloalkyl, cyclopropylmethyl- or phenyl, reacting a corresponding compound having the formula VII

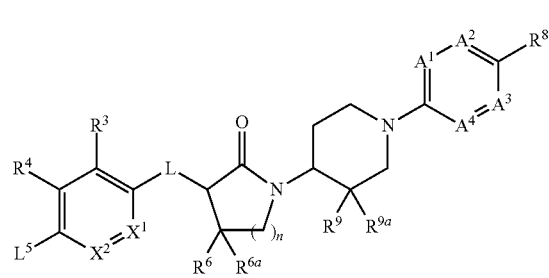

wherein $L^5$ is a leaving atom or group, with a reagent having the formula $R^{5a}SO_2Na$ in the presence of a metal catalyst and a ligand; or (e) for a compound of Formula I wherein $R^8$ is phenyl, pyridyl, pyrimidyl or pyrazolyl, each of which is optionally substituted with one or more substituents independently selected from halogen, (1-4C)alkyl, (1-4C) alkoxy and $CF_3$, reacting a corresponding compound having the formula IV

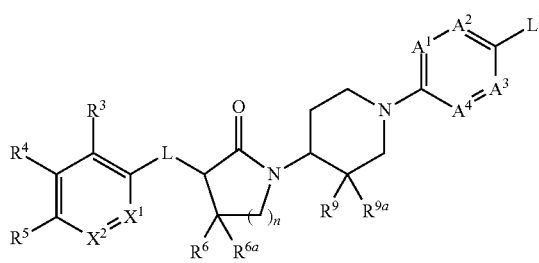

IV wherein $L^3$ is a leaving atom or group, with a corresponding compound having the formula $R^{8a}B(OR^eR^f)_2$, where $R^{8a}$ is phenyl, pyridyl, pyrimidyl or pyrazolyl, each of which is optionally substituted with one or more substituents independently selected from halogen, (1-4C)alkyl, (1-4C)alkoxy and $CF_3$, and $R^e$ and $R^f$ are H or (1-6C)alkyl, or $R^e$ and $R^f$ together with the atoms to which they are connected form a 5-6 membered ring optionally substituted with 1-4 substituents selected from (1-3C alkyl), wherein said coupling takes place in the presence of a palladium catalyst and a base; or (f) for a compound of Formula I wherein $R^5$ is CN, reacting a corresponding compound having the formula VII

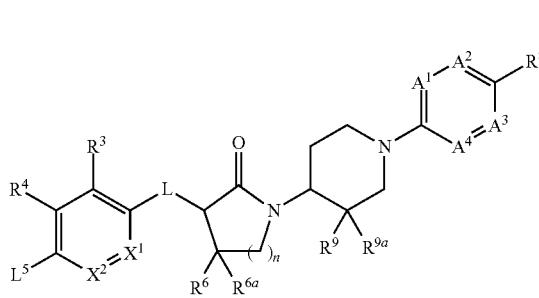

VII wherein $L^5$ is a leaving atom or group, in the presence of a metal catalyst CuCN; or (g) for a compound of Formula I wherein $R^8$ is CH(OH)(1-5C alkyl), reacting a corresponding compound having the formula VIII

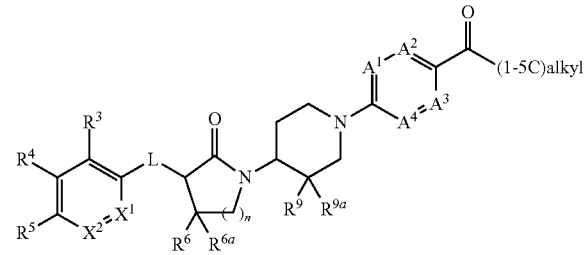

VIII with a reducing agent; or (h) for a compound of Formula I wherein $R^8$ is (1-6C alkyl)sulfanyl, reacting a corresponding compound having the formula IV

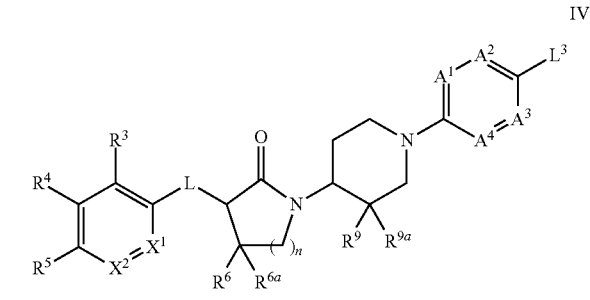

IV wherein $L^3$ is a leaving atom or group, with a reagent having the formula NaS(1-6C alkyl) in the presence of a palladium catalyst, a ligand and a base; and optionally removing any protecting groups and optionally preparing a salt thereof.

* * * * *